US012391671B2

(12) United States Patent
Scott et al.

(10) Patent No.: US 12,391,671 B2
(45) Date of Patent: Aug. 19, 2025

(54) ALLOSTERIC EGFR INHIBITORS AND METHODS OF USE THEREOF

(71) Applicant: Dana-Farber Cancer Institute, Inc., Boston, MA (US)

(72) Inventors: David A. Scott, Newton, MA (US); David Heppner, Brookline, MA (US); Thomas Gero, Stow, MA (US); Courtney A. Cullis, Bedford, MA (US); Ciric To, Medford, MA (US); Shih-Chung Huang, Lexington, MA (US); Yongbo Hu, Winchester, MA (US); Steve Stroud, Cambridge, MA (US); Tyler Beyett, Brookline, MA (US); Michael Eck, Brookline, MA (US); Nathanael S. Gray, Jamaica Plain, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 628 days.

(21) Appl. No.: 17/741,206

(22) Filed: May 10, 2022

(65) Prior Publication Data

US 2022/0411404 A1 Dec. 29, 2022

Related U.S. Application Data

(63) Continuation of application No. PCT/US2020/060001, filed on Nov. 11, 2020.

(60) Provisional application No. 63/030,655, filed on May 27, 2020, provisional application No. 62/933,776, filed on Nov. 11, 2019.

(51) Int. Cl.

| | |
|---|---|
| ***A61K 31/4184*** | (2006.01) |
| ***A61K 31/4439*** | (2006.01) |
| ***A61K 31/454*** | (2006.01) |
| ***A61K 31/4545*** | (2006.01) |
| ***A61K 31/4725*** | (2006.01) |
| ***A61K 31/506*** | (2006.01) |
| ***A61K 31/513*** | (2006.01) |
| ***A61K 31/517*** | (2006.01) |
| ***A61K 31/519*** | (2006.01) |
| ***A61K 31/52*** | (2006.01) |
| ***A61K 31/5377*** | (2006.01) |
| ***A61K 31/541*** | (2006.01) |
| ***A61K 45/06*** | (2006.01) |
| ***A61P 35/00*** | (2006.01) |
| ***C07D 401/14*** | (2006.01) |
| ***C07D 403/06*** | (2006.01) |
| ***C07D 403/14*** | (2006.01) |
| ***C07D 471/04*** | (2006.01) |
| ***C07D 473/00*** | (2006.01) |
| ***C07D 487/04*** | (2006.01) |
| ***C07D 495/14*** | (2006.01) |

(52) U.S. Cl.
CPC ......... *C07D 401/14* (2013.01); *C07D 471/04* (2013.01); *C07D 473/00* (2013.01); *C07D 495/14* (2013.01)

(58) Field of Classification Search
None
See application file for complete search history.

(56) References Cited

U.S. PATENT DOCUMENTS

| | | | |
|---|---|---|---|
| 5,385,894 | A | 1/1995 | de Laszlo et al. |
| 5,409,926 | A | 4/1995 | Reilly et al. |
| 8,981,092 | B2 | 3/2015 | Mirizzi et al. |
| 10,836,722 | B2 | 11/2020 | Gray et al. |
| 2007/0213349 | A1 | 9/2007 | Cheruvallath et al. |
| 2009/0105255 | A1 | 4/2009 | Cheruvallath et al. |
| 2018/0193470 | A1 | 7/2018 | Crew et al. |
| 2018/0290975 | A1 | 10/2018 | Gray et al. |

FOREIGN PATENT DOCUMENTS

| | | | | |
|---|---|---|---|---|
| WO | WO 1995/003055 | A1 | 2/1995 | |
| WO | WO-2009143049 | A1 * | 11/2009 | ........... C07D 239/90 |
| WO | WO 2013/012918 | A1 | 1/2013 | |
| WO | WO 2018115218 | A1 | 6/2018 | |
| WO | WO 2018220149 | A1 | 12/2018 | |
| WO | WO 2019007696 | A1 | 1/2019 | |
| WO | WO 2019149922 | A1 | 8/2019 | |
| WO | WO 2019164945 | A1 | 8/2019 | |
| WO | WO 2020002487 | A1 | 1/2020 | |
| WO | WO 2020036386 | A1 | 2/2020 | |
| WO | WO 2020254544 | A1 | 12/2020 | |
| WO | WO 2020254546 | A1 | 12/2020 | |
| WO | WO 2020254547 | A1 | 12/2020 | |
| WO | WO 2020254562 | A1 | 12/2020 | |
| WO | WO 2020254565 | A1 | 12/2020 | |
| WO | WO 2020254568 | A1 | 12/2020 | |
| WO | WO 2020254572 | A1 | 12/2020 | |
| WO | WO 2020257607 | A1 | 12/2020 | |

(Continued)

OTHER PUBLICATIONS

Golub et al. Science, vol. 286, 1999, pp. 531-537.*
Akritopoulou-Zanze et al. "Synthesis of substituted fused pyridines, pyrazines and pyrimidines by sequential Ugi/inverse electron demand Diels-Alder transformations", *Tetrahedron Letters*, 50:5773-5776, Jul. 2009.
Huang et al., "Synthesis and antitumor activities of novel dipeptide derivatives derived from dehydroabietic acid", *Bioorganic & Medicinal Chemistry Letters*, 24:1511-1518, 2014.
International Search Report for International Application No. PCT/US2020/038672, mailed Sep. 28, 2020, 3 pages.

(Continued)

*Primary Examiner* — Kortney L. Klinkel
*Assistant Examiner* — Alison Azar Salamatian
(74) *Attorney, Agent, or Firm* — Nielsen IP Law LLC

(57) ABSTRACT

The disclosure relates to compounds that act as allosteric inhibitors of epidermal growth factor receptor (EGFR); pharmaceutical compositions comprising the compounds; and methods of treating or preventing kinase-mediated disorders, including cancer and other proliferation diseases.

29 Claims, No Drawings

(56) References Cited

FOREIGN PATENT DOCUMENTS

| | | | |
|---|---|---|---|
| WO | WO 2020257632 | A1 | 12/2020 |
| WO | WO 2021123084 | A1 | 6/2021 |
| WO | WO 2021123087 | A1 | 6/2021 |
| WO | WO 2021127561 | A1 | 6/2021 |

OTHER PUBLICATIONS

International Search Report for International Application No. PCT/US2020/060001, mailed Mar. 10, 2021, 4 pages.

International Search Report for International Application No. PCT/US2021/036657, mailed Nov. 3, 2021, 4 pages.

Pubchem, Substance Record for SID 36584161, Available Date: Dec. 5, 2007 [retrieved on Jan. 6, 2021]. Retrieved from the Internet: <URL: https://pubchem.ncbi.nlm.nih.gov/substance/36584161> entire document.

Pubchem, Substance Record for SID 165334394, Available Date: Nov. 28, 2013 [retrieved on Feb. 22, 2021]. Retrieved from the Internet: <URL: https://pubchem.ncbi.nlm.nih.gov/substance/165334394> entire document.

Pubchem, Substance Record for SID 219108155, Available Date: Oct. 21, 2014 [retrieved on Jan. 6, 2021]. Retrieved from the Internet: <URL: https:/pubchem.ncbi.nlm.nih.gov/substance/219108155> entire document.

Pubchem, Substance Record for SID 273994102, Available Date: Dec. 18, 2015 [retrieved on Jan. 6, 2021]. Retrieved from the Internet: <URL: https://pubchem.ncbi.nlm.nih.gov/substance/273994102> entire document.

Pubchem SID 400025951 Deposit Date: Dec. 7, 2019 (Dec. 7, 2019) (https://pubchem.ncbi.nlm.nih.gov/substance/400025951#section+2D-Structure), pp. 1-5.

Pubchem Compound Record for CID 16611162, '3-(2-Anilino-2-oxo-1-phenylethyl)-4-oxophthalazine-1-carboxylic acid', U.S. National Library of Medicine, Jul. 31, 2007 (Jul. 31, 2007), (https://pubchem.ncbi.nlm.nih.gov/compound/16611162), pp. 1-8.

Pubchem Compound Record for CID 67435267, '(2S)-2-Cyclohexyl-2-(4-oxoquinazolin-3-yl)-N-pyridin-2-ylpropanamide', U.S. National Library of Medicine, Nov. 30, 2012 (Nov. 30, 2012), (https://pubchem.ncbi.nim.nih.gov/compound/67435267), pp. 1-10.

To et al., "Single and Dual Targeting of Mutant EGFR with an Allosteric Inhibitor", Cancer Discovery, 9:926-943, Jul. 2019.

Written Opinion of the International Searching Authority for International Application No. PCT/US2020/038705, mailed Sep. 25, 2020, 4 pages.

Xiang et al., Concise Synthesis of Isoquinoline via the Ugi and Heck Reactions, *Organic Letters*, 6(18):3155-3158, Aug. 2004.

Zhang et al., "Discovery of novel dual-action antidiabetic agents that inhibit glycogen phosphorylase and activate glucokinase", *European Journal of Medicinal Chemistry*, 58:624-639, 2012.

Zhang et al., "Design and Synthesis of Phenylpyrrolidine Phenylglycinamides as Highly Potent and Selective TF-FVIIa Inhibitors", ACS Medicinal Chemistry Letters, 5:188-192, 2014.

International Preliminary Report on Patentability for International Application No. PCT/US2021/036657, mailed Dec. 13, 2022, 7 pages.

Jin et al., "Visible-Light-Mediated Aerobic Oxidation of N-Alkylpyridinium Salts under Organic Photocatalysis", *Journal of the American Chemical Society* 139(40):14237-14243 (2017).

Khodarahmi et al., "Design of novel potential aromatase inhibitors via hybrid pharmacophore approach: docking improvement using the QM/MM method", *RSC Advances* 5(71):58055-58064 (2015).

* cited by examiner

ALLOSTERIC EGFR INHIBITORS AND METHODS OF USE THEREOF

RELATED APPLICATIONS

This application claims priority to U.S. provisional application No. 62/933,776, filed Nov. 11, 2019, and U.S. provisional application No. 63/030,655, filed May 27, 2020, the contents of which are incorporated herein in their entirety.

STATEMENT REGARDING FEDERALLY SPONSORED RESEARCH OR DEVELOPMENT

This invention was made with government support under Grant No. R01 CA201049 awarded by the National Institute of Health (NIH). The government has certain rights in the invention.

BACKGROUND

The epidermal growth factor receptor (EGFR, Erb-B1) belongs to a family of receptor tyrosine kinases that mediate the proliferation, differentiation, and survival of normal and malignant cells (Arteaga, C. L., *J. Clin. Oncol.* 19, 2001, 32-40). Deregulation of EGFR has been implicated in many types of human cancer, with overexpression of the receptor present in at least 70% of human cancers (Seymour, L. K. *Curr. Drug Targets* 2, 2001, 117-133), including non-small lung cell carcinomas, breast cancers, gliomas, squamous cell carcinomas of the head and neck, and prostate cancer (Raymond, E., et al., *Drugs* 60 (Suppl. 1), 2000, 15-23, discussion 41-2; Salomon, D. S., et al., *Crit, Rev. Oncol. Hematol,* 19, 1995, 183-232; Voldborg B. R., et al., *Ann. Oncol.* 8, 1997, 1197-1206). EGFR has, therefore, emerged as an attractive target for the design and development of diagnostic and therapeutic agents that can specifically bind and inhibit the receptor's tyrosine kinase activity and signal transduction pathway in cancer cells. For example, the EGFR tyrosine kinase (EGFR-TK) reversible inhibitor TARCEVA RIM is approved by the FDA for treatment of NSCLC and advanced pancreatic cancer. Other anti-EGFR targeted molecules have also been approved, including LAPATINIB® and IRESSA®.

Epidermal growth factor receptor (EGFR) tyrosine kinase inhibitors (TKIs) are effective clinical therapies for EGFR mutant advanced non-small cell lung cancer (NSCLC) patients (Mok, T. S., et al., *N. Engl. J. Med.* 361, 2009, 947-57; Paez, J. G., et al., *Science* 304, 2004, 1497-500; Lynch, T. J., et al., *N. Engl. J. Med,* 350, 2004, 2129-39; Rosell, R., et al., *Lancet Oncol.* 13, 2012, 239-46). Several random/zed clinical trials have demonstrated that EGFR TKIs are more effective, as measured by response rate (RR) and progression free survival (PFS), than chemotherapy when used as initial systemic treatment for advanced EGFR mutant NSCLC (Mok, T. S., et al., *N. Engl. J. Med.* 361, 2009, 947-57; Rosell, R., et al., *Lancet Oncol.* 13, 2012, 239-46; Sequest, L. V. et al., *J. Clin, Oncol.* 31, 2013, 3327-34; Wu, Y. L, et al., *Lancet Oncol.* 15, 2014, 213-22; Maemondo, M., et al., *N. Engl. J. Med.* 362, 2010, 2380-8; Zhou, C., et al., *Lancet Oncol.* 12, 2011, 735-42; Mitsudomi, T., et al., *Lancet Oncol.* 11, 2010, 121-8). However, the vast majority of patients will develop disease progression following successful treatment with an EGFR TKI. The most common mechanism of acquired resistance, detected in 60% of patients, is a secondary mutation in EGFR at position T790 (T790M) (Yu, H. A., et al., *Clin. Cancer Res.* 19, 2013, 2240-7). This mutation leads to an increase in ATP affinity, thus making it more difficult for reversible EGFR TKIs gefitinib and erlotinib to bind the EGFR TKI domain (Yun C. H., et al., *Proc. Natl. Acad. Sci. USA* 105, 2008, 2070-5).

Covalent EGFR inhibitors have emerged for inhibiting EGFR T790M-containing cancers. However, in lung cancer patients, afatinib is only effective in EGFR TKI naïve EGFR mutant cancers and has a RR of less than 10% in patients with NSCLC that have developed resistance to gefitinib or erlotinib (Miller, V. A., et al., *Lancet Oncol.* 13, 2012, 528-38). Afatinib is a potent inhibitor of both mutant and wild type (WT) EGFR. Inhibition of WT EGFR leads to toxicities, including skin rash and diarrhea, which limits the ability to escalate afatinib doses in patients to those necessary to inhibit EGFR T790M. Irreversible pyrimidine EGFR inhibitors including the tool compound WZ4002 and clinical compounds CO-1686 and AZD9291, overcome many of the limitations of afatinib (Zhou, W., et al., *Nature* 462, 2009, 1070-4; Walter, A. O., et al., *Cancer Discov.* 3, 2013, 1404-15; Cross, D. A. E., et al., *Cancer Discov.* 4, 2014, 1046-61). They are not only more potent on EGFR T790M, but also selectively inhibit mutant over WI EGFR and hence should lead to increased clinical efficacy and less toxicity compared with afatinib (Zhou, W., et al; Walter A. O., et al, Cross, D. A. E., et al.).

However, all current EGFR TKIs target the ATP site, and while third generation irreversible inhibitors can overcome T790M, they are all rendered impotent by the C797S mutation, which is already arising in treated patients. Cetuximab, an anti-EGFR antibody that blocks receptor dimerization, is not effective in EGFR-mutant NSCLC because mutational activation of the kinase is effectively "downstream" of receptor dimerization. Hence, alternative strategies to inhibit EGFR are needed. At present, suitable compounds with alternative mechanisms of action targeting mutant EGFR are not available. Thus, there is a need for potent small molecule EGFR inhibitors with alternative mechanisms of action targeting mutant EGFR.

SUMMARY

In an aspect, provided herein is a compound of Formula I:

(I)

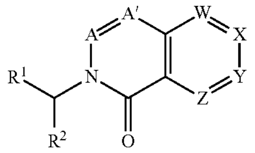

or a pharmaceutically acceptable salt thereof;

wherein:

A and A' are each, independently, CH, $CR^8$, or N;

W and Z are each, independently, N, CH, C-halo, C—($C_1$-$C_3$ alkyl), or C—($C_1$-$C_3$ alkoxy);

X and Y are each, independently, N, CH, or $CR^3$;

provided that at least one of W, X, Y, or Z is CH;

$R^1$ is selected from the group consisting of 6-10 membered aryl, 5-10 membered heteroaryl, 3-10 membered heterocycloalkyl, and 3-10 membered cycloalkyl, all of which are optionally substituted with one, two, or three $R^8$;

$R^2$ is selected from the group consisting of 6-10 membered aryl, 5-10 membered heteroaryl, 3-10 membered heterocycloalkyl, and 3-10 membered cycloalkyl, all of which are optionally substituted with one, two, or three $R^8$;

$R^3$ is independently, at each occurrence, selected from the group consisting of halogen, $OR^4$, $NR^4R^4$, $SO_2R^4$, $SO_2NHR^4$, $NHSO_2R^4$, $C(O)OR^4$, $C(O)NHR^4$, $C(O)R^4$, $C_1$-$C_6$ alkyl, $C_2$-$C_6$ alkenyl, $C_2$-$C_6$ alkynyl, 3-7 membered cycloalkyl, $C_4$-$C_7$ cycloalkenyl, $C_6$-$C_{10}$ aryl, 5-6 membered heteroaryl, and 5-7 membered heterocyclyl, wherein alkyl, alkenyl, or alkynyl are each optionally substituted one, two, or three times with $R^4$, and wherein aryl, heteroaryl, or heterocyclyl are each optionally substituted one, two, or three times with $R^5$;

$R^4$ is independently, at each occurrence, selected from the group consisting of H, $(CH_2)_{0-3}$—($C_3$-$C_7$ cycloalkyl), $(CH_2)_{0-3}$—($C_4$-$C_7$ cycloalkenyl), $(CH_2)_{0-3}$—($C_6$-$C_{10}$ aryl), $(CH_2)_{04}$-(5-6 membered heteroaryl), and $(CH_2)_{0-3}$-(5-7 membered heterocyclyl), wherein the aryl, heteroaryl, or heterocyclyl are each optionally substituted one, two, or three times with $R^5$;

$R^5$ is independently, at each occurrence, selected from the group consisting of $C_1$-$C_6$ alkyl, $C_1$-$C_6$ haloalkyl, $C_1$-$C_8$ alkoxy, $C_1$-$C_6$ haloalkoxy, $C_1$-$C_3$ alkylamine, 3-10 membered cycloalkyl, halogen, COOH, C(O)O($C_1$-$C_6$ alkyl), $O(CH_2)_{1-3}$—OH, $NH_2$, NH($C_1$-$C_6$ alkyl), N($C_1$-$C_6$ alkyl$)_2$, OH, CN, $(CH_2)_{0-3}$—($C_6$-$C_{10}$ aryl), $(CH_2)_{0-3}$-(5-6 membered heteroaryl), and $(CH_2)_{0-3}$-(5-7 membered heterocyclyl), wherein the aryl, heteroaryl, or heterocyclyl are each optionally substituted one, two, or three times with $R^7$;

$R^6$ is independently, at each occurrence, selected from the group consisting of $C_1$-$C_3$ alkyl, $C_1$-$C_3$ haloalkyl, alkoxy, $C_1$-$C_3$ haloalkoxy, $C_1$-$C_3$ alkylamine, halogen, OH, $NO_2$, $NH_2$, NH($C_1$-$C_6$ alkyl), N($C_1$-$C_6$ alkyl$)_2$, $(CH_2)_{1-4}OH$, $S(O)_{0-2}H$, $S(O)_{0-2}NH_2$, or CN;

alternatively, two $R^6$, together with the atoms to which they are attached, can form 5-10 membered heteroaryl, 6-10 membered aryl, 3-10 membered heterocycloalkyl, or 3-10 membered cycloalkyl;

$R^7$ is independently, at each occurrence, selected from the group consisting of substituents independently selected from $C_1$-$C_6$ alkyl, $C_1$-$C_6$ haloalkyl, $C_1$-$C_6$ alkoxy, $C_1$-$C_6$ haloalkoxy, halogen, $NH_2$, NH($C_1$-$C_6$ alkyl), N($C_1$-$C_6$ alkyl$)_2$, $SO_2NH_2$, $SO_2$NH($C_1$-$C_6$ alkyl), $SO_2$N($C_1$-$C_6$ alkyl$)_2$, $(CH_2)_{1-2}$—OH, $C(O)(CH_2)_{1-2}$—OH, C(O)($C_1$-$C_6$ alkyl), and C(O)O($C_1$-$C_6$ alkyl);

alternatively, two $R^7$, together with the atoms to which they are attached, can form 5-10 membered heteroaryl, 6-10 membered aryl, 3-10 membered heterocycloalkyl, or 3-10 membered cycloalkyl; and $R^8$ is independently, at each occurrence, selected from the group consisting of $C_1$-$C_3$ alkyl, $C_1$-$C_3$ haloalkyl, $C_1$-$C_3$ alkoxy, $C_1$-$C_3$ haloalkoxy, $C_1$-$C_3$ alkylamine, 3-6 membered cycloalkyl, halogen, OH, $NO_2$, $NH_2$, NH($C_1$-$C_6$ alkyl), N($C_1$-$C_6$ alkyl$)_2$, $(CH_2)_{1-4}OH$, $S(O)_{0-2}H$, $S(O)_{0-2}NH_2$, or CN.

In another aspect, provided herein is a compound of Formula II:

(II)

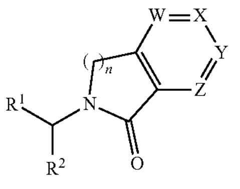

or a pharmaceutically acceptable salt thereof;

wherein

W and Z are each, independently, N, CH, C-halo, C—($C_1$-$C_3$ alkyl), or C—($C_1$-$C_3$ alkoxy);

X and Y are each, independently, N, CH, or $CR^3$;

provided that at least one of W, X, Y, or Z is CH;

$R^1$ is selected from the group consisting of 6-10 membered aryl, 5-10 membered heteroaryl, 3-10 membered heterocycloalkyl, and 3-10 membered cycloalkyl, all of which are optionally substituted with one, two, or three $R^8$;

$R^2$ is selected from the group consisting of 6-10 membered aryl, 5-10 membered heteroaryl, 3-10 membered heterocycloalkyl, and 3-10 membered cycloalkyl, all of which are optionally substituted with one, two, or three $R^6$;

$R^3$ is independently, at each occurrence, selected from the group consisting of halogen, $OR^4$, $NR^4R^4$, $SO_2R^4$, $SO_2NHR^4$, $NHSO_2R^4$, $C(O)OR^4$, $C(O)NHR^4$, $C(O)R^4$, $C_1$-$C_6$ alkyl, $C_2$-$C_6$ alkenyl, $C_2$-$C_6$ alkynyl, 3-7 membered cycloalkyl, $C_4$-$C_7$ cycloalkenyl, $C_6$-$C_{10}$ aryl, 5-6 membered heteroaryl, and 5-7 membered heterocyclyl, wherein alkyl, alkenyl, or alkynyl are each optionally substituted one, two, or three times with $R^4$, and wherein aryl, heteroaryl, or heterocyclyl are each optionally substituted one, two, or three times with $R^5$;

$R^4$ is independently, at each occurrence, selected from the group consisting of H, $(CH_2)_{0-3}$—($C_3$-$C_7$ cycloalkyl), $(CH_2)_{0-3}$—($C_4$-$C_7$ cycloalkenyl), $(CH_2)_{0-3}$—($C_6$-$C_{10}$ aryl), $(CH_2)_{0-3}$-(5-6 membered heteroaryl), and $(CH_2)_{0-3}$-(5-7 membered heterocyclyl), wherein the aryl, heteroaryl, or heterocyclyl are each optionally substituted one, two, or three times with $R^5$;

$R^5$ is independently, at each occurrence, selected from the group consisting of $C_1$-$C_6$ alkyl, $C_1$-$C_6$ haloalkyl, $C_1$-$C_6$ alkoxy, $C_1$-$C_6$ haloalkoxy, $C_1$-$C_3$ alkylamine, 3-10 membered cycloalkyl, halogen, COOH, C(O)O($C_1$-$C_6$ alkyl), $O(CH_2)_{1-3}$—OH, $NH_2$, NH($C_1$-$C_6$ alkyl), N($C_1$-$C_6$ alkyl$)_2$, OH, CN, $(CH_2)_{0-3}$—($C_6$-$C_{10}$ aryl), $(CH_2)_{0-3}$-(5-6 membered heteroaryl), and $(CH_2)_{0-3}$-(5-7 membered heterocyclyl), wherein the aryl, heteroaryl, or heterocyclyl are each optionally substituted one, two, or three times with $R^7$;

$R^6$ is independently, at each occurrence, selected from the group consisting of $C_1$-$C_3$ alkyl, $C_1$-$C_3$ haloalkyl, $C_1$-$C_3$ alkoxy, $C_1$-$C_3$ haloalkoxy, $C_1$-$C_3$ alkylamine, halogen, OH, $NO_2$, $NH_2$, NH($C_1$-$C_6$ alkyl), N($C_1$-$C_6$ alkyl$)_2$, $(CH)_{1-4}OH$, $S(O)_{0-2}H$, $S(O)_{0-2}NH_2$, or CN;

alternatively, two $R^6$, together with the atoms to which they are attached, can form 5-10 membered heteroaryl, 6-10 membered aryl, 3-10 membered heterocycloalkyl, or 3-10 membered cycloalkyl;

$R^7$ is independently, at each occurrence, selected from the group consisting of substituents independently selected from $C_1$-$C_6$ alkyl, $C_1$-$C_6$ haloalkyl, $C_1$-$C_6$ alkoxy, $C_1$-$C_6$ haloalkoxy, halogen, $NH_2$, NH($C_1$-$C_6$ alkyl), N($C_1$-$C_6$ alkyl$)_2$, $SO_2NH_2$, $SO_2$NH($C_1$-$C_6$ alkyl), $SO_2$N($C_1$-$C_6$ alkyl$)_2$, $(CH_2)_{1-2}$—OH, $C(O)(CH_2)_{1-2}$—OH, C(O)($C_1$-$C_6$ alkyl), and C(O)O($C_1$-$C_6$ alkyl);

alternatively, two $R^7$, together with the atoms to which they are attached, can form 5-10 membered heteroaryl, 6-10 membered aryl, 3-10 membered heterocycloalkyl, or 3-10 membered cycloalkyl;

$R^8$ is independently, at each occurrence, selected from the group consisting of $C_1$-$C_3$ alkyl, $C_1$-$C_3$ haloalkyl, $C_1$-$C_3$ alkoxy, $C_1$-$C_3$ haloalkoxy, $C_1$-$C_3$ alkylamine, 3-6 membered cycloalkyl, halogen, OH, $NO_2$, $NH_2$, $NH(C_1-C_6$ alkyl), $N(C_1-C_6$ alkyl$)_2$, $(CH_2)_{1-4}OH$, $S(O)_{0-2}H$, $S(O)_{0-2}NH_2$, or CN; and n is 1 or 2.

In yet another aspect, provided herein is a compound of Formula III:

(III)

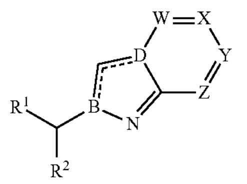

or a pharmaceutically acceptable salt thereof;

wherein

⎓ is an optional double bond;

B and D are each, independently, C or N;

W and Z are each, independently, N, CH, C-halo, C—($C_1$-$C_3$ alkyl), or C—($C_1$-$C_3$ alkoxy);

X and Y are each, independently, N, CH, or $CR^3$;

provided that at least one of W, X, Y, or Z is CH;

$R^1$ is selected from the group consisting of 6-10 membered aryl, 5-10 membered heteroaryl, 3-10 membered heterocycloalkyl, and 3-10 membered cycloalkyl, all of which are optionally substituted with one, two, or three $R^8$;

$R^2$ is selected from the group consisting of 6-10 membered aryl, 5-10 membered heteroaryl, 3-10 membered heterocycloalkyl, and 3-10 membered cycloalkyl, all of which are optionally substituted with one, two, or three $R^6$;

$R^3$ is independently, at each occurrence, selected from the group consisting of halogen, $OR^4$, $NR^4R^4$, $SO_2R^4$, $SO_2NHR^4$, $NHSO_2R^4$, $C(O)OR^4$, $C(O)NHR^4$, $C(O)R^4$, $C_1$-$C_6$ alkyl, $C_2$-$C_6$ alkenyl, $C_2$-$C_6$ alkynyl, 3-7 membered cycloalkyl, $C_4$-$C_7$ cycloalkenyl, $C_6$-$C_{10}$ aryl, 5-6 membered heteroaryl, and 5-7 membered heterocyclyl, wherein alkyl, alkenyl, or alkynyl are each optionally substituted one, two, or three times with $R^4$, and wherein aryl, heteroaryl, or heterocyclyl are each optionally substituted one, two, or three times with $R^5$;

$R^4$ is independently, at each occurrence, selected from the group consisting of H, $(CH_2)_{0-3}$—($C_3$-$C_7$ cycloalkyl), $(CH_2)_{0-3}$—($C_4$-$C_7$ cycloalkenyl), $(CH_2)_{0-3}$—($C_6$-$C_{10}$ aryl), $(CH_2)_{0-3}$-(5-6 membered heteroaryl), and $(CH_2)_{0-3}$-(5-7 membered heterocyclyl), wherein the aryl, heteroaryl, or heterocyclyl are each optionally substituted one, two, or three times with $R^5$;

$R^5$ is independently, at each occurrence, selected from the group consisting of $C_1$-$C_6$ alkyl, $C_1$-$C_6$ haloalkyl, $C_1$-$C_6$alkoxy, $C_1$-$C_6$ haloalkoxy, $C_1$-$C_3$ alkylamine, 3-10 membered cycloalkyl, halogen, COOH, C(O)O ($C_1$-$C_6$ alkyl), $O(CH_2)_{1-3}$—OH, $NH_2$, $NH(C_1-C_6$ alkyl), $N(C_1-C_6$ alkyl$)_2$, OH, CN, $(CH_2)_{0-3}$—($C_6$-$C_{10}$ aryl), $(CH_2)_{0-3}$-(5-6 membered heteroaryl), and $(CH_2)_{0-3}$-(5-7 membered heterocyclyl), wherein the aryl, heteroaryl, or heterocyclyl are each optionally substituted one, two, or three times with $R^7$;

$R^6$ is independently, at each occurrence, selected from the group consisting of $C_1$-$C_3$ alkyl, $C_1$-$C_3$ haloalkyl, $C_1$-$C_3$ alkoxy, $C_1$-$C_3$ haloalkoxy, $C_1$-$C_3$ alkylamine, halogen, OH, $NO_2$, $NH_2$, $NH(C_1-C_6$ alkyl), $N(C_1-C_6$ alkyl$)_2$, $(CH_2)_{1-4}OH$, $S(O)_{0-2}H$, $S(O)_{0-2}NH_2$, or CN;

alternatively, two $R^6$, together with the atoms to which they are attached, can form 5-10 membered heteroaryl, 8-10 membered aryl, 3-10 membered heterocycloalkyl, or 3-10 membered cycloalkyl;

$R^7$ is independently, at each occurrence, selected from the group consisting of substituents independently selected from $C_1$-$C_6$ alkyl, $C_1$-$C_6$ haloalkyl, $C_1$-$C_6$alkoxy, $C_1$-$C_6$ haloalkoxy, halogen, $NH_2$, $NH(C_1-C_6$ alkyl), $N(C_1-C_6$ alkyl$)_2$, $SO_2NH_2$, $SO_2NH(C_1-C_6$ alkyl), $SO_2N(C_1-C_6$ alkyl$)_2$, $(CH_2)_{1-2}$—OH, $C(O)(CH_2)_{1-2}$—OH, C(O)($C_1$-$C_6$ alkyl), and C(O)O($C_1$-$C_6$ alkyl);

alternatively, two $R^7$, together with the atoms to which they are attached, can form 5-10 membered heteroaryl, 6-10 membered aryl, 3-10 membered heterocycloalkyl, or 3-10 membered cycloalkyl; and $R^8$ is independently, at each occurrence, selected from the group consisting of $C_1$-$C_3$ alkyl, $C_1$-$C_3$ haloalkyl, $C_1$-$C_3$ alkoxy, $C_1$-$C_3$ haloalkoxy, $C_1$-$C_3$ alkylamine, 3-6 membered cycloalkyl, halogen, OH, $NO_2$, $NH_2$, $NH(C_1-C_6$ alkyl), $N(C_1-C_6$ alkyl$)_2$, $(CH_2)_{1-4}OH$, $S(O)_{0-2}H$, $S(O)_{0-2}NH_2$, or CN.

In an aspect, provided herein is a method of treating cancer or a proliferation disease, comprising administering to a subject in need thereof an effective amount of a compound of disclosed herein or a pharmaceutical composition comprising a compound disclosed herein and a pharmaceutically acceptable carrier. In one embodiment, the cancer is lung cancer, breast cancer, glioma, squamous cell carcinoma, or prostate cancer. In another embodiment, the method further comprises administering to the subject a second active agent, wherein said second active agent prevents EGFR dimer formation. In another embodiment, the subject is a human.

The disclosure also provides a kit comprising a compound capable of inhibiting EGFR activity selected from a compound of the present disclosure, or a pharmaceutically acceptable salt thereof, and instructions for use in treating cancer. In one embodiment, the kit further comprises components for performing a test to determine whether a subject has an activating mutation in EGFR or a resistance mutation in EGER. In another embodiment, the kit further comprises a second active agent, wherein said second active agent prevents EGFR dimer formation.

DETAILED DESCRIPTION

Definitions

Listed below are definitions of various terms used to describe the compounds and compositions disclosed herein. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e., to at least one) of the grammatical object of the article. By way of example, "an element" means one element or more than one element. Furthermore, use of the term "including" as well as other forms, such as "include," "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, including ±5%, ±1%, and ±0.1% from the specified value, as such variations are appropriate to perform the disclosed methods.

The term "administration" or the like as used herein refers to the providing a therapeutic agent to a subject. Multiple techniques of administering a therapeutic agent exist in the art including, but not limited to, intravenous, oral, aerosol, parenteral, ophthalmic, pulmonary, and topical administration.

The term "treat," "treated," "treating," or "treatment" includes the diminishment or alleviation of at least one symptom associated or caused by the state, disorder or disease being treated. In certain embodiments, the treatment comprises bringing into contact with wild-type or mutant EGFR an effective amount of a compound disclosed herein for conditions related to cancer.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual," or "subject" refers to a human or a non-human mammal. Non-human mammals include, for example, livestock and pets, such as ovine, bovine, porcine, canine, feline and marine mammals. Preferably, the patient, subject, or individual is human.

As used herein, the terms "effective amount," "pharmaceutically effective amount," and "therapeutically effective amount" refer to a nontoxic but sufficient amount of an agent to provide the desired biological result. That result may be reduction or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. The phrase "pharmaceutically acceptable salt" is not limited to a mono, or 1:1, salt. For example, "pharmaceutically acceptable salt" also includes bis-salts, such as a bis-hydrochloride salt. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "prodrug" refers to a precursor compound that will undergo metabolic activation in vivo to produce an active drug. Thus, for example, a prodrug of a compound provided herein will, when administered to a subject, undergo metabolic activation to generate the compound.

As used herein, the term "composition" or "pharmaceutical composition" refers to a mixture of at least one compound useful within the disclosure with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary, and topical administration.

The term "pharmaceutical combination" as used herein means a product that results from the mixing or combining of more than one active ingredient and includes both fixed and non-fixed combinations of the active ingredients. The term "fixed combination" means that the active ingredients, e.g., a compound of the disclosure and a co-agent, are both administered to a patient simultaneously in the form of a single entity or dosage. The term "non-fixed combination" means that the active ingredients, e.g. a compound of the disclosure and a co-agent, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more active ingredients.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the disclosure within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the disclosure, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the present disclosure, and are physiologically acceptable to the patient. Supplementary active compounds may also be incorporated into the compositions. The "pharmaceutically acceptable carrier" may further include a pharmaceutically acceptable salt of the compound disclosed herein. Other additional ingredients that may be included in the pharmaceutical compositions are known in the art and described, for example, in Remington's Pharmaceutical Sciences (Genaro, Ed., Mack Publishing Co., 1985, Easton, Pa.), which is incorporated herein by reference.

As used herein, the term "EGFR" refers to epidermal growth factor receptor (alternately referred to as ErbB-1 or HER1) and may refer to the wild-type receptor or to a receptor containing one or more mutations.

As used herein, the term "HER" or Her" refers to members of the ErbB receptor tyrosine kinase family, including EGFR, ERBB2, HER3, and HER4.

As used herein, the term "allosteric site" refers to a site on EGFR other than the ATP binding site, such as that characterized in a crystal structure of EGFR. An "allosteric site" can be a site that is close to the ATP binding site, such as that characterized in a crystal structure of EGFR. For example, one allosteric site includes one or more of the following amino acid residues of epidermal growth factor receptor (EGFR): Lys745, Leu788, Ala743, Cys755, Leu777, Phe856, Asp855, Met766, Ile759, Glu762, and/or Ala763.

As used herein, the term "agent that prevents EGFR dimer formation," or iterations thereof, refers to an agent that prevents dimer formation in which the C-lobe of the "activator" subunit impinges on the N-lobe of the "receiver" subunit. Examples of agents that prevent EGFR dimer formation include, but are not limited to, cetuximab, trastuzumab, panitumumab, and Mig6.

As used herein, the term "alkyl," by itself or as part of another substituent means, unless otherwise stated, a straight or branched chain hydrocarbon having the number of carbon atoms designated (i.e., $C_1$-$C_6$ alkyl means an alkyl having one to six carbon atoms) and includes straight and branched chains. Examples include methyl, ethyl, propyl, isopropyl, butyl, isobutyl, tert butyl, pentyl, neopentyl, and hexyl. Other examples of $C_1$-$C_6$ alkyl include ethyl, methyl, isopropyl, isobutyl, n-pentyl, and n-hexyl.

As used herein, the term "haloalkyl" refers to an alkyl group, as defined above, substituted with one or more halo substituents, wherein alkyl and halo are as defined herein. Haloalkyl includes, by way of example, chloromethyl, trifluoromethyl, bromoethyl, chlorofluoroethyl, and the like.

As used herein, the term "alkoxy" refers to the group —O-alkyl, wherein alkyl is as defined herein. Alkoxy includes, by way of example, methoxy, ethoxy, n-propoxy, isopropoxy, n-butoxy, sec-butoxy, t-butoxy and the like.

As used herein, the term "alkylamine" refers to the group —NH-alkyl, wherein alkyl is as defined herein. Alkylamine includes, by way of example, methylamine, ethylamine, isopropylamine, n-propylamine, n-butylamine, sec-butylamine, t-butylamine and the like.

As used herein, the term "haloalkoxy" refers to the group —C-haloalkyl, wherein haloalkyl is as defined herein. Haloalkoxy includes, by way of example, chloromethoxy, trifluoromethoxy, bromoethoxy, chlorofluoroethoxy, and the like.

As used herein, the term "alkenyl" refers to a monovalent group derived from a hydrocarbon moiety containing, in certain embodiments, from two to six, or two to eight carbon atoms having at least one carbon-carbon double bond. The alkenyl group may or may not be the point of attachment to another group. The term "alkenyl" includes, but is not limited to, ethenyl, 1-propenyl, 1-butenyl, heptenyl, octenyl and the like.

As used herein, the term "alkynyl" refers to a monovalent group derived from a hydrocarbon moiety containing, in certain embodiments, from two to six, or two to eight carbon atoms having at least one carbon-carbon triple bond. The alkynyl group may or may not be the point of attachment to another group. The term "alkynyl" includes, but is not limited to, ethynyl, 1-propynyl, 1-butynyl, heptynyl, octynyl and the like.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "cycloalkyl" means a non-aromatic carbocyclic system that is fully saturated having 1, 2 or 3 rings wherein such rings may be fused. The term "fused" means that a second ring is present (i.e., attached or formed) by having two adjacent atoms in common (i.e., shared) with the first ring. Cycloalkyl also includes bicyclic structures that may be bridged or spirocyclic in nature with each individual ring within the bicycle varying from 3-8 atoms. The term "cycloalkyl" includes, but is not limited to, cyclopropyl, cyclobutyl, cyclopentyl, cyclohexyl, bicyclo[3.1.0]hexyl, spiro[3.3]heptanyl, and bicyclo[1.1.1]pentyl.

As used herein, the term "cycloalkenyl" means a non-aromatic carbocyclic system that is partially saturated having 1, 2 or 3 rings wherein such rings may be fused, and wherein at least one ring contains an $sp^2$ carbon-carbon bond. The term "cycloalkenyl" includes, but is not limited to, cyclopropenyl, cyclobutenyl, cyclopentenyl, cyclohexenyl, bicyclo[3.1.0]hexenyl, spiro[3.3]heptanenyl, and bicyclo[1.1.1]pentenyl.

As used herein, the term "heterocyclyl" or "heterocycloalkyl" means a non-aromatic carbocyclic system containing 1, 2, 3 or 4 heteroatoms selected independently from N, O, and S and having 1, 2 or 3 rings wherein such rings may be fused, wherein fused is defined above. Heterocyclyl also includes bicyclic structures that may be bridged or spirocyclic in nature with each individual ring within the bicycle varying from 3-8 atoms, and containing 0, 1, or 2 N, O, or S atoms. The term "heterocyclyl" includes cyclic esters (i.e., lactones) and cyclic amides (i.e., lactams) and also specifically includes, but is not limited to, epoxidyl, oxetanyl, tetrahydrofuranyl, tetrahydropyranyl (i.e., oxanyl), pyranyl, dioxanyl, aziridinyl, azetidinyl, pyrrolidinyl, 2,5-dihydro-1H-pyrrolyl, oxazolidinyl, thiazolidinyl, piperidinyl, morpholinyl, piperazinyl, thiomorpholinyl, 1,3-oxazinanyl, 1,3-thiazinanyl, 2-azabicyclo-[2.1.1]hexanyl, 5-azabicyclo[2.1.1]hexanyl, 6-azabicyclo[3.1.1]heptanyl, 2-azabicyclo[2.2.1]-heptanyl, 3-azabicyclo[3.1.1]heptanyl, 2-azabicyclo[3.1.1]heptanyl, 3-azabicyclo[3.1.0]-hexanyl, 2-azabicyclo[3.1.0]hexanyl, 3-azabicyclo[3.2.1]octanyl, 8-azabicyclo[3.2.1]octanyl, 3-oxa-7-azabicyclo[3.3.1]nonanyl, 3-oxa-9-azabicyclo[3.3.1]nonanyl, 2-oxa-5-azabicyclo-[2.2.1]heptanyl, 6-oxa-3-azabicyclo[3.1.1]heptanyl, 2-azaspiro[3.3]heptanyl, 2-oxa-6-azaspiro[3.3]heptanyl, 2-oxaspiro

[3.3]heptanyl, 2-oxaspiro[3.5]nonanyl, 3-oxaspiro[5.3]nonanyl, and 8-oxabicyclo[3.2.1]octanyl.

As used herein, the term "aromatic" refers to a carbocycle or heterocycle with one or more polyunsaturated rings and having aromatic character, i.e., having (4n+2) delocalized π (pi) electrons, where n is an integer.

As used herein, the term "aryl" means an aromatic carbocyclic system containing 1, 2 or 3 rings, wherein such rings may be fused, wherein fused is defined above. If the rings are fused, one of the rings must be fully unsaturated and the fused ring(s) may be fully saturated, partially unsaturated or fully unsaturated. The term "aryl" includes, but is not limited to, phenyl, naphthyl, indanyl, and 1,2,3,4-tetrahydronaphthalenyl. In some embodiments, aryl groups have 6 carbon atoms. In some embodiments, aryl groups have from six to ten carbon atoms. In some embodiments, aryl groups have from six to sixteen carbon atoms.

As used herein, the term "heteroaryl" means an aromatic carbocyclic system containing 1, 2, 3, or 4 heteroatoms selected independently from N, O, and S and having 1, 2, or 3 rings wherein such rings may be fused, wherein fused is defined above. The term "heteroaryl" includes, but is not limited to, furanyl, thienyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridazinyl, pyrimidinyl, pyrazinyl, imidazo[1,2-a]pyridinyl, pyrazolo[1,5-a]pyridinyl, 5,6,7,8-tetrahydroisoquinolinyl, 5,6,7,8-tetrahydroquinolinyl, 6,7-dihydro-5H-cyclopenta[b]pyridinyl, 6,7-dihydro-5H-cyclopenta[c]pyridinyl, 1,4,5,6-tetrahydrocyclopenta[c]pyrazolyl, tetrahydrocyclopenta[c]pyrazolyl, 5,6-dihydro-4H-pyrrolo[1,2-b]pyrazolyl, 6,7-dihydro-5H-pyrrolo[1,2-b][1,2,4]triazolyl, 5,6,7,8-tetrahydro-[1,2,4]triazolo[1,5-a]pyridinyl, 4,5,6,7-tetrahydropyrazolo[1,5-a]pyridinyl, 4,5,6,7-tetrahydro-1H-indazolyl and 4,5,6,7-tetrahydro-2H-indazolyl.

It is to be understood that if an aryl, heteroaryl, cycloalkyl, or heterocyclyl moiety may be bonded or otherwise attached to a designated moiety through differing ring atoms (i.e., shown or described without denotation of a specific point of attachment), then all possible points are intended, whether through a carbon atom or, for example, a trivalent nitrogen atom. For example, the term "pyridinyl" means 2-, 3- or 4-pyridinyl, the term "thienyl" means 2- or 3-thienyl, and so forth.

As used herein, the term "substituted" means that an atom or group of atoms has replaced hydrogen as the substituent attached to another group.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

Compounds

Provided herein are compounds that are allosteric inhibitors of epidermal growth factor receptor (EGFR) useful in the treatment of kinase-mediated disorders, including cancer and other proliferation diseases.

In an aspect, provided herein is a compound of Formula I:

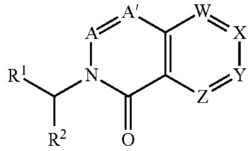

(I)

or a pharmaceutically acceptable salt thereof;

wherein:

A and A' are each, independently; CH, $CR^8$; or N;

W and Z are each, independently; N, CH, C-halo, C—($C_1$-$C_3$ alkyl), or C—($C_1$-$C_3$ alkoxy);

X and Y are each, independently, N, CH, or $CR^3$;

provided that at least one of W, X, Y, or Z is CH;

$R^1$ is selected from the group consisting of 6-10 membered aryl, 5-10 membered heteroaryl, 3-10 membered heterocycloalkyl, and 3-10 membered cycloalkyl, all of which are optionally substituted with one, two, or three $R^8$;

$R^2$ is selected from the group consisting of 6-10 membered aryl, 5-10 membered heteroaryl, 3-10 membered heterocycloalkyl, and 3-10 membered cycloalkyl, all of which are optionally substituted with one, two, or three $R^6$;

$R^3$ is independently, at each occurrence, selected from the group consisting of halogen, $OR^4$, $NR^4R^4$, $SO_2R^4$; $SO_2NHR^4$, $NHSO_2R^4$, $C(O)OR^4$; $C(O)NHR^4$, $C(O)R^4$, $C_1$-$C_6$ alkyl, $C_2$-$C_6$, alkenyl, $C_2$-$C_6$ alkynyl, 3-7 membered cycloalkyl, $C_4$-$C_7$ cycloalkenyl, $C_6$-$C_{10}$ aryl, 5-6 membered heteroaryl, and 5-7 membered heterocyclyl, wherein alkyl, alkenyl, or alkynyl are each optionally substituted one, two, or three times with $R^4$, and wherein aryl, heteroaryl, or heterocyclyl are each optionally substituted one, two, or three times with $R^5$;

$R^4$ is independently, at each occurrence, selected from the group consisting of H, $(CH_2)_{0-3}$—($C_3$-$C_7$ cycloalkyl), $(CH_2)_{0-3}$—($C_4$-$C_7$ cycloalkenyl), $(CH_2)_{0-3}$—($C_6$-$C_{10}$ aryl), $(CH_2)_{0-3}$-(5-6 membered heteroaryl), and $(CH_2)_{0-3}$-(5-7 membered heterocyclyl), wherein the aryl, heteroaryl, or heterocyclyl are each optionally substituted one, two, or three times with $R^5$;

$R^5$ is independently, at each occurrence, selected from the group consisting of $C_1$-$C_6$ alkyl, $C_1$-$C_6$ haloalkyl, $C_1$-$C_6$ alkoxy, haloalkoxy, $C_1$-$C_3$ alkylamine, 3-10 membered cycloalkyl, halogen, COOH, $C(O)O(C_1$-$C_6$ alkyl), $O(CH_2)_{1-3}$—OH, $NH_2$, $NH(C_1$-$C_6$ alkyl), $N(C_1$-$C_6$ alkyl$)_2$, OH, CN, $(CH_2)_{0-3}$—($C_6$-$C_{10}$ aryl), $(CH_2)_{0-3}$-(5-6 membered heteroaryl), and $(CH_2)_{0-3}$-(5-7 membered heterocyclyl), wherein the aryl, heteroaryl, or heterocyclyl are each optionally substituted one, two, or three times with $R^7$;

$R^6$ is independently, at each occurrence, selected from the group consisting of $C_1$-$C_3$ alkyl, $C_1$-$C_3$ haloalkyl, $C_1$-$C_3$ alkoxy, $C_1$-$C_3$ haloalkoxy, $C_1$-$C_3$ alkylamine, halogen, OH, $NO_2$, $NH_2$, $NH(C_1$-$C_6$ alkyl), $N(C_1$-$C_6$ alkyl$)_2$, $(CH_2)_{1-4}OH$, $S(O)_{0-2}H$, $S(O)_{0-2}NH_2$, or CN;

alternatively, two $R^6$, together with the atoms to which they are attached, can form 5-10 membered heteroaryl, 6-10 membered aryl, 3-10 membered heterocycloalkyl, or 3-10 membered cycloalkyl;

$R^7$ is independently, at each occurrence, selected from the group consisting of substituents independently selected from $C_1$-$C_6$ alkyl, $C_1$-$C_6$ haloalkyl, $C_1$-$C_6$ alkoxy, $C_1$-$C_6$ haloalkoxy, halogen, $NH_2$, $NH(C_1$-$C_6$ alkyl), $N(C_1$-$C_6$ alkyl$)_2$, $SO_2NH_2$, $SO_2NH(C_1$-$C_6$ alkyl), $SO_2N(C_1$-$C_6$ alkyl$)_2$, $(CH_2)_{1-2}$—OH, $C(O)(CH_2)_{1-2}$—OH, $C(O)(C_1$-$C_6$ alkyl), and $C(O)O(C_1$-$C_6$ alkyl);

alternatively, two $R^7$, together with the atoms to which they are attached, can form 5-10 membered heteroaryl, 6-10 membered aryl, 3-10 membered heterocycloalkyl, or 3-10 membered cycloalkyl; and $R^8$ is independently, at each occurrence, selected from the group consisting of $C_1$-$C_3$ alkyl, $C_1$-$C_3$ haloalkyl, $C_1$-$C_3$ alkoxy, $C_1$-$C_3$ haloalkoxy, $C_1$-$C_3$ alkylamine, 3-6 membered cycloalkyl, halogen, OH, $NO_2$, $NH_2$, $NH(C_1$-$C_6$ alkyl), $N(C_1$-$C_6$ alkyl$)_2$, $(CH_2)_{1-4}$ OH, $S(O)_{0-2}H$, $S(O)_{0-2}NH_2$, or CN.

In another aspect, provided herein is a compound of Formula I, or a pharmaceutically acceptable salt thereof, wherein W and Z are each, independently, N, CH, C-halo, C—($C_1$-$C_3$ haloalkyl), C—($C_1$-$C_3$ alkyl), or C—($C_1$-$C_3$ alkoxy);

wherein all other variables are defined above.

In an embodiment, the compound of Formula I is a compound of Formula Ia:

(Ia)

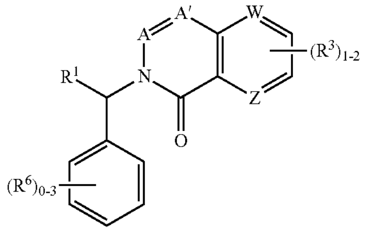

or a pharmaceutically acceptable salt thereof.

In an embodiment of Formula Ia, $R^3$ is $C_6$-$C_{10}$ aryl or 5-6 membered heteroaryl, both of which are optionally substituted one time with $R^5$. In another embodiment of Formula Ia, $R^3$ is $C_6$-$C_{10}$ aryl optionally substituted one time with $R^5$, wherein $R^5$ is 5-7 membered heterocyclyl, $C_6$-$C_{10}$ aryl, 3-10 membered cycloalkyl, or 5-6 membered heteroaryl, all of which are optionally substituted one time with $R^7$. In yet another embodiment of Formula Ia, $R^3$ is phenyl optionally substituted one time with $R^5$, wherein $R^5$ is 5-7 membered heterocyclyl, $C_6$-$C_{10}$ aryl, 3-10 membered cycloalkyl, or 5-6 membered heteroaryl, all of which are optionally substituted one time with $R^7$. In still another embodiment of Formula Ia, $R^3$ is $C_6$-$C_{10}$ aryl optionally substituted one time with $R^5$, wherein $R^5$ is 5 membered heterocyclyl optionally substituted one time with $R^7$. In an embodiment of Formula Ia, $R^3$ is phenyl optionally substituted one time with piperidine, wherein piperidine is substituted one time with $R^7$.

In another embodiment, the compound of Formula I is a compound of Formula Ib:

(Ib)

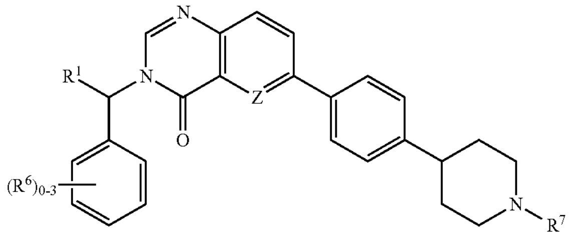

or a pharmaceutically acceptable salt thereof.

In yet another embodiment, Z is CH. In still another embodiment, Z is N. In an embodiment, Z is CF. In another embodiment, $R^6$ is independently, at each occurrence, hydroxy or halo.

In yet another embodiment, $R^1$ is selected from the group consisting of benzimidazole, imidazopyrazine, purine, imidazole, pyrazole, triazole, and imidazopyridine. In still another embodiment, $R^1$ is selected from the group consisting of:

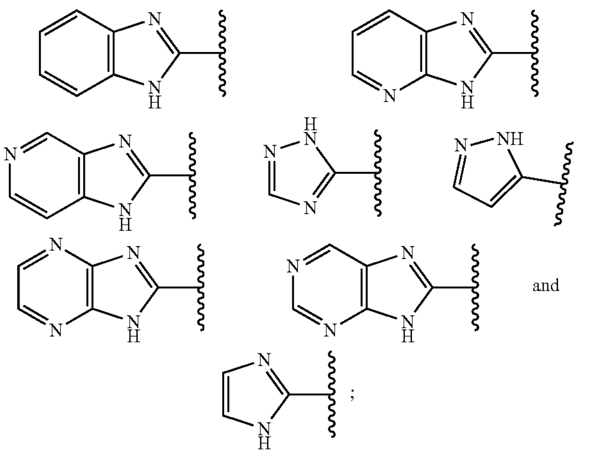

and ;

all of which are optionally substituted with one, two, or three $R^8$.

In another embodiment, $R^6$ is hydroxy, halo, or two $R^6$, together with the atoms to which they are attached, form 5-10 membered heteroaryl, 6-10 membered aryl, 3-10 membered heterocycloalkyl, or 3-10 membered cycloalkyl. In an embodiment, $R^6$ is hydroxy, fluoro, or two $R^6$, together with the atoms to which they are attached, form 5-10 membered heteroaryl, 6-10 membered aryl, 3-10 membered heterocycloalkyl, or 3-10 membered cycloalkyl. In yet another embodiment, $R^6$ is hydroxy. In still another embodiment, $R^6$ is fluoro. In another embodiment, $R^6$ is chloro. In an embodiment, there are two $R^6$ that are hydroxy and fluoro. In another embodiment, there are two $R^6$ that are hydroxy and chloro. In still another embodiment, two $R^6$, together with the atoms to which they are attached, form 5-10 membered heteroaryl, 6-10 membered aryl, 3-10 membered heterocycloalkyl, or 3-10 membered cycloalkyl.

In an embodiment, the compound of Formula i is selected from the group consisting of a compound in Table 1.

TABLE 1
| Compound No. | Structure |
|---|---|
| 001 | 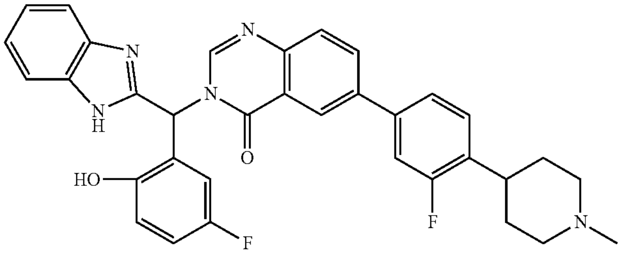 [SMILES: CN1CCC(c2ccc(-c3ccc4ncn(C(c5nc6ccccc6[nH]5)c5cc(F)ccc5O)c(=O)c4c3)cc2F)CC1] |
| 002 | 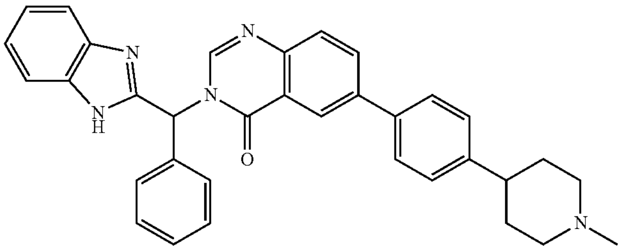 [SMILES: CN1CCC(c2ccc(-c3ccc4ncn(C(c5ccccc5)c5nc6ccccc6[nH]5)c(=O)c4c3)cc2)CC1] |
| 003 | 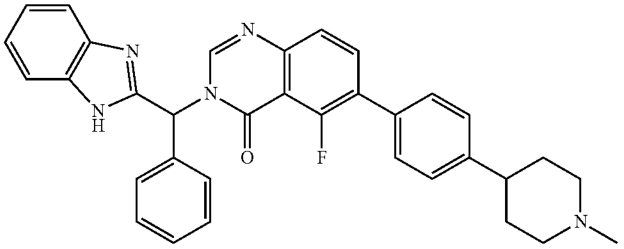 [SMILES: CN1CCC(c2ccc(-c3ccc4ncn(C(c5ccccc5)c5nc6ccccc6[nH]5)c(=O)c4c3F)cc2)CC1] |
| 004 | 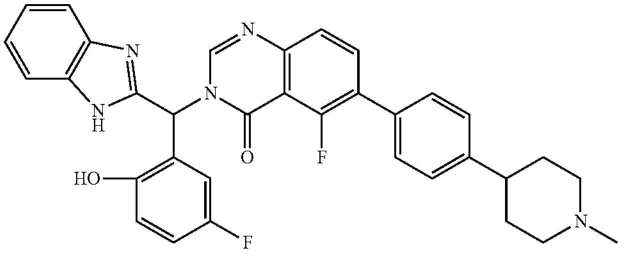 [SMILES: CN1CCC(c2ccc(-c3ccc4ncn(C(c5nc6ccccc6[nH]5)c5cc(F)ccc5O)c(=O)c4c3F)cc2)CC1] |
| 005 | 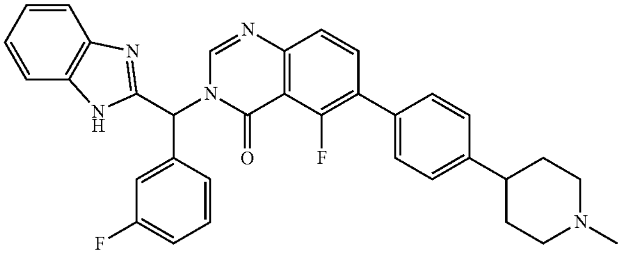 [SMILES: CN1CCC(c2ccc(-c3ccc4ncn(C(c5cccc(F)c5)c5nc6ccccc6[nH]5)c(=O)c4c3F)cc2)CC1] |
| 006 | 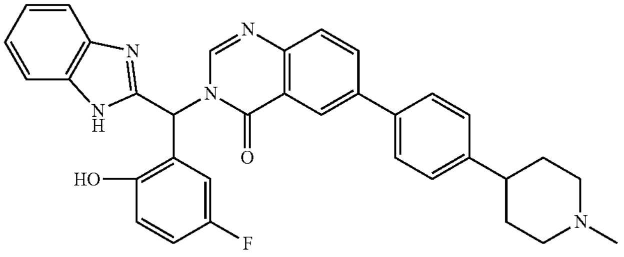 [SMILES: CN1CCC(c2ccc(-c3ccc4ncn(C(c5nc6ccccc6[nH]5)c5cc(F)ccc5O)c(=O)c4c3)cc2)CC1] |

TABLE 1-continued
| Compound No. | Structure |
|---|---|
| 007 | 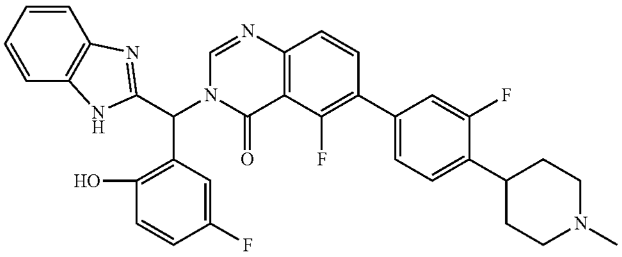 |
| 008 | 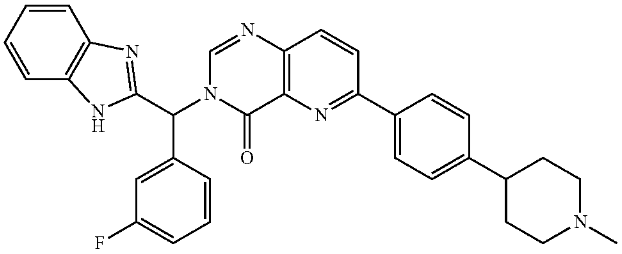 [SMILES: CN1CCC(c2ccc(-c3ccc4ncn(C(c5cccc(F)c5)c5nc6ccccc6[nH]5)c(=O)c4n3)cc2)CC1] |
| 009 | 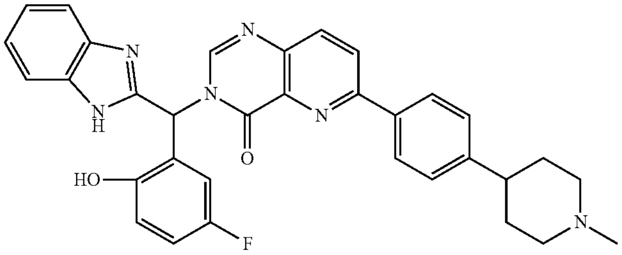 [SMILES: CN1CCC(c2ccc(-c3ccc4ncn(C(c5nc6ccccc6[nH]5)c5cc(F)ccc5O)c(=O)c4n3)cc2)CC1] |
| 053 | 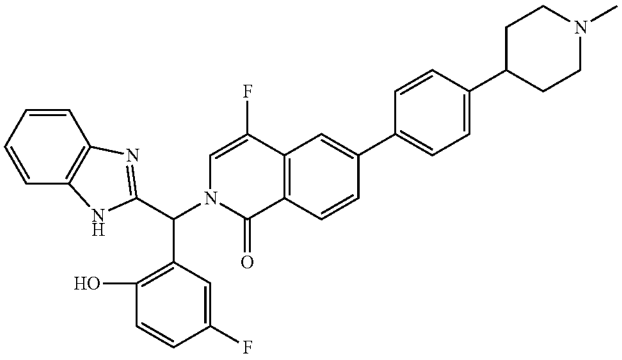 [SMILES: CN1CCC(c2ccc(-c3ccc4c(=O)n(C(c5nc6ccccc6[nH]5)c5cc(F)ccc5O)cc(F)c4c3)cc2)CC1] |
| 054 | 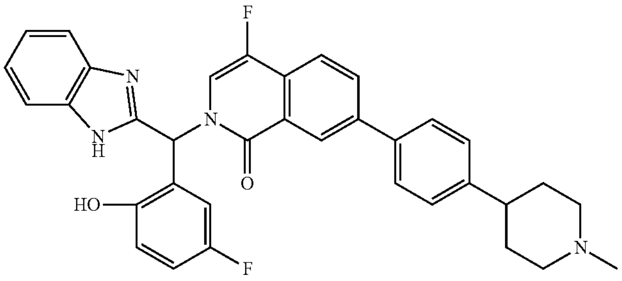 [SMILES: CN1CCC(c2ccc(-c3ccc4c(F)cn(C(c5nc6ccccc6[nH]5)c5cc(F)ccc5O)c(=O)c4c3)cc2)CC1] |

TABLE 1-continued
| Compound No. | Structure |
| --- | --- |
| 055 | 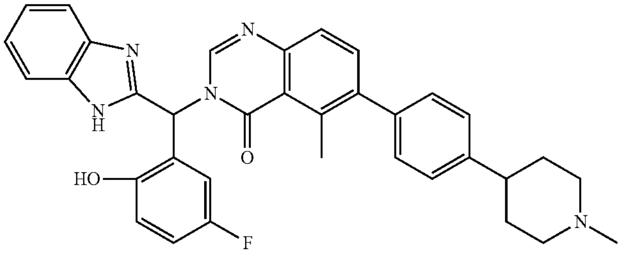 [SMILES: Cc1c(-c2ccc(C3CCN(C)CC3)cc2)ccc2ncn(C(c3nc4ccccc4[nH]3)c3cc(F)ccc3O)c(=O)c12] |
or a pharmaceutically acceptable salt thereof.
In another embodiment, the compound of Formula I is selected from the group consisting of a compound in Table 2.
TABLE 2
| Compound No. | Structure |
| --- | --- |
| 063 | 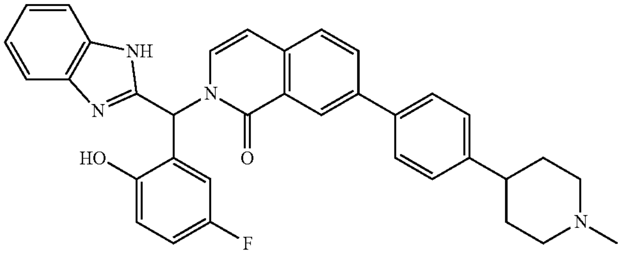 [SMILES: CN1CCC(c2ccc(-c3ccc4ccn(C(c5nc6ccccc6[nH]5)c5cc(F)ccc5O)c(=O)c4c3)cc2)CC1] |
| 064 | 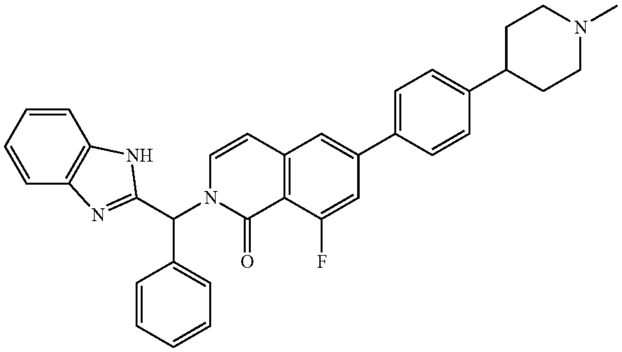 [SMILES: CN1CCC(c2ccc(-c3cc(F)c4c(=O)n(C(c5ccccc5)c5nc6ccccc6[nH]5)ccc4c3)cc2)CC1] |
| 065 | 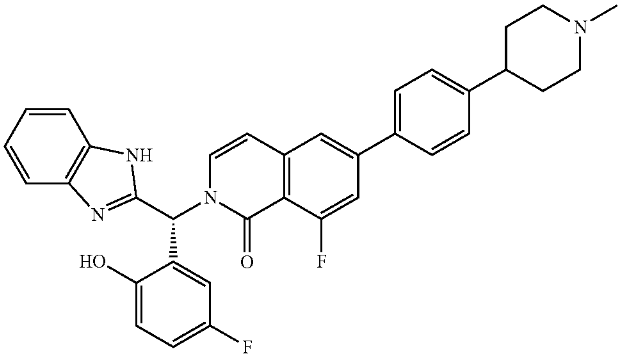 [SMILES: CN1CCC(c2ccc(-c3cc(F)c4c(=O)n([C@@H](c5nc6ccccc6[nH]5)c5cc(F)ccc5O)ccc4c3)cc2)CC1] |

TABLE 2-continued
| Compound No. | Structure |
|---|---|
| 066 | 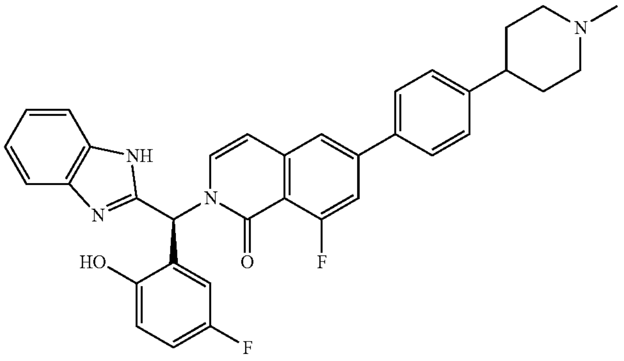 [SMILES: CN1CCC(c2ccc(-c3cc(F)c4c(=O)n([C@H](c5nc6ccccc6[nH]5)c5cc(F)ccc5O)ccc4c3)cc2)CC1] |
| 067 | 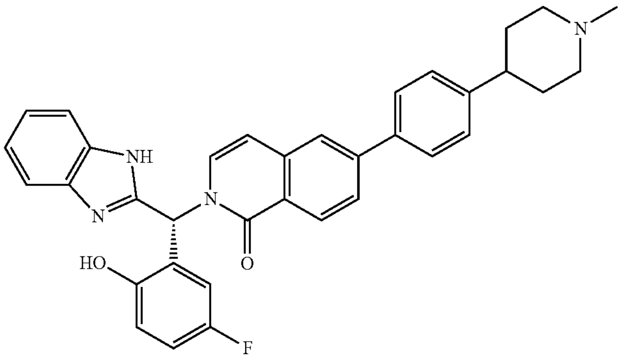 |
| 068 | 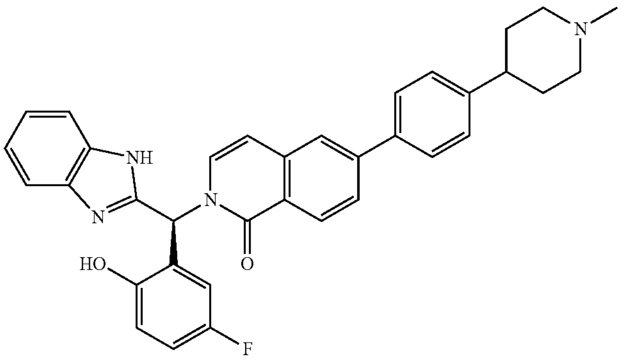 [SMILES: CN1CCC(c2ccc(-c3ccc4c(=O)n([C@H](c5nc6ccccc6[nH]5)c5cc(F)ccc5O)ccc4c3)cc2)CC1] |
| 069 | 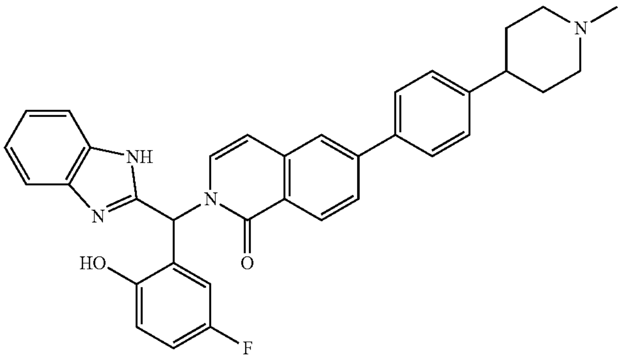 [SMILES: CN1CCC(c2ccc(-c3ccc4c(=O)n(C(c5nc6ccccc6[nH]5)c5cc(F)ccc5O)ccc4c3)cc2)CC1] |

TABLE 2-continued
| Compound No. | Structure |
|---|---|
| 070 | 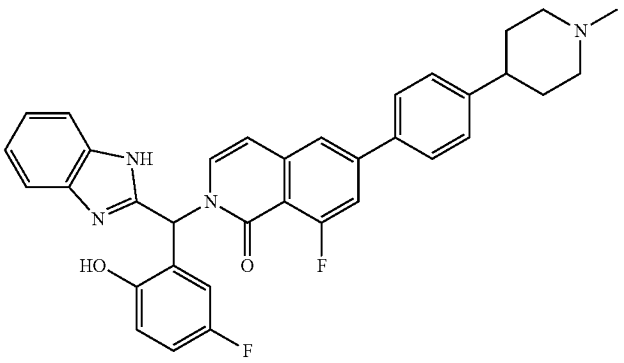 [SMILES: CN1CCC(c2ccc(-c3cc(F)c4c(=O)n(C(c5nc6ccccc6[nH]5)c5cc(F)ccc5O)ccc4c3)cc2)CC1] |
| 071 | 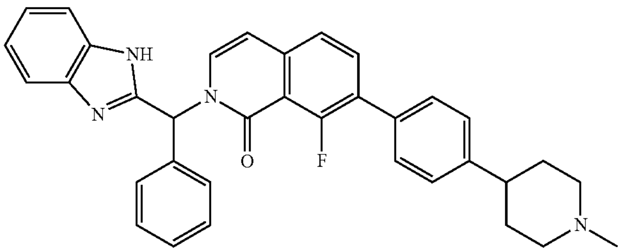 [SMILES: CN1CCC(c2ccc(-c3ccc4ccn(C(c5ccccc5)c5nc6ccccc6[nH]5)c(=O)c4c3F)cc2)CC1] |
| 072 | 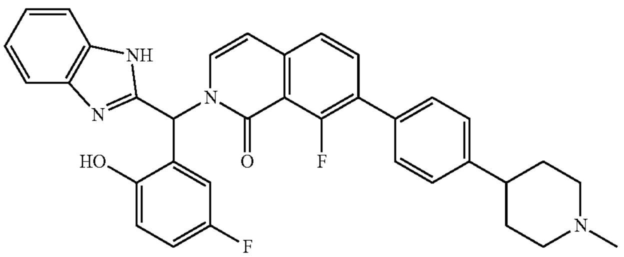 [SMILES: CN1CCC(c2ccc(-c3ccc4ccn(C(c5nc6ccccc6[nH]5)c5cc(F)ccc5O)c(=O)c4c3F)cc2)CC1] |
| 073 | 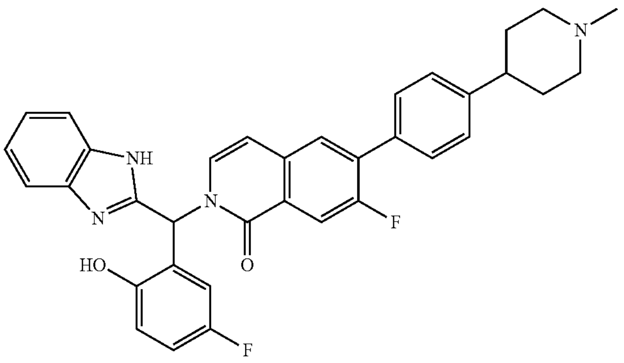 [SMILES: CN1CCC(c2ccc(-c3cc4ccn(C(c5nc6ccccc6[nH]5)c5cc(F)ccc5O)c(=O)c4cc3F)cc2)CC1] |
| 074 | 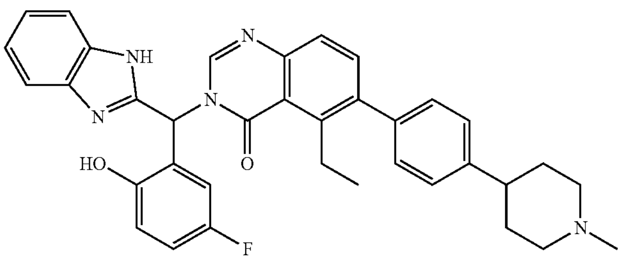 [SMILES: CCc1c(-c2ccc(C3CCN(C)CC3)cc2)ccc2ncn(C(c3nc4ccccc4[nH]3)c3cc(F)ccc3O)c(=O)c12] |

TABLE 2-continued
| Compound No. | Structure |
|---|---|
| 075 | 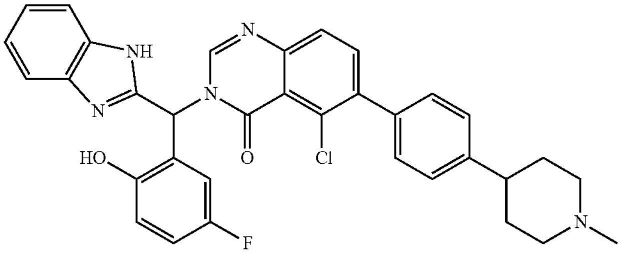 [SMILES: CN1CCC(c2ccc(-c3ccc4ncn(C(c5nc6ccccc6[nH]5)c5cc(F)ccc5O)c(=O)c4c3Cl)cc2)CC1] |
| 076 | 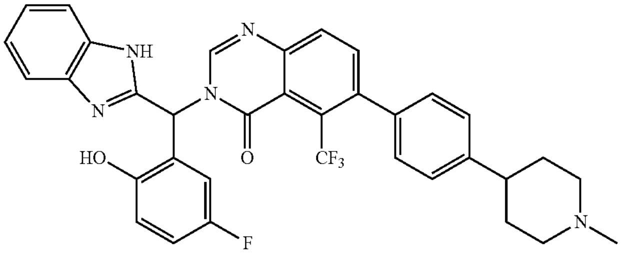 |
| 077 | 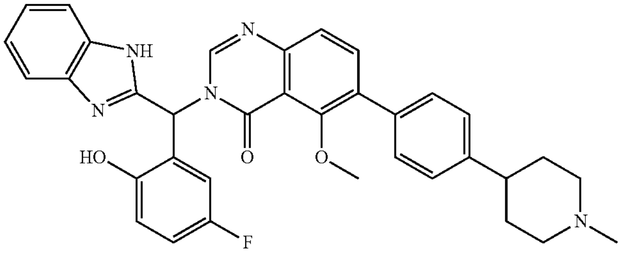 [SMILES: COc1c(-c2ccc(C3CCN(C)CC3)cc2)ccc2ncn(C(c3nc4ccccc4[nH]3)c3cc(F)ccc3O)c(=O)c12] |
| 102 | 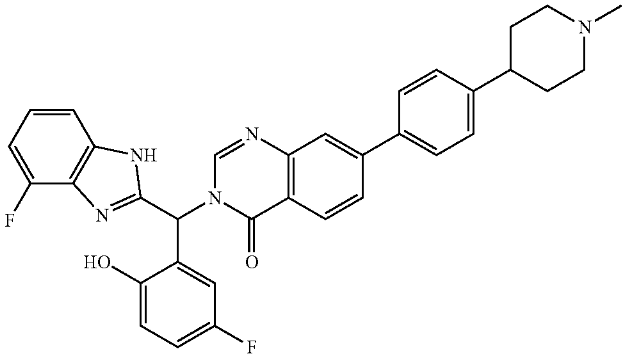 [SMILES: CN1CCC(c2ccc(-c3ccc4c(=O)n(C(c5nc6c(F)cccc6[nH]5)c5cc(F)ccc5O)cnc4c3)cc2)CC1] |
| 108 | 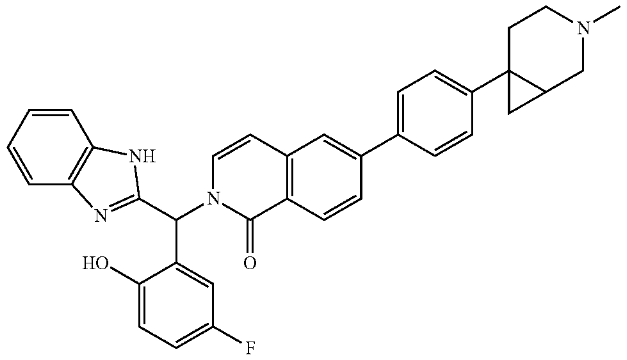 [SMILES: CN1CCC2(c3ccc(-c4ccc5c(=O)n(C(c6nc7ccccc7[nH]6)c6cc(F)ccc6O)ccc5c4)cc3)CC2C1] |

TABLE 2-continued
| Compound No. | Structure |
|---|---|
| 109 | 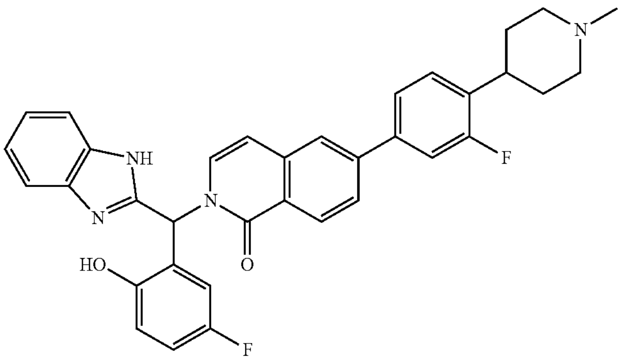 [SMILES: CN1CCC(c2ccc(-c3ccc4c(=O)n(C(c5nc6ccccc6[nH]5)c5cc(F)ccc5O)ccc4c3)cc2F)CC1] |
| 110 | 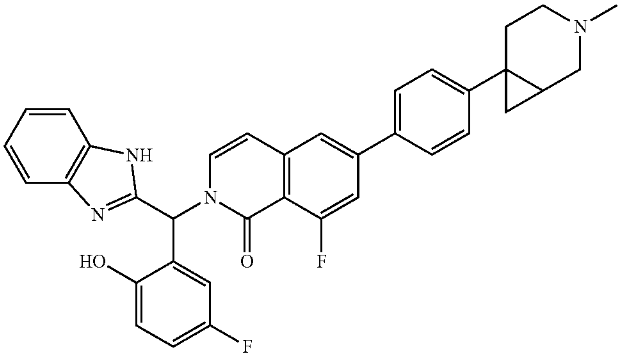 [SMILES: CN1CCC2(c3ccc(-c4cc(F)c5c(=O)n(C(c6nc7ccccc7[nH]6)c6cc(F)ccc6O)ccc5c4)cc3)CC2C1] |
| 111 | 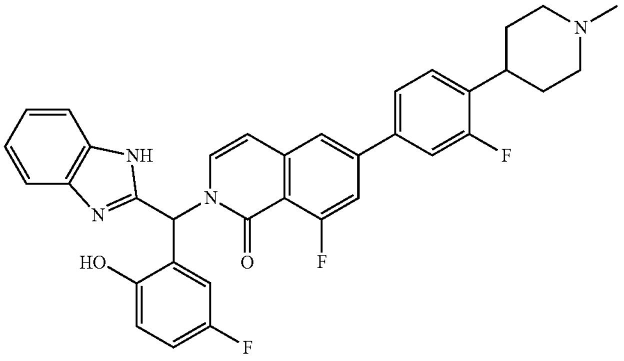 [SMILES: CN1CCC(c2ccc(-c3cc(F)c4c(=O)n(C(c5nc6ccccc6[nH]5)c5cc(F)ccc5O)ccc4c3)cc2F)CC1] |
| 112 | 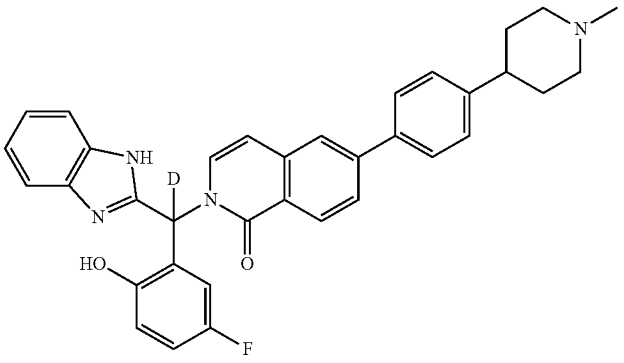 [SMILES: [2H]C(c1nc2ccccc2[nH]1)(c1cc(F)ccc1O)n1ccc2cc(-c3ccc(C4CCN(C)CC4)cc3)ccc2c1=O] |

TABLE 2-continued
| Compound No. | Structure |
| --- | --- |
| 113 | 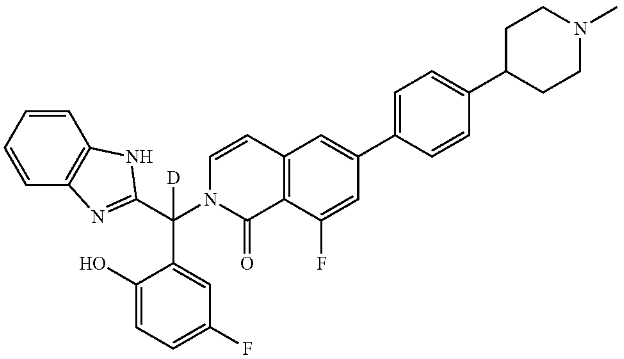 [SMILES: [2H]C(c1nc2ccccc2[nH]1)(c1cc(F)ccc1O)n1ccc2cc(-c3ccc(C4CCN(C)CC4)cc3)cc(F)c2c1=O] |
| 114 | 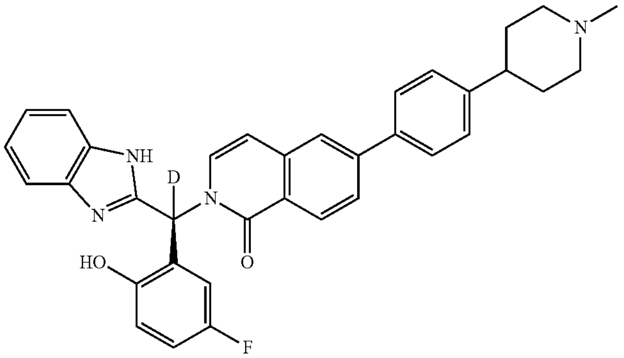 [SMILES: [2H][C@](c1nc2ccccc2[nH]1)(c1cc(F)ccc1O)n1ccc2cc(-c3ccc(C4CCN(C)CC4)cc3)ccc2c1=O] |
| 115 | 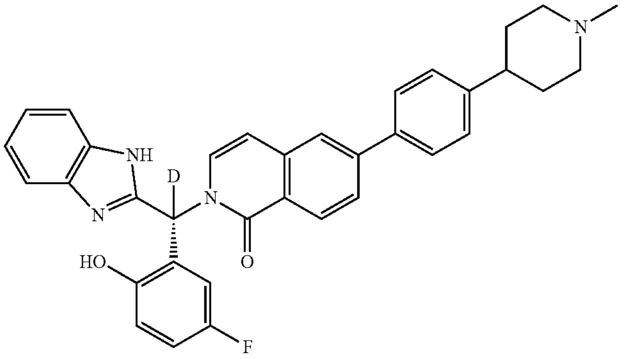 |
| 116 | 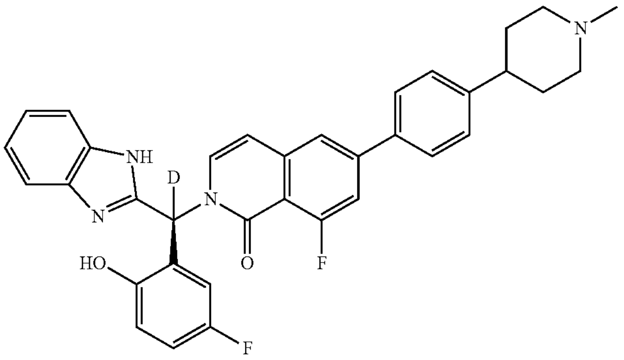 [SMILES: [2H][C@](c1nc2ccccc2[nH]1)(c1cc(F)ccc1O)n1ccc2cc(-c3ccc(C4CCN(C)CC4)cc3)cc(F)c2c1=O] |

TABLE 2-continued

| Compound No. | Structure |
|---|---|
| 117 | 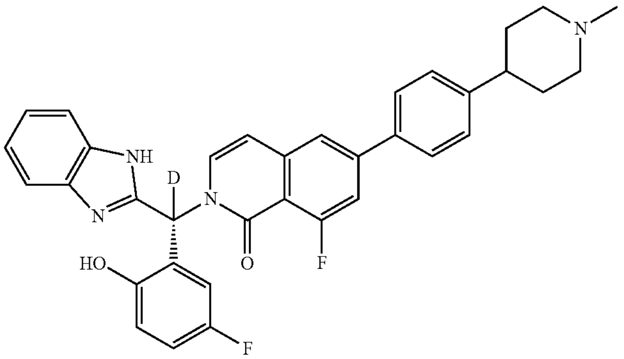 |

or a pharmaceutically acceptable salt thereof.

In embodiments, the compounds 112-117 provided herein have an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In an embodiment of compounds 112-117, each position designated specifically as deuterium has at least 95% incorporation of deuterium.

In another aspect, provided herein is a compound of Formula II:

(II)

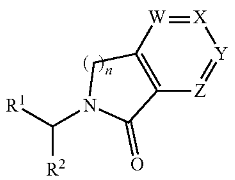

or a pharmaceutically acceptable salt thereof;

wherein

W and Z are each, independently, N, CH, C-halo, C—($C_1$-$C_3$ alkyl), or C—($C_1$-$C_3$ alkoxy);

X and Y are each, independently, N, CH, or $CR^3$;

provided that at least one of W, X, Y, or Z is CH;

$R^1$ is selected from the group consisting of 6-10 membered aryl, 5-10 membered heteroaryl, 3-10 membered heterocycloalkyl, and 3-10 membered cycloalkyl, all of which are optionally substituted with one, two, or three $R^8$;

$R^2$ is selected from the group consisting of 6-10 membered aryl, 5-10 membered heteroaryl, 3-10 membered heterocycloalkyl, and 3-10 membered cycloalkyl, all of which are optionally substituted with one, two, or three $R^6$;

$R^3$ is independently, at each occurrence, selected from the group consisting of halogen, $OR^4$, $NR^4R^4$, $SO_2R^4$, $SO_2NHR^4$, $NHSO_2R^4$, $C(O)OR^4$, $C(O)NHR^4$, $C(O)R^4$, $C_1$-$C_6$ alkyl; $C_2$-$C_6$ alkenyl, $C_2$-$C_6$ alkynyl, 3-7 membered cycloalkyl, $C_4$-$C_7$ cycloalkenyl, $C_5$-$C_{10}$ aryl, 5-6 membered heteroaryl, and 5-7 membered heterocyclyl, wherein alkyl, alkenyl, or alkynyl are each optionally substituted one, two, or three times with $R^4$, and wherein aryl, heteroaryl, or heterocyclyl are each optionally substituted one, two, or three times with $R^5$;

$R^4$ is independently, at each occurrence, selected from the group consisting of H, $(CH_2)_{0-3}$—($C_3$-$C_7$cycloalkyl), $(CH_2)_{0-3}$-($C_4$-$C_7$ cycloalkenyl), $(CH_2)_{0-3}$—($C_6$-$C_{10}$ aryl), $(CH_2)_{0-3}$-(5-6 membered heteroaryl), and $(CH_2)_{0-3}$-(5-7 membered heterocyclyl), wherein the aryl, heteroaryl, or heterocyclyl are each optionally substituted one, two, or three times with $R^5$;

$R^5$ is independently, at each occurrence, selected from the group consisting of $C_1$-$C_6$ alkyl, $C_1$-$C_6$ haloalkyl, $C_1$-$C_6$ alkoxy, $C_1$-$C_6$ haloalkoxy, $C_1$-$C_3$ alkylamine, 3-10 membered cycloalkyl, halogen, COOH, C(O)O($C_1$-$C_6$ alkyl), $O(CH_2)_{1-3}$—OH, $NH_2$, NH($C_1$-$C_6$ alkyl), N($C_1$-$C_6$ alkyl)$_2$, OH, CN, $(CH_2)_{0-3}$—($C_6$-$C_{10}$ aryl), $(CH_2)_{0-3}$-(5-6 membered heteroaryl), and $(CH_2)_{0-3}$-(5-7 membered heterocyclyl), wherein the aryl, heteroaryl, or heterocyclyl are each optionally substituted one, two, or three times with $R^7$;

$R^6$ is independently, at each occurrence, selected from the group consisting of $C_1$-$C_3$ alkyl, $C_1$-$C_3$ haloalkyl, $C_1$-$C_3$ alkoxy, $C_1$-$C_3$ haloalkoxy, $C_1$-$C_3$ alkylamine, halogen, OH, $NO_2$, $NH_2$, NH($C_1$-$C_6$ alkyl), N($C_1$-$C_6$ alkyl)$_2$, $(CH_2)_{1-4}OH$, $S(O)_{0-2}H$, $S(O)_{0-2}NH_2$, or CN;

alternatively, two $R^6$, together with the atoms to which they are attached, can form 5-10 membered heteroaryl, 6-10 membered aryl, 3-10 membered heterocycloalkyl, or 3-10 membered cycloalkyl;

$R^7$ is independently, at each occurrence, selected from the group consisting of substituents independently selected from $C_1$-$C_6$ alkyl, $C_1$-$C_6$ haloalkyl, $C_1$-$C_6$ alkoxy, $C_1$-$C_6$ haloalkoxy, halogen, $NH_2$, NH($C_1$-$C_6$ alkyl), N($C_1$-$C_6$ alkyl)$_2$, $SO_2NH_2$, $SO_2NH$($C_1$-$C_6$ alkyl), $SO_2N$($C_1$-$C_6$ alkyl)$_2$, $(CH_2)_{1-2}$—OH, C(O)$(CH_2)_{1-2}$—OH, C(O)($C_1$-$C_6$ alkyl), and C(O)O($C_1$-$C_6$ alkyl);

alternatively, two $R^7$, together with the atoms to which they are attached, can form 5-10 membered heteroaryl, 6-10 membered aryl, 3-10 membered heterocycloalkyl, or 3-10 membered cycloalkyl;

$R^8$ is independently, at each occurrence, selected from the group consisting of $C_1$-$C_3$ alkyl, $C_1$-$C_3$ haloalkyl, $C_1$-$C_3$ alkoxy, $C_1$-$C_3$ haloalkoxy, $C_1$-$C_3$ alkylamine, 3-6 membered cycloalkyl, halogen, OH, $NO_2$, $NH_2$, $NH(C_1-C_3$ alkyl), $N(C_1-C_6$ alkyl$)_2$, $(CH_2)_{1-4}$ OH, $S(O)_{0-2}H$, $S(O)_{0-2}NH_2$, or CN; and n is 1 or 2.

In an aspect of Formula II, $R^5$ is independently, at each occurrence, selected from the group consisting of $C_1$-$C_6$ alkyl, $C_1$-$C_6$ haloalkyl, $C_1$-$C_6$alkoxy, $C_1$-$C_6$ haloalkoxy, $C_1$-$C_3$ alkylamine, 3-10 membered cycloalkyl, halogen, COOH, C(O)O ($C_1$-$C_6$ alkyl), $O(CH_2)_{1-3}$—OH, $NH_2$, $NH(C_1$-$C_6$ alkyl), $N(C_1$-$C_6$ alkyl$)_2$, OH, CN, $(CH_2)_{0-3}$—($C_6$-$C_{10}$ aryl), $(CH_2)_{0-3}$-(5-6 membered heteroaryl), $O(CH_2)_{0-3}$-(4-7 membered heterocyclyl), and $(CH_2)_{0-3}$-(4-7 membered heterocyclyl), wherein the alkyl, alkoxy, aryl, heteroaryl, or heterocyclyl are each optionally substituted one, two, or three times with $R^7$;

wherein all other variables are defined above.

In an embodiment, the compound of Formula II is a compound of Formula I (IIa)

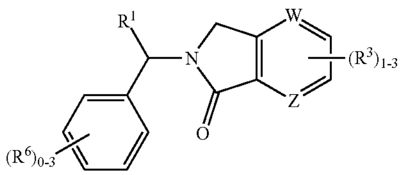

or a pharmaceutically acceptable salt thereof.

In yet another aspect, provided herein is a compound of Formula X:

(X)

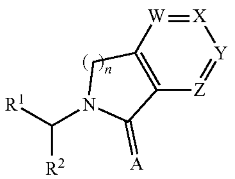

or a pharmaceutically acceptable salt thereof;

wherein

A is O or S;

W and Z are each, independently, N, CH, C-halo, C—($C_1$-$C_3$ alkyl), or C—($C_1$-$C_3$ alkoxy);

X and Y are each, independently, N, CH, or $CR^3$;

provided that at least one of W, X, Y, or Z is CH;

$R^1$ is selected from the group consisting of 6-10 membered aryl, 5-10 membered heteroaryl; 3-10 membered heterocycloalkyl; and 3-10 membered cycloalkyl, all of which are optionally substituted with one; two; or three $R^6$;

$R^2$ is selected from the group consisting of 6-10 membered aryl, 5-10 membered heteroaryl, 3-10 membered heterocycloalkyl, and 3-10 membered cycloalkyl, all of which are optionally substituted with one, two, or three $R^6$;

$R^3$ is independently, at each occurrence, selected from the group consisting of halogen, $OR^4$, $NR^4R^4$, $SO_2R^4$, $SO_2NHR^4$, $NHSO_2R^4$, $C(O)OR^4$, $C(O)NHR^4$, $C(O)R^4$, $C_1$-$C_6$ alkyl, $C_2$-$C_6$ alkenyl, 02-$C_6$ alkynyl, 3-7 membered cycloalkyl, $C_4$-$C_7$ cycloalkenyl. $C_6$-$C_{10}$ aryl, 5-6 membered heteroaryl, and 5-7 membered heterocyclyl, wherein alkyl, alkenyl, or alkynyl are each optionally substituted one, two; or three times with $R^4$, and wherein aryl; heteroaryl, or heterocyclyl are each optionally substituted one, two, or three times with $R^5$;

$R^4$ is independently, at each occurrence, selected from the group consisting of H, $(CH_2)_{0-3}$—($C_3$-$C_7$ cycloalkyl), $(CH_2)_{0-3}$-($C_4$-$C_7$ cycloalkenyl), $(CH_2)_{0-3}$ ($C_6$-$C_{10}$ aryl), $(CH_2)_{0-3}$-(5-6 membered heteroaryl), and $(CH_2)_{0-3}$-(5-7 membered heterocyclyl), wherein the aryl, heteroaryl, or heterocyclyl are each optionally substituted one, two, or three times with $R^5$;

$R^5$ is independently, at each occurrence, selected from the group consisting of $C_1$-$C_6$ alkyl, $C_1$-$C_6$ haloalkyl, $C_1$-$C_6$ alkoxy, $C_1$-$C_6$ haloalkoxy, $C_1$-$C_3$ alkylamine, 3-10 membered cycloalkyl, halogen, COOH, C(O)O ($C_1$-$C_6$ alkyl); $O(CH_2)_{1-3}OH$, $NH_2$, $NH(C_1$-$C_6$ alkyl), $N(C_1$-$C_6$ alkyl$)_2$, OH, CN, $(CH_2)_{0-3}$—($C_6$-$C_{10}$ aryl), $(CH_2)_{0-3}$-(5-6 membered heteroaryl), $O(CH_2)_{0-3}$-(4-7 membered heterocyclyl), and $(CH_2)_{0-3}$-(4-7 membered heterocyclyl), wherein the alkyl, alkoxy, aryl, heteroaryl, or heterocyclyl are each optionally substituted one, two, or three times with $R^7$;

$R^6$ is independently, at each occurrence, selected from the group consisting of $C_1$-$C_3$ alkyl, $C_1$-$C_3$ haloalkyl, $C_1$-$C_3$ alkoxy, $C_1$-$C_3$ haloalkoxy, $C_1$-$C_3$ alkylamine, halogen, OH, $NO_2$, $NH_2$, $NH(C_1$-$C_6$ alkyl), $N(C_1$-$C_6$ alkyl$)_2$, $(CH_2)_{1-4}OH$, $S(O)_{0-2}H$, $S(O)_{0-2}NH_2$, or CN;

alternatively, two $R^6$, together with the atoms to which they are attached, can form 5-10 membered heteroaryl, 6-10 membered aryl, 3-10 membered heterocycloalkyl, or 3-10 membered cycloalkyl;

$R^7$ is independently, at each occurrence, selected from the group consisting of substituents independently selected from $C_1$-$C_6$ alkyl, $C_1$-$C_6$ haloalkyl, $C_1$-$C_6$ alkoxy; $C_1$-$C_6$ haloalkoxy; halogen, $NH_2$, $NH(C_1$-$C_6)$ $N(C_1$-$C_6$ alkyl$)_2$, $SO_2NH_2$; $SO_2NH(C_1$-06 $SO_2N(C_1$-$C_6$ alkyl$)_2$, $(CH_2)_{1-2}$—OH, $C(O)(CH_2)_{1-2}$—OH, $C(O)(C_1$-$C_6$ alkyl); and $C(O)O(C_1$-$C_6$ alkyl);

alternatively, two $R^7$, together with the atoms to which they are attached, can form 5-10 membered heteroaryl; 6-10 membered aryl, 3-10 membered heterocycloalkyl, or 3-10 membered cycloalkyl;

$R^8$ is independently, at each occurrence, selected from the group consisting of $C_1$-$C_3$ alkyl; $C_1$-$C_3$ haloalkyl, $C_1$-$C_3$ alkoxy, $C_1$-$C_3$ haloalkoxy, $C_1$-$C_3$ alkylamine, 3-6 membered cycloalkyl, halogen, OH, $NO_2$, $NH_2$, $NH(C_1$-$C_6$ alkyl), $N(C_1$-$C_6$ alkyl$)_2$, $(CH_2)_{1-4}$ OH, $S(O)_{0-2}H$, $S(O)_{0-2}NH_2$, or CN; and n is 1 or 2.

In an embodiment of Formula IIa, $R^3$ is $C_6$-$C_{10}$ aryl or 5-6 membered heteroaryl, both of which are optionally substituted one time with $R^5$. In another embodiment of Formula IIa, $R^3$ is $C_6$-$C_{10}$ aryl optionally substituted one time with $R^5$, wherein $R^5$ is 5-7 membered heterocyclyl, $C_6$-$C_{10}$ aryl, 3-10 membered cycloalkyl, or 5-6 membered heteroaryl, all of which are optionally substituted one time with $R^7$. In yet another embodiment of Formula IIa, $R^3$ is phenyl optionally substituted one time with $R^5$, wherein $R^5$ is 5-7 membered heterocyclyl, $C_6$-$C_{10}$ aryl, 3-10 membered cycloalkyl, or 5-6 membered heteroaryl, all of which are optionally substituted one time with $R^7$. In still another embodiment of Formula IIa, $R^3$ is $C_6$-$C_{10}$ aryl optionally substituted one time with $R^5$, wherein $R^5$ is 5 membered heterocyclyl optionally substituted one time with $R^7$. In an embodiment of Formula Ile, $R^3$ is phenyl optionally substituted one time with piperidine, wherein piperidine is substituted one time with $R^7$.

In another embodiment, the compound of Formula II is a compound of Formula IIb:

(IIb)

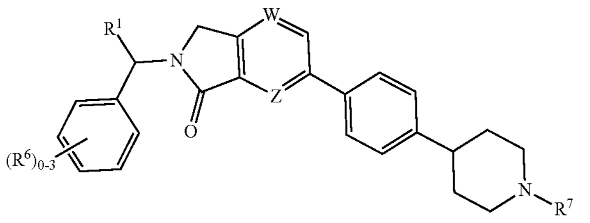

or a pharmaceutically acceptable salt thereof.

In another embodiment, the compound of Formula II is a compound of Formula IIc:

(IIc)

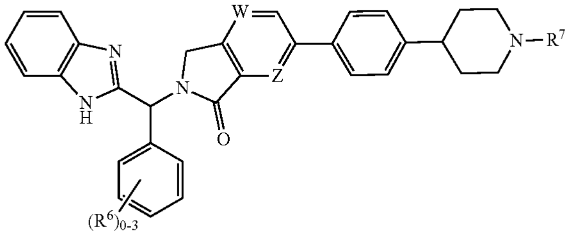

or a pharmaceutically acceptable salt thereof.

In yet another embodiment, wherein $R^6$ is independently, at each occurrence, hydroxy, halo, or two $R^6$, together with the atoms to which they are attached, form 5-10 membered heteroaryl, 6-10 membered aryl, 3-10 membered heterocycloalkyl, or 3-10 membered cycloalkyl. In another embodiment, $R^6$ is hydroxy, fluoro, or two $R^6$, together with the atoms to which they are attached, form 5-10 membered heteroaryl, 6-10 membered aryl, 3-10 membered heterocycloalkyl, or 3-10 membered cycloalkyl. In yet another embodiment, $R^6$ is hydroxy. In still another embodiment, $R^6$ is fluoro. In another embodiment, $R^6$ is chloro.

In an embodiment, there are two $R^6$ that are hydroxy and fluoro. In another embodiment, there are two $R^6$ that are hydroxy and chloro. In still another embodiment, two $R^6$, together with the atoms to which they are attached, form 5-10 membered heteroaryl, 6-10 membered aryl, 3-10 membered heterocycloalkyl, or 3-10 membered cycloalkyl.

In an embodiment of Formulae IIa, and IIb, $R^1$ is selected from the group consisting of benzimidazole, imidazopyrazine, purine, imidazole, pyrazole, triazole, and imidazopyridine. In an embodiment, $R^1$ is selected from the group consisting of:

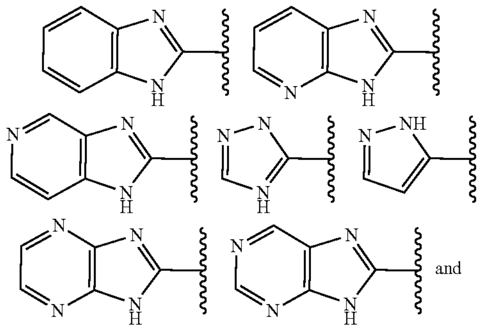

and

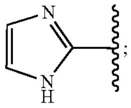

;

all of which are optionally substituted with one, two, or three $R^8$.

In another embodiment, $R^3$ is phenyl or $C_2$-$C_3$ alkynyl, wherein phenyl is optionally substituted one or two times with $R^5$, and alkynyl is optionally substituted one or two times with $R^4$. In yet another embodiment, $R^3$ is phenyl optionally substituted one or two times with $R^5$. In still another embodiment, $R^3$ is $C_2$-$C_3$ alkynyl optionally substituted one or two times with $R^4$. In an embodiment, $R^3$ is phenyl substituted with one or two $R^5$, and $R^5$ is selected from the group consisting of piperidine, pyridine, and thiomorpholine dioxide, all of which are optionally substituted with one or two RT.

In another embodiment, the compound of Formula II is selected from the group consisting of a compound in Table 3.

TABLE 3

| Compound No. | Structure |
|---|---|
| 010 | 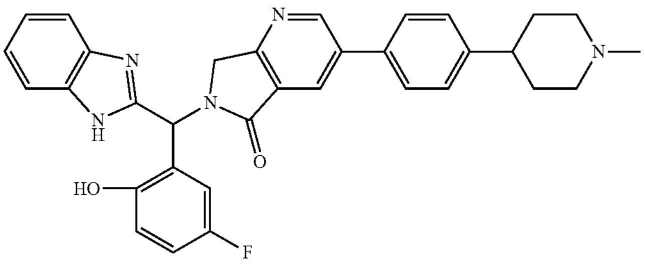 [SMILES: CN1CCC(c2ccc(-c3cnc4c(c3)C(=O)N(C(c3nc5ccccc5[nH]3)c3cc(F)ccc3O)C4)cc2)CC1] |

TABLE 3-continued
| Compound No. | Structure |
|---|---|
| 011 | 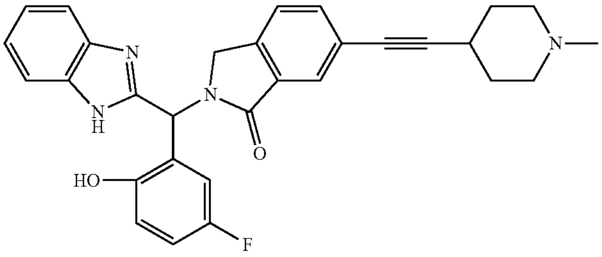 [SMILES: CN1CCC(C#Cc2ccc3c(c2)C(=O)N(C(c2nc4ccccc4[nH]2)c2cc(F)ccc2O)C3)CC1] |
| 012 | 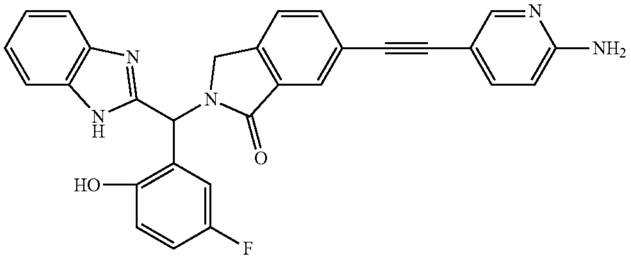 [SMILES: Nc1ccc(C#Cc2ccc3c(c2)C(=O)N(C(c2nc4ccccc4[nH]2)c2cc(F)ccc2O)C3)cn1] |
| 013 | 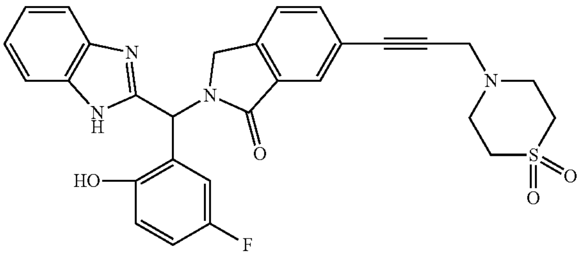 [SMILES: O=C1c2cc(C#CCN3CCS(=O)(=O)CC3)ccc2CN1C(c1nc2ccccc2[nH]1)c1cc(F)ccc1O] |
| 014 | 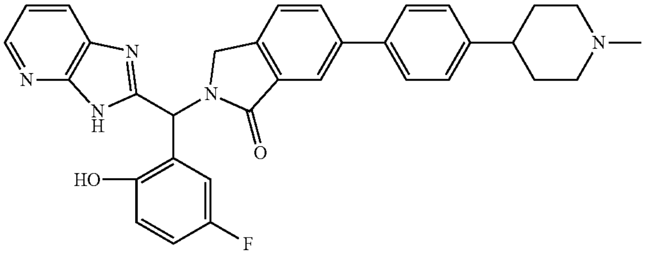 [SMILES: CN1CCC(c2ccc(-c3ccc4c(c3)C(=O)N(C(c3nc5cccnc5[nH]3)c3cc(F)ccc3O)C4)cc2)CC1] |
| 015 | 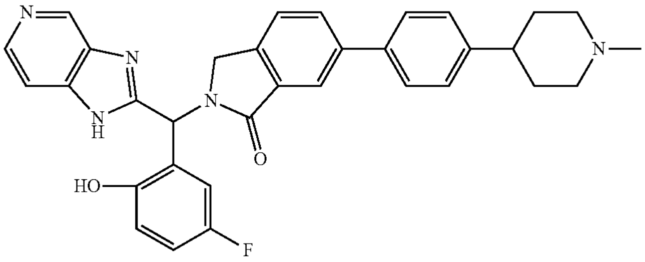 [SMILES: CN1CCC(c2ccc(-c3ccc4c(c3)C(=O)N(C(c3nc5cnccc5[nH]3)c3cc(F)ccc3O)C4)cc2)CC1] |
| 016 | 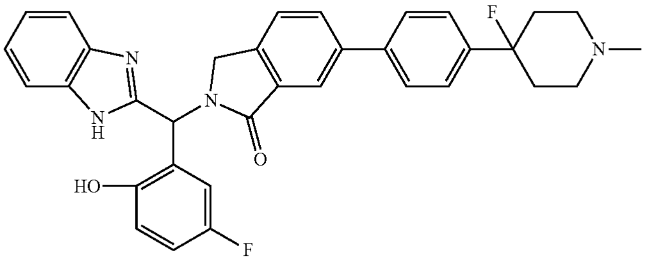 [SMILES: CN1CCC(F)(c2ccc(-c3ccc4c(c3)C(=O)N(C(c3nc5ccccc5[nH]3)c3cc(F)ccc3O)C4)cc2)CC1] |

TABLE 3-continued
| Compound No. | Structure |
| --- | --- |
| 017 | 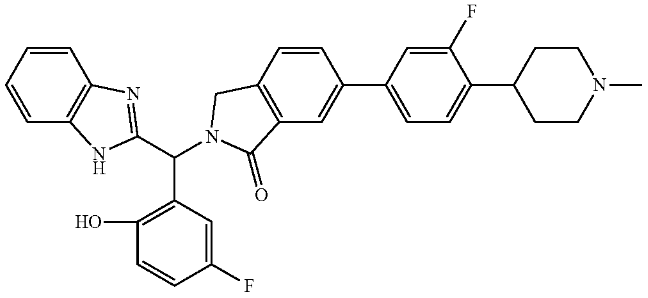 [SMILES: CN1CCC(c2ccc(-c3ccc4c(c3)C(=O)N(C(c3nc5ccccc5[nH]3)c3cc(F)ccc3O)C4)cc2F)CC1] |
| 018 | 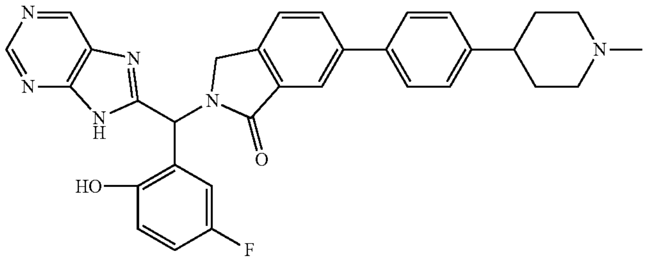 [SMILES: CN1CCC(c2ccc(-c3ccc4c(c3)C(=O)N(C(c3nc5cncnc5[nH]3)c3cc(F)ccc3O)C4)cc2)CC1] |
| 019 | 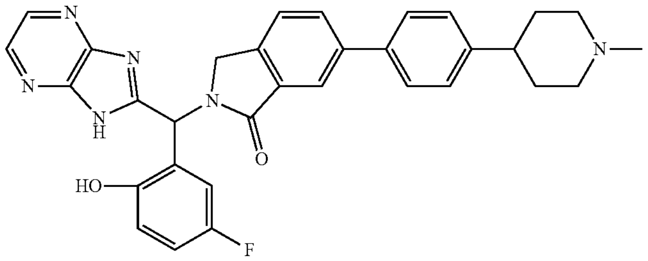 [SMILES: CN1CCC(c2ccc(-c3ccc4c(c3)C(=O)N(C(c3nc5nccnc5[nH]3)c3cc(F)ccc3O)C4)cc2)CC1] |
| 020 | 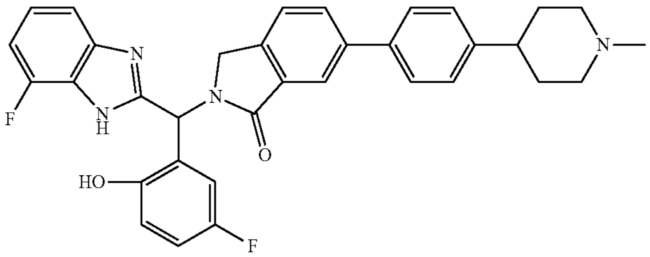 [SMILES: CN1CCC(c2ccc(-c3ccc4c(c3)C(=O)N(C(c3nc5cccc(F)c5[nH]3)c3cc(F)ccc3O)C4)cc2)CC1] |
| 021 | 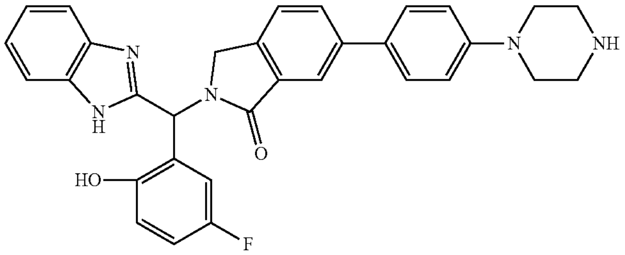 [SMILES: O=C1c2cc(-c3ccc(N4CCNCC4)cc3)ccc2CN1C(c1nc2ccccc2[nH]1)c1cc(F)ccc1O] |

TABLE 3-continued
| Compound No. | Structure |
| --- | --- |
| 022 | 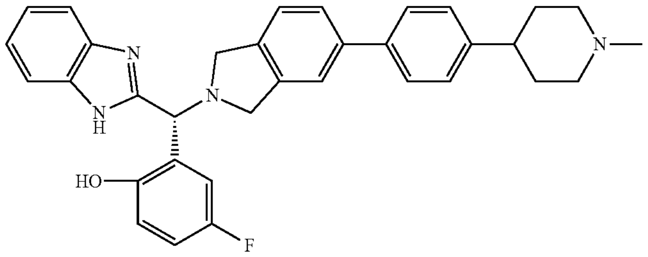 [SMILES: CN1CCC(c2ccc(-c3ccc4c(c3)CN([C@@H](c3nc5ccccc5[nH]3)c3cc(F)ccc3O)C4)cc2)CC1] |
| 023 | 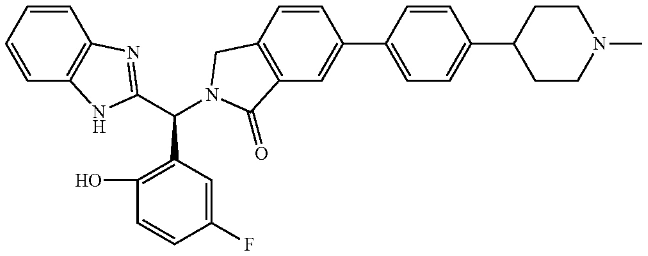 [SMILES: CN1CCC(c2ccc(-c3ccc4c(c3)C(=O)N([C@H](c3nc5ccccc5[nH]3)c3cc(F)ccc3O)C4)cc2)CC1] |
| 024 | 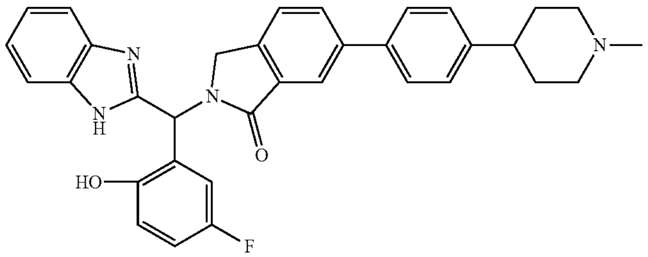 [SMILES: CN1CCC(c2ccc(-c3ccc4c(c3)C(=O)N(C(c3nc5ccccc5[nH]3)c3cc(F)ccc3O)C4)cc2)CC1] |
| 025 | 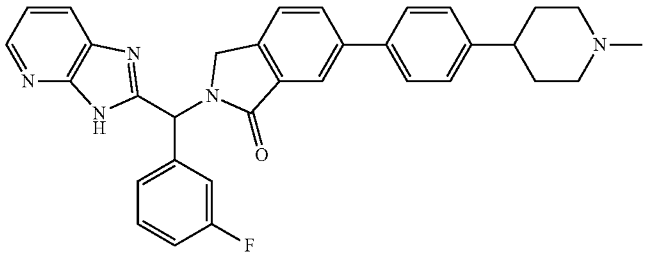 |
| 026 | 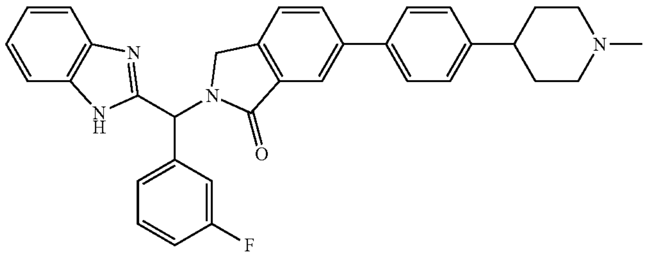 [SMILES: CN1CCC(c2ccc(-c3ccc4c(c3)C(=O)N(C(c3cccc(F)c3)c3nc5cccnc5[nH]3)C4)cc2)CC1] |
| 028 | 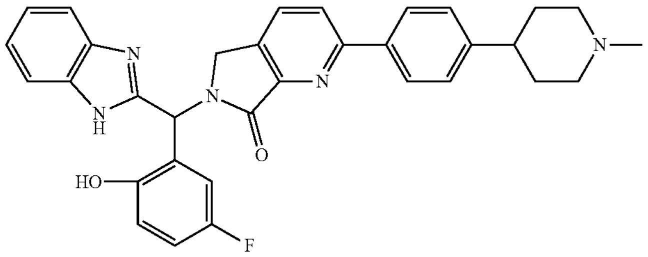 |

TABLE 3-continued
| Compound No. | Structure |
| --- | --- |
| 029 | 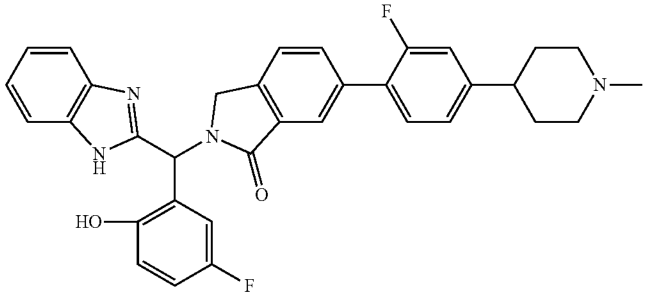 [SMILES: CN1CCC(c2ccc(-c3ccc4c(c3)C(=O)N(C(c3nc5ccccc5[nH]3)c3cc(F)ccc3O)C4)c(F)c2)CC1] |
| 030 | 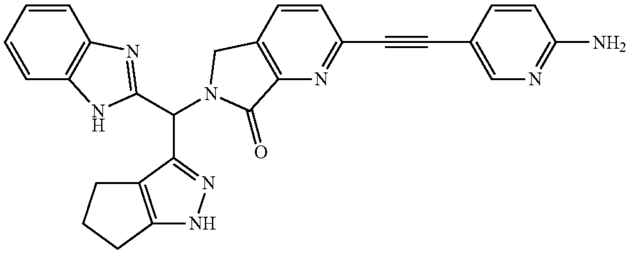 [SMILES: Nc1ccc(C#Cc2ccc3c(n2)C(=O)N(C(c2nc4ccccc4[nH]2)c2n[nH]c4c2CCC4)C3)cn1] |
| 031 | 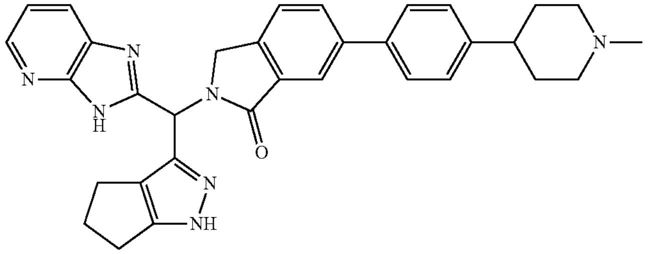 [SMILES: CN1CCC(c2ccc(-c3ccc4c(c3)C(=O)N(C(c3nc5cccnc5[nH]3)c3n[nH]c5c3CCC5)C4)cc2)CC1] |
| 032 | 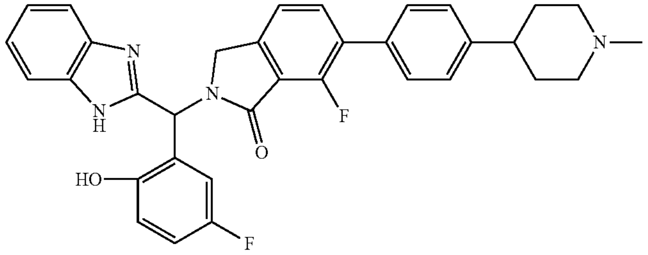 [SMILES: CN1CCC(c2ccc(-c3ccc4c(c3F)C(=O)N(C(c3nc5ccccc5[nH]3)c3cc(F)ccc3O)C4)cc2)CC1] |
| 033 | 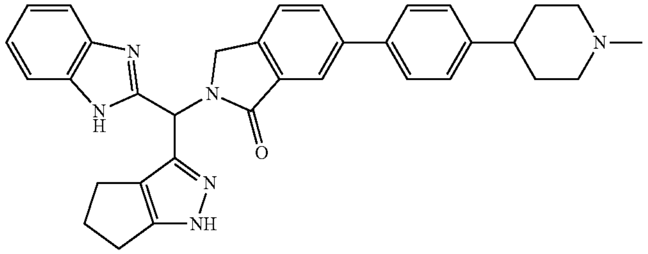 |

TABLE 3-continued
| Compound No. | Structure |
| --- | --- |
| 040 | 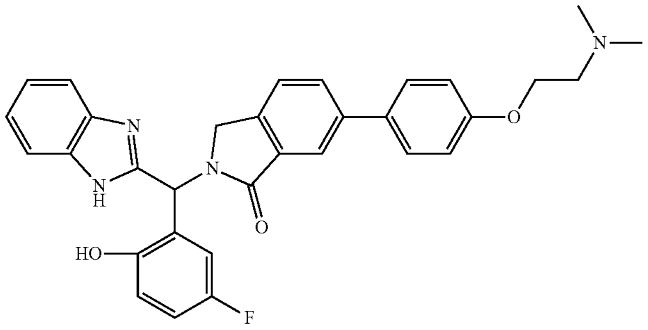 |
| 041 | 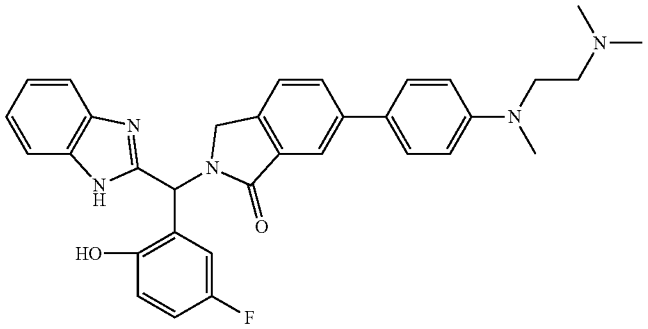 [SMILES: CN(C)CCN(C)c1ccc(-c2ccc3c(c2)C(=O)N(C(c2nc4ccccc4[nH]2)c2cc(F)ccc2O)C3)cc1] |
| 042 | 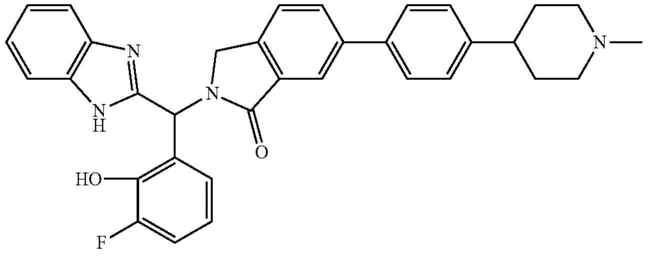 |
| 043 | 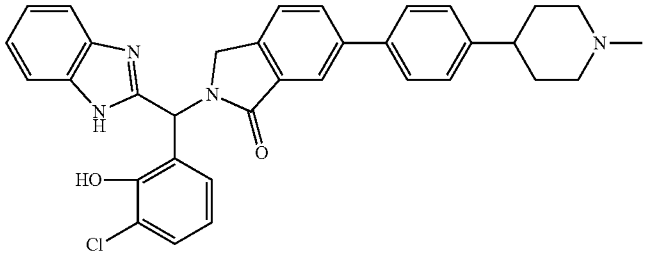 [SMILES: CN1CCC(c2ccc(-c3ccc4c(c3)C(=O)N(C(c3nc5ccccc5[nH]3)c3cccc(Cl)c3O)C4)cc2)CC1] |
| 044 | 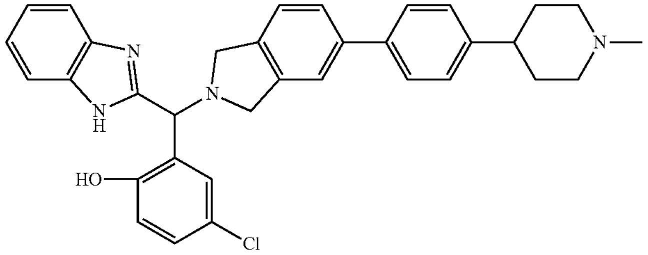 [SMILES: CN1CCC(c2ccc(-c3ccc4c(c3)CN(C(c3nc5ccccc5[nH]3)c3cc(Cl)ccc3O)C4)cc2)CC1] |

TABLE 3-continued
| Compound No. | Structure |
|---|---|
| 045 | 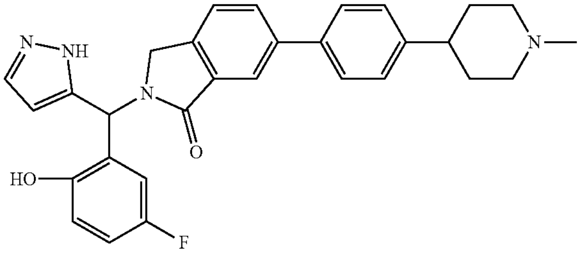 [SMILES: CN1CCC(c2ccc(-c3ccc4c(c3)C(=O)N(C(c3ccn[nH]3)c3cc(F)ccc3O)C4)cc2)CC1] |
| 046 | 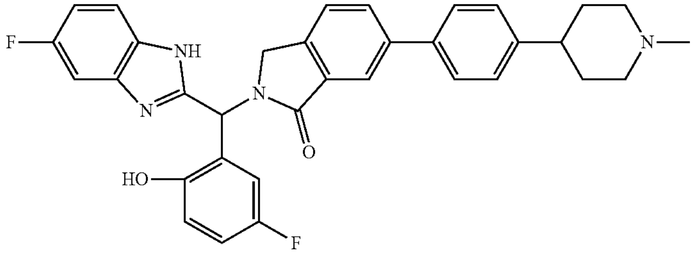 [SMILES: CN1CCC(c2ccc(-c3ccc4c(c3)C(=O)N(C(c3nc5cc(F)ccc5[nH]3)c3cc(F)ccc3O)C4)cc2)CC1] |
| 047 | 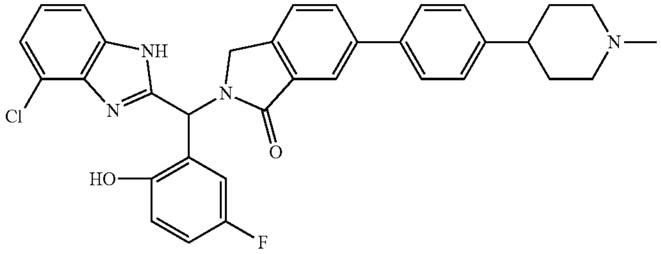 [SMILES: CN1CCC(c2ccc(-c3ccc4c(c3)C(=O)N(C(c3nc5c(Cl)cccc5[nH]3)c3cc(F)ccc3O)C4)cc2)CC1] |
| 048 | 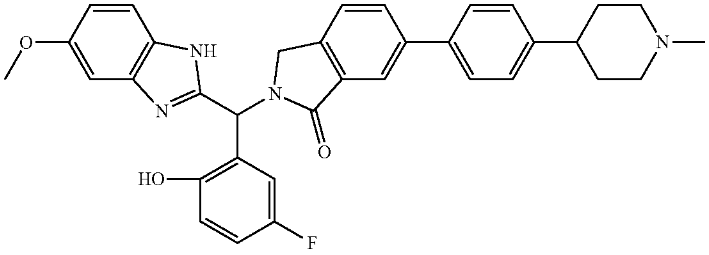 |
| 049 | 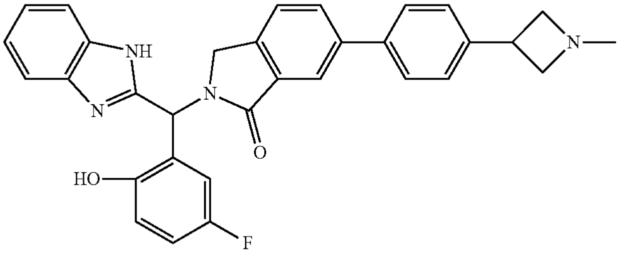 [SMILES: CN1CC(c2ccc(-c3ccc4c(c3)C(=O)N(C(c3nc5ccccc5[nH]3)c3cc(F)ccc3O)C4)cc2)C1] |
| 050 | 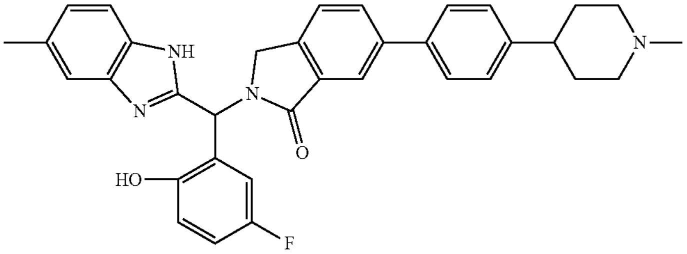 |

TABLE 3-continued
| Compound No. | Structure |
| --- | --- |
| 051 | 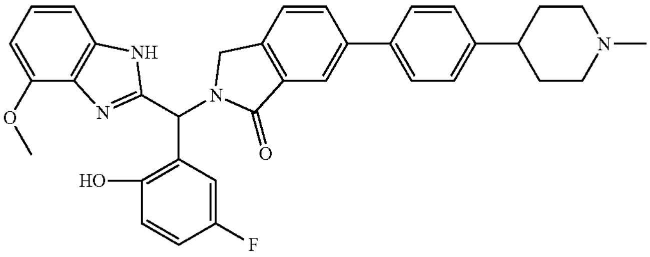 [SMILES: COc1cccc2[nH]c(C(c3cc(F)ccc3O)N3Cc4ccc(-c5ccc(C6CCN(C)CC6)cc5)cc4C3=O)nc12] |
| 052 | 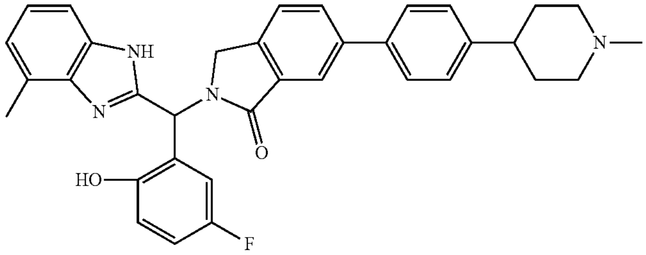 [SMILES: Cc1cccc2[nH]c(C(c3cc(F)ccc3O)N3Cc4ccc(-c5ccc(C6CCN(C)CC6)cc5)cc4C3=O)nc12] |
| 056 | 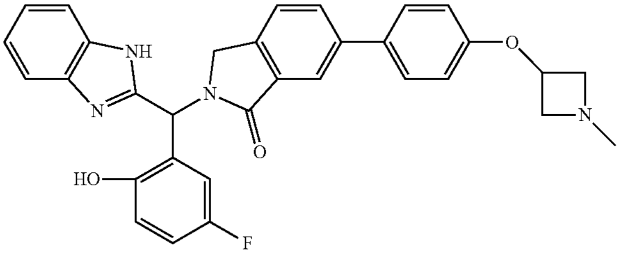 [SMILES: CN1CC(Oc2ccc(-c3ccc4c(c3)C(=O)N(C(c3nc5ccccc5[nH]3)c3cc(F)ccc3O)C4)cc2)C1] |
| 057 | 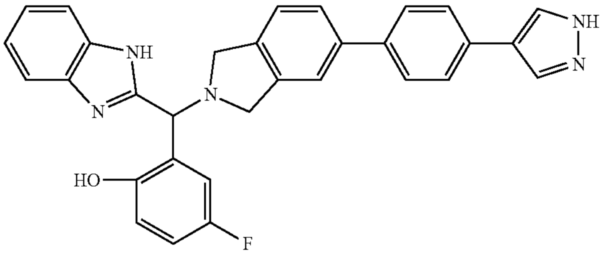 [SMILES: Oc1ccc(F)cc1C(c1nc2ccccc2[nH]1)N1Cc2ccc(-c3ccc(-c4cn[nH]c4)cc3)cc2C1] |
| 058 | 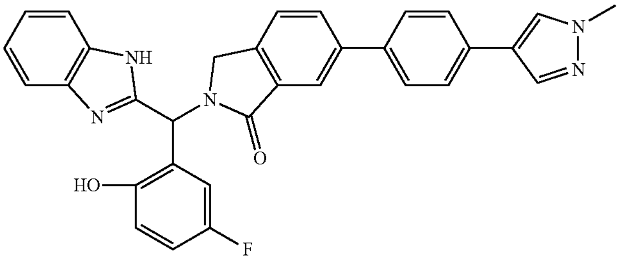 [SMILES: Cn1cc(-c2ccc(-c3ccc4c(c3)C(=O)N(C(c3nc5ccccc5[nH]3)c3cc(F)ccc3O)C4)cc2)cn1] |
| 059 | 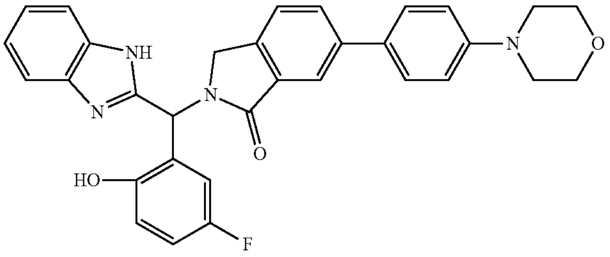 [SMILES: O=C1c2cc(-c3ccc(N4CCOCC4)cc3)ccc2CN1C(c1nc2ccccc2[nH]1)c1cc(F)ccc1O] |

TABLE 3-continued
| Compound No. | Structure |
| --- | --- |
| 060 | 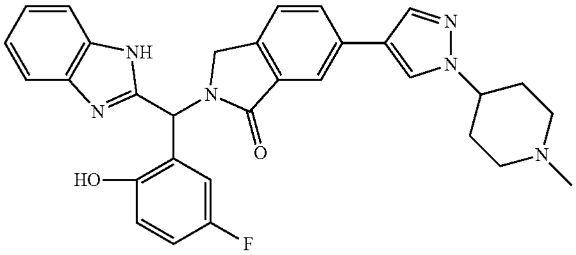 [SMILES: CN1CCC(n2cc(-c3ccc4c(c3)C(=O)N(C(c3nc5ccccc5[nH]3)c3cc(F)ccc3O)C4)cn2)CC1] |
| 061 | 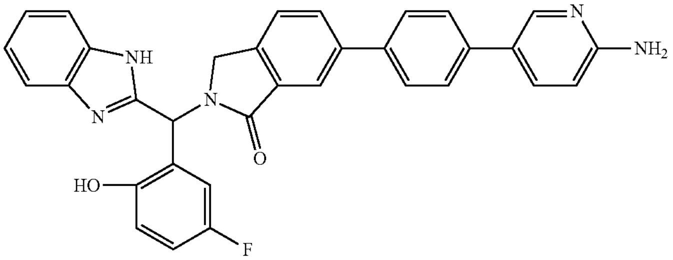 [SMILES: Nc1ccc(-c2ccc(-c3ccc4c(c3)C(=O)N(C(c3nc5ccccc5[nH]3)c3cc(F)ccc3O)C4)cc2)cn1] |
or a pharmaceutically acceptable salt thereof.
In yet another embodiment, the compound of Formula II is selected from the gr consisting of a compound in Table 4.
TABLE 4
| Compound No. | Structure |
| --- | --- |
| 036 | 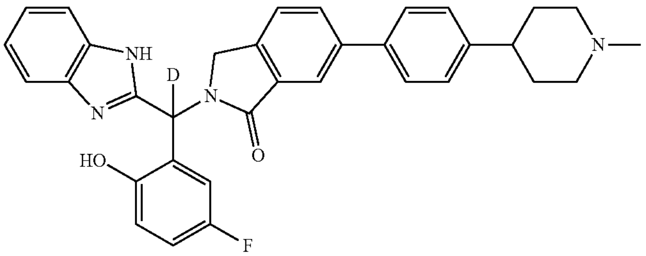 [SMILES: [2H]C(c1nc2ccccc2[nH]1)(c1cc(F)ccc1O)N1Cc2ccc(-c3ccc(C4CCN(C)CC4)cc3)cc2C1=O] |
| 037 and 038 | 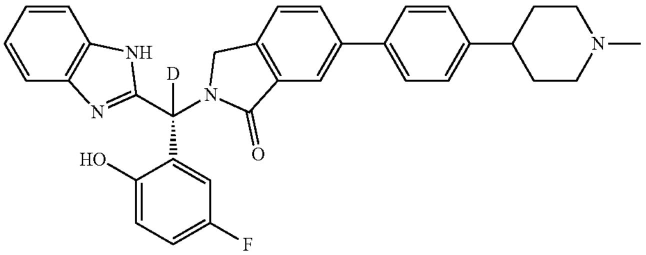 [SMILES: [2H][C@@](c1nc2ccccc2[nH]1)(c1cc(F)ccc1O)N1Cc2ccc(-c3ccc(C4CCN(C)CC4)cc3)cc2C1=O]<br>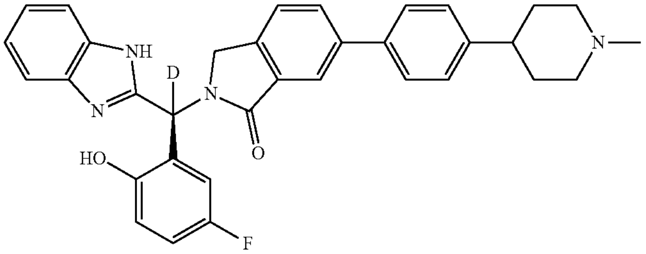 [SMILES: [2H][C@](c1nc2ccccc2[nH]1)(c1cc(F)ccc1O)N1Cc2ccc(-c3ccc(C4CCN(C)CC4)cc3)cc2C1=O] |

TABLE 4-continued

| Compound No. | Structure |
| --- | --- |
| 039 | 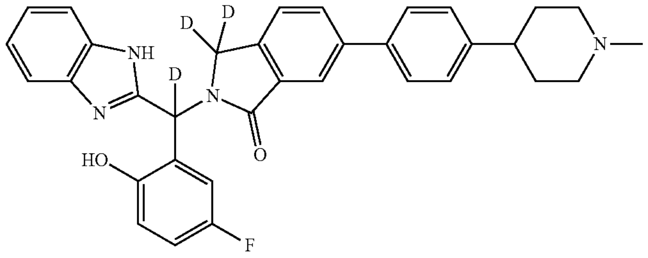 [SMILES: [2H]C1([2H])c2ccc(-c3ccc(C4CCN(C)CC4)cc3)cc2C(=O)N1C([2H])(c1nc2ccccc2[nH]1)c1cc(F)ccc1O] |

or a pharmaceutically acceptable salt thereof.

In embodiments, the compounds 036-039 provided herein have an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In an embodiment of compounds 036-039, each position designated specifically as deuterium has at least 95% incorporation of deuterium.

In another embodiment, the compound of Formula X is selected from the group consisting of a compound in Table 5.

TABLE 5

| Compound No. | Structure |
| --- | --- |
| 078 | 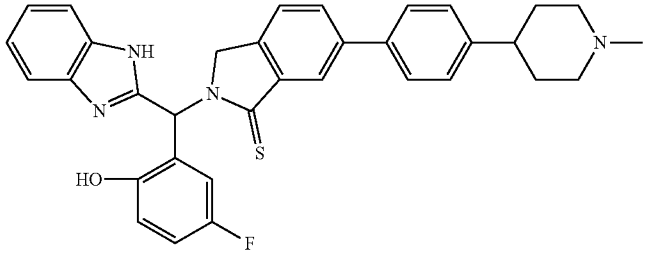 [SMILES: CN1CCC(c2ccc(-c3ccc4c(c3)C(=S)N(C(c3nc5ccccc5[nH]3)c3cc(F)ccc3O)C4)cc2)CC1] |
| 079 | 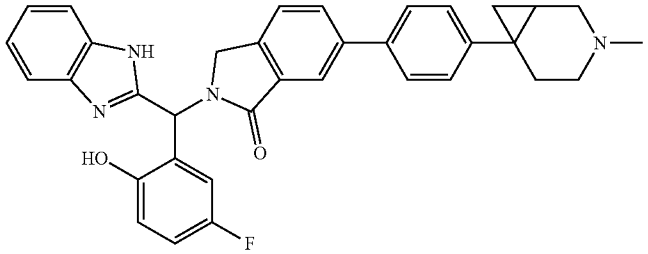 [SMILES: CN1CCC2(c3ccc(-c4ccc5c(c4)C(=O)N(C(c4nc6ccccc6[nH]4)c4cc(F)ccc4O)C5)cc3)CC2C1] |
| 080 | 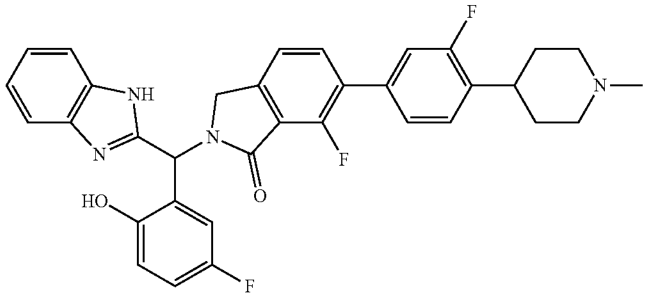 [SMILES: CN1CCC(c2ccc(-c3ccc4c(c3F)C(=O)N(C(c3nc5ccccc5[nH]3)c3cc(F)ccc3O)C4)cc2F)CC1] |

TABLE 5-continued
| Compound No. | Structure |
|---|---|
| 081 | 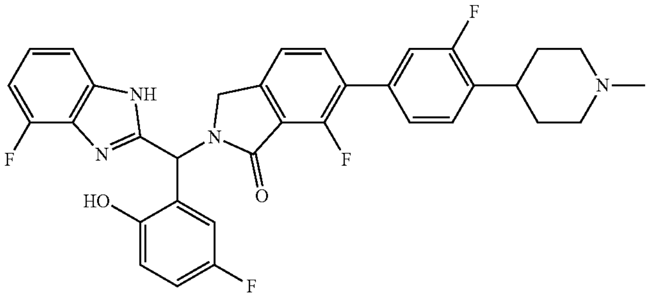 [SMILES: CN1CCC(c2ccc(-c3ccc4c(c3F)C(=O)N(C(c3nc5c(F)cccc5[nH]3)c3cc(F)ccc3O)C4)cc2F)CC1] |
| 082 | 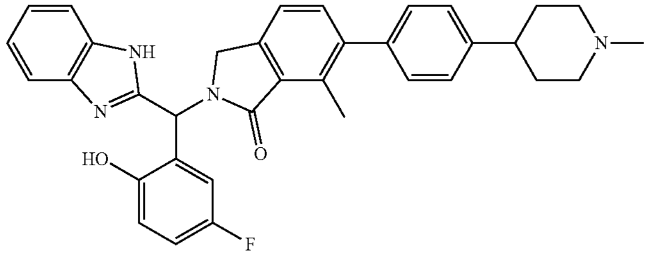 [SMILES: Cc1c(-c2ccc(C3CCN(C)CC3)cc2)ccc2c1C(=O)N(C(c1nc3ccccc3[nH]1)c1cc(F)ccc1O)C2] |
| 083 | 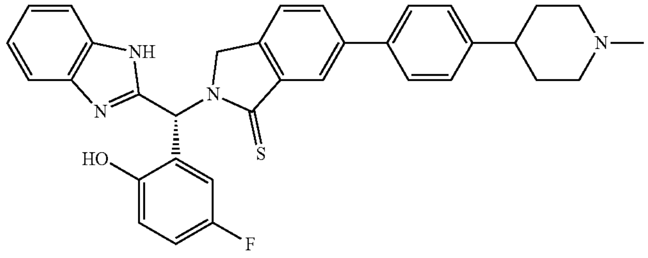 [SMILES: CN1CCC(c2ccc(-c3ccc4c(c3)C(=S)N([C@@H](c3nc5ccccc5[nH]3)c3cc(F)ccc3O)C4)cc2)CC1] |
| 084 | 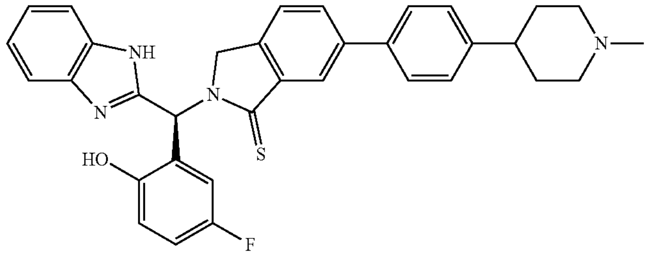 [SMILES: CN1CCC(c2ccc(-c3ccc4c(c3)C(=S)N([C@H](c3nc5ccccc5[nH]3)c3cc(F)ccc3O)C4)cc2)CC1] |
| 085 | 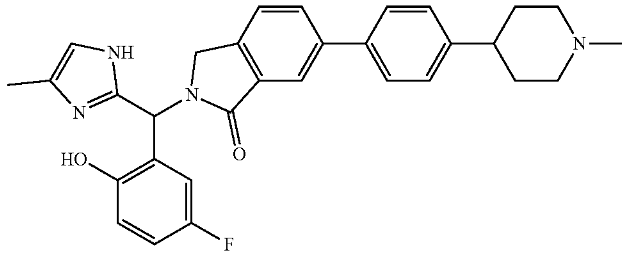 |

TABLE 5-continued
| Compound No. | Structure |
| --- | --- |
| 086 | 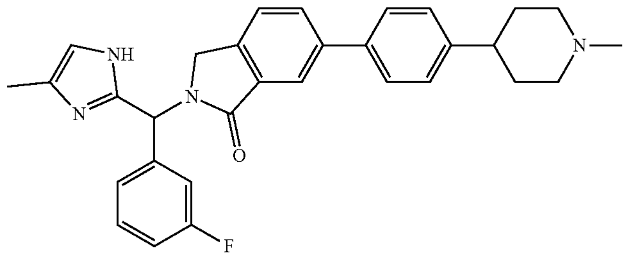 |
| 087 | 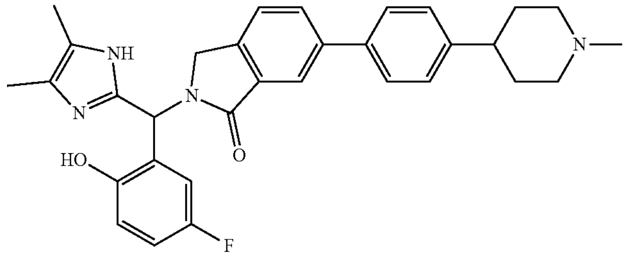 |
| 088 | 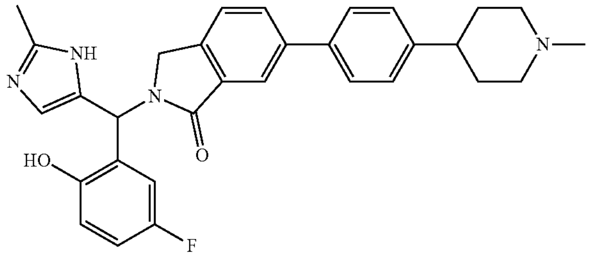 [SMILES: Cc1ncc(C(c2cc(F)ccc2O)N2Cc3ccc(-c4ccc(C5CCN(C)CC5)cc4)cc3C2=O)[nH]1] |
| 089 | 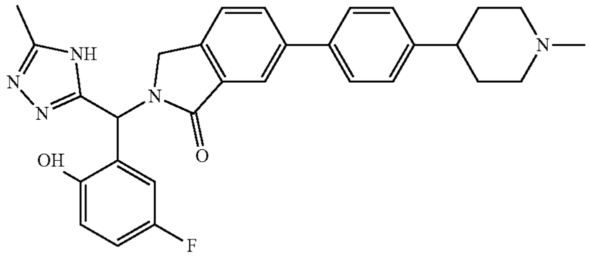 [SMILES: Cc1nnc(C(c2cc(F)ccc2O)N2Cc3ccc(-c4ccc(C5CCN(C)CC5)cc4)cc3C2=O)[nH]1] |
| 090 | 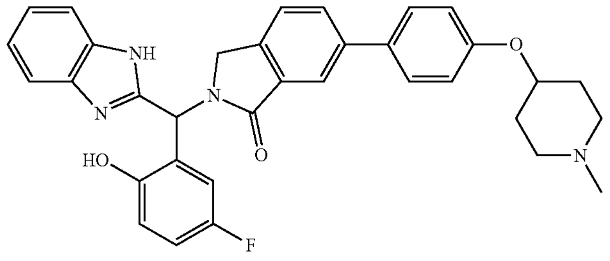 [SMILES: CN1CCC(Oc2ccc(-c3ccc4c(c3)C(=O)N(C(c3nc5ccccc5[nH]3)c3cc(F)ccc3O)C4)cc2)CC1] |
| 091 | 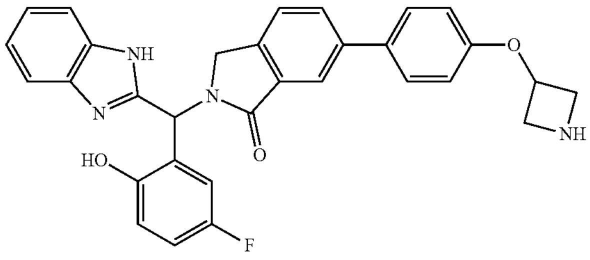 [SMILES: O=C1c2cc(-c3ccc(OC4CNC4)cc3)ccc2CN1C(c1nc2ccccc2[nH]1)c1cc(F)ccc1O] |

TABLE 5-continued
| Compound No. | Structure |
|---|---|
| 093 | 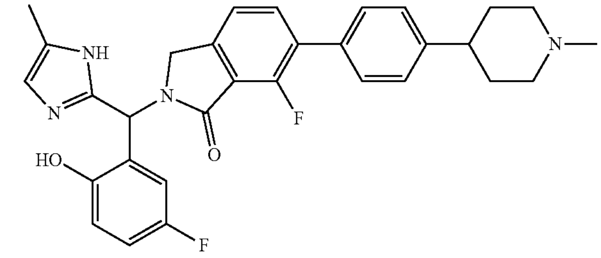 [SMILES: Cc1cnc(C(c2cc(F)ccc2O)N2Cc3ccc(-c4ccc(C5CCN(C)CC5)cc4)c(F)c3C2=O)[nH]1] |
| 094 | 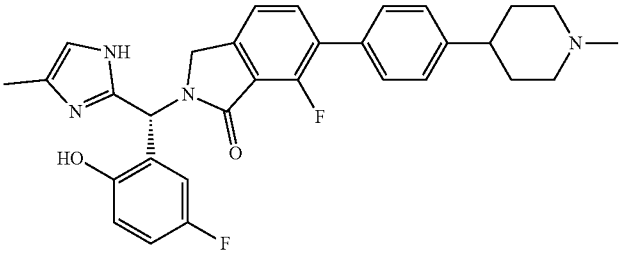 |
| 095 | 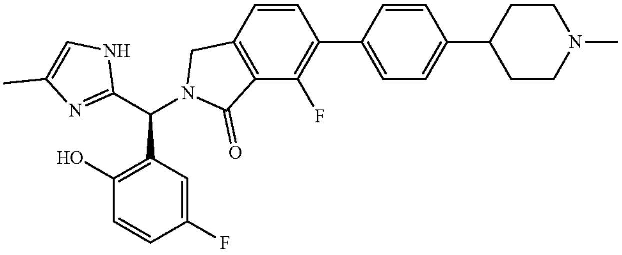 |
| 103 | 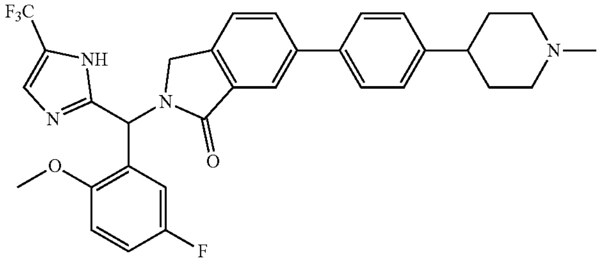 |
| 104 | 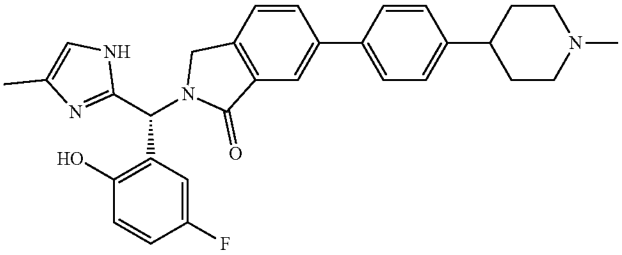 |
| 105 | 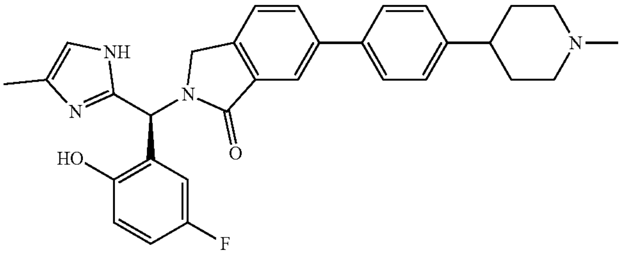 |

TABLE 5-continued

| Compound No. | Structure |
| --- | --- |
| 106 | 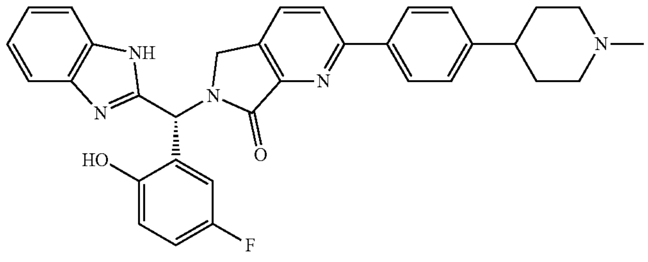 [SMILES: CN1CCC(c2ccc(-c3ccc4c(n3)C(=O)N([C@@H](c3nc5ccccc5[nH]3)c3cc(F)ccc3O)C4)cc2)CC1] |
| 107 | 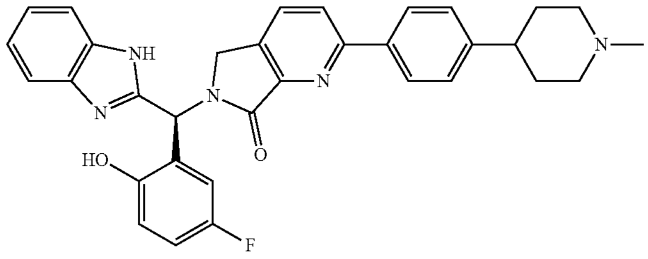 [SMILES: CN1CCC(c2ccc(-c3ccc4c(n3)C(=O)N([C@H](c3nc5ccccc5[nH]3)c3cc(F)ccc3O)C4)cc2)CC1] |

or a pharmaceutically acceptable salt thereof.

In yet another aspect, provided herein is a compound of Formula IIIA (III)

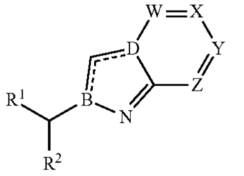

or a pharmaceutically acceptable salt thereof;

wherein

- ⎓ is an optional double bond;
- B and D are each, independently, C or N;
- W and Z are each, independently, N, CH, C-halo, C—($C_1$-$C_3$ alkyl), or C—($C_1$-$C_3$ alkoxy);
- X and Y are each, independently, N, CH, or $CR^3$;
- provided that at least one of W, X, Y, or Z is CH;
- $R^1$ is selected from the group consisting of 6-10 membered aryl, 5-10 membered heteroaryl, 3-10 membered heterocycloalkyl, and 3-10 membered cycloalkyl, all of which are optionally substituted with one, two, or three $R^8$;
- $R^2$ is selected from the group consisting of 6-10 membered aryl, 5-10 membered heteroaryl, 3-10 membered heterocycloalkyl, and 3-10 membered cycloalkyl, all of which are optionally substituted with one, two, or three $R^6$;
- $R^3$ is independently, at each occurrence, selected from the group consisting of halogen, $OR^4$, $NR^4R^4$, $SO_2R^4$, $SO_2NHR^4$, $NHSO_2R^4$, $C(O)OR^4$, $C(O)NHR^4$, $C(O)R^4$, $C_1$-$C_6$ alkyl, $C_2$-$C_6$ alkenyl, $C_2$-$C_6$ alkynyl, 3-7 membered cycloalkyl, $C_4$-$C_7$ cycloalkenyl, $C_6$-$C_{10}$ aryl, 5-6 membered heteroaryl, and 5-7 membered heterocyclyl, wherein alkyl, alkenyl, or alkynyl are each optionally substituted one, two, or three times with $R^4$, and wherein aryl; heteroaryl, or heterocyclyl are each optionally substituted one, two, or three times with $R^5$;
- $R^4$ is independently, at each occurrence, selected from the group consisting of H, $(CH_2)_{0\text{-}3}$—($C_3$-$C_7$ cycloalkyl), $(CH_2)_{0\text{-}3}$—($C_4$-$C_7$ cycloalkenyl), $(CH_2)_{0\text{-}3}$—($C_6$-$C_{10}$ aryl), $(CH_2)_{04}$-(5-6 membered heteroaryl), and $(CH_2)_{0\text{-}3}$-(5-7 membered heterocyclyl), wherein the aryl, heteroaryl, or heterocyclyl are each optionally substituted one, two, or three times with $R^5$;
- $R^5$ is independently, at each occurrence, selected from the group consisting of $C_1$-$C_6$ alkyl, $C_1$-$C_6$ haloalkyl, $C_1$-$C_6$alkoxy, $C_1$-$C_6$ haloalkoxy, $C_1$-$C_3$ alkylamine, 3-10 membered cycloalkyl, halogen, COOH, C(O)O($C_1$-$C_6$ alkyl); 0 $(CH_2)_{1\text{-}3}$—OH, $NH_2$, NH($C_1$-$C_6$ alkyl), N($C_1$-$C_6$ alkyl)$_2$, OH, CN, $(CH_2)_{0\text{-}3}$—($C_6$-$C_{10}$ aryl), $(CH_2)_{0\text{-}3}$-(5-6 membered heteroaryl), and $(CH_2)_{0\text{-}3}$-(5-7 membered heterocyclyl), wherein the aryl, heteroaryl, or heterocyclyl are each optionally substituted one, two, or three times with $R^7$;
- $R^6$ is independently, at each occurrence, selected from the group consisting of $C_1$-$C_3$ alkyl, $C_1$-$C_6$ haloalkyl, $C_1$-$C_3$ alkoxy, $C_1$-$C_3$ haloalkoxy, $C_1$-$C_3$ alkylamine, halogen, OH, $NO_2$, $NH_2$, NH($C_1$-$C_6$ alkyl), N($C_1$-$C_6$ alkyl)$_2$, $(CH_2)_{1\text{-}4}$OH, $S(O)_{0\text{-}2}H$, $S(O)_{0\text{-}2}NH_2$, or CN;
- alternatively, two $R^6$, together with the atoms to which they are attached, can form 5-10 membered heteroaryl, 6-10 membered aryl, 3-10 membered heterocycloalkyl, or 3-10 membered cycloalkyl;
- $R^7$ is independently, at each occurrence, selected from the group consisting of substituents independently selected from $C_1$-$C_6$ alkyl, $C_1$-$C_6$haloalkyl, $C_1$-$C_6$ alkoxy, $C_1$-$C_6$ haloalkoxy, halogen, $NH_2$, NH($C_1$-$C_6$ alkyl), N($C_1$-$C_6$ alkyl)$_2$, $SO_2NH_2$, $SO_2NH$($C_1$-$C_6$ alkyl), $SO_2N$($C_1$-$C_6$ alkyl)$_2$, $(CH_2)_{1\text{-}2}$—OH, $C(O)(CH_2)_{1\text{-}2}$—OH, C(O)($C_1$-$C_5$ alkyl), and C(O)O($C_1$-$C_6$ alkyl);
- alternatively, two $R^7$, together with the atoms to which they are attached, can form 5-10 membered heteroaryl, 6-10 membered aryl, 3-10 membered heterocycloalkyl, or 3-10 membered cycloalkyl; and
- $R^8$ is independently, at each occurrence, selected from the group consisting of $C_1$-$C_3$ alkyl, $C_1$-$C_3$ haloalkyl, $C_1$-$C_3$ alkoxy, $C_1$-$C_3$ haloalkoxy, $C_1$-$C_3$ alkylamine, 3-6 membered cycloalkyl, halogen, OH, $NO_2$, $NH_2$, $NH(C_1\text{-}C_6$ alkyl), $N(C_1\text{-}C_6$ alkyl$)_2$, $(CH_2)_{1\text{-}4}OH$, $S(O)_{0\text{-}2}H$, $S(O)_{0\text{-}2}NH_2$, or CN.

In another aspect, provided herein is a compound of Formula III, or a pharmaceutically acceptable salt thereof, wherein $R^4$ is independently, at each occurrence, selected from the group consisting of H, $C_1\text{-}C_6$ alkyl, $(CH_2)_{0\text{-}3}$—$(C_3\text{-}C_7$ cycloalkyl), $(CH_2)_{0\text{-}3}$—$(C_4\text{-}C_7$ cycloalkenyl), $(CH_2)_{0\text{-}3}$—$(C_6\text{-}C_{10}$ aryl), $(CH_2)_{0\text{-}3}$-(5-6 membered heteroaryl), and $(CH_2)_{0\text{-}3}$-(5-7 membered heterocyclyl), wherein the aryl, heteroaryl, or heterocyclyl are each optionally substituted one, two, or three times with $R^5$;

wherein all other variables are defined above.

In an embodiment, the compound of Formula III is a compound of Formula IIIa:

(IIIa)

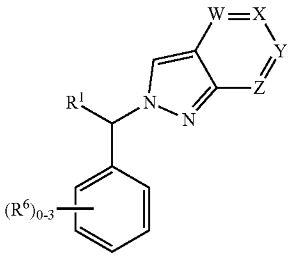

or a pharmaceutically acceptable salt thereof.

In an embodiment of Formula IIIa, $R^3$ is $C_6\text{-}C_{10}$ aryl or 5-6 membered heteroaryl, both of which are optionally substituted one time with $R^5$. In another embodiment of Formula IIIa, $R^3$ is $C_6\text{-}C_{10}$ aryl optionally substituted one time with $R^5$, wherein $R^5$ is 5-7 membered heterocyclyl, aryl, 3-10 membered cycloalkyl, or 5-6 membered heteroaryl, all of which are optionally substituted one time with $R^7$. In yet another embodiment of Formula IIIa, $R^3$ is phenyl optionally substituted one time with $R^5$, wherein $R^5$ is 5-7 membered heterocyclyl, $C_6\text{-}C_{10}$ aryl, 3-10 membered cycloalkyl, or 5-6 membered heteroaryl, all of which are optionally substituted one time with $R^7$. In still another embodiment of Formula IIIa, $R^3$ is $C_6\text{-}C_{10}$ aryl optionally substituted one time with $R^5$, wherein $R^5$ is 5 membered heterocyclyl optionally substituted one time with $R^7$. In an embodiment of Formula Ilia, $R^3$ is phenyl optionally substituted one time with piperidine, wherein piperidine is substituted one time with $R^7$.

In another embodiment, the compound of Formula III is a compound of Formula IIIb:

(IIIb)

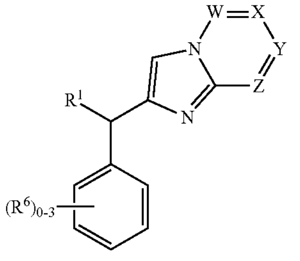

or a pharmaceutically acceptable salt thereof.

In yet another embodiment, the compound of Formula III is a compound of Formula IIIc;

(IIIc)

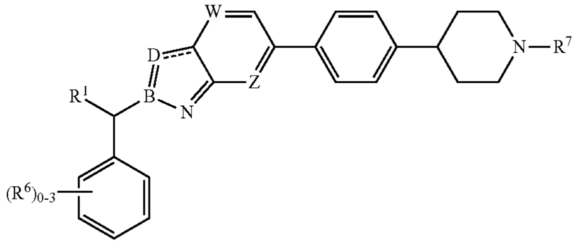

or a pharmaceutically acceptable salt thereof.

In still another embodiment, $R^1$ is selected from the group consisting of benzimidazole, imidazopyrazine, purine, imidazole, pyrazole, triazole, and imidazopyridine. In an embodiment, $R^1$ is selected from the group consisting of:

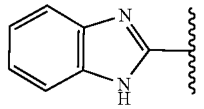
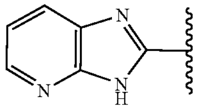
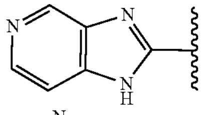
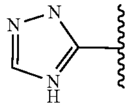
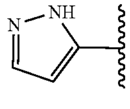
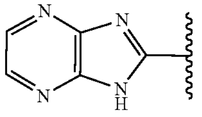
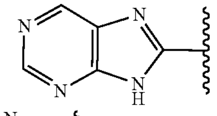
and
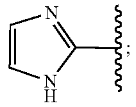
;

all of which are optionally substituted with one, two, or three $R^6$.

In another embodiment, Y is $CR^3$, and $R^3$ is 6-10 membered aryl substituted with one or two $R^5$. In yet another embodiment, Z is CF. In still another embodiment, Z is CH. In an embodiment, Z is N.

In another embodiment, $R^6$ is hydroxy, halo, or two $R^6$, together with the atoms to which they are attached; form 5-10 membered heteroaryl, 6-10 membered aryl; 3-10 membered heterocycloalkyl, or 3-10 membered cycloalkyl. In an embodiment, $R^6$ is hydroxy, fluoro or two $R^6$, together with the atoms to which they are attached, form 5-10 membered heteroaryl, 6-10 membered aryl, 3-10 membered heterocycloalkyl, or 3-10 membered cycloalkyl. In yet another embodiment, $R^6$ is hydroxy. In still another embodiment, $R^6$ is fluoro. In another embodiment, $R^6$ is chloro. In an embodiment, there are two $R^6$ that are hydroxy and fluoro. In another embodiment, there are two $R^6$ that are hydroxy and chloro. In still another embodiment, two $R^6$, together with the atoms to which they are attached, form 5-10 membered heteroaryl, 6-10 membered aryl, 3-10 membered heterocycloalkyl, or 3-10 membered cycloalkyl.

In another embodiment, the compound of Formula III is selected from the group consisting of a compound from Table 6.

TABLE 6
| Compound No. | Structure |
|---|---|
| 034 | 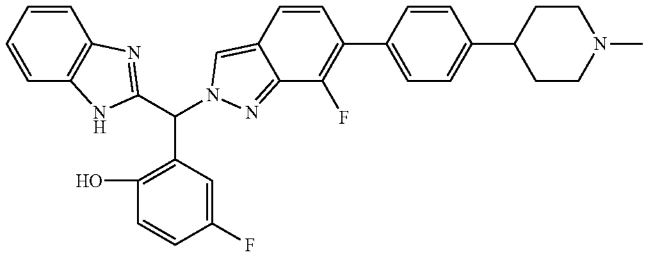 [SMILES: CN1CCC(c2ccc(-c3ccc4cn(C(c5nc6ccccc6[nH]5)c5cc(F)ccc5O)nc4c3F)cc2)CC1] |
| 035 | 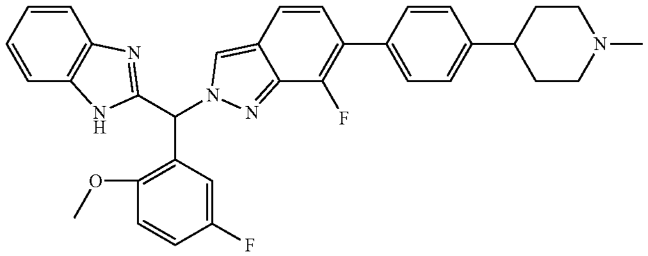 [SMILES: COc1ccc(F)cc1C(c1nc2ccccc2[nH]1)n1cc2ccc(-c3ccc(C4CCN(C)CC4)cc3)c(F)c2n1] |
| 092 | 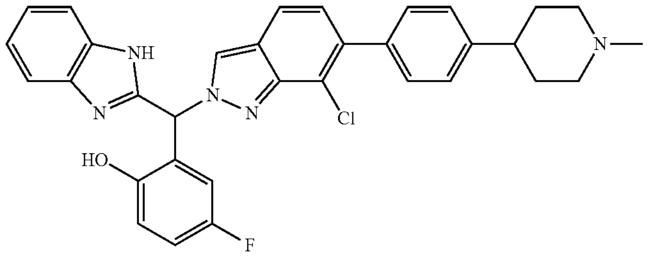 [SMILES: CN1CCC(c2ccc(-c3ccc4cn(C(c5nc6ccccc6[nH]5)c5cc(F)ccc5O)nc4c3Cl)cc2)CC1] |
| 096 | 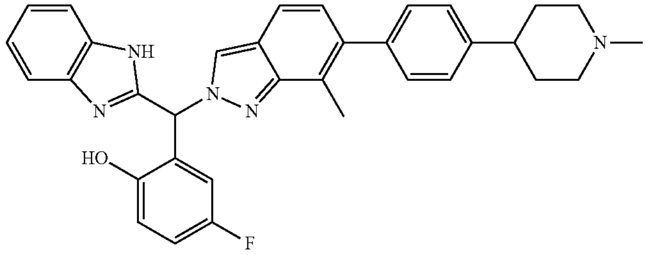 [SMILES: Cc1c(-c2ccc(C3CCN(C)CC3)cc2)ccc2cn(C(c3nc4ccccc4[nH]3)c3cc(F)ccc3O)nc12] |
| 097 | 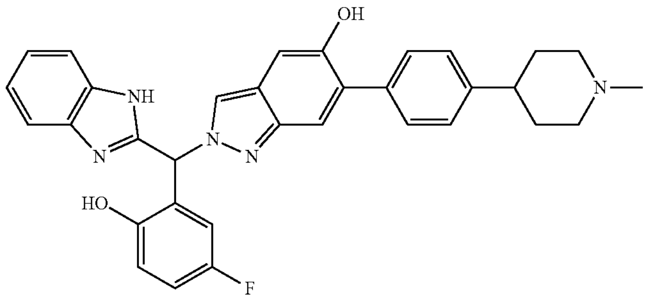 [SMILES: CN1CCC(c2ccc(-c3cc4nn(C(c5nc6ccccc6[nH]5)c5cc(F)ccc5O)cc4cc3O)cc2)CC1] |

TABLE 6-continued
| Compound No. | Structure |
|---|---|
| 098 | 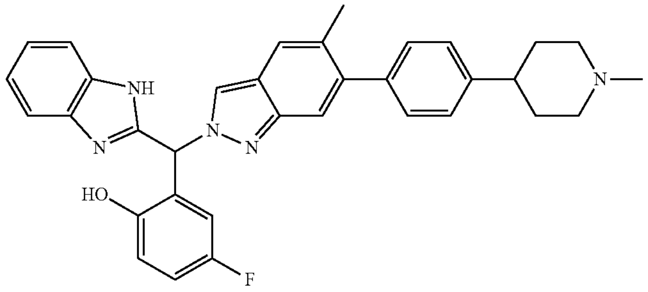 [SMILES: Cc1cc2cn(C(c3nc4ccccc4[nH]3)c3cc(F)ccc3O)nc2cc1-c1ccc(C2CCN(C)CC2)cc1] |
| 099 | 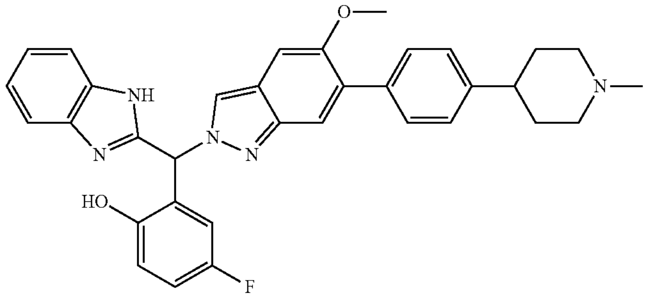 [SMILES: COc1cc2cn(C(c3nc4ccccc4[nH]3)c3cc(F)ccc3O)nc2cc1-c1ccc(C2CCN(C)CC2)cc1] |
| 100 | 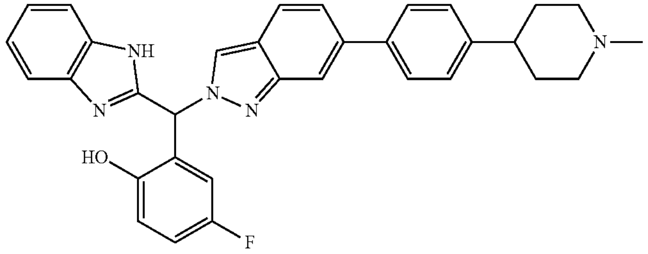 [SMILES: CN1CCC(c2ccc(-c3ccc4cn(C(c5nc6ccccc6[nH]5)c5cc(F)ccc5O)nc4c3)cc2)CC1] |
| 101 | 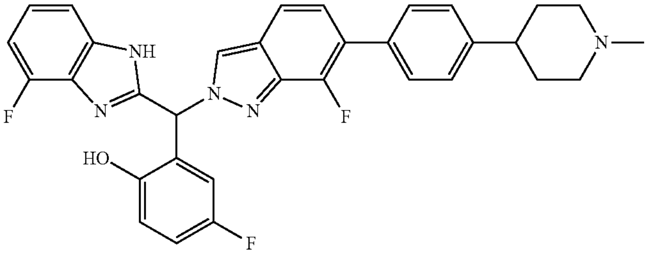 [SMILES: CN1CCC(c2ccc(-c3ccc4cn(C(c5nc6c(F)cccc6[nH]5)c5cc(F)ccc5O)nc4c3F)cc2)CC1] |
| 118 | 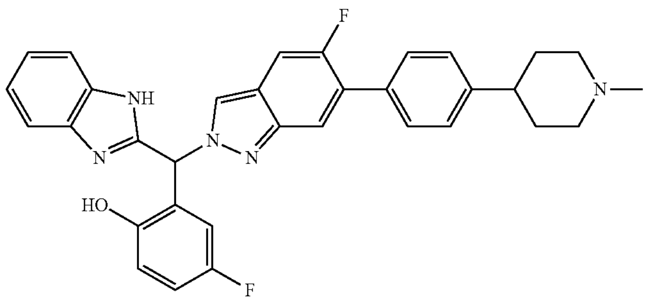 [SMILES: CN1CCC(c2ccc(-c3cc4nn(C(c5nc6ccccc6[nH]5)c5cc(F)ccc5O)cc4cc3F)cc2)CC1] |

TABLE 6-continued

| Compound No. | Structure |
|---|---|
| 119 | 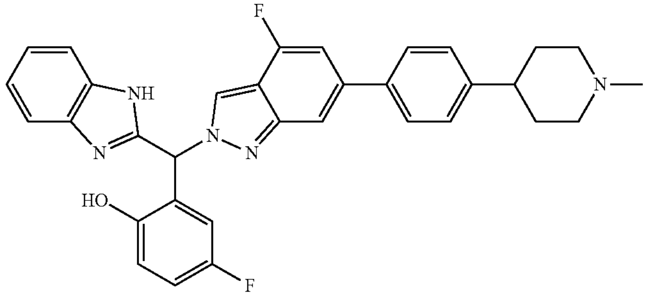 [SMILES: CN1CCC(c2ccc(-c3cc(F)c4cn(C(c5nc6ccccc6[nH]5)c5cc(F)ccc5O)nc4c3)cc2)CC1] |

or a pharmaceutically acceptable salt thereof.

In an embodiment of Formulas I, II, and III, $R^7$ is $C_1$-$C_3$ alkyl.

The compounds disclosed herein may exist as tautomers and optical isomers (e.g., enantiomers, diastereomers, diastereomeric mixtures, racemic mixtures, and the like).

It is generally well known in the art that any compound that will be converted in vivo to provide a compound disclosed herein is a prodrug within the scope of the present disclosure.

Compounds provided herein can also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the invention can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7, 8, 9, 10, 11 or 12 deuterium atoms. Synthetic methods for including isotopes into organic compounds are known in the art (Deuterium Labeling in Organic Chemistry by Alan F. Thomas (New York, N.Y., Appleton-Century-Crofts, 1971; The Renaissance of HID Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can used in various studies such as NMR spectroscopy, metabolism experiments, and/or assays.

In the compounds provided herein, any atom not specifically designated as a particular isotope is meant to represent any stable isotope of that atom. Unless otherwise stated, when a position is designated specifically as "H" or "hydrogen," the position is understood to have hydrogen at its natural abundance isotopic composition. Also, unless otherwise stated, when a position is designated specifically as "D" or "deuterium", the position is understood to have deuterium at an abundance that is at least 3000 times greater than the natural abundance of deuterium, which is 0.015% (i.e., at least 45% incorporation of deuterium).

In an aspect, provided herein is a pharmaceutical composition comprising any one of the compounds disclosed herein, or a pharmaceutically acceptable salt thereof, and at least one pharmaceutically acceptable carrier.

In an embodiment, the composition further comprises a second active agent. In another embodiment, the second active agent is selected from the group consisting of a MEK inhibitor, a PI3K inhibitor, and an mTor inhibitor. In yet another embodiment, the second active agent prevents EGFR dimer formation in a subject. In still another embodiment, the second active agent is selected from the group consisting of cetuximab, trastuzumab, and panitumumab. In an embodiment, the second active agent is an ATP competitive EGFR inhibitor. In another embodiment, the ATP competitive EGFR inhibitor is osimertinib, gefitinib, or erlotinib. In another embodiment, the ATP competitive EGFR inhibitor is osimertinib.

In another aspect, provided herein are pharmaceutical compositions comprising a compound of the present disclosure, or a pharmaceutically acceptable salt thereof, and a pharmaceutically acceptable carrier. In another aspect, the pharmaceutical composition further comprises a second active agent, wherein said second active agent prevents EGFR dimer formation, and a pharmaceutically acceptable carrier. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab.

A compound that binds to an allosteric site in EGFR, such as the compounds of the present disclosure (e.g., the compounds of the formulae disclosed herein), optionally in combination with a second active agent, wherein said second active agent prevents EGFR dimer formation, are capable of modulating EGFR activity. In some embodiments, the compounds of the present disclosure are capable of inhibiting or decreasing EGFR activity without a second active agent (e.g., an antibody such as cetuximab, trastuzumab, or panitumumab). In other embodiments, the compounds of the present disclosure in combination with a second active agent. In an embodiment, the second active agent prevents EGFR dimer formation and/or are capable of inhibiting or decreasing EGFR activity. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib, gefitinib or erlotinib. In another embodiment, the ATP competitive EGFR inhibitor is osimertinib.

Methods of Treatment

In an aspect, provided herein is a method of treating cancer in an individual in need thereof, comprising administering to the individual a therapeutically effective amount of a compound disclosed herein. In an embodiment, the cancer is selected from the group consisting of lung cancer, colon cancer, breast cancer, endometrial cancer, thyroid cancer, glioma, squamous cell carcinoma, and prostate cancer. In another embodiment, the cancer is non-small cell lung cancer (NSCLC).

In another aspect, provided herein is a method of inhibiting a kinase in an individual in need thereof, comprising administering to the individual a therapeutically effective amount of a compound provided herein. In an embodiment, the kinase is EGFR.

In yet another aspect, provided herein is a method of treating or preventing a kinase-mediated disorder in an individual in need thereof, comprising administering to the individual a therapeutically effective amount of a compound of the present disclosure. In an embodiment, the kinase-mediated disorder is resistant to an EGFR-targeted therapy. In another embodiment, the EGFR-treated therapy is selected from the group consisting of gefitinib, erlotinib, osimertinib, CO-1686, and WZ4002.

In some embodiments, the compounds of the present disclosure are capable of modulating (e.g., inhibiting or decreasing) the activity of EGFR containing one or more mutations. In some embodiments, the mutant EGFR contains one or more mutations selected from T790M, L718Q, L844V, V948R, L858R, I941R, C797S, and Del. In other embodiments, the mutant EGFR contains a combination of mutations, wherein the combination is selected from Del/L718Q, Del/L844V, Del/T790M, Del/T790M/L718Q, Del/T790M/L844V, L858R/L718Q, L858R/L844V, L858R/T790M, L858R/T790M/I941R, Del/T790M, Del/T790M/C797S, L858R/T790M/C797S, and L858R/T790M/L718Q. In other embodiments, the mutant EGFR contains a combination of mutations, wherein the combination is selected from Del/L844V, L858R/L844V, L858R/T790M, L858R/T790M/I941R, L858R/T790M/C797S, Del/T790M, Del/T790M, Del/T790M/C797S, and L858R/T790M. In other embodiments, the mutant EGFR contains a combination of mutations, wherein the combination is selected from L858R/T790M, L858R/T790M/I941R, L858R/T790M/C797S, Del/T790M, Del/T790M/C797S, and L858R/T790M.

In some embodiments, the compounds of the present disclosure in combination with a second active agent, wherein said second active agent prevents EGFR dimer formation, are capable of modulating (e.g., inhibiting or decreasing) the activity of EGFR containing one or more mutations. In some embodiments, the mutant EGFR contains one or more mutations selected from T790M, L718Q, L844V, V948R, L858R, I941R, C797S, and Del. In other embodiments, the mutant EGFR contains a combination of mutations, wherein the combination is selected from Del/L718 Q, Del/L844V, Del/T790M, Del/T790M/L718Q, Del/T790M/L844V, L858R/L718Q, L858R/L844V, L858R/T790M, L858R/T790M/I941R, Del/T790M, Del/T790M/C797S, L858R/T790M/C797S, and L858R/T790M/L718Q. In other embodiments, the mutant EGFR contains a combination of mutations, wherein the combination is selected from Del/L844V, L858R/L844V, L858R/T790M, L858R/T790M/I941R, L858R/T790M/C797S, Del/T790M, Del/T790M/C797S, and L858R/T790M. In other embodiments, the mutant EGFR contains a combination of mutations, wherein the combination is selected from L858R/T790M, L858R/T790M/I941R, L858R/T790M/C797S, Del/T790M, Del/T790M/C797S, and L858R/T790M. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib, gefitinib or erlotinib.

In some embodiments, the compounds of the present disclosure are capable of modulating (e.g., inhibiting or decreasing) the activity of EGFR containing one or more mutations, but do not affect the activity of a wild-type EGFR.

In other embodiments, the compounds of the present disclosure in combination with a second active agent, wherein said second active agent prevents EGFR dimer formation, are capable of modulating (e.g., inhibiting or decreasing) the activity of EGFR containing one or more mutations, but do not affect the activity of a wild-type EGFR. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib, gefitinib or erlotinib. In another embodiment, the ATP competitive EGFR inhibitor is osimertinib.

Modulation of EGFR containing one or more mutations, such as those described herein, but not a wild-type EGFR, provides an approach to the treatment, prevention, or amelioration of diseases including, but not limited to, cancer and metastasis, inflammation, arthritis, systemic lupus erythematosus, skin-related disorders, pulmonary disorders, cardiovascular disease, ischemia, neurodegenerative disorders, liver disease, gastrointestinal disorders, viral and bacterial infections, central nervous system disorders, Alzheimer's disease, Parkinson's disease, Huntington's disease, amyotrophic lateral sclerosis, spinal cord injury, and peripheral neuropathy.

In some embodiments, the compounds of the disclosure exhibit greater inhibition of EGFR containing one or more mutations as described herein relative to a wild-type EGFR. In certain embodiments, the compounds of the disclosure exhibit at least 2-fold, 3-fold, 5-fold, 10-fold, 25-fold, 50-fold or 100-fold greater inhibition of EGFR containing one or more mutations as described herein relative to a wild-type EGFR. In various embodiments, the compounds of the disclosure exhibit up to 1000-fold greater inhibition of EGFR containing one or more mutations as described herein relative to a wild-type EGFR. In various embodiments, the compounds of the disclosure exhibit up to 10000-fold greater inhibition of EGFR having a combination of mutations described herein (e.g., L858R/T790M, L858R/T790M/I941R, L858R/T790M/C797S, Del/T790M, Del/T790M/C797S, and L858R/T790M) relative to a wild-type EGFR.

In other embodiments, the compounds of the disclosure in combination with a second active agent, wherein said second active agent prevents EGFR dimer formation, exhibit greater inhibition of EGFR containing one or more mutations as described herein relative to a wild-type EGFR. In certain embodiments, the compounds of the disclosure in combination with a second active agent, wherein said second active agent prevents EGFR dimer formation, exhibit at least 2-fold, 3-fold, 5-fold, 10-fold, 25-fold, 50-fold or 100-fold greater inhibition of EGFR containing one or more mutations as described herein relative to a wild-type EGFR. In various embodiments, the compounds of the disclosure in combination with a second active agent, wherein said second active agent prevents EGFR dimer formation, exhibit up to 1000-fold greater inhibition of EGFR containing one or more mutations as described herein relative to a wild-type EGFR. In various embodiments, the compounds of the disclosure in combination with a second active agent, wherein said second active agent prevents EGFR dirtier formation, exhibit up to 10000-fold greater inhibition of EGFR having a combination of mutations described herein (e.g., L858R/T790M, L858R/T790M/I941R, L858R/T790M/C797S, Del/T790M, Del/T790M/C797S, and L858R/T790M) relative to a wild-type EGFR. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGER dimer formation is cetuximab. In an embodiment, the second active agent is an ATP competitive EGFR inhibitor. In another embodiment, the ATP competitive EGFR inhibitor is osimertinib, gefitinib or erlotinib. In another embodiment, the ATP competitive EGFR inhibitor is osimertinib.

In some embodiments, the compounds of the disclosure exhibit from about 2-fold to about 10-fold greater inhibition of EGFR containing one or more mutations as described herein relative to a wild-type EGFR. In various embodiments, the compounds of the disclosure exhibit from about 10-fold to about 100-fold greater inhibition of EGFR containing one or more mutations as described herein relative to a wild-type EGFR. In various embodiments, the compounds of the disclosure exhibit from about 100-fold to about 1000-fold greater inhibition of EGFR containing one or more mutations as described herein relative to a wild-type EGFR. In various embodiments, the compounds of the disclosure exhibit from about 1000-fold to about 10000-fold greater inhibition of EGFR containing one or more mutations as described herein relative to a wild-type EGFR.

In other embodiments, the compounds of the disclosure in combination with a second active agent, wherein said second active agent prevents EGFR dimer formation, exhibit from about 2-fold to about 10-fold greater inhibition of EGFR containing one or more mutations as described herein relative to a wild-type EGFR. In other embodiments, the compounds of the disclosure in combination with a second active agent, wherein said second active agent prevents EGFR dimer formation, exhibit from about 10-fold to about 100-fold greater inhibition of EGFR containing one or more mutations as described herein relative to a wild-type EGFR. In other embodiments, the compounds of the disclosure in combination with a second active agent wherein said second active agent prevents EGFR dimer formation exhibit from about 100-fold to about 1000-fold greater inhibition of EGFR containing one or more mutations as described herein relative to a wild-type EGFR. In other embodiments, the compounds of the disclosure in combination with a second active agent, wherein said second active agent prevents EGFR dimer formation, exhibit from about 1000-fold to about 10000-fold greater inhibition of EGFR containing one or more mutations as described herein relative to a wild-type EGFR. In other embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGER inhibitor. In another embodiment, the ATP competitive EGFR inhibitor is osimertinib, gefitinib or erlotinib. In another embodiment, the ATP competitive EGFR inhibitor is osimertinib.

In certain embodiments, the compounds of the disclosure exhibit at least 2-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR. In certain embodiments, the compounds of the disclosure exhibit at least 3-fold greater inhibition of EGER having a combination of mutations selected from L858R/T790M, L858R/T790M/I941R, L858R/T790M/C797S, Del/T790M, Del/T790M/C797S, and L858R/T790M relative to a wild-type EGFR. In certain embodiments, the compounds of the disclosure exhibit at least 5-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR. In certain embodiments, the compounds of the disclosure exhibit at least 10-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR. In certain embodiments, the compounds of the disclosure exhibit at least 25-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGER. In certain embodiments, the compounds of the disclosure exhibit at least 50-fold greater inhibition of EGFR having a combination of mutations selected from L L858R/T790M, L858R/T790M/I941R, L858R/T790M/C797S, Del/T790M, Del/T790M/C797S, and L858R/T790M relative to a wild-type EGER. In certain embodiments, the compounds of the disclosure exhibit at least 100-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGER.

In certain embodiments, the compounds of the disclosure in combination with a second active agent, wherein said second active agent prevents EGFR dimer formation, exhibit at least 2-fold greater inhibition of EGER having a combination of mutations selected from L858R/T790M, L858R/T790M/I941R, L858R/T790M/C797S, Del/T790M, Del/T790M/C797S, and L858R/T790M relative to a wild-type EGER. In certain embodiments, the compounds of the disclosure in combination with a second active agent, wherein said second active agent prevents EGFR dimer formation, exhibit at least 3-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR. In certain embodiments, the compounds of the disclosure in combination with a second active agent, wherein said second active agent prevents EGFR dimer formation, exhibit at least 5-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR. In certain embodiments, the compounds of the disclosure in combination with a second active agent, wherein said second active agent prevents EGFR dialer formation, exhibit at least 10-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR. In certain embodiments, the compounds of the disclosure in combination with a second active agent, wherein said second active agent prevents EGFR dimer formation, exhibit at least 25-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR. In certain embodiments, the compounds of the disclosure in combination with a second active agent, wherein said second active agent prevents EGFR dimer formation, exhibit at least 50-fold greater inhibition of EGFR having a combination of mutations selected from L L858R/T790M, L858R/T790M/I941R, L858R/T790M/C797S, Del/T790M, Del/T790M/C797S, and L858R/T790M relative to a wild-type EGFR. In certain embodiments, the compounds of the disclosure in combination with a second active agent, wherein said second active agent prevents EGFR dimer formation, exhibit at least 100-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib.

In some embodiments, the inhibition of EGFR activity is measured by $IC_{50}$.

In some embodiments, the inhibition of EGFR activity is measured by $EC_{50}$.

In some embodiments, the inhibition of EGFR by a compound of the disclosure can be measured via a biochemical assay. By illustrative and non-limiting example, a homogenous time-resolved fluorescence (HTRF) assay may be used to determine inhibition of EGFR activity using conditions and experimental parameters disclosed herein. The HTRF assay may, for example, employ concentrations of substrate (e.g., biotin-Lck-peptide substrate) of about 1 μM; concentrations of EGFR (mutant or WT) from about 0.2 nM to about 40 nM; and concentrations of inhibitor from about 0.000282 μM to about 50 μM. A compound of the disclosure screened under these conditions may, for example, exhibit an $IC_{50}$ value from about 1 nM to >1 μM; from about 1 nM to about 400 nM; from about 1 nM to about 150 nM; from about 1 nM to about 75 nM; from about 1 nM to about 40 nM; from about 1 nM to about 25 nM; from about 1 nM to about 15 nM; or from about 1 nM to about 10 nM. In certain embodiments, a compound of the disclosure screened under the above conditions for inhibition of EGFR having a mutation or combination of imitations selected from L858R/T790M, L858R, and T790M may, for example, exhibit an $IC_{50}$ value from about 1 nM to >1 μM; from about 1 nM to about 400 nM; from about 1 nM to about 150 nM; from about 1 nM to about 75 nM; from about 1 nM to about 40 nM; from about 1 nM to about 25 nM; from about 1 nM to about 15 nM; or from about 1 nM to about 10 nM.

In some embodiments, the compounds of the disclosure bind to an allosteric site in EGFR. In some embodiments, the compounds of the disclosure interact with at least one amino acid residue of epidermal growth factor receptor (EGFR) selected from Lys745, Leu788, and Ala 743. In other embodiments, the compounds of the disclosure interact with at least one amino acid residue of epidermal growth factor receptor (EGFR) selected from Cys755, Leu777, Phe856, and Asp855. In other embodiments, the compounds of the disclosure interact with at least one amino acid residue of epidermal growth factor receptor (EGFR) selected from Met766. Ile759, Glu762, and Ala763. In other embodiments, the compounds of the disclosure interact with at least one amino acid residue of epidermal growth factor receptor (EGFR) selected from Lys745, Leu788, and Ala 743; at least one amino acid residue of epidermal growth factor receptor (EGFR) selected from Cys755, Leu777, Phe856, and Asp855; and at least one amino acid residue of epidermal growth factor receptor (EGFR) selected from Met766, Ile759, Glu762, and Ala763. In other embodiments, the compounds of the disclosure do not interact with any of the amino acid residues of epidermal growth factor receptor (EGFR) selected from Met793, Gly796, and Cys797.

In some embodiments, the disclosure provides a compound comprising an allosteric kinase inhibitor, wherein the compound is a more potent inhibitor of a drug-resistant EGFR mutant relative to a wild type EGFR. For example, the compound can be at least about 2-fold, 3-fold, 5-fold, 10-fold, 25-fold, 50-fold or about 100-fold more potent at inhibiting the kinase activity of the drug-resistant EGFR mutant relative to a wild-type EGFR. In some embodiments, the drug-resistant EGFR mutant is resistant to one or more known EGFR inhibitors, including but not limited to gefitinib, erlotinib, lapatinib, WZ4002, HKI-272, CL-387785, and osimertinib.

In some embodiments, the drug-resistant EGFR mutant comprises a sensitizing mutation, such as Del and L858R.

In some embodiments, the disclosure provides a compound comprising an allosteric kinase inhibitor in combination with a second active agent, wherein said second active agent prevents EGFR dimer formation, wherein the compound is a more potent inhibitor of a drug-resistant EGFR mutant relative to a wild type EGFR. For example, the compound in combination with a second active agent, wherein said second active agent prevents EGFR dimer formation, can be at least about 2-fold, 3-fold, 5-fold, 10-fold, 25-fold, 50-fold or about 100-fold more potent at inhibiting the kinase activity of the drug-resistant EGFR mutant relative to a wild-type EGFR. In some embodiments, the drug-resistant EGFR mutant is resistant to one or more known EGFR inhibitors, including but not limited to gefitinib, erlotinib, lapatinib, WZ4002, HKI-272, CL-387785, and osimertinib. In some embodiments, the drug-resistant EGFR mutant comprises a sensitizing mutation, such as Del and L858R. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib.

In some embodiments, the disclosure provides a compound comprising an allosteric kinase inhibitor, wherein the compound inhibits kinase activity of a drug-resistant EGFR mutant harboring a sensitizing mutation (e.g., Del and L858R) and a drug-resistance mutation (e.g., T7901.1, L718Q, C797S, and L844V) with less than a 10-fold difference in potency (e.g., as measured by $IC_{50}$) relative to an EGFR mutant harboring the sensitizing mutation but not the drug-resistance mutation. In some embodiments, the difference in potency is less than about 9-fold, 8-fold, 7-fold, 6-fold, 5-fold, 4-fold, 3-fold, or 2-fold. In other embodiments, the disclosure provides a compound comprising an allosteric kinase inhibitor in combination with a second active agent, wherein said second active agent prevents EGFR dimer formation, wherein the compound in combination with the second active agent inhibits kinase activity of a drug-resistant EGFR mutant harboring a sensitizing mutation (e.g., Del and L858R) and a drug-resistance mutation (e.g., T790M, L718Q, C797S, and L844V) with less than a 10-fold difference in potency (e.g., as measured by $IC_{50}$) relative to an EGFR mutant harboring the sensitizing mutation but not the drug-resistance mutation. In some embodiments, the difference in potency is less than about 9-fold, 8-fold, 7-fold, 6-fold, 5-fold, 4-fold, 3-fold, or 2-fold. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib, gefitinib or erlotinib. In another embodiment, the ATP competitive EGFR inhibitor is osimertinib.

In some embodiments, the disclosure provides a compound comprising an allosteric kinase inhibitor, wherein the compound is more potent than one or more known EGFR inhibitors, including but not limited to gefitinib, erlotinib, lapatinib, WZ4002, HKI-272, CL-387785, and osimertinib, at inhibiting the activity of EGFR containing one or more mutations as described herein, such as T790M, L718Q, L844V, L858R, C797S, and Del. For example, the compound can be at least about 2-fold, 3-fold, 10-fold, 25-fold, 50-fold or about 100-fold more potent (e.g., as measured by $IC_{50}$) than gefitinib, erlotinib, lapatinib, WZ4002, HKI-272, CL-387785, and osimertinib at inhibiting the activity of the EGFR containing one or more mutations as described herein.

In other embodiments, the disclosure provides a compound comprising an allosteric kinase inhibitor in combination with a second active agent, wherein said second active agent prevents EGFR dimer formation, wherein the compound in combination with the second active agent is more potent than one or more known EGFR inhibitors, including but not limited to gefitinib, erlotinib, lapatinib, WZ4002, NISI-272, CL-387785, and osimertinib, at inhibiting the activity of EGFR containing one or more mutations as described herein, such as T790M, L718Q, L844V, L858R, C797S, and Del. For example, the compound in combination with a second active agent, wherein said second active agent prevents EGFR dimer formation, can be at least about 2-fold, 3-fold, 5-fold, 10-fold, 25-fold, 50-fold or about 100-fold more potent (e.g., as measured by $IC_{50}$) than gefitinib, erlotinib, lapatinib, WZ4002, HKI-272, CL-387785, and osimertinib at inhibiting the activity of the EGFR containing one or more mutations as described herein. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib, gefitinib or erlotinib. In another embodiment, the ATP competitive EGFR inhibitor is osimertinib.

In some embodiments, the disclosure provides a compound comprising an allosteric kinase inhibitor, wherein the compound is less potent than one or more known EGFR inhibitors, including but not limited to gefitinib, erlotinib, lapatinib, WZ4002, HKI-272, CL-387785, and osimertinib, at inhibiting the activity of a wild-type EGFR. For example, the compound can be at least about 2-fold, 3-fold, 5-fold, 10-fold, 25-fold, 50-fold or about 100-fold less potent (e.g., as measured by $IC_{50}$) than gefitinib, erlotinib, lapatinib, WZ4002, HKI-272, CL-387785, and osimertinib, at inhibiting the activity of a wild-type EGFR.

In other embodiments, the disclosure provides a compound comprising an allosteric kinase inhibitor in combination with a second active agent, wherein said second active agent prevents EGFR dimer formation, wherein the compound in combination with the second active agent is less potent than one or more known EGFR inhibitors, including but not limited to gefitinib, erlotinib, lapatinib, WZ4002, HKI-272, CL-387785, and osimertinib, at inhibiting the activity of a wild-type EGFR. For example, the compound in combination with a second active agent, wherein said second active agent prevents EGFR dimer formation can be at least about 2-fold, 3-fold, 5-fold, 10-fold, 25-fold, 50-fold or about 100-fold less potent (e.g., as measured by $IC_{50}$) than gefitinib, erlotinib, lapatinib, WZ4002, HKI-272, CL-387785, and osimertinib, at inhibiting the activity of a wild-type EGFR. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib, gefitinib or erlotinib. In another embodiment, the ATP competitive EGFR inhibitor is osimertinib.

Potency of the inhibitor can be determined by $EC_{50}$ value. A compound with a lower $EC_{50}$ value, as determined under substantially similar conditions, is a more potent inhibitor relative to a compound with a higher $EC_{50}$ value. In some embodiments, the substantially similar conditions comprise determining an EGFR-dependent phosphorylation level, in vitro or in vivo (e.g., in 3T3 cells expressing a wild type EGFR, a mutant EGFR, or a fragment of any thereof).

Potency of the inhibitor can also be determined by $IC_{50}$ value. A compound with a lower $IC_{50}$ value, as determined under substantially similar conditions, is a more potent inhibitor relative to a compound with a higher $IC_{50}$ value. In some embodiments, the substantially similar conditions comprise determining an EGFR-dependent phosphorylation level, in vitro or in vivo (e.g., in 3T3 cells expressing a wild type EGFR, a mutant EGFR, or a fragment of any thereof).

An EGFR sensitizing mutation comprises without limitation L858R, G719S, G719C, G719A, L861Q, a deletion in exon 19 and/or an insertion in exon 20. A drug-resistant EGFR mutant can have without limitation a drug resistance mutation comprising T790M, T854A, L718Q, C797S, or D761Y.

The selectivity between wild-type EGFR and EGFR containing one or more mutations as described herein can also be measured using cellular proliferation assays where cell proliferation is dependent on kinase activity. For example, murine Ba/F3 cells transfected with a suitable version of wild-type EGER (such as VIII; containing a WT EGFR kinase domain), or Ba/F3 cells transfected with L858R/T790M, Del/T790M/L718Q, L858R/T790M/L718Q, L858R/T790M/C797S, Del/T790M/C797S, L858R/T790M/I941R, or Exon 19 deletion/T790M can be used. Proliferation assays are performed at a range of inhibitor concentrations (10 μM, 3 μM, 1.1 μM, 330 nM, 110 nM, 33 nM, 11 nM, 3 nM, 1 nM) and an $EC_{50}$ is calculated.

An alternative method to measure effects on EGER activity is to assay EGFR phosphorylation. Wild type or mutant (L858R/T790M, Del/T790M, Del/T790M/L718Q, L558R/T790M/C797S, Del/T790M/C797S, L858R/T790M/I941R, or L856R/T790M/L718Q) EGFR can be transfected into NIH-3 T3 cells (which do not normally express endogenous EGFR) and the ability of the inhibitor (using concentrations as above) to inhibit EGFR phosphorylation can be assayed. Cells are exposed to increasing concentrations of inhibitor for 6 hours and stimulated with EGF for 10 minutes. The effects on EGFR phosphorylation are assayed by Western Blotting using phospho-specific (Y106B) EGFR antibodies.

In another aspect, the present disclosure relates to a compound that binds to an allosteric site in EGFR, wherein the compound exhibits greater than 2-fold, 3-fold, 5-fold, 10-fold, 25-fold, 50-fold, 100-fold, or 1000-fold inhibition of EGFR containing one or more mutations as described herein (e.g., L858R/T790M, Del/I790M, Del/T790M/L715Q, L858R/T790M/C797S, Del/T790M/C797S, L858R/T790M/I941R, or L858R/T790M/L718Q) relative to a wild-type EGFR.

In other embodiments, the disclosure provides a compound that binds to an allosteric site in EGFR in combination with a second active agent, wherein said second active agent prevents EGFR dimer formation, wherein the compound in combination with the second active agent greater than 2-fold, 3-fold, 5-fold, 10-fold, 25-fold, 50-fold, 100-fold, or 1000-fold inhibition of EGER containing one or more mutations as described herein (e.g., L858R/T790M, Del/T790M, Del/T790M/L718Q, Del/T790M/C797S, L858R/T790M/C797S, L858R/T790M/I941R, or L858R/T790M/L718Q) relative to a wild-type EGER. In some embodiments, the second active agent that prevents EGFR dimer formation is an antibody. In further embodiments, the second active agent that prevents EGER dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib, gefitinib or erlotinib. In another embodiment, the ATP competitive EGFR inhibitor is osimertinib.

In still another aspect, the disclosure provides a method of inhibiting epidermal growth factor receptor (EGFR), the method comprising administering to a subject in need thereof an effective amount of a compound of disclosed herein, or a pharmaceutically acceptable salt thereof. In some embodiments, the method further comprises administering a second active agent, wherein said second active agent prevents EGFR dimer formation. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib, gefitinib or erlotinib. In another embodiment, the ATP competitive EGFR inhibitor is osimertinib.

In another aspect, provided herein is a method of treating or preventing a disease, the method comprising administering to a subject in need thereof an effective amount of a compound of disclosed herein, or a pharmaceutically acceptable salt thereof. In some embodiments, the disease is mediated by a kinase. In further embodiments, the kinase comprises a mutated cysteine residue. In further embodiments, the mutated cysteine residue is located in or near the position equivalent to Cys 797 in EGFR, including such positions in Jak3, Blk, Bmx, Btk, HER2 (ErbB2), HER4 (ErbB4), Itk, Tec, and Txk. In some embodiments, the method further comprises administering a second active agent, wherein said second active agent prevents dimer formation of the kinase. In some embodiments, the second active agent that prevents kinase dimer formation is an antibody. In further embodiments, the second active agent prevents EGFR dimer formation. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib, gefitinib or erlotinib. In another embodiment, the ATE competitive EGFR inhibitor is osimertinib.

In some embodiments, the disease is mediated by EGFR (e.g., EGFR plays a role in the initiation or development of the disease). In some embodiments, the disease is mediated by a Her-kinase. In further embodiments, the Her-kinase is HER1, HER2, or HER4.

In certain embodiments, the disease is resistant to a known EGFR inhibitor, including but not limited to, gefitinib, erlotinib, osimertinib, CO-1686, or WZ4002. In certain embodiments, a diagnostic test is performed to determine if the disease is associated with an activating mutation in EGFR. In certain embodiments, a diagnostic test is performed to determine if the disease is associated with an EGFR harboring an activating mutation and/or a drug resistance mutation. Activating mutations comprise without limitation L858R, G719S, G719C, G719A, L718Q. L861Q, a deletion in exon 19 and/or an insertion in exon 20. Drug resistant EGFR mutants can have without limitation a drug resistance mutation comprising T790M, T854A, L718Q, C797S, or D761Y. The diagnostic test can comprise sequencing, pyrosequencing, PCR, RT-PCR, or similar analysis techniques known to those of skill in the art that can detect nucleotide sequences.

In certain embodiments, the disease is cancer or a proliferation disease.

In further embodiments, the disease is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors. In further embodiments, the disease is lung cancer, breast cancer, glioma, squamous cell carcinoma, or prostate cancer. In still further embodiments, the disease is non-small cell lung cancer.

In certain embodiments, the disease is resistant to a known EGFR inhibitor, including but not limited to, gefitinib, erlotinib, osimertinib, CO-1686, or WZ4002. In certain embodiments, a diagnostic test is performed to determine if the disease is associated with an activating mutation in EGFR. In certain embodiments, a diagnostic test is performed to determine if the disease is associated with an EGFR harboring an activating mutation and/or a drug resistance mutation. Activating mutations comprise without limitation L858R, G719S, G719C, G719A, L718Q, L861Q, a deletion in exon 19 and/or an insertion in exon 20. Drug resistant EGFR mutants can have without limitation a drug resistance mutation comprising T790M, T854A, L718Q, C797S, or D761Y. The diagnostic test can comprise sequencing, pyrosequencing, PCR, RT-PCR, or similar analysis techniques known to those of skill in the art that can detect nucleotide sequences.

In yet another aspect, provided herein is a method of treating a kinase-mediated disorder comprising administering to a subject in need thereof an effective amount of a compound disclosed herein, or a pharmaceutically acceptable salt thereof. In some embodiments, the compound is an inhibitor of HER1, HER2, or HER4. In other embodiments, the subject is administered an additional therapeutic agent. In other embodiments, the compound and the additional therapeutic agent are administered simultaneously or sequentially.

In another aspect, the disclosure provides a method of treating a kinase mediated disorder, the method comprising administering to a subject in need thereof an effective amount of a compound of disclosed herein, or a pharmaceutically acceptable salt thereof, and a second active agent, wherein said second active agent prevents EGFR dimer formation. In some embodiments, the compound is an inhibitor of HER1, HER2, or HER4. In other embodiments, the subject is administered an additional therapeutic agent. In other embodiments, the compound, the second active agent that prevents EGFR dimer formation, and the additional therapeutic agent are administered simultaneously or sequentially. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib, gefitinib or erlotinib. In another embodiment, the ATP competitive EGFR inhibitor is osimertinib.

In other embodiments, the disease is cancer. In further embodiments, the cancer is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors. In further embodiments, the disease is lung cancer, breast cancer, glioma, squamous cell carcinoma, or prostate cancer. In still further embodiments, the disease is non-small cell lung cancer.

In another aspect, provided herein is a method of treating cancer, wherein the cancer cell comprises activated EGFR, comprising administering to a subject in need thereof an effective amount of a compound of disclosed herein, or a pharmaceutically acceptable salt thereof.

In another aspect, provided herein is a method of treating cancer, wherein the cancer cell comprises activated EGFR, comprising administering to a subject in need thereof an effective amount of a compound of disclosed herein, or a pharmaceutically acceptable salt thereof and a second active agent, wherein said second active agent prevents EGFR dimer formation. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib, gefitinib or erlotinib. In another embodiment, the ATP competitive EGFR inhibitor is osimertinib.

In certain embodiments, the EGFR activation is selected from mutation of EGFR, amplification of EGFR, expression of EGFR, and ligand mediated activation of EGFR.

In further embodiments, the mutation of EGFR is selected from G719S, G719C, G719A, L858R, L861Q, an exon 19 deletion mutation, and an exon 20 insertion mutation.

In still another aspect, provided herein is a method of treating cancer in a subject, wherein the subject is identified as being in need of EGFR inhibition for the treatment of cancer, comprising administering to the subject an effective amount of a compound disclosed herein, or a pharmaceutically acceptable salt thereof.

In certain embodiments, the subject identified as being in need of EGFR inhibition is resistant to a known EGFR inhibitor, including but not limited to, gefitinib, erlotinib, osimertinib, CO-1686, or WZ4002. In certain embodiments, a diagnostic test is performed to determine if the subject has an activating mutation in EGFR. In certain embodiments, a diagnostic test is performed to determine if the subject has an EGFR harboring an activating mutation and/or a drug resistance mutation. Activating mutations comprise without limitation L858R, G719S, G719C, G719A, L718Q, L861Q, a deletion in exon 19 and/or an insertion in exon 20. Drug resistant EGFR mutants can have without limitation a drug resistance mutation comprising T790M, T854A, L718Q, C797S, or D761Y. The diagnostic test can comprise sequencing, pyrosequencing, FOR, RT-PCR, or similar analysis techniques known to those of skill in the art that can detect nucleotide sequences.

In an aspect, provided herein is a method of preventing resistance to a known EGFR inhibitor (including but not limited to gefitinib, erlotinib, osimertinib, CO-1686, or WZ4002) in a subject, comprising administering to a subject in need thereof an effective amount of a compound disclosed herein, or a pharmaceutically acceptable salt thereof.

In another aspect, provided herein is a method of preventing resistance to a known EGFR inhibitor (including but not limited to gefitinib, erlotinib, osimertinib, CO-1686, or WZ4002) in a disease, comprising administering to a subject in need thereof an effective amount of a compound disclosed herein, or a pharmaceutically acceptable salt thereof, and a second active agent, wherein said second active agent prevents EGFR dimer formation. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab.

In an embodiment of the methods disclosed herein, the subject is a human.

In another aspect, the disclosure provides a compound disclosed herein, or a pharmaceutically acceptable salt thereof, for use in the manufacture of a medicament for treating or preventing a disease in which EGFR plays a role.

In an aspect, provided herein is a method of treating or preventing a condition selected from the group consisting of autoimmune diseases, inflammatory diseases, proliferative and hyperproliferative diseases, immunologically-mediated diseases, bone diseases, metabolic diseases, neurological and neurodegenerative diseases, cardiovascular diseases, hormone related diseases, allergies, asthma, and Alzheimer's disease. In other embodiments, said condition is selected from a proliferative disorder and a neurodegenerative disorder.

One aspect of this disclosure provides compounds that are useful for the treatment of diseases, disorders, and conditions characterized by excessive or abnormal cell proliferation. Such diseases include, but are not limited to, a proliferative or hyperproliferative disease, and a neurodegenerative disease. Examples of proliferative and hyperproliferative diseases include, without limitation, cancer. The term "cancer" includes, but is not limited to, the following cancers: breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, colorectal, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon, rectum, large intestine, rectum, brain and central nervous system, chronic myeloid leukemia (CML), and leukemia. The term "cancer" includes, but is not limited to, the following cancers: myeloma, lymphoma, or a cancer selected from gastric, renal, head and neck, oropharangeal, non-small cell lung cancer (NSCLC), endometrial, hepatocarcinoma, non-Hodgkin's lymphoma, and pulmonary.

The term "cancer" refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute non-lymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodysplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, nasopharyngeal and esophageal), genitourinary cancers (e.g., prostate, bladder, renal, uterine, ovarian, testicular), lung cancer (e.g., small-cell and non-small cell), breast cancer, pancreatic cancer, melanoma and other skin cancers, stomach cancer, brain tumors, tumors related to Gorlin syndrome (e.g., medulloblastoma, meningioma, etc.), and liver cancer. Additional exemplary forms of cancer which may be treated by the subject compounds include, but are not limited to, cancer of skeletal or smooth muscle, stomach cancer, cancer of the small intestine, rectum carcinoma, cancer of the salivary gland, endometrial cancer; adrenal cancer, anal cancer, rectal cancer, parathyroid cancer; and pituitary cancer.

Additional cancers that the compounds described herein may be useful in preventing, treating and studying are, for example, colon carcinoma, familial adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma; testis carcinoma, urinary carcinoma, melanoma; brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma. In one aspect of the disclosure, the present disclosure provides for the use of one or more compounds of the disclosure in the manufacture of a medicament for the treatment of cancer, including without limitation the various types of cancer disclosed herein.

In some embodiments, the compounds of this disclosure are useful for treating cancer, such as colorectal, thyroid, breast, and lung cancer; and myeloproliferative disorders, such as polycythemia vera, thrombocythemia, myeloid metaplasia with myelofibrosis, chronic myelogenous leukemia, chronic myelomonocytic leukemia; hypereosinophilic syndrome, juvenile myelomonocytic leukemia, and systemic mast cell disease. In some embodiments, the compounds of this disclosure are useful for treating hematopoietic disorders, in particular, acute-myelogenous leukemia (AML); chronic-myelogenous leukemia (CML), acute-promyelocytic leukemia, and acute lymphocytic leukemia (ALL).

The term "cancerous cell" as provided herein, includes a cell afflicted by any one of the above-identified conditions.

The disclosure further provides a method for the treatment or prevention of cell proliferative disorders such as hyperplasias; dysplasias and pre-cancerous lesions. Dysplasia is the earliest form of pre-cancerous lesion recognizable in a biopsy by a pathologist. The subject compounds may be administered for the purpose of preventing said hyperplasias, dysplasias, or pre-cancerous lesions from continuing to expand or from becoming cancerous. Examples of pre-cancerous lesions may occur in skin, esophageal tissue, breast and cervical intra-epithelial tissue.

Examples of neurodegenerative diseases include, without limitation, adrenoleukodystrophy (ALD), Alexander's disease, Alper's disease, Alzheimer's disease, amyotrophic lateral sclerosis (Lou Gehrig's Disease), ataxia telangiectasia, Batten disease (also known as Spielmeyer-Vogt-Sjogren-Batten disease), bovine spongiform encephalopathy (BSE), Canavan disease, Cockayne syndrome, corticobasal degeneration, Creutzfeldt-Jakob disease, familial fatal insomnia, frontotemporal lobar degeneration, Huntington's disease, HIV-associated dementia, Kennedy's disease, Krabbe's disease, Lewy body dementia, neuroborreliosis, Machado-Joseph disease (spinocerebellar ataxia type 3), multiple system atrophy, multiple sclerosis, narcolepsy, Niemann Pick disease, Parkinson's disease, Pelizaeus-Merzbacher disease, Pick's disease, primary lateral sclerosis, prion diseases, progressive supranuclear palsy, Refsum's disease, Sandhoff disease, Schilder's disease, subacute combined degeneration of spinal cord secondary to pernicious anaemia, Spielmeyer-Vogt-Sjogren-Batten disease (also known as Batten disease), spinocerebellar ataxia (multiple types with varying characteristics), spinal muscular atrophy, Steele-Richardson-Olszewski disease, tabes dorsalis, and toxic encephalopathy.

Another aspect of this disclosure provides a method for the treatment or lessening the severity of a disease selected from a proliferative or hyperproliferative disease, or a neurodegenerative disease, comprising administering an effective amount of a compound, or a pharmaceutically acceptable composition comprising a compound, to a subject in need thereof. In other embodiments, the method further comprises administering a second active agent, wherein said second active agent prevents EGFR dimer formation. In some embodiments, the second active agent that prevents EGFR dimer formation is an antibody. In further embodiments, the second active agent that prevents EGER dialer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib, gefitinib or erlotinib. In another embodiment, the ATP competitive EGER inhibitor is osimertinib.

The activity of the compounds and compositions of the present disclosure as EGFR kinase inhibitors may be assayed in vitro, in vivo, or in a cell line. In vitro assays include assays that determine inhibition of either the kinase activity or ATPase activity of the activated kinase. Alternate in vitro assays quantitate the ability of the inhibitor to bind to the protein kinase and may be measured either by radio labelling the inhibitor prior to binding, isolating the inhibitor/kinase complex and determining the amount of radio label bound, or by running a competition experiment where new inhibitors are incubated with the kinase bound to known radioligands. Detailed conditions for assaying a compound utilized in this disclosure as an inhibitor of various kinases are set forth in the Examples below.

In accordance with the foregoing, the present disclosure further provides a method for preventing or treating any of the diseases or disorders described above in a subject in need of such treatment, which method comprises administering to said subject a therapeutically effective amount of a compound of the disclosure, or a pharmaceutically acceptable salt thereof, and optionally a second active agent, wherein said second active agent prevents EGFR dimer formation. For any of the above uses, the required dosage will vary depending on the mode of administration, the particular condition to be treated and the effect desired.

In other embodiments, the compound and the second active agent that prevents EGFR dimer formation are administered simultaneously or sequentially.

Administration/Dosages/Formulations

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils); glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations (for example, sterile injectable aqueous or oleaginous suspensions) may be formulated according to the known art using suitable dispersing or wetting agents and suspending agents. The sterile injectable preparation may also be a sterile injectable solution; suspension, or emulsion in a nontoxic parenterally acceptable diluent or solvent, for example, as a solution in 1,3-butanediol. Among the acceptable vehicles and solvents that may be employed are water, Ringers solution, U.S.P., and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing the compounds of this disclosure with suitable non-irritating excipients or carriers such as cocoa butter, polyethylene glycol, or a suppository wax which are solid at ambient temperature but liquid at body temperature and therefore melt in the rectum or vaginal cavity and release the active compound.

Solid compositions of a similar type may also be employed as fillers in soft and hard filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets, and pills, the dosage forms may also comprise buffering agents.

Dosage forms for topical or transdermal administration of a compound of this disclosure include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this disclosure.

The ointments, pastes, creams and gels may contain, in addition to an active compound of this disclosure, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this disclosure, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present disclosure, disorders are treated or prevented in a subject, such as a human or other animal, by administering to the subject a therapeutically effective amount of a compound of the disclosure, in such amounts and for such time as is necessary to achieve the desired result. The term "therapeutically effective amount" of a compound of the disclosure, as used herein, means a sufficient amount of the compound so as to decrease the symptoms of a disorder in a subject. As is well understood in the medical arts a therapeutically effective amount of a compound of this disclosure will be at a reasonable benefit/risk ratio applicable to any medical treatment.

In general, compounds of the disclosure will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g., humans, is in the range from about 0.5 mg to about 100 mg, conveniently administered, e.g., in divided doses up to four times a day or in retard form. Suitable unit dosage forms for oral administration comprise from ca. 1 to 50 mg active ingredient.

In certain embodiments, a therapeutic amount or dose of the compounds of the present disclosure may range from about 0.1 mg/Kg to about 500 mg/Kg, alternatively from about 1 to about 50 mg/Kg. In general, treatment regimens according to the present disclosure comprise administration to a patient in need of such treatment from about 10 mg to about 1000 mg of the compound(s) of this disclosure per day in single or multiple doses.

Therapeutic amounts or doses will also vary depending on route of administration, as well as the possibility of co-usage with other agents.

Upon improvement of a subject's condition, a maintenance dose of a compound, composition or combination of this disclosure may be administered, if necessary. Subsequently, the dosage or frequency of administration, or both, may be reduced, as a function of the symptoms, to a level at which the improved condition is retained; when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present disclosure will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The disclosure also provides for a pharmaceutical combination, e.g., a kit, comprising a) a first agent which is a compound of the disclosure as disclosed herein, in free form or in pharmaceutically acceptable salt form, and b) at least one co-agent. The kit can comprise instructions for its administration.

In certain embodiments, these compositions optionally further comprise one or more additional therapeutic agents. For example, an agent that prevents EGFR dimer formation, chemotherapeutic agents or other antiproliferative agents may be combined with the compounds of this disclosure to treat proliferative diseases and cancer.

Some examples of materials which can serve as pharmaceutically acceptable carriers include, but are not limited to, ion exchangers; alumina; aluminum stearate; lecithin; serum proteins, such as human serum albumin; buffer substances such as phosphates, glycine, sorbic acid, or potassium sorbate; partial glyceride mixtures of saturated vegetable fatty acids; water; salts or electrolytes, such as protamine sulfate; disodium hydrogen phosphate; potassium hydrogen phosphate; sodium chloride; zinc salts; colloidal silica; magnesium trisilicate; polyvinyl pyrrolidone; polyacrylates; waxes; polyethylenepolyoxypropylene-block polymers; wool fat; sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols, such a propylene glycol or polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; and phosphate buffer solutions. Further, non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The protein kinase inhibitors or pharmaceutical salts thereof may be formulated into pharmaceutical compositions for administration to animals or humans. These pharmaceutical compositions, which comprise an amount of the protein inhibitor effective to treat or prevent a protein kinase-mediated condition and a pharmaceutically acceptable carrier, are other embodiments of the present disclosure.

Kits

In an aspect, provided herein is a kit comprising a compound capable of inhibiting kinase activity selected from one or more compounds of disclosed herein, or pharmaceutically acceptable salts thereof, and instructions for use in treating cancer. In certain embodiments, the kit further comprises components for performing a test to determine whether a subject has activating and/or drug resistance mutations in EGFR.

In another aspect, the disclosure provides a kit comprising a compound capable of inhibiting EGFR activity selected from a compound disclosed herein, or a pharmaceutically acceptable salt thereof.

In another aspect, the disclosure provides a kit comprising a compound capable of inhibiting kinase activity selected from one or more compounds of disclosed herein, or pharmaceutically acceptable salts thereof; a second active agent, wherein said second active agent prevents EGFR dimer formation; and instructions for use in treating cancer. In certain embodiments, the kit further comprises components for performing a test to determine whether a subject has activating and/or drug resistance mutations in EGFR. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab.

In another aspect, the disclosure provides a kit comprising a compound capable of inhibiting EGFR activity selected from a compound of disclosed herein, or a pharmaceutically acceptable salt thereof and a second active agent, wherein said second active agent prevents EGFR dimer formation. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib, gefitinib or erlotinib. In another embodiment, the ATP competitive EGFR inhibitor is osimertinib.

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

EXAMPLES

The application is further illustrated by the following examples, which should not be construed as further limiting. The practice of the present disclosure will employ, unless otherwise indicated, conventional techniques of organic synthesis, cell biology, cell culture, and molecular biology, which are within the skill of the art.

Abbreviations

- ACN acetonitrile
- dba dibenzylideneacetone
- DCM dichloromethane
- DIPEA diisopropylethylamine
- DMF dimethylformamide
- DMSO dimethylsulfoxide
- dppf 1,1'-bis(diphenylphosphino)ferrocene
- EtOAc ethyl acetate
- EtOH ethanol
- HATU 1-[dis(dimethylamino)methylene]-1H-1,2,3-triazolo[4,5-b]pyridinium 3-oxide hexafluorophosphate
- LDA lithium diisopropylamide
- MeOH methanol
- SPhos 2-dicyclohexylphosphino-2',6'-dimethoxybiphenyl
- TBTU 2-(1H-benzotriazole-1-yl)-1,1,3,3-tetramethylaminium tetrafluoroborate
- TEA triethylamine
- TFA trifluoroacetic acid
- THF tetrahydrofuran
- XPhos 2-dicyclohexylphosphino-2',4',6''-triisopropylbiphenyl Example 1: Preparation of 2-[1H-Benzimidazol-2-yl-(3-fluorophenyl)methyl]-6-[4-(1-methyl-4-piperidyl)phenyl]isoindolin-1-one (Compound 026)

Scheme 1.

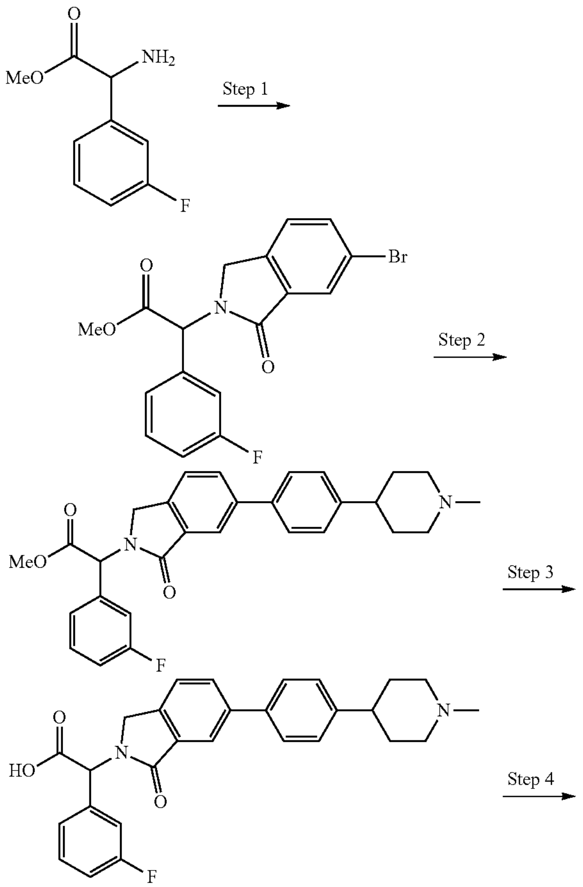

-continued

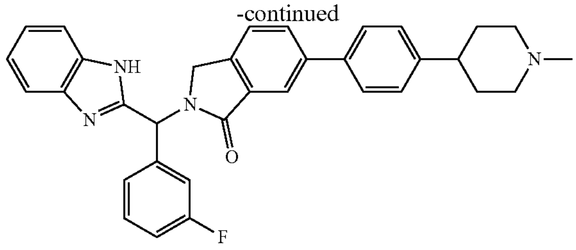

026

Step 1. Methyl 2-(6-bromo-1-oxo-isoindolin-2-yl)-2-(3-fluorophenyl)acetate

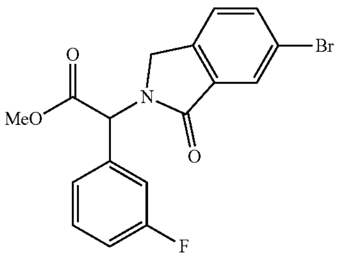 [SMILES: COC(=O)C(c1cccc(F)c1)N1Cc2ccc(Br)cc2C1=O]

To a solution of methyl 2-amino-2-(3-fluorophenyl)acetate (4.00 g, 21.8 mmol) in DMF (109 mL) was added DIPEA (10.6 mL, 61.0 mmol). The reaction mixture was stirred at room temperature for 5 min before methyl 5-bromo-2-(bromomethyl)benzoate (6.71 g, 21.8 mmol) was added. The reaction mixture was heated at 80 overnight. After cooling to room temperature, the reaction mixture was poured into water and extracted with ethyl acetate three times. The combined organic extracts were washed with water, brine, dried over sodium sulfate, filtered and concentrated under reduced pressure. The crude product was purified by silica gel column chromatography eluting with 0-20% ethyl acetate in hexane to give the title compound (4.75 g, 58%). MS m/z: 379.1 $[M+1]^+$.

Step 2. Methyl 2-(3-fluorophenyl)-2-[6-[4-(1-methyl-4-piperidyl)phenyl]-1-oxo-isoindolin-2-yl]acetate

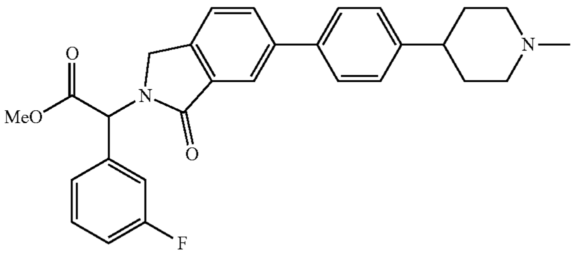 [SMILES: COC(=O)C(c1cccc(F)c1)N1Cc2ccc(-c3ccc(C4CCN(C)CC4)cc3)cc2C1=O]

A mixture of methyl 2-(6-bromo-1-oxo-isoindolin-2-yl)-2-(3-fluorophenyl)acetate (4.13 g, 10.9 mmol), 1-methyl-4-[4-(4,4,5,5-tetramethyl-1,3,2-dioxaborolan-2-yl)phenyl]piperidine (4.91 g, 16.3 mmol), 1.0 M sodium carbonate solution (21.8 mL, 21.8 mmol) and dioxane (109 mL) was degassed with nitrogen twice. [1,1' bis(diphenylphosphino)

ferrocene]dichloropalladium(II), complex with dichloromethane (0.534 g, 0.654 mmol) and XPhos (0.519 g, 1.09 mmol) were added and then the reaction was degassed with nitrogen once more. The reaction mixture was heated at 100° C. for 2 h. After cooling to room temperature, the reaction mixture was poured into water and extracted with dichloromethane twice. The combined organic extracts were washed with brine, dried over sodium sulfate, filtered and concentrated under reduced pressure. The crude product was purified by C18 column chromatography eluting with 0-80% ACN/water containing 10 mM ammonium acetate to give the title compound (4.17 g, 81%). MS m/z: 473.2 $[M+1]^+$.

Step 3. 2-(3-Fluorophenyl)-2-[6-[4-(1-methyl-4-piperidyl)phenyl]-1-oxo-isoindolin-2-yl]acetic acid

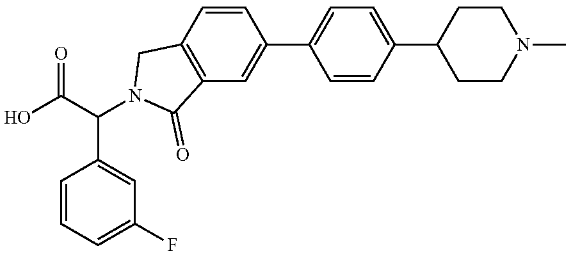 [SMILES: CN1CCC(c2ccc(-c3ccc4c(c3)C(=O)N(C(C(=O)O)c3cccc(F)c3)C4)cc2)CC1]

A mixture of methyl 2-(6-bromo-1-oxo-isoindolin-2-yl)-2-(3-fluorophenyl)acetate (4.13 g, 10.9 mmol), 1-methyl-4-[4-(4,4,5,5-tetramethyl-1,3,2-dioxaborolan-2-yl)phenyl]piperidine (4.91 g, 16.3 mmol), 1.0 M sodium carbonate solution (21.8 mL, 21.8 mmol) and dioxane (109 mL) was degassed with nitrogen twice. [1,1' bis(diphenylphosphino) ferrocene]dichloropalladium(II), complex with dichloromethane (0.534 g, 0.654 mmol) and XPhos (0.519 g, 1.09 mmol) were added and then the reaction was degassed with nitrogen once more. The reaction mixture was heated at 100° C. for 2 h. After cooling to room temperature, the reaction mixture was poured into water and extracted with dichloromethane twice. The combined organic extracts were washed with brine, dried over sodium sulfate, filtered and concentrated under reduced pressure. The crude product was purified by C18 column chromatography eluting with 0-80% ACN/water containing 10 mM ammonium acetate to give the title compound (4.17 g, 81%). MS m/z: 473.2 $[M+1]^+$.

Step 4: 2-[1H-Benzimidazol-2-yl-(3-fluorophenyl)methyl]-6-[4-(1-methyl-4-piperidyl)phenyl]isoindolin-1-one (026)

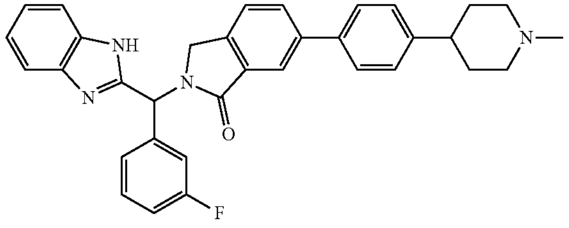 [SMILES: CN1CCC(c2ccc(-c3ccc4c(c3)C(=O)N(C(c3cccc(F)c3)c3nc5ccccc5[nH]3)C4)cc2)CC1]

To a solution of 2-(3-fluorophenyl)-2-[6-[4-(1-methyl-4-piperidyl)phenyl]-1-oxo-isoindolin-2-yl]acetic acid (0.100 g, 0.218 mmol), 1,2-diaminobenzene (0.053 g, 0.491 mmol)

and HATU (0.166 g, 0.436 mmol) in DMF (4.4 mL) was added DIPEA (0.150 mL, 0.872 mmol). After stirring at room temperature overnight, the reaction mixture was added sat. sodium chloride solution. The resulting solid was collected by filtration and washed with water to give the amide intermediate which was used in the next reaction without further purification. MS m/z: 549.3 [M+1]'.

To the above amide intermediate was added acetic acid (5 mL). After stirring at 80° C. overnight, the solvent was removed under reduced pressure. The crude product was purified by C18 column chromatography eluting with 0-100% ACN/water containing 10 mM ammonium acetate to give the title compound (18 mg, 17%). $^1$H NMR (400 MHz, DMSO-d6) δ: 8.22-8.26 (m, 1H), 7.89-7.97 (m, 2H), 7.63-7.71 (m, 3H), 7.52-7.63 (m, 2H), 7.44-7.51 (m, 1H), 7.36 (d, 2H), 7.16-7.26 (m, 5H), 6.96 (s, 1H), 4.92 (d, 1H), 4.31 (d, 1H), 2.89-2.98 (m, 2H), 2.53-2.66 (m, 1H), 2.24 (s, 3H), 2.01-2.10 (m, 2H), 1.66-1.81 (m, 4H); MS m/z: 531.3 $[M+1]^+$.

Compound 025 was prepared by a similar method to Example 1 from 2-(3-fluorophenyl)-2-[6-[4-(1-methyl-4-piperidyl)phenyl]-1-oxo-isoindolin-2-yl]acetic acid and pyridine-2,3-diamine:

-continued

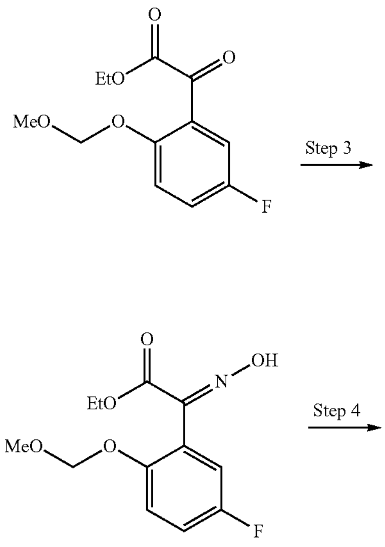

| No. | Structure/Name | m/z $[M + 1]^+$ | $^1$H NMR (DMSO-$d_6$) δ |
|---|---|---|---|
| 025 | 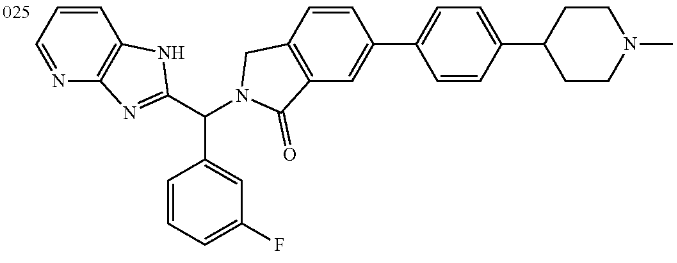 2-[(3-Fluorophenyl)-(3H-imidazo-[4,5-b]pyridin-2-yl)methyl]-6-[4-(1-methyl-4-piperidyl)phenyl]-isoindolin-1-one | 532.3 | 8.23-8.32 (m, 1H), 7.77-7.98 (m, 3H), 7.54-7.68 (m, 3H), 7.34-7.47 (m, 1H), 7.25-7.33 (m, 2H) 7.09-7.25 (m. 4H), 6.88 (s, 1H), 4.85 (d, 1H), 4.23 (d, 1H), 2.80-3.24 (m, 2H), 2.52-2.70 (m, 1H), 1.91-2.38 (m, 5H), 1.58-1.89 (m, 4H) |

Example 2: Preparation of 2-[(5-fluoro-2-hydroxyphenyl)-(1H-imidazo[4,5-c]pyridin-2-yl)methyl]-6-[4-(1-methyl-4-piperidyl)phenyl]isoindolin-1-one; hydrochloride (Compound 015)

Scheme 2.

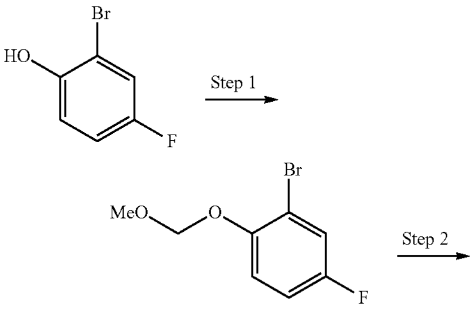

-continued

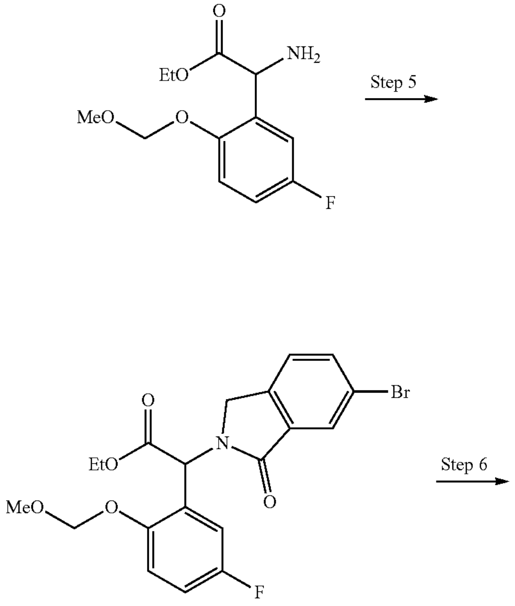

-continued

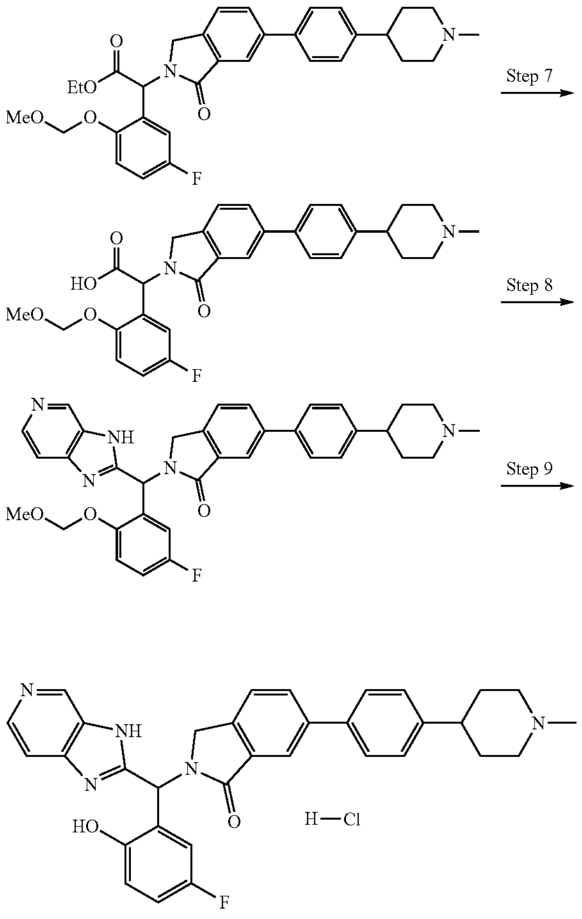

015

Step 1. 2-Bromo-4-fluoro-1-(methoxymethoxy)benzene

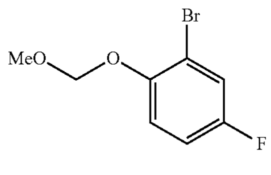 [SMILES: COCOc1ccc(F)cc1Br]

To a solution of 2-bromo-4-fluoro-phenol (100 g, 523 mmol) in THF (1 L) was added sodium hydride (23.0 g, 575 mmol, 60% in mineral oil) at 0° C. for 4 h, followed by addition of methoxymethyl chloride (44.9 mL, 601 mmol). After stirring at room temperature for 10 h, the reaction mixture was quenched by water and extracted with ethyl acetate three times. The combined organic extracts were washed with brine, dried over sodium sulfate, filtered and concentrated under reduced pressure. The crude product was purified by silica gel column chromatography eluting with 1-10% ethyl acetate in petroleum ether to give the title compound (80 g, 65%). $^1$H NMR (400 MHz, $CDCl_3$) δ: 7.30 (dd, 1H), 7.12 (dd, 1H), 6.97 (m, 1H), 5.07-5.24 (m, 2H), 3.46-3.62 (m, 3H).

Step 2. Ethyl 2-[5-fluoro-2-(methoxymethoxy)phenyl]-2-oxo-acetate

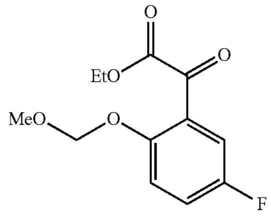 [SMILES: CCOC(=O)C(=O)c1cc(F)ccc1OCOC]

To a solution of 2-bromo-4-fluoro-1-(methoxymethoxy)benzene (80.0 g, 340 mmol) in THF (1 L) at −78° C. was added dropwise n-butyllithium (2.5 M in hexane, 142 mL, 357 mmol). After stirring at −78° C. for 1 h, the reaction mixture was cannulated to a pre-cooled (−78° C.) solution of diethyl oxalate (74.4 g, 510 mmol) in THF (500 mL). Upon completion of addition, the reaction mixture was allowed to warm to room temperature. The reaction mixture was quenched by water and extracted with ethyl acetate three times. The combined organic extracts were washed with brine, dried over sodium sulfate, filtered and concentrated under reduced pressure. The crude product was purified by silica gel column chromatography eluting with 10% ethyl acetate in petroleum ether to give the title compound (70 g, 80%). $^1$H NMR (400 MHz, $CDCl_3$) δ: 7.57 (dd, 1H), 7.26-7.31 (m, 1H), 7.18-7.23 (m, 1H), 5.15 (s, 2H), 4.37-4.43 (m, 2H), 3.46-3.50 (m, 3H), 1.35-1.41 (m, 3H).

Step 3. Ethyl-2-[5-fluoro-2-(methoxymethoxy)phenyl]-2-hydroxyimino-acetate

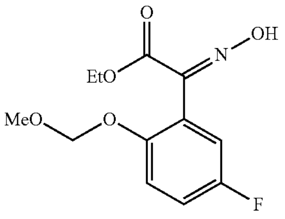 [SMILES: CCOC(=O)C(=NO)c1cc(F)ccc1OCOC]

To a solution of hydroxylamine hydrochloride (37.9 g, 546 mmol) in ethanol (500 mL) was added ethyl 2-[5-fluoro-2-(methoxymethoxy)phenyl]-2-oxo-acetate (70.0 g, 273 mmol) and sodium acetate (44.7 g, 132 mmol). After stirring at 80° C. for 2.5 h, the solvent was removed under reduced pressure and the resulting residue was partitioned between water and dichloromethane. The aqueous phase was extracted with additional dichloromethane. The combined organic extracts were washed with brine, dried over sodium sulfate, filtered and concentrated under reduced pressure to give the title compound (68 g, 92%). $^1$H NMR (400 MHz, $CDCl_3$) δ: 9.76 (br s, 1H), 7.17-7.23 (m, 1H), 7.07-7.14 (m, 2H), 5.10 (s, 2H), 4.31-4.39 (m, 2H), 3.44-3.48 (m, 3H), 1.35-1.40 (m, 3H).

Step 4. Ethyl 2-amino-2-[5-fluoro-2-(methoxymethoxy)phenyl]acetate

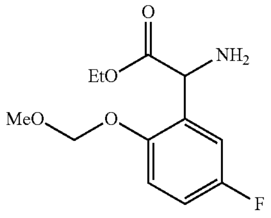 [SMILES: CCOC(=O)C(N)c1cc(F)ccc1OCOC]

To a solution of Raney Ni (1.46 g, 25.0 mmol) in EtOH/THF (650 mL, 4/1) was added ethyl-2-[5-fluoro-2-(methoxymethoxy)phenyl]-2-hydroxyimino-acetate (34.0 g, 125 mmol). The flask was evacuated and backfilled with hydrogen and the reaction mixture was allowed to stir at 70° C. under an atmosphere of hydrogen (50 psi) for 24 h. The reaction mixture was filtered through a pad of Celite which was washed several times with ethanol. The filtrate was concentrated under reduced pressure and purified by silica gel chromatography eluting with 33% ethyl acetate in petroleum ether to give the title compound (30.6 g, 48%). $^1$H NMR (400 MHz, DMSO-d6) δ: 7.23 (dd, 1H), 7.04-7.08 (m, 2H), 5.14-5.18 (m, 2H), 4.66 (s, 1H), 3.92-4.12 (m, 2H), 3.37 (s, 3H), 1.06-1.22 (m, 3H).

Step 5. Ethyl 2-(6-bromo-1-oxo-isoindolin-2-yl)-2-[5-fluoro-2-(methoxymethoxy)phenyl]acetate

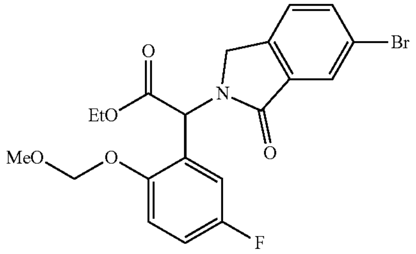

To a solution of ethyl 2-amino-2-[5-fluoro-2-(methoxymethoxy)phenyl]acetate (30.6 g, 118 mmol) in DMF (300 mL) was added DIPEA (58.4 mL, 354 mmol). The reaction mixture was stirred at room temperature for 5 min before methyl 5-bromo-2-(bromomethyl)benzoate (32.6 g, 106 mmol) was added. The reaction mixture was heated at 100° C. for 10 h. After cooling to room temperature, the reaction mixture was poured into water and extracted with ethyl acetate three times. The combined organic extracts were washed with water, brine, dried over sodium sulfate, filtered and concentrated under reduced pressure. The crude product was purified by silica gel column chromatography eluting with 33% ethyl acetate in petroleum ether to give the title compound (35 g, 66%). $^1$H NMR (400 MHz, $CDCl_3$) δ: 8.00 (d, 1H), 7.63 (dd, 1H), 7.22-7.36 (m, 1H), 7.10-7.19 (m, 1H), 6.94-7.08 (m, 2H), 6.36-6.54 (m, 1H), 5.06-5.21 (m, 2H), 4.72 (d, 1H), 4.13-4.34 (m, 2H), 3.94 (d, 1H), 3.31-3.45 (m, 3H), 1.24-1.28 (m, 3H); MS m/z: 453.8 $[M+1]^+$.

Step 6. Ethyl 2-[5-fluoro-2-(methoxymethoxy)phenyl]2-[6-[4-(1-methyl-4-piperidyl)phenyl]-1-oxo-isoindolin-2-yl]acetate

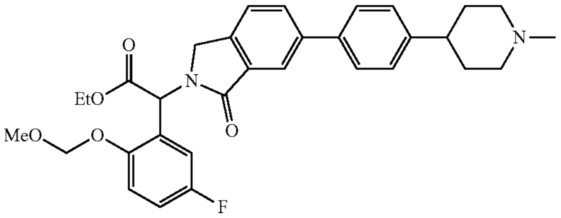 [SMILES: CCOC(=O)C(c1cc(F)ccc1OCOC)N1Cc2ccc(-c3ccc(C4CCN(C)CC4)cc3)cc2C1=O]

A mixture of ethyl 2-(6-bromo-1-oxo-isoindolin-2-yl)-2-[5-fluoro-2-(methoxymethoxy)-phenyl]acetate (5.34 g, 11.8 mmol), 1-methyl-4-[4-(4,4,5,5-tetramethyl-1,3,2-dioxaborolan-2-yl)phenyl]piperidine (4.60 g, 15.3 mmol), sodium carbonate (3.12 g, 29.5 mmol) and dioxane/water (125 mL, 4/1) was degassed under nitrogen twice. [1.1 bis(diphenylphosphino)-ferrocene]dichloropalladium(II), complex with dichloromethane (1.44 g, 1.77 mmol) was added and then the reaction was degassed under nitrogen once more. The reaction mixture was heated at 100° C. for 2 h. After cooling to room temperature, the reaction mixture was poured into water and extracted with ethyl acetate three times. The combined organic extracts were washed with brine, dried over sodium sulfate, filtered and concentrated under reduced pressure. The crude product was purified by silica gel column chromatography eluting with 0-15% methanol in dichloromethane to give the title compound (4.91 g, 76%). MS m/z: 547.3 $[M+1]^+$.

Step 7. 2-[5-Fluoro-2-(methoxymethoxy)phenyl]2-[6-[4-(1-methyl-4-piperidyl)phenyl]-1-oxo-isoindolin-2-yl]acetic acid

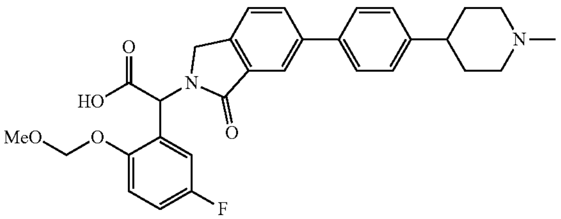 [SMILES: COCOc1ccc(F)cc1C(C(=O)O)N1Cc2ccc(-c3ccc(C4CCN(C)CC4)cc3)cc2C1=O]

To a solution of ethyl 2-[5-fluoro-2-(methoxymethoxy) phenyl]-2-[6-[4-(1-methyl-4-piperidyl)phenyl]-1-oxo-isoindolin-2-yl]acetate (4.91 g, 8.98 mmol) in THF/MeOH/water (90 mL, 1/1/1) was added lithium hydroxide monohydrate (1.50 g, 35.9 mmol). After stirring at room temperature for 2 h, the solvent was removed under reduced pressure and the resulting residue was neutralized with conc. HD. The crude product was purified by $C_{18}$ column chromatography eluting with 0-45% ACN/water containing 0.1% formic acid to give the title compound (4.01 g, 86%). MS m/z: 519.3 [M+1]'.

Step 8. 2-[[5-Fluoro-2-(methoxymethoxy)phenyl]-(1H-imidazo[4,5-c]pyridin-2-yl)methyl]-6-[4-(1-methyl-4-piperidyl)phenyl]isoindolin-1-one

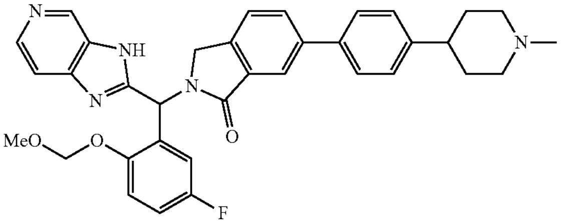 [SMILES: COCOc1ccc(F)cc1C(c1nc2ccncc2[nH]1)N1Cc2ccc(-c3ccc(C4CCN(C)CC4)cc3)cc2C1=O]

To a solution of 2-[5-fluoro-2-(methoxymethoxy)phenyl]-2-[6-[4-(1-methyl-4-piperidyl)-phenyl]-1-oxo-isoindolin-2-yl]acetic acid (0.200 g, 0.385 mmol), 3,4-diaminopyridine (0.084 g, 0.770 mmol) and HATU (0.219 g, 0.577 mmol) in DMF (4 mL) was added DIPEA (0,265 mL, 1.53 mmol). After stirring at room temperature for 2 h, the reaction mixture was diluted with ethyl acetate and washed twice with sat. sodium bicarbonate solution and brine. The organic layer was dried over sodium sulfate, filtered and concentrated under reduced pressure. The crude product was purified by C18 column chromatography eluting with 0-50% ACN/water containing 0.1% formic acid to give the amide intermediate (172 mg, 73%) as a white solid. MS m/z: 610.3 $[M+1]^+$.

To the above amide intermediate (0.172 g, 0.282 mmol) was added acetic acid (3.66 mL). After stirring 30 min at 80° C., the solvent was removed under reduced pressure. The crude product was purified by C18 column chromatography eluting with 0-40% ACN/water containing 0.1% formic acid. The product fractions were pooled and concentrated under reduced pressure to remove the organic solvent. The remaining aqueous solution was basified with sat. sodium bicarbonate solution and extracted twice with ethyl acetate. The combined organic extracts were washed with brine, dried over sodium sulfate, filtered and concentrated under reduced pressure to give the title compound (143 mg, 86%). MS m/z: 592.3 $[M+1]^+$.

Step 9. 2-[(5-Fluoro-2-hydroxy-phenyl)-(1H-imidazo[4,5-c]pyridin-2-yl)methyl]-6-[4-(1-methyl-4-piperidyl)phenyl]isoindolin-1-one;hydrochloride (Compound 015)

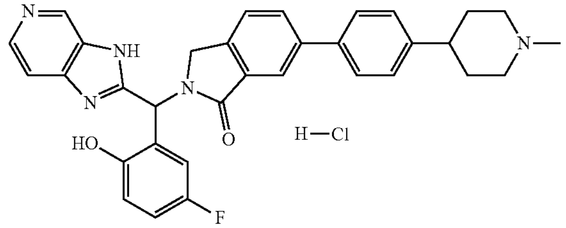 [SMILES: CN1CCC(c2ccc(-c3ccc4c(c3)C(=O)N(C(c3nc5ccncc5[nH]3)c3cc(F)ccc3O)C4)cc2)CC1 ; Cl]

To a solution of 2-[[5-fluoro-2-(methoxymethoxy)phenyl]-(1H-imidazo[4,5-c]pyridin-2-yl)methyl]-6-[4-(1-methyl-4-piperidyl)phenyl]isoindolin-1-one (0.143 g, 0.241 mmol) in dichloromethane (5.2 mL) was added HCl in dioxane (4 M, 0.6 mL, 2.40 mmol). After stirring 1 h at room temperature, the solvent was removed under reduced pressure. Diethyl ether was added to the residue and the resulting solid was isolated via filtration to give the title compound (131 mg, 93%). 1H NMR (400 MHz, DMSO-d6) δ: 10.52 (br s, 1H), 10.09 (s, 1H), 9.31 (br s, 1H), 8.50 (d, 1H), 8.00 (d, 1H), 7.84-7.89 (m, 2H), 7.62-7.68 (m, 3H), 7.30 (d, 2H), 7.01-7.09 (m, 2H), 6.91-6.96 (m, 1H), 6.85 (m, 1H), 4.74 (d, 1H), 4.16 (d, 1H), 3.38-3.50 (m, 2H), 2.92-3.08 (m, 2H), 2.74-2.85 (m, 1H), 2.66-2.73 (m, 3H), 1.84-2.08 (m, 4H); MS m/z: 548.3 $[M+1]^+$.

The following compounds were prepared by a similar method to Example 2 from ethyl 2-amino-2-[5-fluoro-2-(methoxymethoxy)phenyl]acetate and either methyl 5-bromo-2-(bromo-methyl)-benzoate or methyl 5-bromo-2-(bromomethyl)nicotinate, and the corresponding boronate and diamino aryl starting materials:

| No. | Structure/Name | m/z $[M + 1]^+$ | $^1H$ NMR (DMSO-$d_6$) δ | Starting materials |
|---|---|---|---|---|
| 024 | 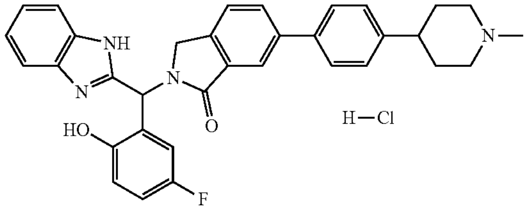 [SMILES: CN1CCC(c2ccc(-c3ccc4c(c3)C(=O)N(C(c3nc5ccccc5[nH]3)c3cc(F)ccc3O)C4)cc2)CC1 ; Cl] 2-[1H-Benzimidazol-2-yl-(5-fluoro-2-hydroxy-phenyl)methyl]-6-[4-(1-methyl-4-piperidyl)phenyl]isoindolin-1-one; hydrochloride | 547.3 | 10.53 (br s, 1H), 10.29 (br s, 1H), 7.94-8.00 (m, 2H), 7.68-7.77 (m, 5H), 7.48 (s, 2H), 7.38 (d, 2H), 7.09-7.22 (m, 3H), 6.95-7.09 (m, 1H), 4.79 (d, 1H), 4.27 (d, 1H), 3.48-3.54 (m, 2H), 3.02-3.15 (m, 2H), 2.84-2.92 (m, 1H), 2.78 (d, 3H), 1.92-2.15 (m, 4H) | 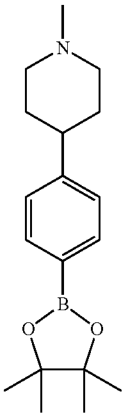 and 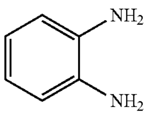 |

-continued

| No. | Structure/Name | m/z [M + 1]+ | $^1H$ NMR (DMSO-$d_6$) δ | Starting materials |
|---|---|---|---|---|
| 020 | 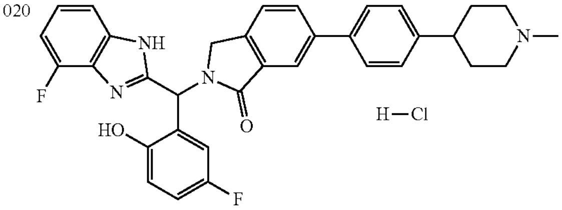 2-[(7-Fluoro-1H-benzimidazol-2-yl)-(5-fluoro-2-hydroxy-phenylmethyl]-6-(4-(1-methy-4-piperidyl)phenyl]isoindolin-1-one; hydrochloride | 565.3 | 10.27 (br s, 1H), 9.96 (br s, 1H), 7.83-7.88 (m, 2H), 7.61-7.68 (m, 3H), 7.26-7.33 (m, 3H), 7.11-7.19 (m, 1H), 6.94-7.06 (m, 3H), 6.88 (m, 1H), 6.75-6.82 (m, 1H), 4.72 (d, 1H), 4.13 (d, 1H), 3.38-3.50 (m, 2H), 2.93-3.07 (m, 2H), 2.68-2.84 (m, 4H), 1.84-2.06 (m, 4H) | 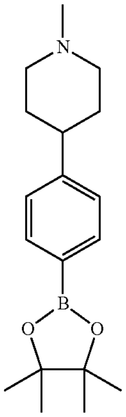 and 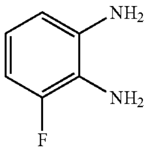 |
| 017 | 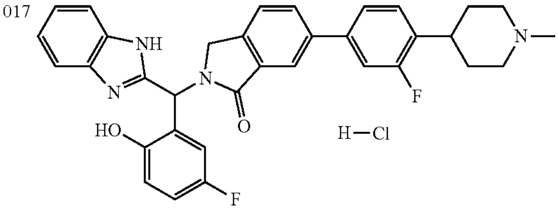 2-[1H-Benzimidazol-2-yl-(5-fluoro-2-hydroxy-phenyl)methyl]-6-[3-fluoro-4-(1-methyl-4-piperidyl)phenyl]isoindolin-1-one; hydrochloride | 565.3 | 10.42 (br s, 1H), 10.28 (br s, 1H), 8.04 (s, 1H), 8.00 (d, 1H), 7.60-7.77 (m. 5H), 7.35-7.54 (m, 3H), 7.08-7.22 (m, 3H), 6.97-7.06 (m, 1H), 4.80 (d, 1H), 4.27 (d, 1H), 3.55-3.59 (m, 2H), 3.04-3.20 (m, 3H), 2.69-2.84 (m, 3H), 1.93-2.16 (m, 4H) | 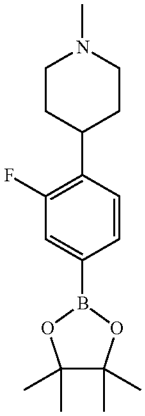 and 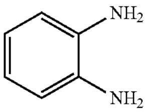 |

-continued

| No. | Structure/Name | m/z [M + 1]+ | $^1H$ NMR (DMSO-$d_6$) δ | Starting materials |
|---|---|---|---|---|
| 016 | 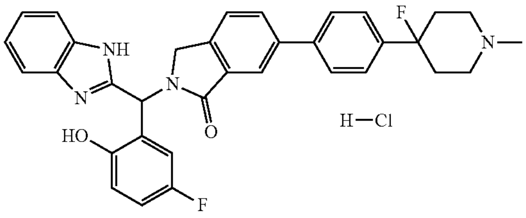 [SMILES: CN1CCC(F)(c2ccc(-c3ccc4c(c3)C(=O)N(C(c3nc5ccccc5[nH]3)c3cc(F)ccc3O)C4)cc2)CC1 ; Cl] 2-[1H-Benzimidazol-2-yl-(5-fluoro-2-hydroxy-phenyl)methyl]-6-[4-(4-fluoro-1-methyl-4-piperidyl)phenyl]isoindolin-1-one; hydrochloride | 565.3 | 11.10 (br s, 1H), 10.29 (br s, 1H), 7.96-8.05 (m, 2H), 7.82-7.88 (m, 2H), 7.64-7.80 (m, 3H), 7.51-7.58 (m, 2H), 7.43-7.50 (m, 2H), 7.09-7.23 (m, 3H), 6.99-7.05 (m, 1H), 4.80 (d, 1H), 4.28 (d, 1H), 3.10-3.36 (m, 4H), 2.81-2.90 (m, 3H), 2.54-2.73 (m, 2H), 2.21-2.30 (m, 2H) | 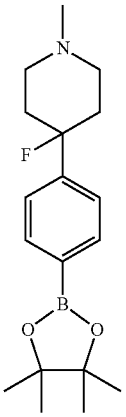 and 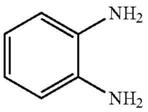 |
| 019 | 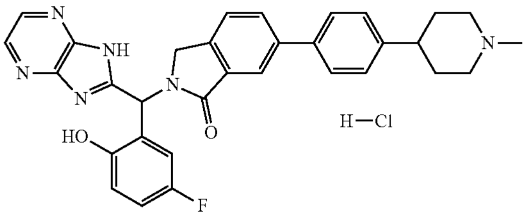 [SMILES: CN1CCC(c2ccc(-c3ccc4c(c3)C(=O)N(C(c3nc5nccnc5[nH]3)c3cc(F)ccc3O)C4)cc2)CC1 ; Cl] 2-[(5-Fluoro-2-hydroxy-phenyl)-(1H-imidazo[4,5-b]pyrazin-2-yl)methyl]-6-[4-(1-methyl-4-piperidyl)phenyl]isoindolin-1-one; hydrochloride | 549.3 | 10.10 (br s, 1H), 10.03 (br s, 1H), 8.40 (s, 2H), 7.91-7.97 (m, 2H), 7.69-7.76 (m, 3H), 7.37 (d, 2H), 7.07-7.15 (m, 1H), 7.05 (s, 1H), 6.93-6.99 (m, 1H), 6.87-6.92 (m, 1H), 4.84 (d, 1H), 4.19 (d, 1H), 3.50-3.54 (m, 2H), 3.04-3.15 (m, 2H), 2.77-2.93 (m, 4H), 1.92-2.11 (m, 4H) | 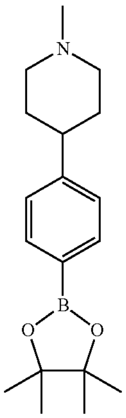 and 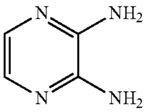 |

-continued

| No. | Structure/Name | m/z [M + 1]$^+$ | $^1$H NMR (DMSO-$d_6$) δ | Starting materials |
|---|---|---|---|---|
| 018 | 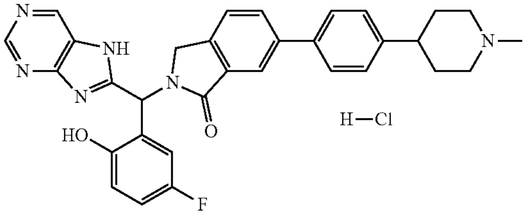 [SMILES: CN1CCC(c2ccc(-c3ccc4c(c3)C(=O)N(C(c3nc5ncncc5[nH]3)c3cc(F)ccc3O)C4)cc2)CC1 ; Cl]<br>2-[(5-Fluoro-2-hydroxy-phenyl)-(9H-purin-8-yl)methyl]-6-[4-(1-methyl-4-piperidyl)phenyl]isoindoiin-1-one; hydrochloride | 549.3 | 10.37 (br s, 1H), 10.00 (br s, 1H), 9.06 (s, 1H), 8.90 (s, 1H), 7.81-7.90 (m, 2H), 7.60-7.68 (m, 3H), 7.29 (d, 2H), 7.01-7.09 (m, 1H), 6.98 (s, 1H), 6.90 (m, 1H), 6.76-6.82 (m, 1H), 4.73 (d, 1H), 4.12 (d, 1H), 3.38-3.48 (m, 2H), 2.95-3.08 (m, 2H), 2.67-2.83 (m, 4H), 1.84-2.07 (m, 4H) | 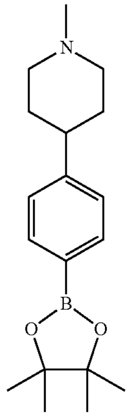<br>and<br>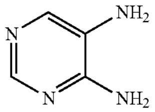 |
| 021 | 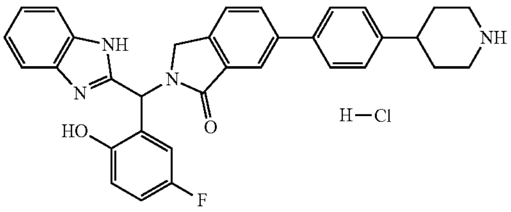 [SMILES: O=C1c2cc(-c3ccc(C4CCNCC4)cc3)ccc2CN1C(c1nc2ccccc2[nH]1)c1cc(F)ccc1O ; Cl]<br>2-[1H-Benzimidazol-2-yl-(5-fluoro-2-hydroxy-phenyl)methyl]-6-(4-piperazin-1-yiphenyl)isoindolin-1-one;hydrochioride | 534.2 | 10.43 (br s, 1H), 9.35 (br s, 2H), 7.92-7.96 (m, 2H), 7.66-7.78 (m, 5H), 7.51-7.59 (m, 2H), 7.04-7.23 (m, 6H), 4.77 (d, 1H), 4.29 (d, 1H), 3.42-3.52 (m, 4H), 3.15-3.28 (m, 4H) | 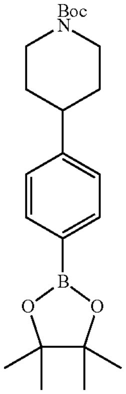<br>and<br>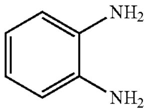 |

-continued

| No. | Structure/Name | m/z [M + 1]+ | $^1H$ NMR (DMSO-$d_6$) δ | Starting materials |
|---|---|---|---|---|
| 014 | 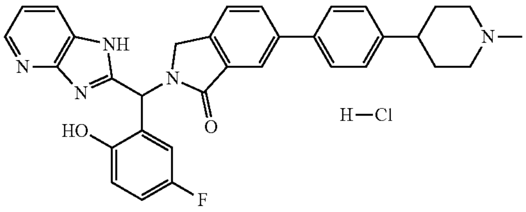 [SMILES: CN1CCC(c2ccc(-c3ccc4c(c3)C(=O)N(C(c3nc5ncccc5[nH]3)c3cc(F)ccc3O)C4)cc2)CC1 ; Cl] 2-[(5-Fluoro-2-hydroxy-phenyl)-(3H-imidazo[4,5-b]pyridin-2-yl)methyl]-6-[4-(1-methyl-4-piperidyl)phenyl]isoindolin-1-one; hydrochloride | 548.3 | 10.62 (br s, 1H), 10.06 (br s, 1H), 8.41 (d, 1H), 8.15 (d, 1H), 7.84-7.89 (m, 2H), 7.61-7.68 (m, 3H), 7.33-7.45 (m, 1H), 7.29 (d, 2H), 6.97-7.08 (m, 2H), 6.79-6.97 (m, 2H), 4.74 (d, 1H), 4.13 (d, 1H), 3.37-3.45 (m, 2H), 2.94-3.07 (m, 2H), 2.64-2.83 (m, 4H), 1.84-2.09 (m, 4H) | 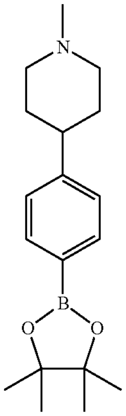 and 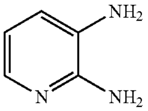 |
| 010 | 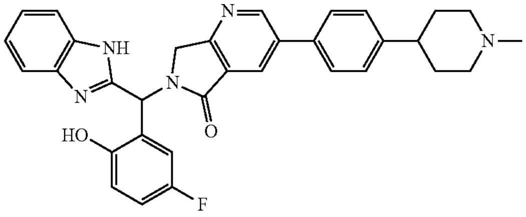 [SMILES: CN1CCC(c2ccc(-c3cnc4c(c3)C(=O)N(C(c3nc5ccccc5[nH]3)c3cc(F)ccc3O)C4)cc2)CC1] 6-[1H-Benzimidazol-2-yl-(5-fluoro-2-hydroxy-phenyl)methyl]-3-[4-(1-methyl-4-piperidyl)phenyl]-7H-pyrrolo[3,4-b]pyridin-5-one | 548.3 | 9.08 (d, 1H), 8.33 (d, 1H), 7.71-7.81 (m, 2H), 7.49-7.60 (m, 2H), 7.36-7.45 (m, 2H), 7.15-7.23 (m, 2H), 7.04-7.11 (m, 2H), 6.80-6.95 (m, 2H), 4.85 (d, 1H), 4.21 (d, 1H), 3.11-3.19 (m, 1H), 2.85-2.92 (m, 2H) 2.21 (s, 3H), 1.96-2.05 (m, 2H), 1.64-1.79 (m, 4H) | 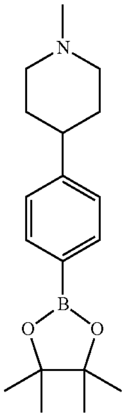 and 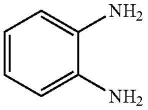 |

The following compounds were prepared by a similar method to Example 2 from ethyl 2-amino-2-(5-fluoro-2-(methoxymethoxy)phenyl)acetate and either methyl 5-bromo-2-(bromo-methyl)-benzoate or methyl 6-(bromomethyl)-3-chloro-2-fluorobenzoate, and the corresponding boronate and diamino aryl starting materials:

| No. | Structure/Name | m/z [M + 1]+ | $^1$H NMR (DMSO-$d_6$) δ | Starting materials |
|---|---|---|---|---|
| 079 | 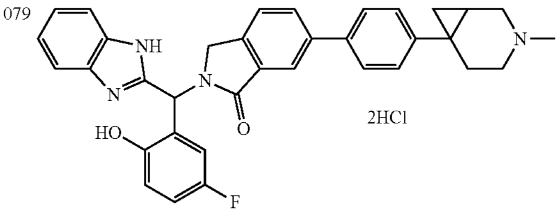 2-[1H-benzimidazol-2-yl-(5-fluoro-2-hydroxy-phenyl)methyl]-6-[4-(3-methyl-3-azabicyclo[4.1.0]heptan-6-yl)phenyl]isoindolin-1-one; dihydrochloride | 559.4 | 10.63 (br s, 1H), 10.37 (br s, 1H), 7.92-8.05 (m, 2H), 7.67-7.75 (m, 5H) 7.44-7.64 (m, 4H), 7.10-7.25 (m, 3H), 6.98-7.07 (m, 1H), 4.78 (d, 1H), 4.27 (d, 1H), 3.22-3.31 (m, 1H), 2.97-3.07 (m, 1H), 2.81-2.94 (m, 1H), 2.77-2.90 (m, 1H), 2.68 (d, 3H), 2.55-2.61 (m, 1H), 2.26-2.35 (m, 1H) 1.43-1.59 (m, 1H), 1.07-1.27 (m, 2H) | 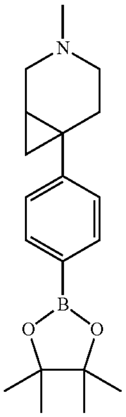 and 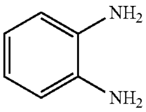 |
| 080 | 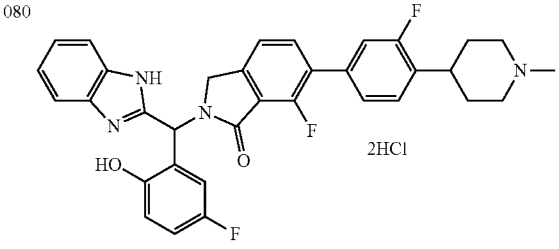 2-[1H-benzimidazol-2-yl-(5-fluoro-2-hydroxy-phenyl)methyl]-7-fluoro-6-[3-fluoro-4-(1-methyl-4-piperidyl)phenyl]isoindolin-1-one; dihydrochloride | 583.5 | $^1$H NMR (methanol-$d_6$) δ: 7.73-7.88 (m, 3H), 7.60-7.67 (m, 2H), 7.37-7.55 (m, 4H), 7.26-7.31 (m, 1H), 7.18-7.25 (m, 1H), 7.13-7.17 (m, 1H), 7.00-7.06 (m. 1H), 4.81-4.87 (m, 2H), 4.46 (d, 1H), 3.61-3.72 (m, 2H), 3.20-3.29 (m, 2H), 2.96 (s, 3H), 2.12-2.24 (m, 4H) | 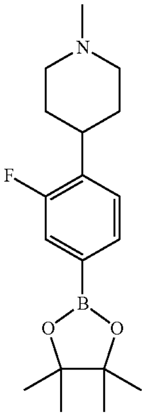 and 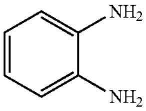 |

-continued

| No. | Structure/Name | m/z [M + 1]+ | $^1H$ NMR (DMSO-$d_6$) δ | Starting materials |
|---|---|---|---|---|
| 081 | 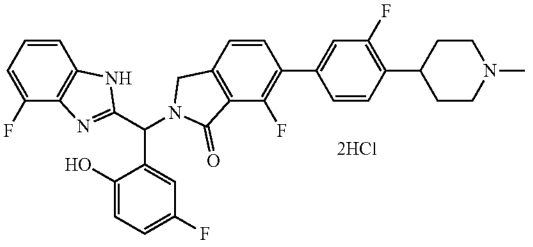 [SMILES: CN1CCC(c2ccc(-c3ccc4c(c3F)C(=O)N(C(c3nc5c(F)cccc5[nH]3)c3cc(F)ccc3O)C4)cc2F)CC1 ; "2HCl"] 7-fluoro-2-[(4-fluoro-1H-benzimidazol-2-yl)-(5-fluoro-2-hydroxy-phenyl)methyl]-6-[3-fluoro-4-(1-methyl-4-piperidyl)phenyl]isoindolin-1-one; dihydrochloride | 601.1 | 10.64 (br s, 1H), 10.29 (br s, 1H), 7.73-7.84 (m, 1H), 7.52 (d, 1H), 7.36-7.47 (m, 4H), 7.24-7.32 (m, 1H), 7.09-7.19 (m, 2H), 6.97-7.04 (m, 2H), 6.89-6.96 (m, 1H), 4.80 (d, 1H), 4.20 (d, 1H), 3.40-3.51 (m, 2H), 3.09-3.19 (m, 3H), 2.76 (d, 3H), 2.03-2.20 (m, 2H), 1.89-2.02 (m, 2H) | 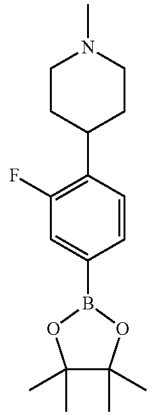 and 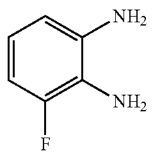 |

Example 3: Preparation of 2-[(R)-1H-benzimidazol-2-yl-(5-fluoro-2-hydroxy-phenyl)methyl]-6-[4-(1-methyl-4-piperidyl)phenyl]isoindolin-1-one and 2-[(S)-1H-benzimidazol-2-yl-(5-fluoro-2-hydroxy-phenyl)methyl]-6-[4-(1-methyl-4-piperidyl)phenyl]isoindolin-1-one (Compounds 022 and 023)

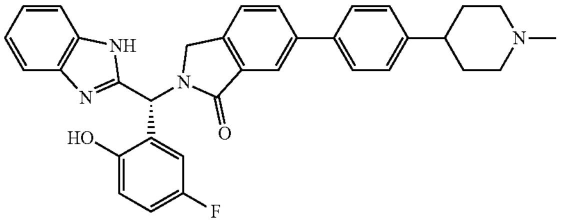

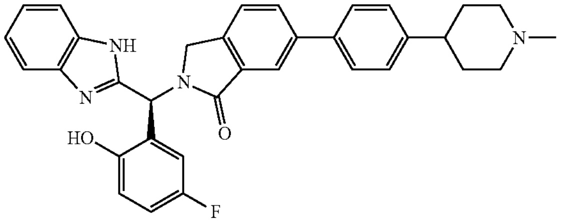

2-[1H-Benzimidazol-2-yl-(5-fluoro-2-hydroxy-phenyl)methyl]-6-[4-(1-methyl-4-piperidyl)-phenyl]isoindolin-1-one;hydrochloride (0.600 g, 1.02 mmol) was partitioned between sat. sodium bicarbonate solution and ethyl acetate. The aqueous phase was extracted with additional ethyl acetate three times. The combined organic extracts were washed with brine, dried over sodium sulfate, filtered and concentrated under reduced pressure. The crude product was purified by prep SFC with Chiralpak IA column eluting with 45% (0.3% TEA in MeOH)/55% 002 at 10 MPa to separate enantiomers. Absolute configuration of the chiral center for each isolated enantiomer is unknown. First eluting peak (022) (120 mg, 22% yield, 94:6 er); $[\alpha]_D^{20}$−34.2° (c=0.12, MeOH); $^1H$ NMR (400 MHz, methanol-$d_4$) δ: 8.02 (s, 1H), 7.84-7.90 (m, 1H), 7.52-7.63 (m, 5H), 7.36 (d, 2H), 7.20-7.27 (m, 2H), 7.14 (s, 1H), 6.97-7.05 (m, 1H), 6.86-6.91 (m, 1H), 6.73-6.79 (m, 1H), 4.76 (d, 1H), 4.26 (d, 1H), 2.99-3.08 (m, 2H), 2.56-2.66 (m, 1H), 2.35 (s, 3H), 2.21 (m, 2H), 1.77-1.94 (m, 4H); MS m/z: 547.2 $[M+1]^+$. Second eluting peak (023) (154 mg, 28% yield, 89:11 er); $[\alpha]_D^{20}$ +28.0° (c=0.1, MeOH); $^1H$ NMR (400 MHz, methanol-d4) δ: 8.02 (s, 1H), 7.84-7.89 (m, 1H), 7.52-7.64 (m, 5H), 7.36 (d, 2H), 7.20-7.27 (m, 2H), 7.14 (s, 1H), 6.96-7.06 (m, 1H), 6.86-6.92 (m, 1H), 6.74-6.79 (m, 1H), 4.76 (d, 1H), 4.27 (d, 1H), 3.00-3.09 (m, 2H), 2.56-2.68 (m, 1H), 2.36 (s, 3H), 2.23 (m, 2H), 1.78-1.94 (m, 4H); MS m/z: 547.3 $[M+1]^+$.

Example 4: Preparation of 6-[2-(6-amino-3-pyridyl)ethynyl]-2-[1H-benzimidazol-2-yl-(5-fluoro-2-hydroxy-phenyl)methyl]isoindolin-1-one (Compound 012)

Scheme 3.

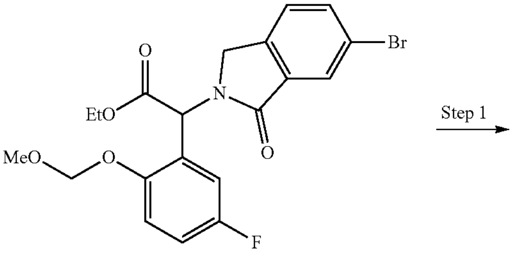

-continued

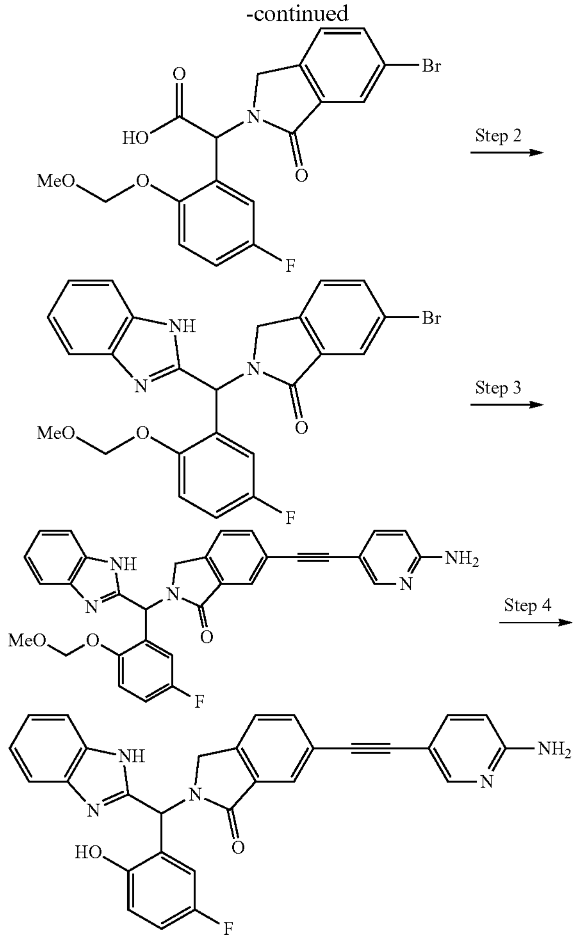

012

Step 1. 2-(6-Bromo-1-oxo-isoindolin-2-yl)-2-[5-fluoro-2-(methoxymethoxy)phenyl]acetic acid

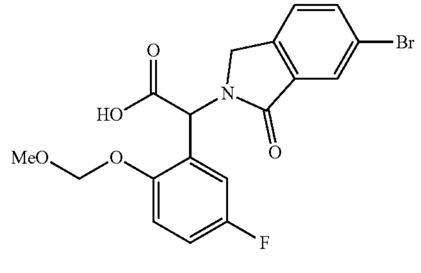 [SMILES: COCOc1ccc(F)cc1C(C(=O)O)N1Cc2ccc(Br)cc2C1=O]

To a solution of ethyl 2-(6-bromo-1-oxo-isoindolin-2-yl)-2-[5-fluoro-2-(methoxymethoxy)-phenyl]acetate (22.0 g, 48.6 mmol) in THF/MeOH/water (300 mL, 1/1/1) was added lithium hydroxide monohydrate (6.10 g, 145 mmol). After stirring at room temperature for 3 h, the solvent was removed under reduced pressure and the resulting residue was adjusted to pH 3 by HCl (1 M). The solid was collected by filtration and washed with water to give the title compound (18.2 g, 88%). $^1$H NMR (400 MHz, $CDCl_3$) δ: 820 (br s, 1H), 7.90 (d, 1H), 7.56 (dd, 1H), 7.19 (s, 1H), 6.94-7.15 (m, 3H), 6.35 (s, 1H), 5.03-5.10 (m, 2H), 4.63 (d, 1H), 3.89 (d, 1H), 3.27-3.36 (m, 3H).

Step 2. 2-[1H-Benzimidazol-2-yl-[5-fluoro-2-(methoxymethoxy)phenyl]methyl]-6-bromo-isoindolin-1-one

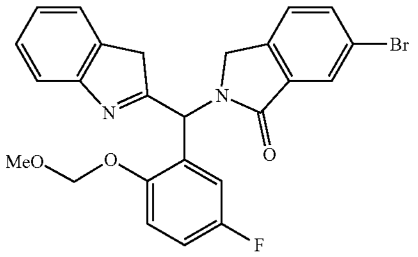 [SMILES: COCOc1ccc(F)cc1C(C1=Nc2ccccc2C1)N1Cc2ccc(Br)cc2C1=O]

To a solution of 2-(6-bromo-1-oxo-isoindolin-2-yl)-2-[5-fluoro-2-(methoxymethoxy)-phenyl]acetic acid (18.2 g, 42.9 mmol), 1,2-diaminobenzene (9.27 g, 85.8 mmol) and HATU (32.6 g, 85.8 mmol) in DMF (200 mL) was added DIPEA (30.3 mL, 42.4 mmol). After stirring at room temperature for 10 h, the reaction mixture was diluted with ethyl acetate and washed twice with sat. sodium bicarbonate solution and brine. The organic layer was dried over sodium sulfate, filtered and concentrated under reduced pressure. The crude product was purified by silica gel column chromatography eluting with $NH_4OH$/MeOH/DCM (1/5/100) to give the amide intermediate (15.5 g, 70%) as a yellow solid. $^1$H NMR (400 MHz, DMSO-d6) δ: 9.72 (s, 1H), 7.88 (d, 1H), 7.75-7.85 (m, 1H), 7.51-7.69 (m, 1H), 7.08-7.23 (m, 4H), 6.89-6.96 (m, 1H), 6.74 (dd, 1H), 6.53-6.60 (m, 1H), 6.31 (s, 1H), 5.11-5.27 (m, 2H), 4.85 (br s, 2H), 4.62 (d, 1H), 3.94-4.08 (m, 1H), 3.25 (s, 3H).

To the above amide intermediate (15.5 g, 30.1 mmol) was added acetic acid (150 mL). After stirring 30 min at 80° C., the solvent was removed under reduced pressure. The reaction mixture was neutralized with sat. sodium bicarbonate solution and extracted with ethyl acetate three times. The combined organic extracts were dried over sodium sulfate, filtered and concentrated under reduced pressure. The crude product was re-crystallized from ethyl acetate to give the title compound (12.5 g, 84%). MS m/z: 497.3 $[M+1]^+$.

Step 3. 6-[2-(6-Amino-3-pyridyl)ethynyl]-2-[1H-benzimidazol-2-yl-[5-fluoro-2-(methoxymethoxy)-phenyl]methyl]isoindolin-1-one

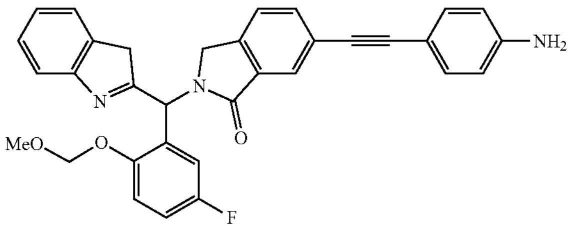 [SMILES: COCOc1ccc(F)cc1C(C1=Nc2ccccc2C1)N1Cc2ccc(C#Cc3ccc(N)cc3)cc2C1=O]

A mixture of 2-[1H-benzimidazol-2-yl-[5-fluoro-2-(methoxymethoxy)-phenyl]methyl]-6-bromo-isoindolin-1-one (0.150 g, 0.302 mmol), 5-ethynylpyridin-2-amine (0.071 g, 0.604 mmol), bis(triphenylphosphine)palladium (II) dichloride (0.012 g, 0.017 mmol), copper(I) iodide (0.006 g, 0.030 mmol), and TEA/DMF (3 mL, 1/1) was degassed under nitrogen twice. The reaction mixture was heated at 100° C. overnight. After cooling to room temperature, the reaction mixture was poured into water and extracted with ethyl acetate twice. The combined organic extracts were washed with brine, dried over sodium sulfate, filtered and concentrated under reduced pressure. The crude product was purified by C18 column chromatography eluting with 5-100% ACN/water containing 0.1% formic acid to give the title compound (66 g, 41%). MS m/z: 534.2 $[M+1]^+$.

Step 4. 6-[2-(6-Amino-3-pyridyl)ethynyl]-2-[1H-benzimidazol-2-yl-(5-fluoro-2-hydroxy-phenyl)methyl]isoindolin-1-one (Compound 012)

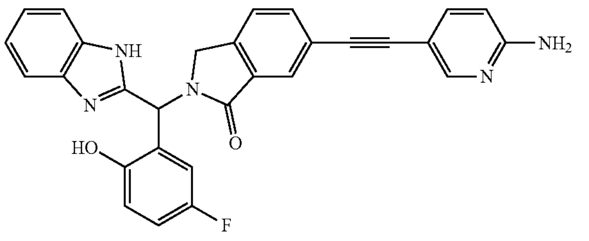 [SMILES: Nc1ccc(C#Cc2ccc3c(c2)C(=O)N(C(c2nc4ccccc4[nH]2)c2cc(F)ccc2O)C3)cn1]

To a solution of 6-[2-(6-amino-3-pyridyl)ethynyl]-2-[1H-benzimidazol-2-yl-[5-fluoro-2-(methoxymethoxy)phenyl]methyl]isoindolin-1-one (0.066 g, 0.123 mmol) in dichloromethane (2.6 mL) was added HCl in dioxane (4 M, 0.305 mL, 1.22 mmol). After stirring 2 h at room temperature, the solvent was removed under reduced pressure. The crude product was purified by reverse phase HPLC eluting with 0-100% ACN/water containing 10 mM ammonium acetate to give the title compound (6 mg, 10%). $^1H$ NMR (400 MHz, DMSO-$d_6$) δ: 8.16 (s, 1H), 7.68-7.78 (m, 2H), 7.59-7.64 (m, 1H), 7.44-7.56 (m, 3H), 7.11-7.19 (m, 2H), 7.00-7.09 (m, 1H), 6.77-6.97 (m, 3H), 6.43-6.48 (m, 3H), 4.70-4.86 (m, 1H), 4.20-4.36 (m, 1H); MS m/z: 490.2 $[M+1]^+$.

The following compounds were prepared by a similar method to Example 4 from 2-[1H-benzimidazol-2-yl-[5-fluoro-2-(methoxymethoxy)phenyl]methyl]-6-bromo-isoindolin-1-one and the corresponding acetylene starting materials:

| No. | Structure/Name | m/z $[M + 1]^+$ | $^1H$ NMR (DMSO-$d_6$) δ |
|---|---|---|---|
| 013 | 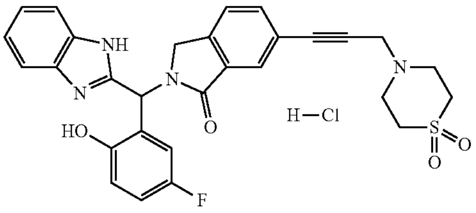 [SMILES: O=C1c2cc(C#CCN3CCS(=O)(=O)CC3)ccc2CN1C(c1nc2ccccc2[nH]1)c1cc(F)ccc1O ; Cl] 2-[1H-benzimidazol-2-yl-(5-fluoro-2-hydroxy-phenyl)methyl]-6-[3-(1,1-dioxo-1,4-thiazinan-4-yl)prop-1-ynyl]isoindolin-1-one; hydrochloride | 545.2 | 10.39 (br s, 1H), 7.83-7.89 (m, 1H), 7.67-7.82 (m, 4H), 7.50-7.58 (m, 2H), 7.17-7.26 (m, 2H), 7.13 (s, 1H), 6.99-7.08 (m, 1H), 4.78 (d, 1H), 4.29 (d, 1H), 4.09 (s, 2H), 3.30-3.53 (m, 8H) |
| 011 | 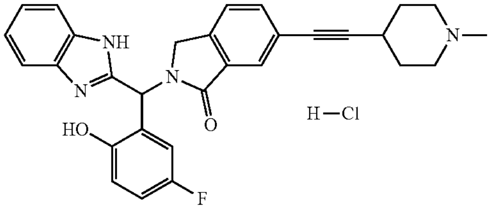 [SMILES: CN1CCC(C#Cc2ccc3c(c2)C(=O)N(C(c2nc4ccccc4[nH]2)c2cc(F)ccc2O)C3)CC1 ; Cl] 2-[1H-benzimidazol-2-yl-(5-fluoro-2-hydroxy-phenyl)methyl]-6-[2-(1-methyl-4-piperidyl)-ethynyl]isoindolin-1-one; hydrochloride | 495.2 | 7.49-7.64 (m, 5H), 7.14-7.19 (m, 2H). 7.02-7.08 (m, 1H), 6.97 (s, 1H), 6.87-6.92 (m, 1H), 6.75-6.81 (m, 1H), 4.78 (d, 1H), 4.20 (d, 1H), 2.58-2.66 (m, 3H), 2.16 (s, 3H), 2.02-2.13 (m, 2H), 1.83-1.90 (m, 2H), 1.59-1.69 (m, 2H) |

Example 5: Preparation of 2-[1H-benzimidazol-2-yl-(5-fluoro-2-hydroxy-phenyl)methyl]-7-fluoro-6-[4-(1-methyl-4-piperidyl)phenyl]isoindolin-1-one; hydrochloride (Compound 032)

Scheme 4.

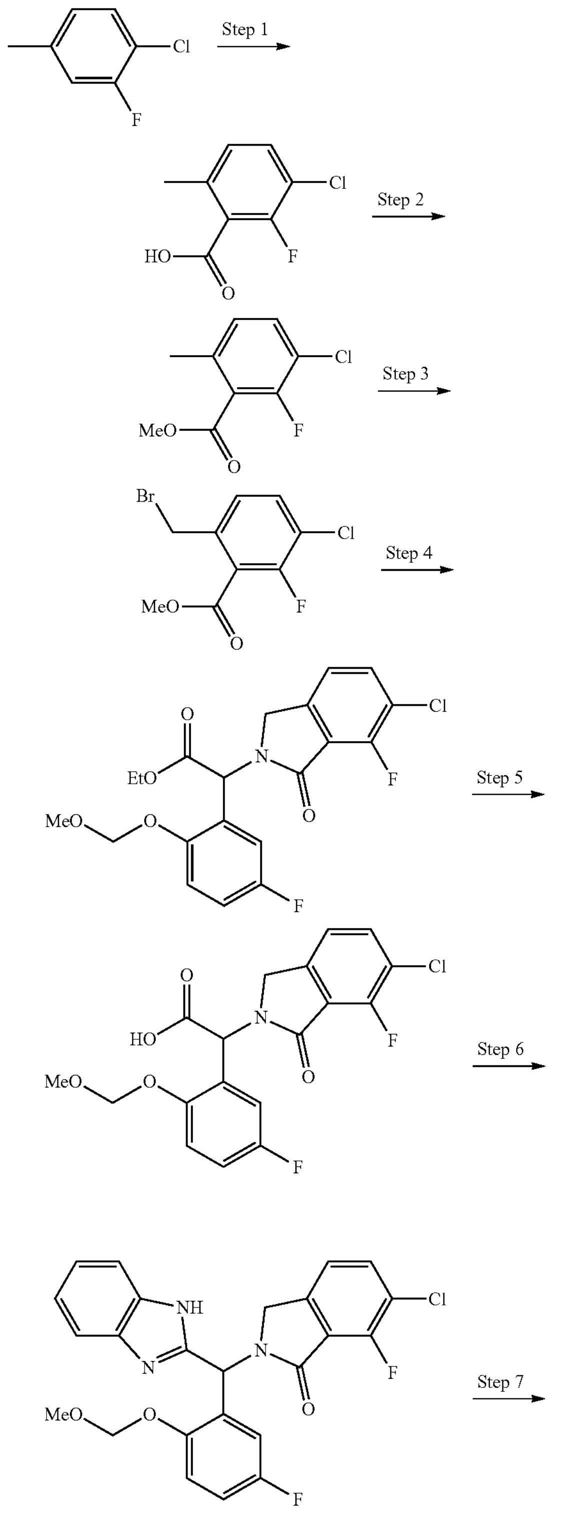

-continued

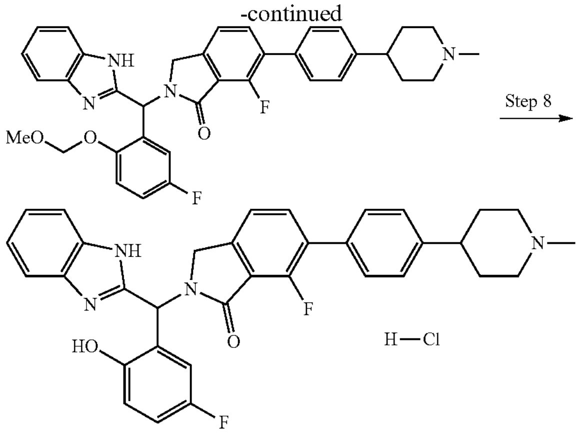

032

Step 1: 3-Chloro-2-fluoro-6-methyl-benzoic acid

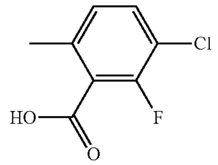

To a solution of 1-chloro-2-fluoro-4-methyl-benzene (10.0 g, 69.1 mmol) in THE (100 mL) at −70° C. was added dropwise LDA (2 M in THF, 36.2 mL, 72.5 mmol). After stirring at −70° C. for 0.5 h, CO2 (9.10 g) was added to the reaction mixture and stirred at the same temperature for 1 h. After warming to room temperature, the solvent was removed under reduced pressure. Water was added to the residue and the mixture was washed with ethyl acetate twice. The aqueous phase was adjusted to pH 1 by NCI (1 M) and extracted with ethyl acetate three times. The combined organic extracts were washed with brine, dried over sodium sulfate, filtered and concentrated under reduced pressure to give the title compound (3.5 g, 27%). 1H NMR (400 MHz, DMSO-d6) δ: 13.38 (br s, 1H), 7.51-7.58 (m, 1H), 7.16 (d, 1H), 2.33 (s, 3H).

Step 2: Methyl 3-chloro-2-fluoro-6-methyl-benzoate

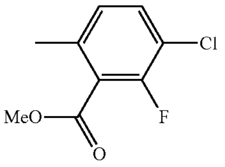

To a solution of 3-chloro-2-fluoro-6-methyl-benzoic add (3.50 g, 18.5 mmol) in dichloromethane (50 mL) was added oxalyl chloride (4.69 g, 37.0 mmol) at 0° C. After stirring at the same temperature for 0.5 h, the solvent was removed under reduced pressure. The residue was dissolved in methanol (20 mL) and was added triethylamine (7.47 g, 74.0 mmol). After stirring at room temperature for 1 h, the solvent was removed under reduced pressure and the crude product was purified by silica gel column chromatography eluting with 3% ethyl acetate in petroleum ether to give the title compound (1.9 g, 51%). $^1H$ NMR (400 MHz, DMSO-d5) δ: 7.60-7.66 (m, 1H), 7.20 (d, 1H), 3.90 (s, 3H), 2.32 (s, 3H).

Step 3: Methyl 6-(bromomethyl)-3-chloro-2-fluorobenzoate

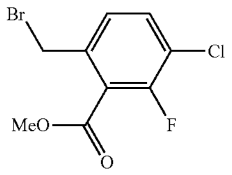 [SMILES: COC(=O)c1c(CBr)ccc(Cl)c1F]

To a solution of methyl 3-chloro-2-fluoro-6-methyl-benzoate (1.90 g, 9.37 mmol) in carbon tetrachloride (20 mL) was added N-bromosuccinimide (1.66 g, 9.37 mmol) and benzoyl peroxide (0.452 g, 1.87 mmol). After stirring at 80° C. for 12 h, the solvent was removed under reduced pressure. The crude product was purified by silica gel column chromatography eluting with 1% ethyl acetate in petroleum ether to give the title compound (0.9 g, 34%). $^1H$ NMR (400 MHz, $CDCl_3$) δ: 7.45-7.52 (m, 1H), 7.19 (d, 1H), 4.62 (s, 2H), 4.02 (s, 3H).

Step 4: Ethyl 2-(6-chloro-7-fluoro-1-oxo-isoindolin-2-yl)-2-[5-fluoro-2-(methoxymethoxy)-phenyl]acetate

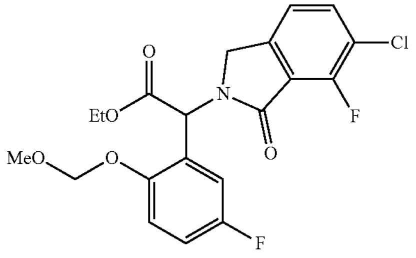 [SMILES: CCOC(=O)C(c1cc(F)ccc1OCOC)N1Cc2ccc(Cl)c(F)c2C1=O]

To a solution of ethyl 2-amino-2-[5-fluoro-2-(methoxymethoxy)phenyl]acetate (1.06 g, 4.14 mmol) in DMF (15 mL) was added DIPEA (1.23 g, 9.57 mmol). The reaction mixture was stirred at room temperature for 5 min before methyl 6-(bromomethyl)-3-chloro-2-fluorobenzoate (0.900 g, 3.19 mmol) was added. The reaction mixture was heated at 100° C. for 1 h. After cooling to room temperature, the reaction mixture was poured into water and extracted with ethyl acetate three times. The combined organic extracts were washed with water, brine, dried over sodium sulfate, filtered and concentrated under reduced pressure. The crude product was purified by silica gel column chromatography eluting with 33% ethyl acetate in petroleum ether to give the title compound (800 mg, 59%). MS m/z: 426.1 [M+1]$^+$.

Step 5: 2-(6-Chloro-7-fluoro-1-oxo-isoindolin-2-yl)-2-[5-fluoro-2-(methoxymethoxy)phenyl]acetic add

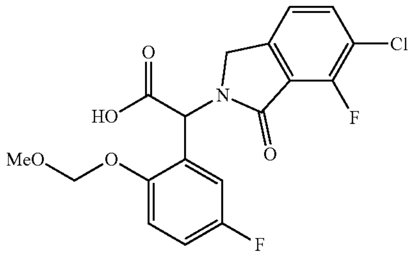 [SMILES: COCOc1ccc(F)cc1C(C(=O)O)N1Cc2ccc(Cl)c(F)c2C1=O]

To a solution of ethyl 2-(6-chloro-7-fluoro-1-oxo-isoindolin-2-yl)-2-[5-fluoro-2-(methoxy-methoxy)phenyl]acetate (0.800 g, 1.87 mmol) in THF/MeOH/water (15 mL, 1/1/1) was added lithium hydroxide monohydrate (0.314 g, 7.48 mmol). After stirring at room temperature for 1 h, the solvent was removed under reduced pressure and the resulting residue was adjusted to pH 3 by HCl (1 M). The resulting solid was collected by filtration and washed with water to give the title compound (750 mg, quant.). MS m/z: 398.0 [M+1]$^+$.

Step 6: 2-[1H-Benzimidazol-2-yl-[5-fluoro-2-(methoxymethoxy)phenyl]methyl]-6-chloro-7-fluoro-isoindolin-1-one

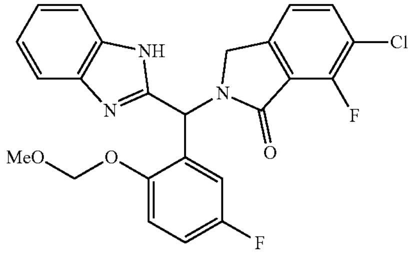 [SMILES: COCOc1ccc(F)cc1C(c1nc2ccccc2[nH]1)N1Cc2ccc(Cl)c(F)c2C1=O]

To a solution of 2-(6-chloro-7-fluoro-1-oxo-isoindolin-2-yl)-2-[5-fluoro-2-(methoxy-methoxy)phenyl]acetic acid (0.750 g, 1.88 mmol), 1,2-diaminobenzene (0.213 g, 1.97 mmol) and HATU (1.07 g, 2.82 mmol) in DMF (10 mL) was added DIPEA (0.728 g, 5.64 mmol). After stirring at room temperature overnight, the reaction mixture was partitioned between water and ethyl acetate. The aqueous phase was extracted with additional ethyl acetate three times. The combined organic extracts were washed with brine, dried over sodium sulfate, filtered and concentrated under reduced pressure to give the amide intermediate (800 mg, 87%) which was used in the next reaction without further purification. MS m/z: 488.3 [M+1]$^+$.

To the above amide intermediate was added acetic acid (15 mL). After stirring at 80 for 0.5 h, the solvent was removed under reduced pressure. The reaction mixture was neutralized with sat. sodium bicarbonate solution and extracted with ethyl acetate three times. The combined organic extracts were dried over sodium sulfate, filtered and concentrated under reduced pressure. The crude product was re-crystallized from ethyl acetate to give the title compound (550 mg, 72%). MS m/z: 470.0 [M+1]$^+$.

Step 7: 2-[1H-Benzimidazol-2-yl-[5-fluoro-2-(methoxymethoxy)phenyl]methyl]-7-fluoro-6-[4-(1-methyl-4-piperidyl)phenyl]isoindolin-1-one

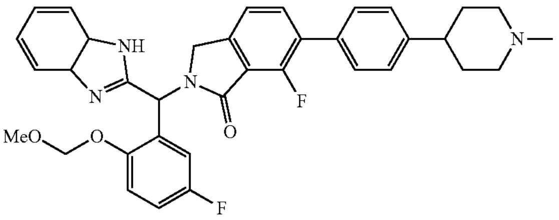 [SMILES: COCOc1ccc(F)cc1C(C1=NC2C=CC=CC2N1)N1Cc2ccc(-c3ccc(C4CCN(C)CC4)cc3)c(F)c2C1=O]

A mixture of 2-[1H-benzimidazol-2-yl-[5-fluoro-2-(methoxymethoxy)phenyl]methyl]-6-chloro-7-fluoro-isoindolin-1-one (0.550 g, 1.17 mmol), 1-methyl-4-[4-(4,4,5,5-tetramethyl-1,3,2-dioxaborolan-2-yl)phenyl]piperidine (0.385 g, 1.28 mmol), sodium carbonate (0.487 g, 3.51 mmol), SPhos (0.192 g, 0.468 mmol), Pd2(dba)3 (0.321 g, 0.351 mmol) and dioxane (10 mL) was degassed with nitrogen twice. The reaction mixture was heated at 105° C. for 4 h. After cooling to room temperature, the solvent was removed under reduced pressure. The crude product was purified by silica gel column chromatography eluting with 10% methanol in dichloromethane to give the title compound (120 mg, 17%). MS m/z; 609.3 $[M+1]^+$.

Step 8: 2-[1H-Benzimidazol-2-yl-[5-fluoro-2-hydroxy-phenyl)methyl]-7-fluoro-6-[4-(1-methyl-4-piperidyl)phenyl]isoindolin-1-one;hydrochloride (Compound 032)

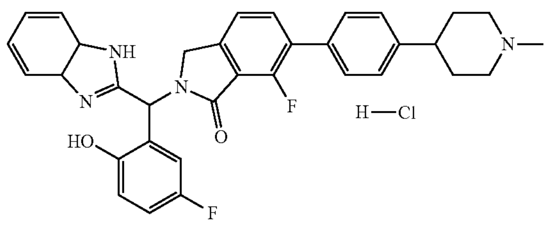

To a solution of 2-[1H-benzimidazol-2-yl-[5-fluoro-2-(methoxymethoxy)phenyl]methyl]-7-fluoro-6-[4-(1-methyl-4-piperidyl)phenyl]isoindolin-1-one (0.120 g, 0.197 mmol) in dichloromethane (5 mL) was added HCl in dioxane (4 M, 0.985 mL, 3.94 mmol). After stirring 1 h at room temperature, the solvent was removed under reduced pressure. Diethyl ether was added to the residue and the resulting solid was isolated via filtration to give the title compound (112 mg, 94%). 1H NMR (400 MHz, DMSO-d6) δ: 10.51 (br s, 1H), 10.29 (br s, 1H), 7.74-7.82 (m, 1H), 7.65-7.73 (m, 2H), 7.49-7.59 (m, 3H), 7.35-7.49 (m, 4H), 6.97-7.22 (m, 4H), 4.80 (d, 1H), 4.25 (d, 1H), 3.48-3.51 (m, 2H), 3.03-3.13 (m, 2H), 2.85-2.93 (m, 1H), 2.73-2.81 (m, 3H), 1.91-2.15 (m, 4H); MS m/z: 565.3 $[M+1]^+$.

Example 6: Preparation of 2-[1H-benzimidazol-2-yl-(5-fluoro-2-methoxy-phenyl)methyl]-7-fluoro-6-[4-(1-methyl-4-piperidyl)phenyl]indazole (035) and 2-[1H-benzimidazol-2-yl-[7-fluoro-6-[4-(1-methyl-4-piperidyl)phenyl]indazol-2-yl]methyl]-4-fluorophenol;hydrochloride (034)

Scheme 5.

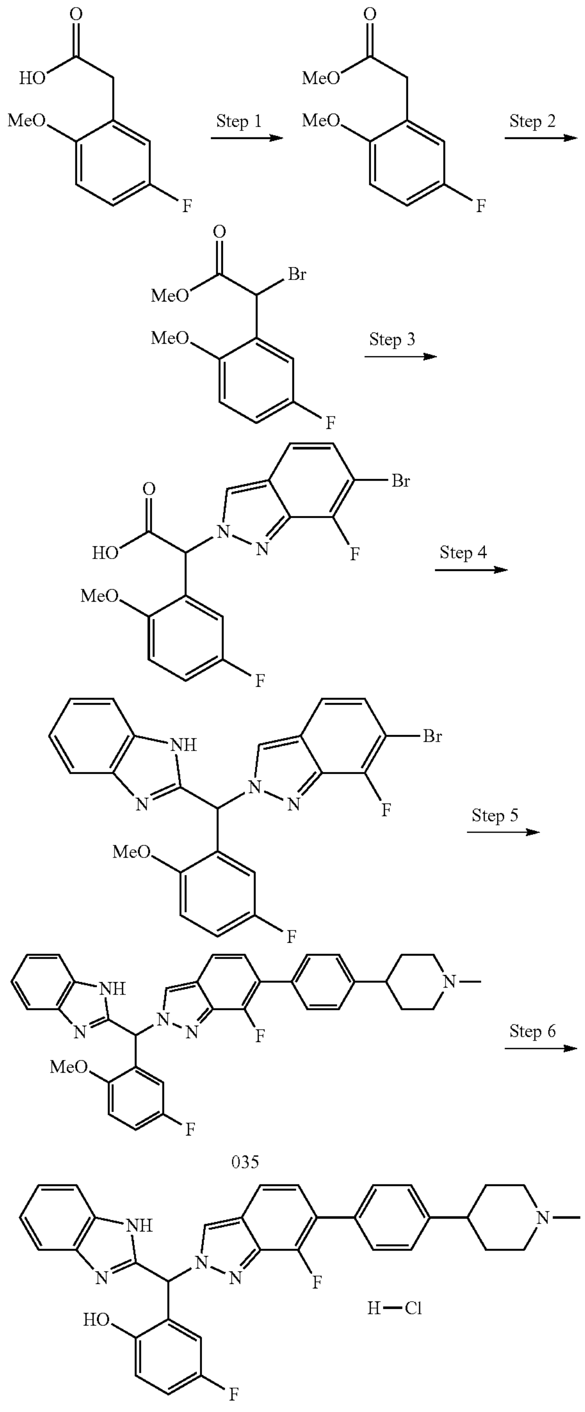

035

034

Step 1. Methyl 2-(5-fluoro-2-methoxy-phenyl)acetate

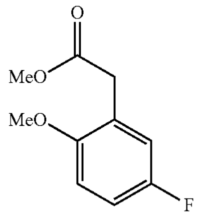 [SMILES: COC(=O)Cc1cc(F)ccc1OC]

To a solution of 2-(5-fluoro-2-methoxy-phenyl)acetic add (0.900 g, 4.88 mmol) in methanol (20 mL) was added sulfuric acid (0.983 mL, 18.5 mmol). After stirring at 70 CC for 2 h, the solvent was removed under reduced pressure and the resulting residue was diluted with ethyl acetate and washed with sat. sodium bicarbonate three times, dried over sodium sulfate, filtered and concentrated under reduced pressure to give the title compound (900 mg, 93%). $^1$H NMR (400 MHz, $CDCl_3$) δ: 7.01-6.90 (m, 2H), 6.85-6.77 (m, 1H), 3.81 (s, 3H), 3.72 (s, 3H), 3.66-3.61 (m, 2H).

Step 2. Methyl 2-bromo-2-(5-fluoro-2-methoxy-phenyl)acetate

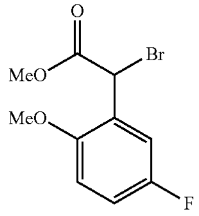 [SMILES: COC(=O)C(Br)c1cc(F)ccc1OC]

To a solution of methyl 2-(5-fluoro-2-methoxy-phenyl) acetate (0.900 g, 5.44 mmol) in carbon tetrachloride (20 mL) was added N-bromosuccinimide (0.968 g, 5.44 mmol) and benzoyl peroxide (0.109 g, 0.454 mmol). After stirring at 80° C. for 16 h, the solvent was removed under reduced pressure. The crude compound was purified by silica gel column chromatography eluting with 12% ethyl acetate in petroleum ether to give the title compound (1.2 g, 96%). $^1$H NMR (400 MHz, $CDCl_3$) δ: 7.42 (dd, 1H), 6.98-7.07 (m, 1H), 6.83 (dd, 1H), 5.90-5.80 (m, 1H), 3.87 (s, 3H), 3.82 (s, 3H).

Step 3. 2-(6-Bromo-7-fluoro-indazol-2yl)-2-(5-fluoro-2-methoxy-phenyl)acetic acid

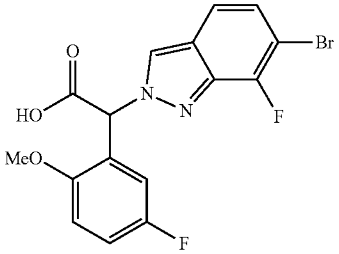 [SMILES: COc1ccc(F)cc1C(C(=O)O)n1cc2ccc(Br)c(F)c2n1]

To a solution of methyl 2-bromo-2-(5-fluoro-2-methoxy-phenyl)acetate (0.579 g, 2.09 mmol) and 6-bromo-7-fluoro-1H-indazole (0.450 g, 2.09 mmol) in acetonitrile (15 mL) was added cesium carbonate (0.814 g, 2.50 mmol). After stirring at 0° C. for 30 min and then room temperature for 1 h, the reaction mixture was partitioned between water and ethyl acetate. The aqueous phase was extracted with additional ethyl acetate three times. The combined organic extracts were washed with brine, dried over sodium sulfate, filtered and concentrated under reduced pressure to give the ester intermediate. MS m/z: 412.9 $[M+1]^+$. To a solution of the above intermediate in THF/MeOH/water (15 mL, 1/1/1) was added lithium hydroxide monohydrate (0.336 g, 8.01 mmol). After stirring at room temperature for 1 h, the solvent was removed under reduced pressure and the resulting residue was partitioned between water and ethyl acetate. The aqueous phase was adjusted to pH 3 with 5% citric acid and extracted with ethyl acetate three times. The combined organic extracts were dried over sodium sulfate, filtered and concentrated under reduced pressure. The crude product was purified by silica gel column chromatography eluting with 35% ethyl acetate in petroleum ether to give the title compound (280 mg, 26%). 1H NMR (400 MHz, DMSO-d6) δ: 8.57 (d, 1H), 7.53 (d, 1H), 7.38-7.11 (m, 4H), 6.82 (s, 1H), 3.82 (s, 3H). MS m/z: 398.8 $[M+1]^+$.

Step 4. 2-[1H-Benzimidazol-2-yl-(5-fluoro-2-methoxy-phenyl)methyl]-6-bromo-7-fluoro-indazole

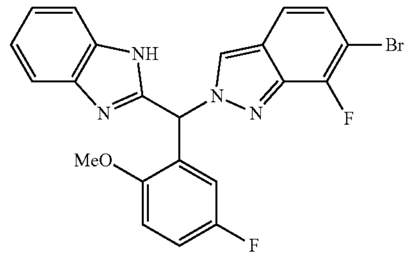 [SMILES: COc1ccc(F)cc1C(c1nc2ccccc2[nH]1)n1cc2ccc(Br)c(F)c2n1]

To a solution of 2-(6-bromo-7-fluoro-indazol-2-yl)-2-(5-fluoro-2-methoxy-phenyl)acetic add (0.280 g, 0.704 mmol), 1,2-diaminobenzene (0.091 g, 0.844 mmol) and TBTU (0.270 g, 0.844 mmol) in DMF (10 mL) was added DIPEA (0.091 g, 0.704 mmol). After stirring at room temperature for 16 h, the reaction mixture was partitioned between sat. sodium chloride and ethyl acetate. The aqueous phase was extracted with ethyl acetate three times, and the combined organic extracts were dried over sodium sulfate, filtered and concentrated under reduced pressure. The crude product was purified by silica gel column chromatography eluting with 35% ethyl acetate in petroleum ether to give the amide intermediate. MS m/z: 488.8 $[M+1]^+$.

To the above amide intermediate was added acetic acid (15 mL). After stirring at 80 for 30 min, the solvent was removed under reduced pressure. The reaction mixture was diluted with ethyl acetate and washed three times with sat. sodium bicarbonate. The organic layer was dried over sodium sulfate, filtered and concentrated under reduced pressure to give the title compound (330 mg, 67%). 1H NMR (400 MHz, $CDCl_3$) δ: 10.75 (br s, 1H), 8.20 (d, 1H), 7.67 (s, 1H), 7.56 (s, 1H), 7.46-7.36 (m, 1H), 7.29-7.20 (m, 2H), 7.07 (dd, 1H), 7.00 (dd, 1H), 6.90-6.99 (m, 1H), 6.75 (dd, 1H), 6.64 (s, 1H), 3.69 (s, 3H); MS m/z: 470.8 $[M+1]^+$.

Step 5. 2-[1H-Benzimidazol-2-yl-(5-fluoro-2-methoxy-phenyl)methyl]-7-fluoro-6-[4-(1-ethyl-4-piperidyl)phenyl]indazole (Compound 035)

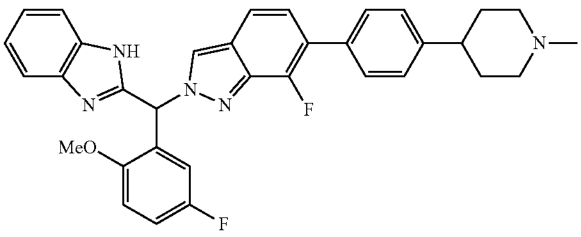 [SMILES: COc1ccc(F)cc1C(c1nc2ccccc2[nH]1)n1cc2ccc(-c3ccc(C4CCN(C)CC4)cc3)c(F)c2n1]

A mixture of 2-[1H-benzimidazol-2-yl-(5-fluoro-2-methoxy-phenyl)methyl]-6-bromo-7-fluoro-indazole (0.200 g, 0.426 mmol), 1-methyl-4-[4-(4,4,5,5-tetramethyl-1,3,2-dioxaborolan-2-yl)phenyl]piperidine (0.140 g, 0.468 mmol), sodium carbonate (0.146 g, 1.06 mmol), [1,1' bis-(diphenylphosphino)ferrocene]dichloropalladium(II), complex with dichloromethane (0.047 g, 0.064 mmol) and dioxane/water (8 mL, 4/1) was degassed with nitrogen twice. The reaction mixture was heated at 100 CC for 20 h. After cooling to room temperature, the reaction mixture was poured into water and extracted with ethyl acetate three times. The combined organic extracts were washed with brine, dried over sodium sulfate, filtered and concentrated under reduced pressure. The crude product was purified by silica gel column chromatography eluting with 6% methanol in dichloromethane to give the title compound (150 mg, 62%). 1H NMR (400 MHz, DMSO-d6) δ: 12.67 (s, 1H), 8.58 (d, 1H), 7.60-7.65 (m, 3H), 7.49-7.57 (m, 3H), 7.37 (d, 2H), 7.14-7.33 (m, 5H), 6.98 (m, 1H), 3.80 (s, 3H), 2.99-3.14 (m, 2H), 2.56-2.65 (m, 1H), 2.19-2.42 (m, 5H), 1.68-1.91 (m, 4H); MS m/z: 564.3 $[M+1]^+$.

Step 6. 2-[1H-Benzimidazol-2-yl-[7-fluoro-6-[4-(1-methyl-4-piperidyl)phenyl]indazol-2-yl]methyl]-4-fluoro-phenol;hydrochloride (Compound 034)

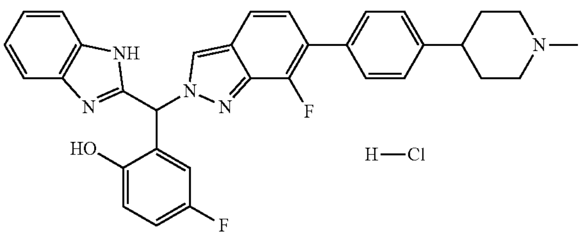 [SMILES: CN1CCC(c2ccc(-c3ccc4cn(C(c5nc6ccccc6[nH]5)c5cc(F)ccc5O)nc4c3F)cc2)CC1 ; Cl]

To a solution of 2-[1H-benzimidazol-2-yl-(5-fluoro-2-methoxy-phenyl)methyl]-7-fluoro-6-[4-(1-methyl-4-piperidyl) phenyl]indazole (0.150 g, 0,266 mmol) in dichloromethane (8 mL) at 0 was added boron tribromide (0,666 g, 2.66 mmol). After stirring at the room temperature for 2 h, the reaction mixture was diluted with dichloromethane and poured into ice-water. The aqueous phase was extracted with dichloromethane three times. The combined organic extracts were washed with brine, dried over sodium sulfate, filtered and concentrated under reduced pressure. The crude product was purified by reverse phase HPLC eluting with 0-100% ACN/water (0.05% HCl modifier) to give the title compound (25 mg, 30%). $^1H$ NMR (400 MHz, DMSO-$d_6$) δ: 10.10-10.47 (m, 2H), 8.65 (d, 1H), 7.51-7.72 (m, 6H), 7.29-7.42 (m, 4H), 7.11-7.23 (m, 2H), 6.99 (m, 1H), 6.90 (m, 1H), 3.48-3.57 (m, 2H), 3.00-3.14 (m, 2H), 2.76-2.93 (m, 4H), 1.92-2.10 (m, 4H); MS m/z: 550.3 $[M+1]^+$.

The following examples were prepared by a similar method to Example 6 from methyl 2-bromo-2-(5-fluoro-2-methoxyphenyl)acetate or methyl 2-bromo-2-phenylacetate and the corresponding bicyclic starting materials:

| No. | Structure/Name | m/z $[M + 1]^+$ | $^1H$ NMR (DMSO-$d_6$) δ | Starting materials |
|---|---|---|---|---|
| 063 | 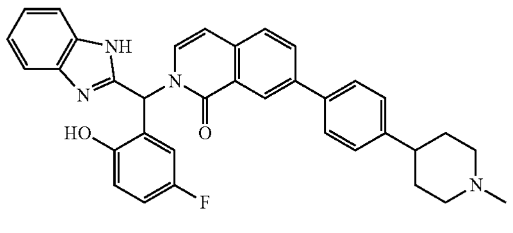 [SMILES: CN1CCC(c2ccc(-c3ccc4ccn(C(c5nc6ccccc6[nH]5)c5cc(F)ccc5O)c(=O)c4c3)cc2)CC1] 2-[1H-benzimidazol-2-yl-(5-fluoro-2-hydroxy-phenyl)methyl]-7-[4-(1-methyl-4-piperidyl)phenyl]isoquinolin-1-one | 559.5 | 12.79 (br s, 1H), 10.02 (br s, 1H), 8.44 (d, 1H), 8.01-8.09 (m, 1H), 7.75 (d, 1H), 7.65-7.71 (m, 3H), 7.41-7.62 (m, 2H), 7.37 (d, 2H), 7.12-7.30 (m, 3H), 7.03-7.11 (m, 1H), 6.82-6.93 (m, 1H), 6.63-6.71 (m, 2H), 2.91 (d, 2H), 2.53-2.58 (m, 1H), 2.23 (s, 3H), 1.98-2.12 (m, 2H), 1.65-1.81 (m, 4H) | 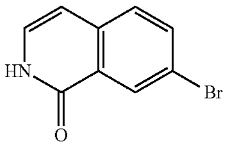 [SMILES: O=c1[nH]ccc2ccc(Br)cc12] |

-continued

| No. | Structure/Name | m/z $[M + 1]^+$ | $^1H$ NMR (DMSO-$d_6$) δ | Starting materials |
|---|---|---|---|---|
| 082 | 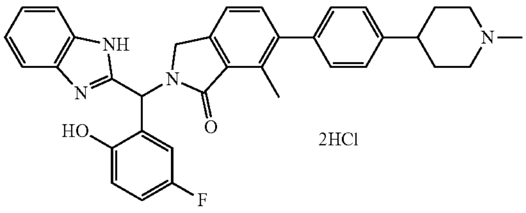 [SMILES: Cc1c(-c2ccc(C3CCN(C)CC3)cc2)ccc2c1C(=O)N(C(c1nc3ccccc3[nH]1)c1cc(F)ccc1O)C2] 2-[1H-benzimidazol-2-yl-(5-fluoro-2-hydroxy-phenyl)methyl]-7-methyl-6-[4-(1-methyl-4-piperidyl)phenyl]isoindolin-1-one; dihydrochloride | 561.2 | 10.68 (br s, 1H), 10.35 (br s, 1H), 7.67-7.78 (m, 2H), 7.42-7.56 (m, 4H), 7.28-7.40 (m, 4H), 7.07-7.26 (m, 3H), 6.96-7.04 (m, 1H), 4.70 (d, 1H), 4.17 (d, 1H), 3.50 (d, 2H), 3.00-3.17 (m, 2H), 2.84-2.92 (m, 1H), 2.77 (d, 3H), 2.57 (s, 3H), 1.91-2.16 (m, 4H) | 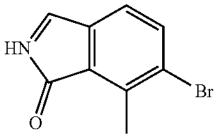 |
| 064 | 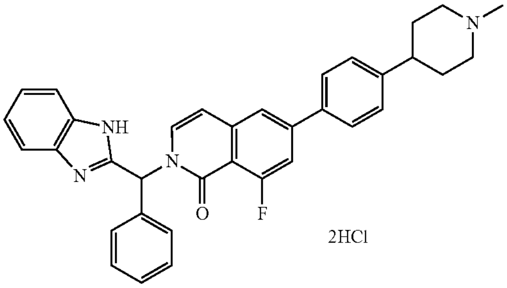 [SMILES: CN1CCC(c2ccc(-c3cc(F)c4c(=O)n(C(c5ccccc5)c5nc6ccccc6[nH]5)ccc4c3)cc2)CC1] 2-[1H-benzimidazol-2-yl(phenyl)methyl]-8-fluoro-6-[4-(1-methyl-4-piperidyl) phenyl]-isoquinolin-1-one; dihydrochloride | 543.1 | 10.81 (br s, 1H), 7.80-7.87 (m, 3H), 7.60-7.72 (m, 4H), 7.45-7.52 (m, 6H), 7.33-7.44 (m, 4H), 6.78 (d, 1H), 3.48 (d, 2H), 3.01-3.13 (m, 2H), 2.82-2.90 (m, 1H), 2.76 (d, 3H), 1.95-2.14 (m, 4H) | 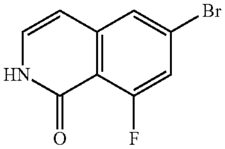 [SMILES: O=c1[nH]ccc2cc(Br)cc(F)c12] |
| 069 | 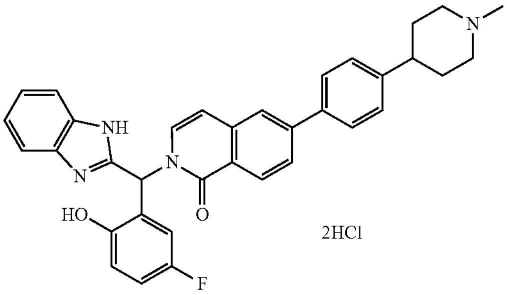 [SMILES: CN1CCC(c2ccc(-c3ccc4c(=O)n(C(c5nc6ccccc6[nH]5)c5cc(F)ccc5O)ccc4c3)cc2)CC1] 2-[1H-benzimidazol-2-yl-(5-fluoro-2-hydroxy-phenyl)methyl]-6-[4-(1-methyl-4-piperidyl) phenyl]-isoquinolin-1-one; dihydrochloride | 559.6 | 10.54 (br s, 1H), 10.33 (br s, 1H), 8.28 (d, 1H), 8.01 (d, 1H), 7.82-7.89 (m, 1H), 7.80 (d, 2H), 7.59-7.70 (m, 3H), 7.35-7.48 (m, 4H), 7.33 (d, 1H), 7.12-7.23 (m, 1H), 6.89-7.05 (m, 2H), 6.79 (d, 1H), 2.98-3.22 (m, 4H), 2.72-2.94 (m, 4H), 1.97-2.11 (m. 4H) | 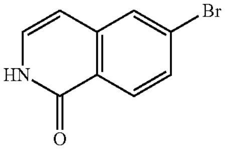 [SMILES: O=c1[nH]ccc2cc(Br)ccc12] |
| 070 | 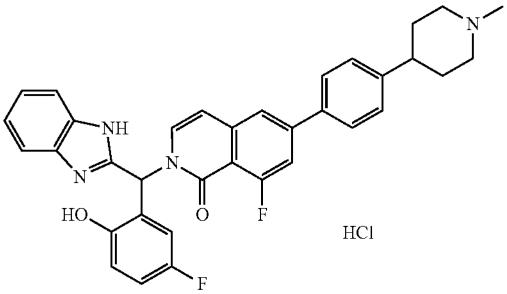 [SMILES: CN1CCC(c2ccc(-c3cc(F)c4c(=O)n(C(c5nc6ccccc6[nH]5)c5cc(F)ccc5O)ccc4c3)cc2)CC1 ; Cl] 2-[1H-benzimidazol-2-yl-(5-fluoro-2-hydroxy-phenyl)methyl]-8-fluoro-6-[4-(1-methyl-4-piperidyl)phenyl]-isoquinolin-1-one; hydrochloride | 577.1 | 10.58 (br s, 1H), 10.35 (br s, 1H), 7.81-7.91 (m, 3H), 7.60-7.71 (m, 3H), 7.55 (s, 1H), 7.28-7.44 (m, 5H), 7.12-7.23 (m, 1H), 6.88-7.04 (m, 2H), 6.77 (d, 1H), 3.17-3.29 (m, 2H), 2.98-3.14 (m, 2H), 2.83-2.91 (m, 1H), 2.77 (d, 3H), 1.90-2.09 (m, 4H) | 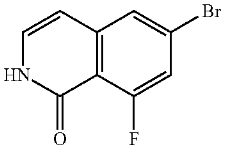 [SMILES: O=c1[nH]ccc2cc(Br)cc(F)c12] |

-continued

| No. | Structure/Name | m/z [M + 1]$^+$ | $^1$H NMR (DMSO-$d_6$) δ | Starting materials |
|---|---|---|---|---|
| 071 | 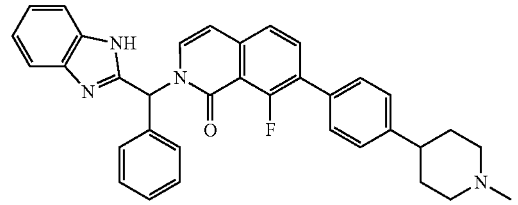 [SMILES: CN1CCC(c2ccc(-c3ccc4ccn(C(c5ccccc5)c5nc6ccccc6[nH]5)c(=O)c4c3F)cc2)CC1] 2-((1H-benzo[d]imidazol-2-yl)(phenyl)methyl)-8-fiuoro-7-(4-(1-methylpiperidin-4-yl)phenylisoquinolin-1(2H)-one | | 9.44 (br s, 1H), 7.83 (m, 1H), 7.64 (s, 1H) 7.59-7.55 (m, 5H), 7.47-7.42 (m, 4H), 7.38 (d, 2H), 7.34 (d, 2H), 7.25 (m, 2H), 6.71 (m, 1H), 3.60 (m, 2H), 3.10 (m, 2H), 2.88 (m, 1H), 2.83 (d, 3H), 2.07 (m, 2H) 1.87 (m, 2H) | 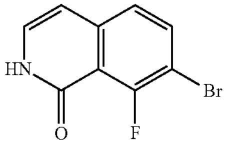 |
| 072 | 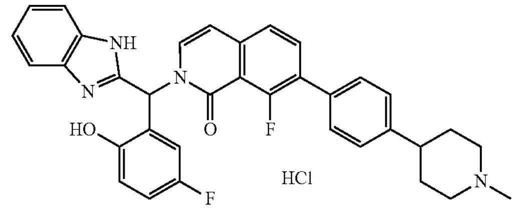 [SMILES: CN1CCC(c2ccc(-c3ccc4ccn(C(c5nc6ccccc6[nH]5)c5cc(F)ccc5O)c(=O)c4c3F)cc2)CC1 ; Cl] HCl 2-[1H-benzimidazol-2-yl-(5-fluoro-2-hydroxy-phenyl)methyl]-8-fluoro-7-[4-(1-methyl-4-piperidyl)phenyl]-isoquinolin-1-one; hydrochloride | 577.5 | 9.98-10.27 (m, 2H), 7.78-7.87 (m, 1H), 7.52-7.62 (m, 6H), 7.37 (d, 2H), 7.22-7.32 (m, 3H), 7.10-7.20 (m, 1H), 7.07-7.19 (m, 1H), 6.67-6.83 (m, 2H), 3.15-3.22 (m, 2H), 3.03-3.10 (m, 2H), 2.75-2.90 (m, 4H), 1.92-2.08 (m, 4H) | 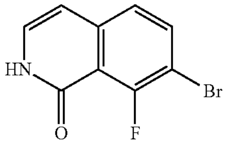 |
| 073 | 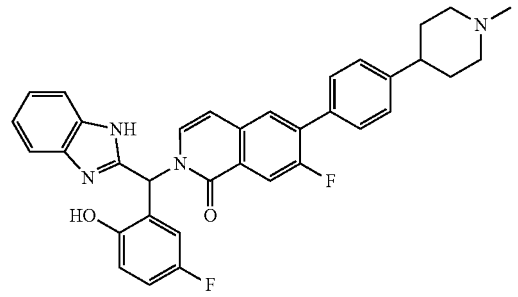 [SMILES: CN1CCC(c2ccc(-c3cc4ccn(C(c5nc6ccccc6[nH]5)c5cc(F)ccc5O)c(=O)c4cc3F)cc2)CC1] 2-[1H-benzimidazol-2-yl-(5-fluoro-2-hydroxy-phenyl)methyl]-7-fluoro-6-[4-(1-methyl-4-piperidy)phenyl]-isoquinolin-1-one | 577.2 | 12.79 (br s, 1H), 10.08 (br s, 1H), 8.21 (s, 1H), 7.97 (d, 1H). 7.88 (d, 1H), 7.55-7.68 (m, 4H), 7.41 (d, 2H), 7.27 (d, 1H), 7.16-7.23 (m, 2H), 7.07-7.15 (m, 1H), 6.88-6.94 (m, 1H), 6.71 (d, 1H), 6.62-6.68 (m, 1H), 2.94 (d, 2H), 2.54-2.59 (m, 1H), 2.26 (s, 3H), 2.04-2.12 (m, 2H), 1.67-1.85 (m, 4H) | 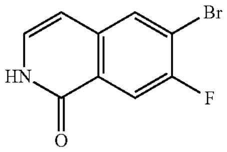 [SMILES: O=c1[nH]ccc2cc(Br)c(F)cc12] |
| 092 | 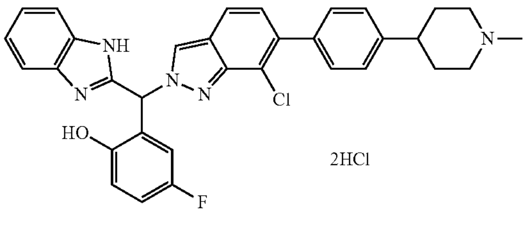 [SMILES: CN1CCC(c2ccc(-c3ccc4cn(C(c5nc6ccccc6[nH]5)c5cc(F)ccc5O)nc4c3Cl)cc2)CC1 ; "2HCl"] 2HCl 2-[1H-benzimidazol-2-yl-[7-chloro-6-[4-(1-methyl-4-piperidyl)phenyl]-indazol-2-yl]methyl]-4-fluoro-phenol; dihydrochloride | 566.4 | $^1$H NMR (methanol-$d_4$) δ: 8.62 (s, 1H), 7.90 (s, 1H), 7.72-7.80 (m, 3H), 7.56-7.62 (m, 2H), 7.50 (d, 2H), 7.39 (d, 2H), 7.12-7.19 (m, 2H), 6.94-7.01 (m, 1H), 6.80-6.88 (m, 1H), 3.58-3.69 (m, 2H), 3.14-3.25 (m, 2H), 2.95-3.04 (m, 1H), 2.93 (s, 3H), 2.13-2.24 (m, 2H), 1.97-2.11 (m, 2H) | 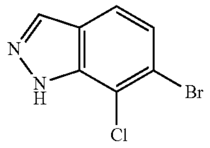 [SMILES: Clc1c(Br)ccc2cn[nH]c12] |

-continued

| No. | Structure/Name | m/z [M + 1]$^+$ | $^1$H NMR (DMSO-$d_6$) δ | Starting materials |
|---|---|---|---|---|
| 074 | 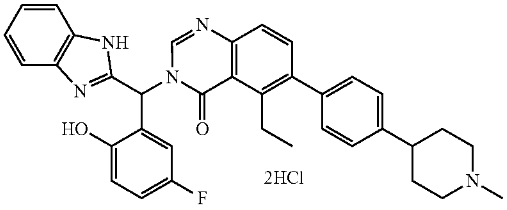 [SMILES: CCc1c(-c2ccc(C3CCN(C)CC3)cc2)ccc2ncn(C(c3nc4ccccc4[nH]3)c3cc(F)ccc3O)c(=O)c12 ; "2HCl"] 2HCl 3-[1H-benzimidazol-2-yl-(5-fluoro-2-hydroxy-phenyl)methyl]-5-ethyl-6-[4-(1-methyl-4-piperidyl)phenyl]-quinazolin-4-one; dihydrochloride | 588.4 | $^1$H NMR (methanol-$d_4$) δ: 8.53-8.66 (m, 1H), 7.76-7.83 (m, 2H). 7.62-7.74 (m, 4H), 7.58 (s, 1H), 7.42 (d, 2H), 7.22-7.37 (m, 4H), 7.01-7.09 (m, 1H), 3.60-3.72 (m, 2H), 3.13-3.27 (m, 4H), 2.89-3.06 (m, 4H), 2.00-2.28 (m, 4H), 1.00 (t, 3H) | 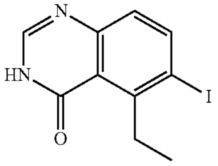 |

Compounds 067 and 068: Preparation of 2-[(R)-1H-benzimidazol-2-yl-(5-fluoro-2-hydroxy-phenyl)methyl]-6-[4-(1-methyl-4-piperidyl)phenyl]isoquinolin-1-one and 2-[((S)-1H-benzimidazol-2-yl-(5-fluoro-2-hydroxy-phenyl)methyl]-6-[4-(1-methyl-4-piperidyl)phenyl]isoquinolin-1-one

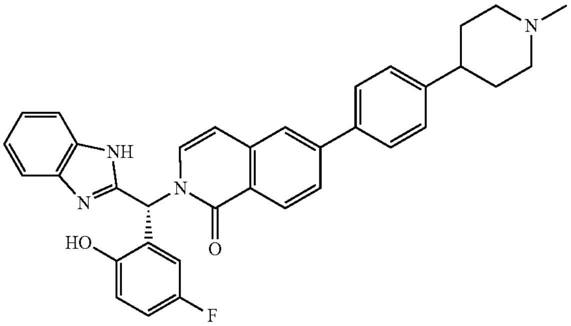

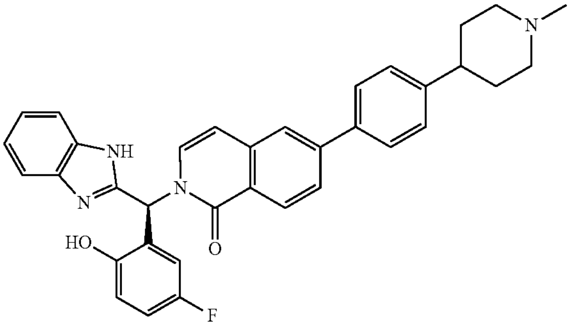

2-[(rac)-1H-benzimidazol-2-yl-(5-fluoro-2-hydroxy-phenyl)methyl]-6-[4-(1-methyl-4-piperidyl)-phenyl]isoquinolin-1-one; dihydrochloride (069, 0.050 g, 0.079 mmol) was purified by prep SFC with a Chiral Technologies Chiralpak IG (5 micron 250×10 mm) column @ 40° C. eluting with 55% (0.3% TEA in MeOH)/45% CO2 at 10 MPa BPR to separate enantiomers. Absolute configuration of the chiral center for each isolated enantiomer is unknown. First eluting peak (067) (17.0 mg, 38% yield, 98.5:1.5 er); $[\alpha]^{20}_D$ −12.9 (c=0.31, MeOH); $^1$H NMR (DMSO-$d_6$) δ: 12.6-12.9 (m, 1H), 9.9-10.2 (m, 1H), 8.28 (d, 1H), 7.94 (s, 1H), 7.82 (dd, 1H), 7.74 (d, 2H), 7.65 (s, 1H), 7.54 (br s, 2H), 7.39 (d, 2H), 7.29 (d, 1H), 7.19 (br dd, 2H), 7.1 (m, 1H), 6.89 (dd, 1H), 6.6-6.7 (m, 2H), 2.88 (d, 2H), 2.5-2.6 (m, 1H), 2.20 (s, 3H), 1.9-2.1 (m, 2H), 1.6-1.8 (m, 4H); MS m/z: 559.3 [M+1]$^+$. Second eluting peak (068) (14.1 mg, 31% yield, 1.5:98.5 er); $[\alpha]_D^{20}$ +14.1 (c=0.64, MeOH); $^1$H NMR (DMSO-$d_6$) δ: 12.6-12.9 (m, 1H), 9.9-10.2 (m, 1H), 8.28 (d, 1H), 7.94 (s, 1H), 7.82 (dd, 1H), 7.74 (d, 2H), 7.65 (s, 1H), 7.54 (br s, 2H), 7.39 (d, 2H), 7.29 (d, 1H), 7.19 (br dd, 2H), 7.1 (m, 1H), 6.89 (dd, 1H), 6.6-6.7 (m, 2H), 2.88 (d, 2H), 2.5-2.6 (m, 1H), 2.20 (s, 3H), 1.9-2.1 (m, 2H), 1.6-1.8 (m, 4H); MS m/z: 559.3 [M+1]$^+$.

Compounds 065 and 066: Preparation of 2-[(R)-1H-benzimidazol-2-yl-(5-fluoro-2-hydroxy-phenyl)methyl]-8-fluoro-6-[4-(1-methyl-4-piperidyl)phenyl]isoquinolin-1-one and 2-[(S)-1H-benzimidazol-2-yl-(5-fluoro-2-hydroxy-phenyl)methyl]-8-fluoro-6-[4-(1-methyl-4-piperidyl)phenyl]isoquinolin-1-one

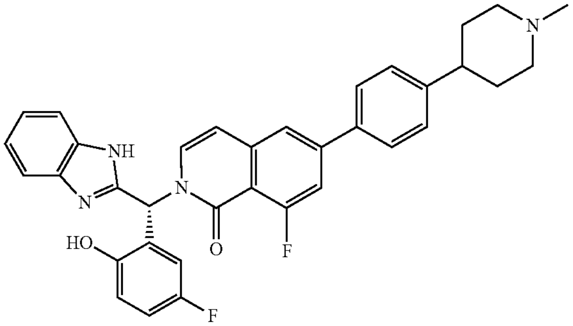

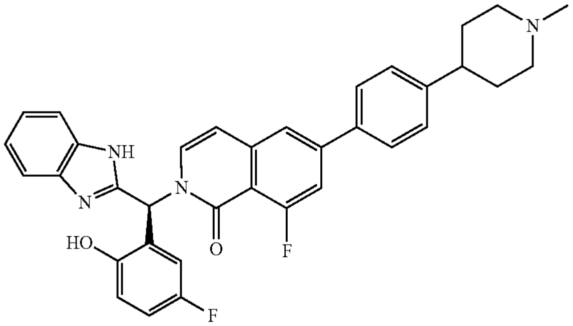

2-[1H-benzimidazol-2-yl-(5-fluoro-2-hydroxy-phenyl)methyl]-8-fluoro-6-[4-(1-methyl-4-piperidyl)phenyl]isoquinolin-1-one; hydrochloride (070, 0.012 g, 0.020 mmol) was purified by prep SFC with Phenomenex Lux Cellulose-4 column eluting with 55% (0.3% TEA in MeOH)/45% CO2 at 10 MPa to separate enantiomers. Absolute configuration of the chiral center for each isolated enantiomer is unknown. First eluting peak (065) (3 mg, 27% yield, 100:0 er); $[\alpha]^{20}_{D}$ −13.3 (c=0.37, MeOH); $^1H$ NMR (DMSO-$d_6$) δ: 12.69 (br s, 1H), 9.95 (br s, 1H), 7.68-7.73 (m, 3H), 7.37-7.58 (m, 4H), 7.32 (d, 2H), 7.22 (d, 1H), 7.08-7.16 (m, 2H), 6.99-7.07 (m, 1H), 6.80-6.86 (m, 1H), 6.56-6.63 (m, 2H), 2.81 (d, 2H), 2.45-2.50 (m, 1H), 2.13 (s, 3H), 1.85-1.96 (m, 2H), 1.57-1.73 (m, 4H); MS m/z: 577.3 $[M+1]^+$. Second eluting peak (066) (4 mg, 36% yield, 100:0 er); $[\alpha]_D^{20}$ +14.8 (c=0.27, MeOH); $^1H$ NMR (DMSO-$d_6$) δ: 12.69 (br s, 1H), 9.98 (br s, 1H), 7.68-7.73 (m, 3H), 7.38-7.58 (m, 4H), 7.32 (d, 2H), 7.22 (d, 1H), 7.08-7.18 (m, 2H), 6.99-7.06 (m, 1H), 6.80-6.86 (m, 1H), 6.56-6.63 (m, 2H), 2.81 (d, 2H), 2.45-2.52 (m, 1H), 2.13 (s, 3H), 1.83-1.96 (m, 2H), 1.57-1.73 (m, 4H); MS m/z: 577.3 $[M+1]^+$.

Example 7: Preparation of 3-[1H-benzimidazol-2-yl-(5-fluoro-2-hydroxy-phenyl)methyl]-6-[4-(1-methyl-4-piperidyl)phenyl]quinazolin-4-one;hydrochloride (compound 006)

Scheme 6.

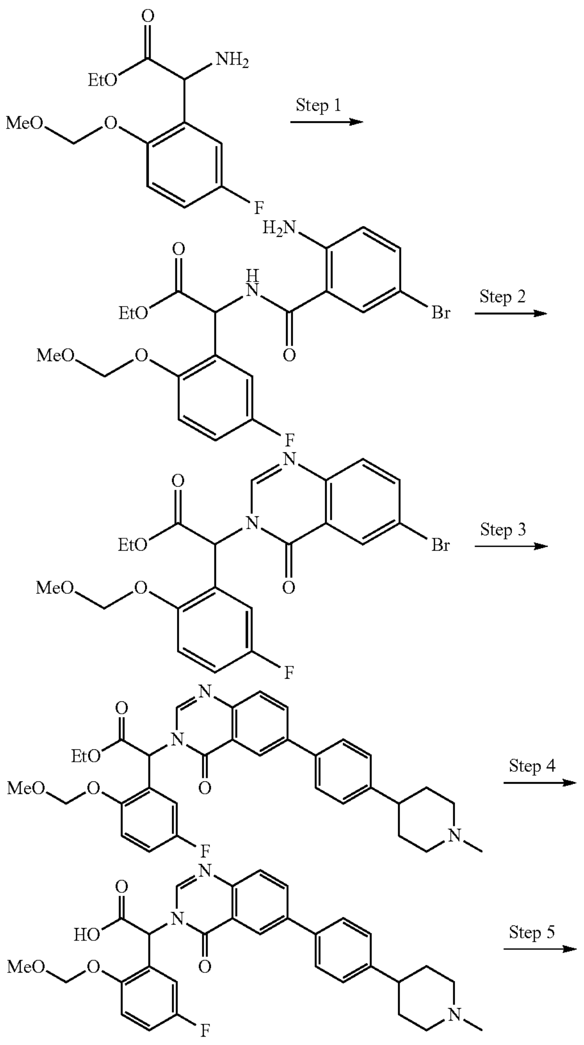

-continued

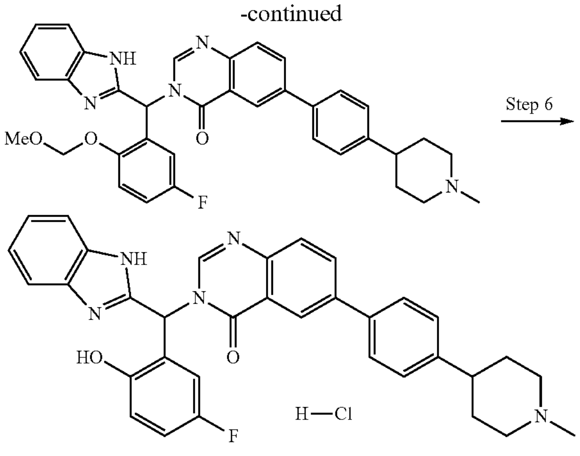

006

Step 1. Ethyl 2-[(2-amino-5-bromo-benzoyl)aminol-2-[5-fluoro-2-(methoxymethoxy)phenyl]-acetate

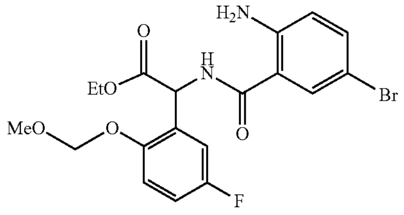 [SMILES: CCOC(=O)C(NC(=O)c1cc(Br)ccc1N)c1cc(F)ccc1OCOC]

To a solution of ethyl 2-amino-2-[5-fluoro-2-(methoxymethoxy)phenyl]acetate (10.0 g, 38.8 mmol) and 6-bromo-2,4-dihydro-1H-3,1-benzoxazine-2,4-dione (10.3 g, 42.6 mmol) In THF (80 mL) was added triethylamine (7.85 g, 77.6 mmol). After stirring at 40° C. for 3 h, the solvent was removed under reduced pressure. The crude product was purified by silica gel column chromatography eluting with 25% ethyl acetate in petroleum ether to give the title compound (5 g, 28%). $^1H$ NMR (400 MHz, DMSO-$d_6$) δ: 8.95 (d, 1H), 7.77 (d, 1H), 7.29 (dd, 1H), 7.15-7.22 (m, 3H), 6.69 (d, 1H), 6.57 (s, 2H), 5.99 (d, 1H), 5.19-5.27 (m, 2H), 4.09-4.18 (m, 2H), 3.38 (s, 3H), 1.14-1.18 (m, 3H).

Step 2. Ethyl 2-(6-bromo-4-oxo-quinazolin-3-yl)-2-[5-fluoro-2-(methoxymethoxy)phenyl]acetate

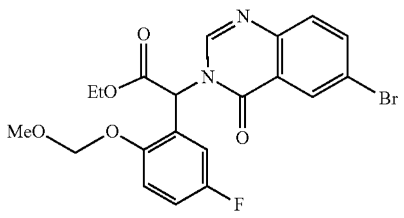 [SMILES: CCOC(=O)C(c1cc(F)ccc1OCOC)n1cnc2ccc(Br)cc2c1=O]

A solution of ethyl 2-[(2-amino-5-bromo-benzoyl) amino]-2-[5-fluoro-2-(methoxymethoxy)-phenyl]acetate (5.25 g, 11.5 mmol) in triethoxy methane (20 mL) was stirred at 110° C. for 22 h. After cooling to room temperature, the solvent was removed under reduced pressure. The crude product was purified by silica gel column chromatography eluting with 10-33% ethyl acetate in petroleum ether to give the title compound (2.2 g, 41%). $^1$H NMR (400 MHz, DMSO-$d_6$) δ: 8.25-8.29 (m, 2H), 8.02 (dd, 1H), 7.66 (d, 1H), 7.26-7.37 (m, 2H), 7.14-7.21 (m, 1H), 6.68 (s, 1H), 5.17-5.25 (m, 2H), 4.22-4.30 (m, 2H), 3.26 (s, 3H) 1.15-1.25 (m, 3H).

Step 3. Ethyl 2-[5-fluoro-2-(methoxymethoxy)phenyl]-2-[6-[4-(1-methyl-4-piperidyl)phenyl]-4-oxo-quinazolin-3-yl]acetate

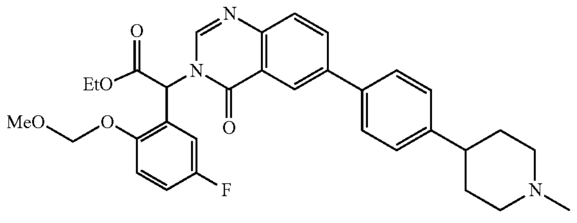 [SMILES: CCOC(=O)C(c1cc(F)ccc1OCOC)n1cnc2ccc(-c3ccc(C4CCN(C)CC4)cc3)cc2c1=O]

A mixture of ethyl 2-(6-bromo-4-oxo-quinazolin-3-yl)-2-[5-fluoro-2-(methoxymethoxy)-phenyl]acetate (22 g, 4.72 mmol), 1-methyl-4-[4-(4,4,5,5-tetramethyl-1,3,2-dioxaborolan-2-yl)phenyl]piperidine (1.98 g, 6.60 mmol), potassium carbonate (1.96 g, 14.1 mmol) and dioxane/water (20 mL, 4/1) was degassed with nitrogen gas. [1,1'-Bis(diphenylphosphino)-ferrocene]dichloropalladium(II) complex with dichloromethane (0.690 g, 0.944 mmol) was added and then the reaction was degassed under nitrogen once more. The reaction mixture was heated at 105° C. for 3 h. After cooling to room temperature, the reaction mixture was poured into water and extracted with ethyl acetate three times. The combined organic extracts were washed with brine, dried over sodium sulfate, filtered and concentrated under reduced pressure. The crude product was purified by silica gel column chromatography eluting with 0-15% methanol in dichloromethane to give the title compound (1.8 g, 68%). MS m/z: 560.4 $[M+1]^+$.

Step 4. 2-[5-Fluoro-2-(methoxymethoxy)phenyl]2-[6-[4-(1-ethyl-4-piperidyl)phenyl]-4-oxo-quinazolin-3-yl]acetic acid

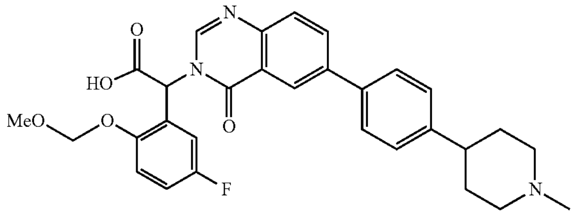

To a solution of ethyl 2-[5-fluoro-2-(methoxymethoxy) phenyl]-2-[6-[4-(1-methyl-4-piperidyl)-phenyl]-4-oxo-quinazolin-3-yl]acetate (1.80 g, 3.21 mmol) in THF/MeOH/water (30 mL, 1/1/1) was added lithium hydroxide monohydrate (0.404 g, 9.62 mmol). After stirring at the room temperature for 3 h, the solvent was removed under reduced pressure and the resulting residue was adjusted to pH 3 by HCl (1 M). The resulting solid was collected by filtration and washed with water to give the title compound (1.5 g, 88%). MS m/z: 532.1 $[M+1]^+$.

Step 5. 3-[1H-Benzimidazol-2-yl-[5-fluoro-2-(methoxymethoxy)phenyl]methyl]-6-[4-(1-ethyl-4-piperidyl)phenyl]quinazolin-4-one

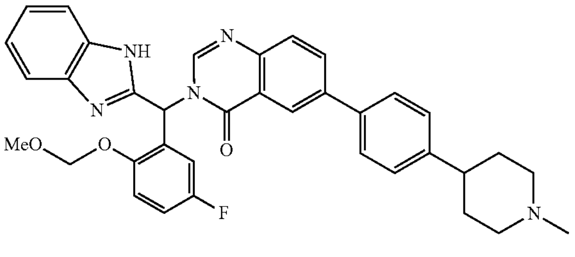 [SMILES: COCOc1ccc(F)cc1C(c1nc2ccccc2[nH]1)n1cnc2ccc(-c3ccc(C4CCN(C)CC4)cc3)cc2c1=O]

To a solution of 2-[5-fluoro-2-(methoxymethoxy)phenyl]-2-[6-[4-(1-methyl-4-piperidyl)-phenyl]-4-oxo-quinazolin-3-yl)acetic acid (0.900 g, 1.69 mmol), 1,2-diaminobenzene (0.218 g, 2.02 mmol) and HATU (0.962 g, 2.53 mmol) in DMF (10 mL) was added DIPEA (0.545 g, 4.22 mmol). After stirring at room temperature for 10 h, sat. sodium chloride was added to the reaction mixture. The resulting solid was collected by filtration and washed with water. The crude product was purified by silica gel column chromatography eluting with 0-10% methanol in dichloromethane to give the amide intermediate. MS m/z: 622.3 $[M+1]^+$.

To the above amide intermediate was added acetic acid (8 mL). After stirring at 80° C. for 3 h, the solvent was removed under reduced pressure. The reaction mixture was neutralized with sat. sodium bicarbonate and extracted with ethyl acetate three times. The combined organic extracts were dried over sodium sulfate, filtered and concentrated under reduced pressure. The crude product was re-crystallized from ethyl acetate to give the title compound (170 mg, 50%). MS m/z: 604.3 [M+1]".

Step 6. 3-[1H-Benzimidazol-2-yl-(5-fluoro-2-hydroxy-phenyl)methyl]-6-[4-(1-methyl-4-piperidyl)-phenyl]quinazolin-4-one;hydrochloride (Compound 006)

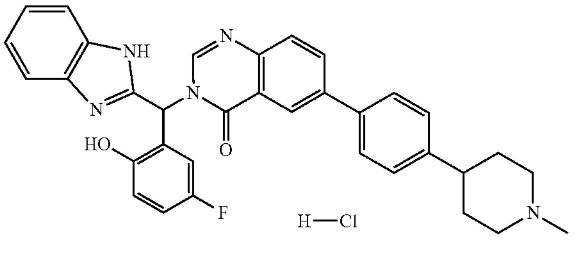 [SMILES: CN1CCC(c2ccc(-c3ccc4ncn(C(c5nc6ccccc6[nH]5)c5cc(F)ccc5O)c(=O)c4c3)cc2)CC1 ; Cl]

To a solution of 3-[1H-benzimidazol-2-yl-[5-fluoro-2-(methoxymethoxy)phenyl]methyl]-6-[4-(1-methyl-4-piperidyl)phenyl]quinazolin-4-one (0.120 g, 0.198 mmol) in dichloromethane (10 mL) was added HCl in dioxane (4 M, 0.495 mL, 1.98 mmol). After stirring 1 h at room temperature, the solvent was removed under reduced pressure. To the residue was added diethyl ether and the resulting solid was isolated via filtration to give the title compound (160 mg, 91%), $^{1}H$ NMR (400 MHz, DMSO-$d_6$) δ: 10.28-10.48 (m, 2H), 8.38 (s, 1H), 8.29 (s, 1H), 8.22 (d, 1H), 7.75-7.86 (m, 3H), 7.68 (m, 2H), 7.59 (s, 1H), 7.34-7.45 (m, 4H), 7.20 (m, 1H), 6.96-7.06 (m, 2H), 3.47-3.54 (m, 2H), 3.00-3.15 (m, 2H), 2.75-2.92 (m, 4H), 1.92-2.13 (m, 4H); MS m/z: 560.3 $[M+1]^+$.

The following compounds were prepared by a similar method to Example 7 from ethyl 2-(6-bromo-4-oxo-quinazolin-3-yl)-2-[5-fluoro-2-(methoxymethoxy)phenyl]acetate and the corresponding boronate, or from ethyl 2-amino-2-phenylacetate:

Example 8: Preparation of 2-[1H-benzimidazol-2-yl(1,4,5,6-tetrahydrocyclopenta[c]pyrazol-3-yl)methyl]-6-[4-(1-methyl-4-piperidyl)phenyl]isoindolin-1-one (Compound 033)

Scheme 7.

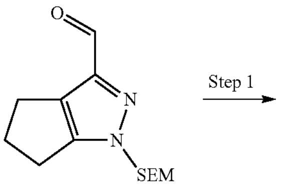

| No. | Structure/Name | m/z $[M + 1]^+$ | $^{1}H$ NMR (DMSO-$d_6$) δ |
|---|---|---|---|
| 001 | 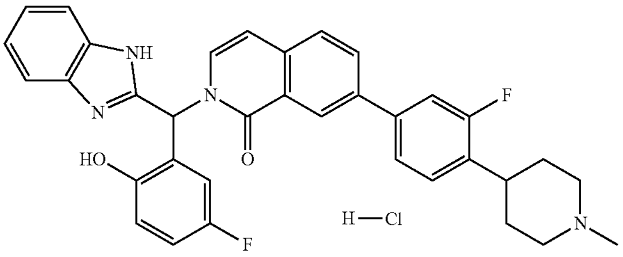 3-[1H-Benzimidazol-2-yl-(5-fluoro-2-hydroxyphenyl)methyl]-6-[3-fluoro-4-(1-methyl-4-piperidyl)phenyl]quinazolin-4-one; hydrochloride | 578.3 | 10.32 (br s, 1H), 8.35-8.46 (m, 1H), 8.14-8.32 (m, 2H), 7.83 (d, 1H), 7.60-7.69 (m, 4H), 7.57 (s, 1H), 7.38-7.45 (m, 1H), 7.24-7.36 (m, 2H), 7.13-7.23 (m, 1H), 6.94-7.04 (m, 1H), 6.78-6.93 (m, 1H), 3.52-3.56 (m, 3H), 3.08-3.19 (m, 2H), 2.74-2.95 (m, 3H), 1.94-2.14 (m, 4H) |
| 002 | 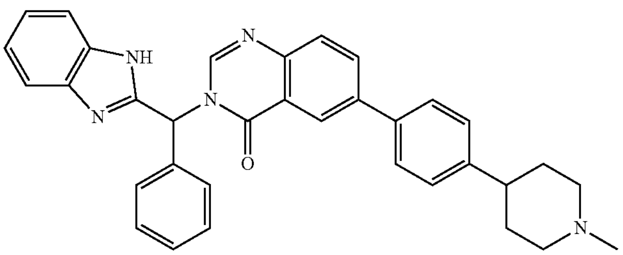 [SMILES: CN1CCC(c2ccc(-c3ccc4ncn(C(c5ccccc5)c5nc6ccccc6[nH]5)c(=O)c4c3)cc2)CC1] 3-[1H-Benzimidazol-2-yl(phenyl)methyl]-6-[4-(1-methyl-4-piperidyl)phenyl]quinazolin-4-one | 526.3 | 9.44 (br s, 1H), 8.39-8.44 (m, 1H), 8.35 (s, 1H), 8.19 (d, 1H), 7.75-7.83 (m, 3H), 7.56-7.63 (m, 3H), 7.37-7.51 (m, 7H), 7.22-7.27 (m, 2H), 3.55 (d, 2H), 3.10 (d, 2H), 2.81-2.95 (m, 4H), 2.07 (d, 2H), 1.81-1.94 (m, 2H) |

-continued

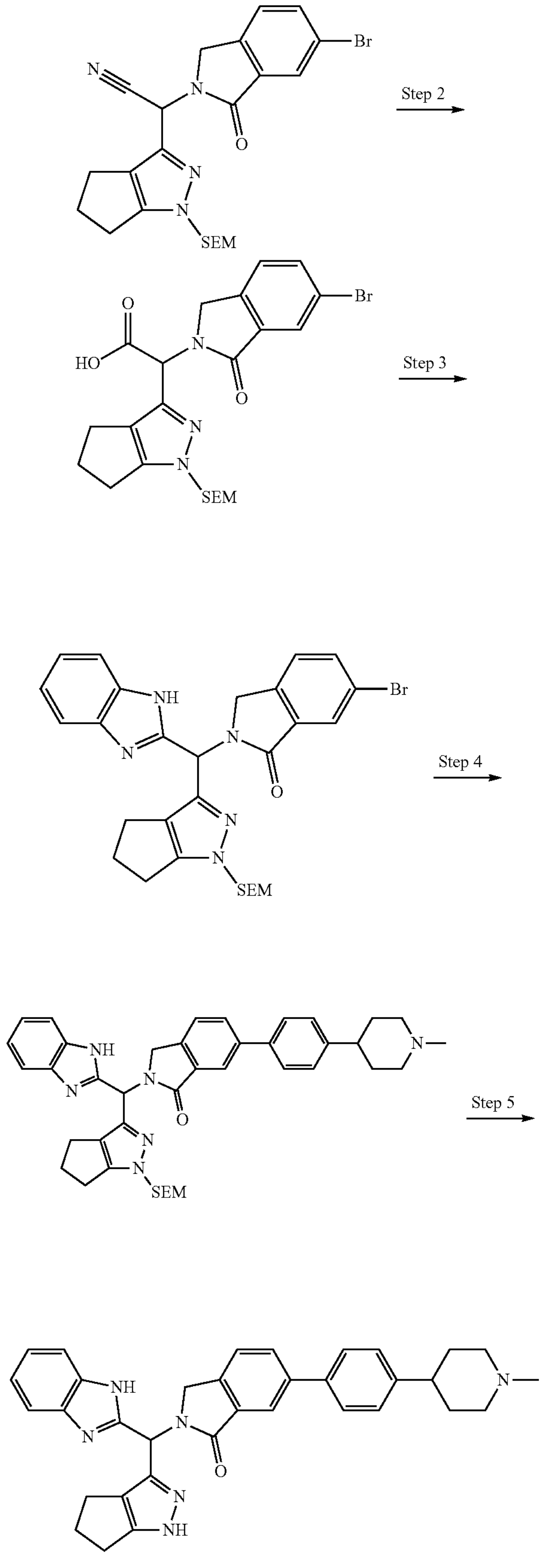

033

Step 1. 2-(6-Bromo-1-oxo-isoindolin-2-yl)-2-[1-(2-trimethylsilylethoxymethyl)-5,6-dihydro-4H-cyclopenta[c]pyrazol-3-yl]acetonitrile

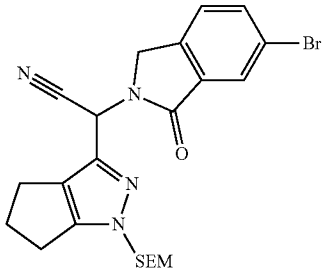 [SMILES: C[Si](C)(C)CCOCn1nc(C(C#N)N2Cc3ccc(Br)cc3C2=O)c2c1CCC2]

To a solution of 1-(2-trimethylsilylethoxymethyl)-5,6-dihydro-4H-cyclopenta[c]pyrazole-3-carbaldehyde (3.25 g, 11.5 mmol) in acetonitrile (30 mL) was added methyl 2-(aminomethyl)-5-bromobenzoate hydrochloride (3.25 g, 11.5 mmol), DIPEA (4.73 mL, 28.7 mmol) and trimethylsilyl cyanide (1.35 g, 13.7 mmol). The reaction mixture was heated at 75° C. for 16 h. After cooling to room temperature, the reaction mixture was poured into water and extracted with ethyl acetate three times. The combined organic extracts were washed with water, brine, dried over sodium sulfate, filtered and concentrated under reduced pressure. The crude product was purified by silica gel column chromatography eluting with 1-20% ethyl acetate in petroleum ether to give the title compound (1.77 g, 32%). MS m/z: 488.2 $[M+1]^+$.

Step 2. 2-(6-Bromo-1-oxo-isoindolin-2-yl)-2-[1-(2-trimethylsilylethoxymethyl)-5,6-dihydro-4H-cyclopenta[c]pyrazol-3-yl]acetic add

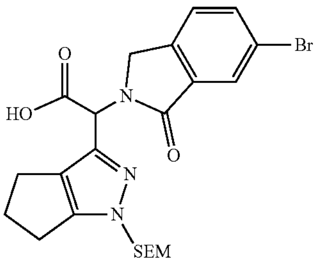 [SMILES: C[Si](C)(C)CCOCn1nc(C(C(=O)O)N2Cc3ccc(Br)cc3C2=O)c2c1CCC2]

To a solution of 2-(6-bromo-1-oxo-isoindolin-2-yl)-2-[1-(2-trimethylsilylethoxymethyl)-5,6-dihydro-4H-cyclopenta[c]pyrazol-3-yl]acetonitrile (0.950 g, 1.94 mmol) in ethanol (10 mL) in an ice bath was added dropwise potassium hydroxide aqueous solution (2 M, 4.85 mL, 9.70 mmol). After stirring at 100° C. for 2 h, the reaction mixture was diluted with water and adjusted to pH 5 by acetic acid. The aqueous phase was extracted with ethyl acetate three times. The combined organic extracts were dried over sodium sulfate, filtered and concentrated under reduced pressure. The crude product was purified by C18 column chromatography eluting with 0-70% ACN/water containing 10 mM ammonium acetate to give the title compound (420 mg, 43%). MS m/z: 507.1 $[M+1]^+$.

Step 3: 2-[1H-Benzimidazol-2-yl-[1-(2-trimethylsilylethoxymethyl)-5,6-dihydro-4H-cyclopenta[c]pyrazol-3-yl]methyl]-6-bromo-isoindolin-1-one

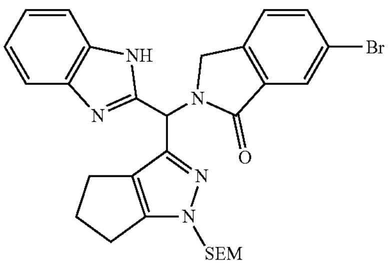 [SMILES: C[Si](C)(C)CCOCn1nc(C(c2nc3ccccc3[nH]2)N2Cc3ccc(Br)cc3C2=O)c2c1CCC2]

To a solution of 2-(6-bromo-1-oxo-isoindolin-2-yl)-2-[1-(2-trimethylsilylethoxymethyl)-5,6-dihydro-4H-cyclopenta[c]pyrazol-3-yl]acetic acid (0,250 g, 0.494 mmol), 1,2-diaminobenzene (0.120 g, 1.11 mmol) and HATU (0.377 g, 0.987 mmol) in DMF (10 mL) was added DIPEA (0,342 mL, 1.97 mmol). After stirring at room temperature for 5 h, sat. sodium chloride was added to the reaction mixture. The resulting solid was collected by filtration and washed with water to give the amide intermediate which was used in the next reaction without further purification. MS m/z: 597.2 $[M+1]^+$.

To the above amide intermediate was added acetic acid (8 mL). After stirring at 80° C. for 1 h, the solvent was removed under reduced pressure. The crude product was purified by C18 column chromatography eluting with 0-100% ACN/water containing 0.1% formic acid to give the title compound (220 mg, 58%). MS m/z: 579.2 $[M+1]^+$.

Step 4. 2-[1H-Benzimidazol-2-yl-[1(2-trimethylsilylethoxymethyl)-5,6-dihydro-4H-cyclopenta[c]pyrazol-3-yl]methyl]-6-[4-[1-methyl-4-piperidyl)phenyl]isoindolin-1-one

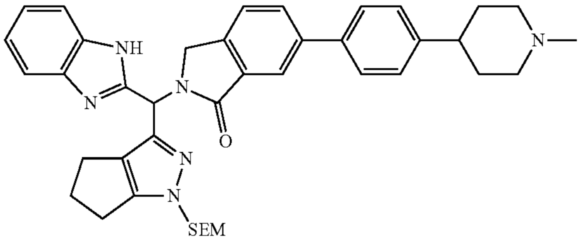 [SMILES: CN1CCC(c2ccc(-c3ccc4c(c3)C(=O)N(C(c3nc5ccccc5[nH]3)c3nn(COCC[Si](C)(C)C)c5c3CCC5)C4)cc2)CC1]

A mixture of 2-[1H-benzimidazol-2-yl-[1-(2-trimethylsilylethoxymethyl)-5,6-dihydro-4H-cyclopenta[c]pyrazol-3-yl]methyl]-6-bromo-isoindolin-1-one (0.100 g, 0.173 mmol), 1-methyl-4-[4-(4,4,5,5-tetramethyl-1,3,2-dioxaborolan-2-yl)phenyl]piperidine (0,060 g, 0.199 mmol), sodium carbonate (0.024 g, 0.222 mmol) in dioxane/water (4.5 mL, 7/2) was degassed with nitrogen twice. [1,1'-Bis(diphenylphosphino)ferrocene]dichloropalladium(II) complex with dichloro-methane (0.028 g, 0.035 mmol) was added and then the reaction was degassed with nitrogen once more. The reaction mixture was heated at 105° C. for 1.5 h. After cooling to room temperature, the reaction mixture was poured into water and extracted with ethyl acetate three times. The combined organic extracts were washed with brine, dried over sodium sulfate, filtered and concentrated under reduced pressure. The crude product was purified by C18 column chromatography eluting with 0-100% ACN/water containing 0.1% formic acid to give the title compound (88 mg, 76%). MS m/z: 673.4 $[M+1]^+$.

Step 5. 2-[1H-Benzimidazol-2-yl(1,4,5,6-tetrahydrocyclopenta[c]pyrazol-3-yl)methyl]-6-[4-(1-methyl-4-piperidyl)phenyl]isoindolin-1-one (Compound 033)

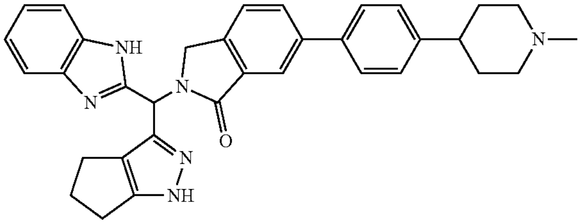 [SMILES: CN1CCC(c2ccc(-c3ccc4c(c3)C(=O)N(C(c3nc5ccccc5[nH]3)c3n[nH]c5c3CCC5)C4)cc2)CC1]

To a solution of 2-[1H-benzimidazol-2-yl-[1-(2-trimethylsilylethoxymethyl)-5,6-dihydro-4H-cyclopenta[c]pyrazol-3-yl]methyl]-6-[4-(1-methyl-4-piperidyl)phenyl]isoindolin-1-one (0.087 g, 0.129 mmol) in water (0.464 mL) was added trifluoroacetic acid (2 mL). After stirring overnight at room temperature, the solvent was removed under reduced pressure. The crude product was purified by C18 column chromatography eluting with 0-100% ACN/water containing 0.1% formic acid to give the title compound (44 mg, 63%). $^1H$ NMR (400 MHz, DMSO-$d_6$) δ: 12.56 (br s, 1H), 8.20 (s, 1H), 7.87-7.98 (m, 2H), 7.64-7.75 (m, 3H), 7.47-7.62 (m, 2H), 7.37 (d, 2H), 7.12-7.24 (m, 2H), 6.85 (s, 1H), 4.92 (d, 1H), 4.35 (d, 1H), 2.98-3.05 (m, 2H), 2.54-2.66 (m, 3H), 2.27-2.38 (m, 5H), 2.14-2.27 (m, 3H), 1.89-2.01 (m, 1H), 1.69-1.86 (m, 4H); MS m/z: 543.4 $[M+1]^+$.

Compound 031 was prepared by a similar method to Example 8 from 2-(6-bromo-1-oxo-isoindolin-2-yl)-2-[1-(2-trimethylsilylethoxymethyl)-5,6-dihydro-4H-cyclopenta[c]pyrazol-3-yl]acetic add and pyridine-2,3-diamine:

| No. | Structure/Name | m/z [M + 1]+ | $^1$H NMR (DMSO-$d_6$) δ |
|---|---|---|---|
| 031 | 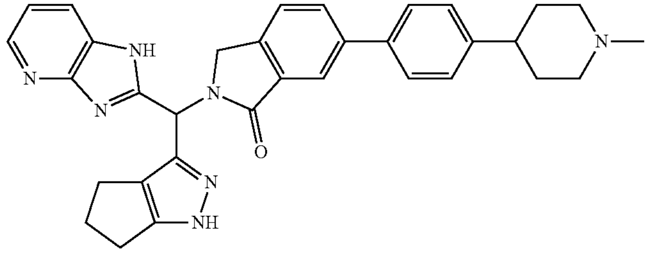 [SMILES: CN1CCC(c2ccc(-c3ccc4c(c3)C(=O)N(C(c3nc5ncccc5[nH]3)c3n[nH]c5c3CCC5)C4)cc2)CC1] 2-[1H-Imidazo[4,5-b]pyridin-2-yl(1,4,5,6-tetrahydrocyclopenta[c]pyrazol-3-yl)methyl]-6-[4-(1-methyl-4-piperidy)phenyl]isoindolin-1-one | 544.4 | 8.30-8.38 (m, 1H), 8.24 (s, 1H), 7.86-7.98 (m, 3H), 7.63-7.74 (m, 3H), 7.36 (d, 2H), 7.18-7.25 (m, 1H), 6.84 (s, 1H), 4.95 (d, 1H), 4.33 (d, 1H), 2.87-2.96 (m, 2H), 2.55-2.67 (m, 2H), 2.17-2.38 (m, 6H), 1.93-2.08 (m, 3H), 1.64-1.85 (m, 5H) |

Example 9: Preparation of 3-((1H-benzo[d]imidazol-2-yl)(5-fluoro-2-hydroxyphenyl)methyl)-6-4-(1-methylpiperidin-4-yl)phenyl)pyrido[3,2-d]pyrimidin-4(3H)-one 2,2,2-trifluoroacetate (Compound 009)

Scheme 8.

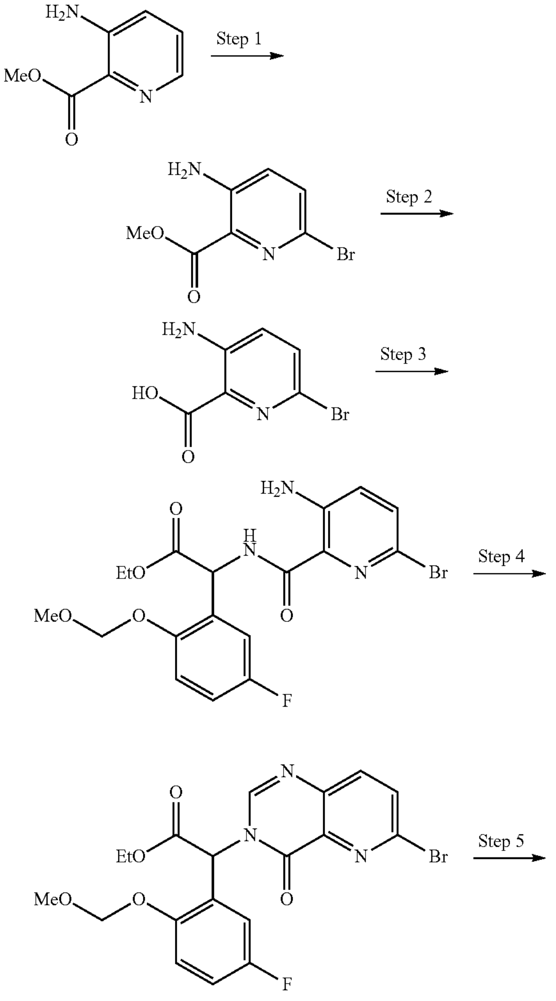

-continued

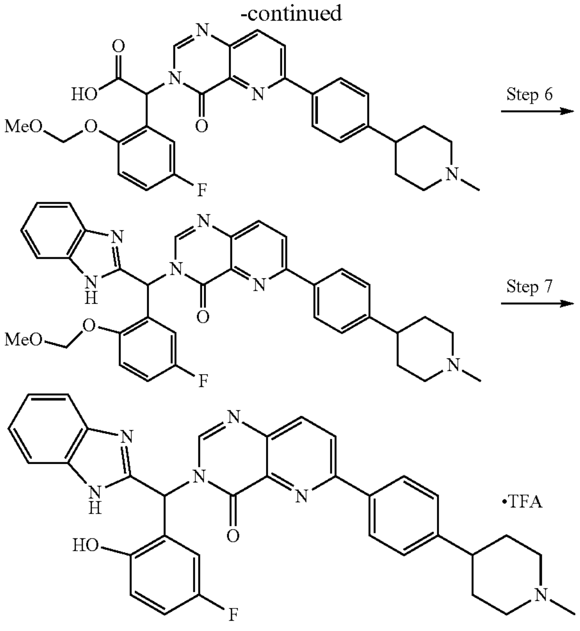

009

Step. 1. Methyl 3-amino-6-bromopicolinate

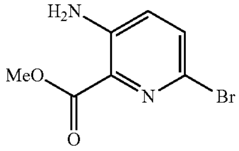 [SMILES: COC(=O)c1nc(Br)ccc1N]

A mixture of methyl 3-aminopicolinate (650 mg, 4.27 mmol) in a solution of $H_2SO_4$ (207 mL, 4 mmol) and water (13 mL) was treated dropwise over one minute with a solution of bromine (200 mL, 4.27 mmol) in acetic acid (800 mL). The reaction mixture was stirred at room temperature for 15 minutes and basified with 10N NaOH to pH 6. The mixture was extracted with EtOAc three times. The combined organic extracts were washed with saturated brine, dried over $Na_2SO_4$, filtered and concentrated under reduced pressure. The residue was purified by silica gel chromatography eluting with 0-60% EtOAc in hexane to give the title compound (600 mg, 61%). $^1$H NMR (500 MHz, DMSO-$d_6$) δ ppm 7.45 (d, 1H) 7.22 (d, 1H) 6.89 (s, 2H) 3.82 (s, 3H); MS m/z: 232.9 $[M+1]^+$.

Step 2. 3-Amino-6-bromopicolinic acid

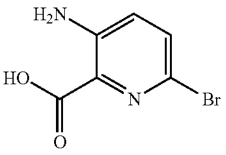 [SMILES: Nc1ccc(Br)nc1C(=O)O]

A mixture of methyl 3-amino-6-bromopicolinate (600 mg, 2.6 mmol), lithium hydroxide monohydrate (600 mg 14.3 mmol) in THF (6 mL), MeOH (1.5 mL) and water (1.5 mL) was stirred at room temperature for 45 minutes. The solvent was removed under reduced pressure. The residue was dissolved in water (20 mL) and treated with 2N HCl to pH 6. The white solid was collected by filtration, washed with cold water, and dried to give the title compound (400 mg, 71%). $^1$H NMR (500 MHz, DMSO-$d_6$) d ppm 7.19 (d, 1H) 7.43 (d, 1H); MS m/z: 218.9 $[M+1]^+$.

Step 3. Ethyl 2-(3-amino-6-bromopicolinamido)-2-(5-fluoro-2-(methoxymethoxy)phenyl)acetate

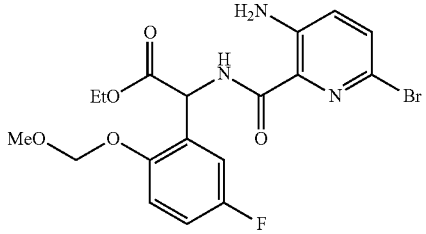 [SMILES: CCOC(=O)C(NC(=O)c1nc(Br)ccc1N)c1cc(F)ccc1OCOC]

A mixture of 3-amino-6-bromopicolinic acid (167 mg, 0.77 mmol), ethyl 2-amino-2-(5-fluoro-2-(methoxymethoxy)phenyl)acetate (237 mg, 0.92 mmol), HATU (585 mg, 1.54 mmol), and DIPEA (401 mL, 2.31 mmol) in degassed DMF (2 mL) was stirred at 60° C. for 1 h. After cooling, the reaction mixture was poured into saturated brine (20 mL) and extracted three times with EtOAc. The combined organic extracts were dried over $Na_2SO_4$, filtered and concentrated under reduced pressure. The residue was purified by silica gel chromatography eluting with 0-55% EtOAc in hexane to give the title compound (315 mg, 90%). MS m/z: 458.0 $[M+1]^+$.

Step 4. Ethyl 2-(6-bromo-4-oxopyrido[3,2-d]pyrimidin-3(4H)-yl)-2-(5-fluoro-2-(methoxymethoxy)-phenyl)acetate

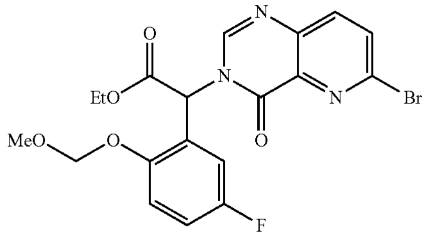 [SMILES: CCOC(=O)C(c1cc(F)ccc1OCOC)n1cnc2ccc(Br)nc2c1=O]

A mixture of ethyl 2-(3-amino-6-bromopicolinamido)-2-(5-fluoro-2-(methoxymethoxy)-phenyl)acetate (315 mg, 0.68 mmol) in triethylorthoformate (4 mL) in a sealed vial was heated in a microwave for 2 h at 210° C. After cooling, excess triethylorthoformate was removed under reduced pressure, and the residue was purified by silica gel chromatography, eluting with 0-65% EtOAc in hexane to give the title compound (310 mg, 98%). $^1$H NMR (500 MHz, DMSO-$d_6$) δ ppm 8.37 (s, 1H) 8.06-8.09 (m, 2H) 7.36 (dd, 1H) 7.25-7.32 (m, 1H) 7.17-7.23 (m, 1H) 6.71 (s, 1H) 5.19-5.25 (m, 2H) 4.27 (q, 2H) 3.29 (s, 3H) 1.19-1.23 (m, 3H); MS m/z: 468.0 $[M+1]^+$.

Step 5. 2-(5-Fluoro-2-(methoxymethoxy)phenyl)-2-(6-(4-(1-methylpiperidin-4-yl)phenyl)-4-oxopyrido[3,2-d]pyrimidin-3(4H)-yl)acetic acid

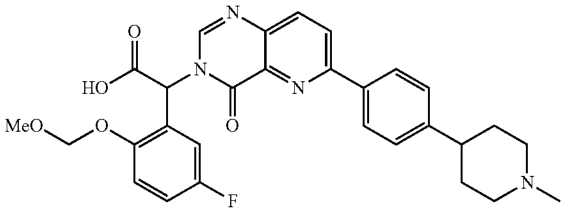 [SMILES: COCOc1ccc(F)cc1C(C(=O)O)n1cnc2ccc(-c3ccc(C4CCN(C)CC4)cc3)nc2c1=O]

A mixture of ethyl 2-(6-bromo-4-oxopyrido[3,2-d]pyrimidin-3(4H)-yl)-2-(5-fluoro-2-(methoxymethoxy)phenyl) acetate (310 mg, 0.73 mmol), 1-methyl-4-(4-(4,4,5,5-tetramethyl-1,3,2-dioxaborolan-2-yl)phenyl)piperidine (265 mg, 0.88 mmol), Pd(dppf)$Cl_2$. DCM (119 mg, 0.146 mmol) and sodium carbonate (232 mg, 2.19 mmol) in dioxane: water (4:1, 7.5 mL) was heated at 100° C. for 24 h under nitrogen. After cooling, the reaction mixture was filtered, and the filtrate was concentrated and purified by reverse phase HPLC, eluting with 0-80% ACN/water (0.035% TFA modifier) to give the title compound (151 mg, 39%). $^1$H NMR (500 MHz, DMSO-$d_6$) δ ppm 9.36 (br s, 1H) 8.43 (d, 1H) 8.33 (d, 1H) 8.20 (m, 3H) 7.44 (d, 2H) 7.41 (dd, 1H) 7.24-7.33 (m, 1H) 7.19 (dd, 1H) 6.67 (s, 1H) 5.25 (d, 1H) 5.22 (d, 1H) 3.56 (d, 2H) 3.28 (s, 3H) 3.11 (m, 2H) 2.91 (m, 1H) 2.84 (d, 3H) 2.03-2.13 (m, 2H) 1.81-1.96 (m, 2H). MS m/z: 533 $[M+1]^+$.

Step 6, 3-((1H-Benzo[d]imidazol-2-0(5-fluoro-2-(methoxymethoxy)phenyl)methyl)-6-(4-(1-methylpiperidin-4-yl)phenyl)pyrido[3,2-d]pyrimidin-4(3H)-one

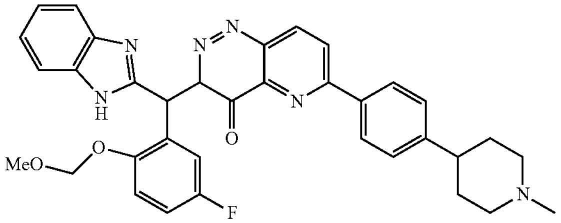 [SMILES: COCOc1ccc(F)cc1C(c1nc2ccccc2[nH]1)C1N=Nc2ccc(-c3ccc(C4CCN(C)CC4)cc3)nc2C1=O]

A mixture of 2-(5-fluoro-2-(methoxymethoxy)phenyl)-2-(6-(4-(1-methylpiperidin-4-yl)phenyl)-4-oxopyrido[3,2-d]pyrimidin-3(4H)-yl)acetic acid (75 mg, 0.14 mmol), ortho phenylenediamine (31 mg, 0.28 mmol), HATU (106 mg, 0.28 mmol), and DIPEA (156 mL, 0.90 mmol) in degassed DMF (3 mL) was stirred at 60° C. for 1.5 h. The reaction mixture was purified by reverse phase HPLC, eluting with 0-80% AC-NI/water (0.035% TFA modifier) to give the amide intermediate. MS m/z: 623.7 $[M+1]^+$.

The above amide intermediate was dissolved in acetic acid (5 mL) and heated at 110° C. for 1 h. Excess acetic acid was removed under reduced pressure to give the title compound, used without further purification. MS m/z: 605.4 $[M+1]^+$.

Step 7. 3-((1H-Benzo[d]imidazol-2-yl)(5-fluoro-2-hydroxyphenyl)methyl)-6-(4-(1-methylpiperidin-4-yl)phenyl)pyrido[3,2-d]pyrimidin-4(3H)-one 2,2,2-trifluoroacetate (Compound 009)

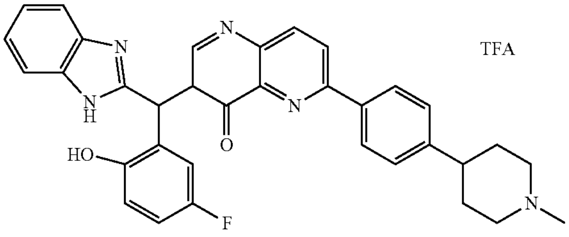 [SMILES: CN1CCC(c2ccc(-c3ccc4c(n3)C(=O)C(C(c3nc5ccccc5[nH]3)c3cc(F)ccc3O)C=N4)cc2)CC1]

TFA

The above material of 3-((1H-benzo[d]imidazol-2-yl)(5-fluoro-2-(methoxymethoxy)-phenyl)methyl)-6-(4-(1-methylpiperidin-4-yl)phenyl)pyrido[3,2-d]pyrimidin-4(3H)-one was treated with 5 mL of 1:1 DCM/TFA for 6 h. Solvents were removed under reduced pressure, and the residue was purified by reverse phase HPLC, eluting with 0-80% ACN/water (0.035% TFA modifier) to give the title compound (14 mg, 15%), $^1$H NMR (500 MHz, DMSO-$d_6$) δ ppm 10.20 (s, 1H) 9.30 (br s, 1H) 8.46 (d, 1H) 8.31 (s, 1H) 8.23 (d, 1H) 8.21 (d, 2H) 7.58 (m, 3H) 7.43 (d, 2H) 7.24 (m, 2H) 7.17 (m, 1H) 6.94 (dd, 1H) 6.80 (m, 1H) 3.55 (d, 2H) 3.10 (m, 2H) 2.90 (m, 1H) 2.85 (d, 3H) 2.08 (m, 2H) 1.87 (m, 2H); MS m/z: 561.3 $[M+1]^+$.

The following compounds were prepared by a similar method to Example 9 from the corresponding amine and add starting materials:

| No. | Structure/Name | m/z $[M + 1]^+$ | $^1$H NMR (DMSO-$d_6$) δ | Starting materials |
|---|---|---|---|---|
| 008 | 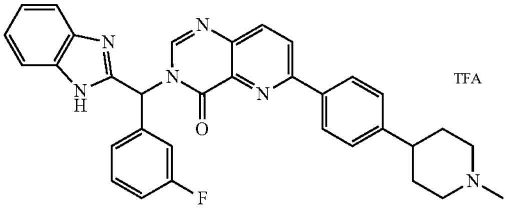 [SMILES: CN1CCC(c2ccc(-c3ccc4ncn(C(c5cccc(F)c5)c5nc6ccccc6[nH]5)c(=O)c4n3)cc2)CC1] TFA<br>3-((1H-Benzo[d]imidazol-2-yl)(3-fluorophenyl)methyl)-6-(4-(1-methylpiperidin-4-yl)phenyl)-pyrido[3,2-d]pyrimidin-4(3H)-one 2,2,2-trifluoroacetate | 545.3 | 9.29 (br s, 1H) 8.45-8.47 (m, 2H) 8.21-8.24 (m, 3H) 7.60 (m, 2H) 7.58 (s, 1H) 7.50-7.53 (m, 1H) 7.43 (d, 2H) 7.39 (d, 1H) 7.27-7.31 (m, 2H) 7.25 (m, 2H) 3.55 (d, 2H) 3.07-3.14 (m, 2H) 2.89-2.95 (m, 1H) 2.84 (d, 3H) 2.08 (d, 2H) 1.82-1.91 (m, 2H) | 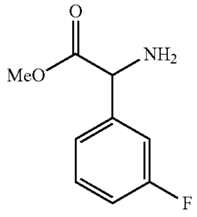 [SMILES: COC(=O)C(N)c1cccc(F)c1]<br>and<br>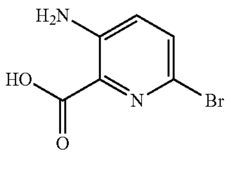 [SMILES: Nc1ccc(Br)nc1C(=O)O] |

-continued

| No. | Structure/Name | m/z [M + 1]+ | $^1$H NMR (DMSO-$d_6$) δ | Starting materials |
|---|---|---|---|---|
| 004 | 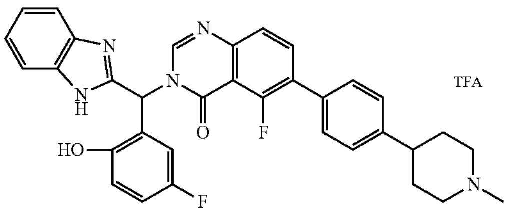 [SMILES: CN1CCC(c2ccc(-c3ccc4ncn(C(c5nc6ccccc6[nH]5)c5cc(F)ccc5O)c(=O)c4c3F)cc2)CC1] TFA<br>3-((1H-Benzo[d]imidazol-2-yl)(5-fluoro-2-hydroxyphenyl)methyl)-5-fluoro-6-(4-(1-methylpiperidin-4-yl)phenyl)quinazolin-4(3H)-one 2,2,2-trifluoroacetate | 578.2 | 10.19 (s, 1H) 9.29 (br, s, 1H) 8.22 (s, 1H) 7.97 (m, 1H) 7.62 (d, 1H) 7.58 (m, 4H) 7.50 (s, 1H) 7.39 (d, 2H) 7.24 (dd, 2H) 7.16 (m, 1H) 6.94 (dd, 1H) 6.75 (dd, 1H) 3.54 (d, 2H) 3.09 (m, 2H) 2.87 (m, 1H) 2.82 (d, 3H) 2.07 (m, 2H) 1.85 (m, 2H) | 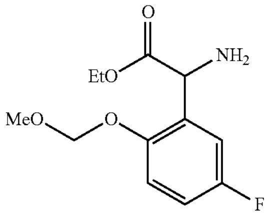 [SMILES: CCOC(=O)C(N)c1cc(F)ccc1OCOC]<br>and<br>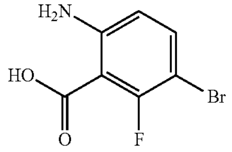 [SMILES: Nc1ccc(Br)c(F)c1C(=O)O] |
| 005 | 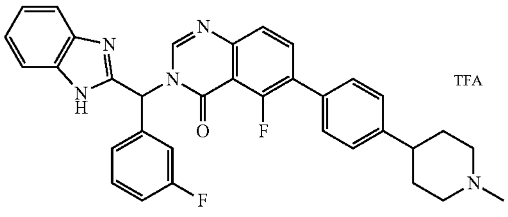 [SMILES: CN1CCC(c2ccc(-c3ccc4ncn(C(c5cccc(F)c5)c5nc6ccccc6[nH]5)c(=O)c4c3F)cc2)CC1] TFA<br>3-((1H-Benzo[d]imidazol-2-yl)(3-fluorophenyl)methyl)-5-fluoro-6-(4-(1-methylpiperidin-4-yl)phenyl)-quinazolin-4(3H)-one 2,2,2-trifluoroacetate | 562.3 | 9.43 (br s, 1H) 8.31 (s, 1H) 7.90 (m, 1H) 7.51-7.56 (m, 5H) 7.42-7.47 (m, 2H) 7.32 (d, 2H) 7.28 (d, 1H) 7.23 (m, 1H) 7.18 (m, 3H) 3.48 (d, 2H) 2.99-3.06 (m, 2H) 2.78-2.83 (m, 1H) 2.7 7(d, 3H) 2.00 (d, 2H) 1.76-1.85 (m, 2H) | 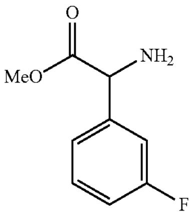 [SMILES: COC(=O)C(N)c1cccc(F)c1]<br>and<br>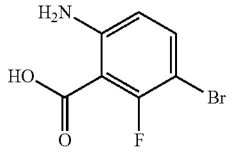 [SMILES: Nc1ccc(Br)c(F)c1C(=O)O] |

The following compounds were prepared by a similar method to Example 9 from ethyl 2-amino-2-(5-fluoro-2-(methoxymethoxy)phenyl)acetate and the corresponding acid starting materials:

| No. | Structure/Name | m/z [M + 1]+ | $^1$H NMR (DMSO-$d_6$) δ | Starting materials |
|---|---|---|---|---|
| 075 | 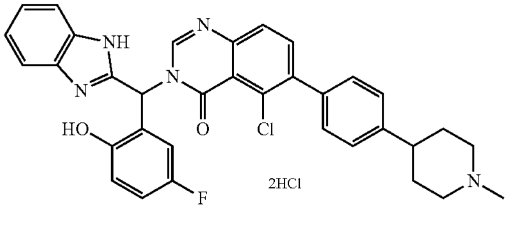 [SMILES: CN1CCC(c2ccc(-c3ccc4ncn(C(c5nc6ccccc6[nH]5)c5cc(F)ccc5O)c(=O)c4c3Cl)cc2)CC1] 2HCl<br>3-[1H-benzimidazol-2-yl-(5-fluoro-2-hydroxy-phenyl)methyl]-5-chloro-6-[4-(1-methyl-4-piperidy)phenyl]-quinazolin-4-one; dihydrochloride | 594.3 | 11.00 (br s, 1H), 10.77 (br s, 1H), 8.35 (s, 1H), 7.74-7.85 (m, 4H), 7.50-7.57 (m, 3H), 7.32-7.47 (m, 4H), 7.17-7.28 (m, 2H), 7.09-7.15 (m, 1H), 3.48 (d, 2H), 2.97-3.21 (m, 2H), 2.84-2.91 (m, 1H), 2.75 (d, 3H), 1.96-2.19 (m, 4H) | 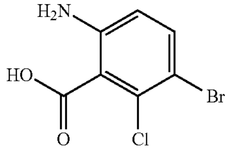 [SMILES: Nc1ccc(Br)c(Cl)c1C(=O)O] |

-continued

| No. | Structure/Name | m/z [M + 1]+ | $^1H$ NMR (DMSO-$d_6$) δ | Starting materials |
|---|---|---|---|---|
| 076 | 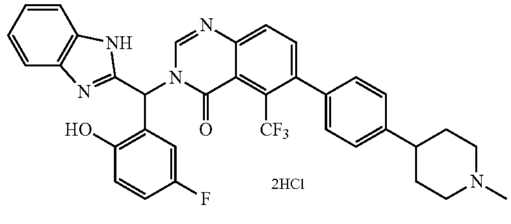 [SMILES: CN1CCC(c2ccc(-c3ccc4ncn(C(c5nc6ccccc6[nH]5)c5cc(F)ccc5O)c(=O)c4c3C(F)(F)F)cc2)CC1] 3-[1H-benzimidazol-2-yl-(5-fluoro-2-hydroxy-phenyl)methyl]-6-[4-(1-methyl-4-piperidyl)phenyl]-5-(trifluoromethyl)quinazolin-4-one; dihydrochloride | 628.1 | 10.72 (br s, 1H), 10.59 (br s, 1H), 8.42 (s, 1H), 8.01 (d, 1H), 7.86 (d, 1H), 7.66-7.78 (m, 2H), 7.56 (s, 1H), 7.42-7.50 (m, 2H), 7.35-7.41 (m, 4H), 7.16-7.28 (m, 1H), 6.99-7.13 (m, 2H), 3.51 (d, 2H), 3.02-3.16 (m, 2H), 2.84-2.96 (m, 1H), 2.78 (d, 3H), 1.87-2.18 (m, 4H) | 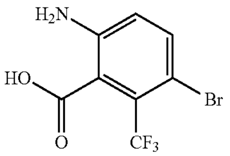 |

Compound 077: 3-[1H-benzimidazol-2-yl-(5-fluoro-2-hydroxy-phenyl)methyl]-5-methoxy-6-[4-(1-methyl-4-piperidyl)phenyl]quinazolin-4-one;dihydrochloride Scheme 9

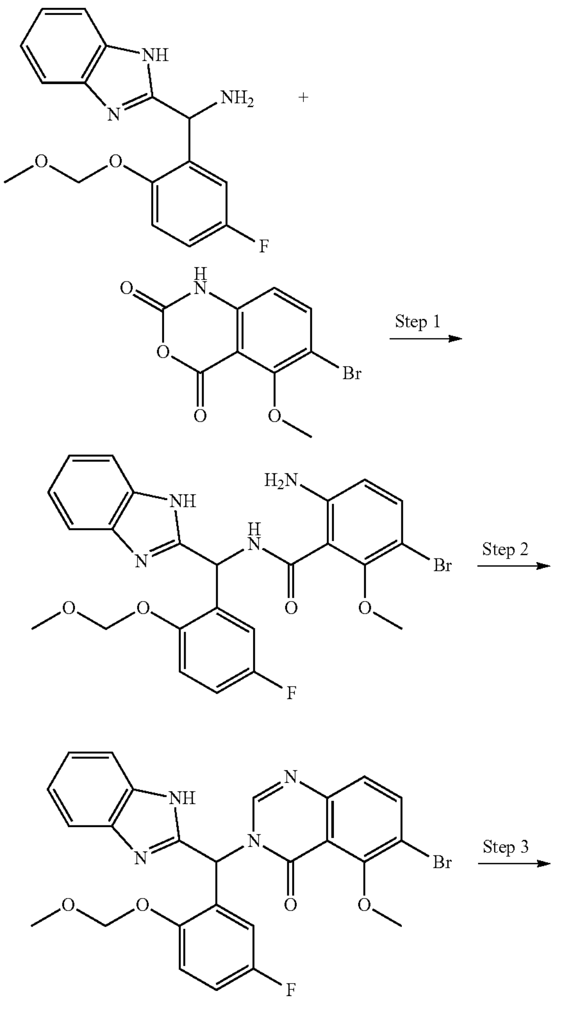

-continued

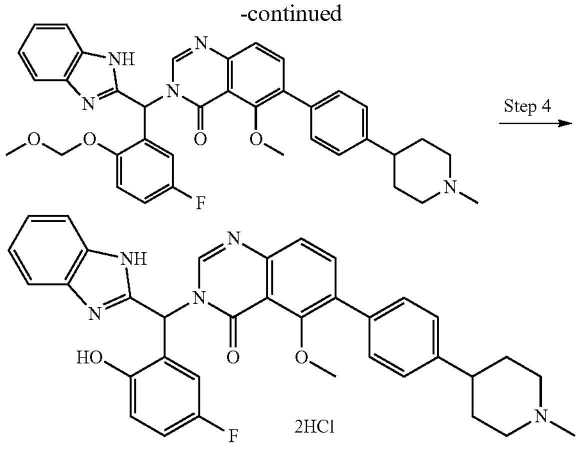

Step 1. 6-amino-N-[1H-benzimidazol-2-yl-[5-fluoro-2-(methoxymethoxy)phenyl]methyl]-3-bromo-2-methoxy-benzamide

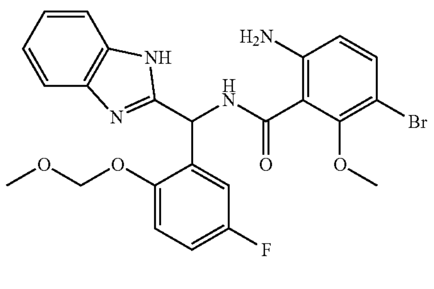 [SMILES: COCOc1ccc(F)cc1C(NC(=O)c1c(N)ccc(Br)c1OC)c1nc2ccccc2[nH]1]

To a solution of 6-bromo-5-methoxy-2,4-dihydro-1H-3,1-benzoxazine-2,4-dione (0.350 g, 1.28 mmol) in THF (30 mL) was added ethyl 2-amino-2-(5-fluoro-2-(methoxymethoxy)phenyl)-acetate (0.385 g, 1.28 mmol). After stirring at 70° C. for 12 h, the reaction mixture was concentrated under reduced pressure, and purified by reverse phase HPLC eluting with 0-100% ACN/water (0.035% TFA modifier) to give the title compound (0.21 g, 31%). $^1H$ NMR (DMSO-$d_6$) δ: 12.28-12.38 (m, 1H), 9.34-9.45 (m, 1H), 7.52-7.60 (m, 1H), 7.39-7.48 (m, 1H), 7.26-7.32 (m, 2H), 7.13-7.20 (m, 4H), 6.83 (d, 1H), 6.46 (d, 1H), 6.11 (s, 2H), 5.24 (d, 1H), 5.17 (d, 1H), 3.62 (s, 3H), 3.26 (s, 3H); MS m/z: 529.1 [M+1]$^+$.

Step 2. 3-[1H-benzimidazol-2-yl-[5-fluoro-2-(methoxymethoxy)phenyl]methyl]-6-bromo-5-methoxy-quinazolin-4-one

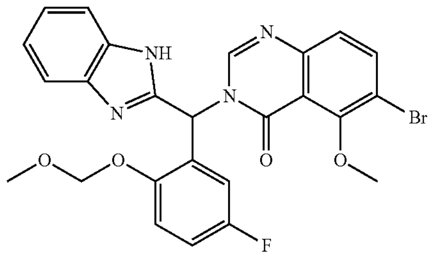 [SMILES: COCOc1ccc(F)cc1C(c1nc2ccccc2[nH]1)n1cnc2ccc(Br)c(OC)c2c1=O]

A mixture of 6-amino-N-[1H-benzimidazol-2-yl-[5-fluoro-2-(methoxymethoxy)phenyl]-methyl]-3-bromo-2-methoxy-benzamide (0.200 g, 0.377 mmol) in triethylorthoformate (20 mL) was heated at 210° C. for 2 h. After cooling to room temperature, the reaction mixture was concentrated under reduced pressure, and purified by reverse phase HPLC eluting with 0-100% ACN/water (0.035% TFA modifier) to give the title compound (0.14 g, 69%). $^1$H NMR (DMSO-d6) δ: 12.88 (br s, 1H), 8.18-8.32 (m, 1H), 7.94-8.14 (m, 1H), 7.59-7.75 (m, 2H), 7.47-7.56 (m, 1H), 7.38-7.47 (m, 1H), 7.23 (d, 4H), 6.76-6.96 (m, 1H), 5.10-5.26 (m, 2H), 3.82 (s, 3H), 3.13 (s, 3H); MS m/z: 539.1 [M+1]$^+$.

Step 3. 3-[1H-benzimidazol-2-yl-[5-fluoro-2-(methoxymethoxy)phenyl]methyl]-5-methoxy-6-[4-(1-methyl-4-piperidyl)phenyl]quinazolin-4-one

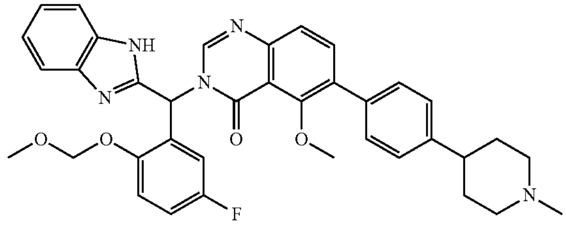

A mixture of 3-[1H-benzimidazol-2-yl-[5-fluoro-2-(methoxymethoxy)phenyl]methyl]-6-bromo-5-methoxy-quinazolin-4-one (0.100 g, 0.185 mmol), 1-methyl-4-(4-(4,4,5,5-tetramethyl-1,3,2-dioxaborolan-2-yl)phenyl) piperidine (0.056 g, 0.185 mmol), Pd(dppf)$Cl_2$ (0,014 g, 0.019 mmol) and potassium carbonate (0.050 g, 0.370 mmol) in dioxane:DMF:water (1:1:1, 10 mL) was heated at 100° C. for 12 h under nitrogen. After cooling, the reaction mixture was filtered, and the filtrate was concentrated under reduced pressure, and purified by reverse phase HPLC eluting with 0-100% ACN/water (0.035% TFA modifier) to give the title compound (0.085 g, 73%). $^1$H NMR (400 MHz, methanol-$d_4$) δ: 8.27-8.37 (m, 2H), 8.11-8.19 (m, 1H), 7.81-7.90 (m, 1H), 7.70-7.74 (m, 1H), 7.59-7.64 (m, 4H), 7.35-7.43 (m, 2H), 7.28-7.31 (m, 2H), 7.19-7.25 (m, 1H), 6.82-6.88 (m, 1H), 5.17-5.25 (m, 2H), 3.60-3.68 (m, 2H), 3.53 (s, 3H), 3.11-3.25 (m, 5H), 2.93-2.97 (m, 4H), 1.98-2.24 (m, 4H); MS m/z: 634.5 [M+1]$^+$.

Step 4. 3-[1H-benzimidazol-2-yl-(5-fluoro-2-hydroxy-phenyl)methyl]-5-methoxy-6-[4-(1-methyl-4-piperidyl)phenyl]quinazolin-4-one;dihydrochloride

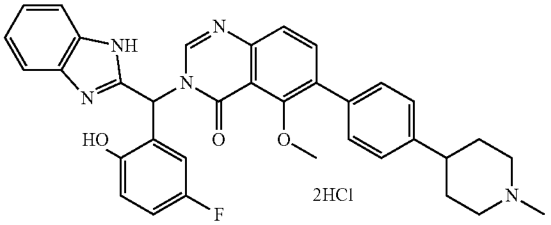 [SMILES: COc1c(-c2ccc(C3CCN(C)CC3)cc2)ccc2ncn(C(c3nc4ccccc4[nH]3)c3cc(F)ccc3O)c(=O)c12]

To a solution of 3-[1H-benzimidazol-2-yl-[5-fluoro-2-(methoxymethoxy)phenyl]methyl]-5-methoxy-6-[4-(1-methyl-4-piperidyl)phenyl]quinazolin-4-one (0.075 g, 0,118 mmol) in dichloromethane (10 mL) was added HO in methanol (4 M, 0.590 mL, 2.36 mmol). After stirring 12 h at room temperature, the solvent was removed under reduced pressure. The crude product was purified by reverse phase HPLC eluting with 0-100% ACN/water (0.05% HCl modifier) to give the title compound (0,026 g, 37%). $^1$H NMR (400 MHz, methanol-$d_4$) δ: 8.41 (5, 1H), 7.92 (d, 1H), 7.73-7.82 (m, 2H), 7.52-7.69 (m, 6H), 7.37-7.45 (m, 2H), 7.21-7.35 (m, 2H), 6.99-7.07 (m, 1H), 3.60-3.68 (m, 2H), 3.53 (s, 3H), 3.15-3.26 (m, 2H), 2.89-3.05 (m, 4H), 1.98-2.20 (m, 4H); MS m/z: 590.7 [M+1]$^+$.

Compound 078: 2-[1H-benzimidazol-2-yl-(5-fluoro-2-hydroxy-phenyl)methyl]-6-[4-(1-methyl-4-piperidyl)phenyl]isoindoline-1-thione;dihydrochloride Scheme 10

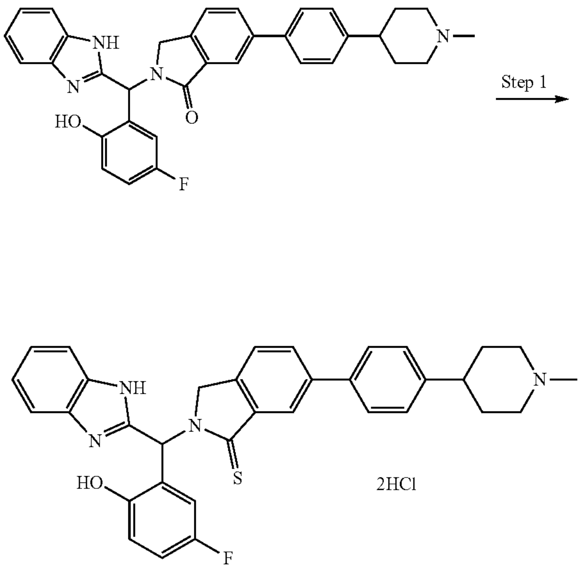

Step 1. 2-[1H-benzimidazol-2-yl-(5-fluoro-2-hydroxy-phenyl)methyl]-6-[4-(1-methyl-4-piperidyl)phenyl]isoindoline-1-thione;dihydrochloride

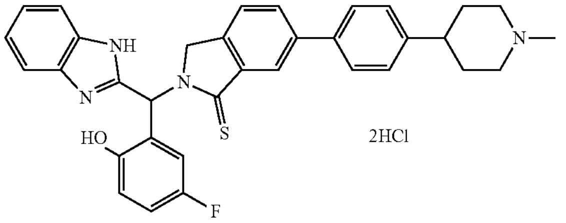 [SMILES: CN1CCC(c2ccc(-c3ccc4c(c3)C(=S)N(C(c3nc5ccccc5[nH]3)c3cc(F)ccc3O)C4)cc2)CC1]

To a solution of 2-[1H-benzimidazol-2-yl-(5-fluoro-2-hydroxy-phenyl)methyl]-6-[4-(1-methyl-4-piperidyl)phenyl]isoindolin-1-one (1.00 g, 1.82 mmol) in toluene (20 mL) was added Lawesson reagent (3.68 g, 9.10 mmol). After stirring at 120° C. for 72 h, the solvent was removed under reduced pressure. The crude product was purified by reverse phase HPLC eluting with 0-100% ACN/water (0.05% HCl modifier) to give the title compound (0.026 g, 3%). $^{1}$H NMR (DMSO-$d_6$) δ: 10.33-10.99 (m, 2H), 7.96-8.21 (m, 2H), 7.63-7.90 (m, 6H), 7.36-7.54 (m, 4H), 7.14-7.24 (m, 1H), 6.92-7.16 (m, 2H), 5.08-5.26 (m, 1H), 4.40-4.57 (m, 1H), 3.00-3.14 (m, 3H), 2.86-2.98 (m, 2H), 2.80 (s, 3H), 1.96-2.19 (m, 4H); MS m/z: 563.1 [M+1]$^+$.

Compounds 083 and 084: Preparation of 2-[(R)-1H-benzimidazol-2-yl-(5-fluoro-2-hydroxy-phenyl)methyl]-6-[4-(1-methyl-4-piperidyl)phenyl]isoindoline-1-thione and 2-[(S)-1H-benzimidazol-2-yl-(5-fluoro-2-hydroxy-phenyl)methyl]-6-[4-(1-methyl-4-piperidyl)phenyl]isoindoline-1-thione

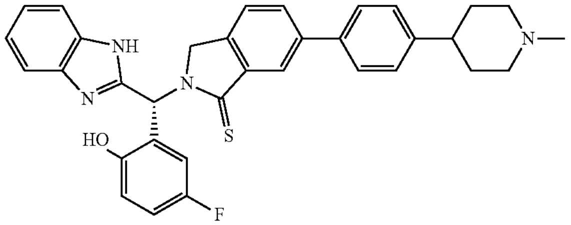

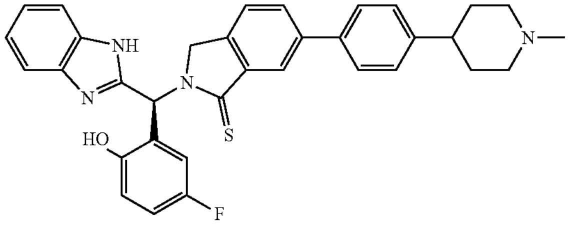

2-[1H-benzimidazol-2-yl-(5-fluoro-2-hydroxy-phenyl)methyl]-6-[4-(1-methyl-4-piperidyl)phenyl]isoindoline-1-thione;dihydrochloride (0.013 g, 0.020 mmol) was purified by prep SFC with Phenomenex Lux Cellulose-4 column eluting with 45% (0.3% TEA in MeOH)/55% CO2 at 10 MPa to separate enantiomers. Absolute configuration of the chiral center for each isolated enantiomer is unknown. First eluting peak (083) (4 mg, 31% yield, 100:0 er); $[\alpha]^{20}_{D}$ −88.9 (c=0.18, MeOH); $^{1}$H NMR (DMSO-$d_6$) δ: 12.74 (br s, 1H), 10.06 (br s, 1H), 8.06 (s, 1H), 7.93 (d, 1H), 7.73 (d, 1H), 7.45-7.69 (m, 5H), 7.39 (d, 2H), 7.08-7.26 (m, 3H), 6.88-6.98 (m, 1H), 6.62-6.71 (m, 1H), 5.08-5.20 (m, 1H), 4.38-4.49 (m, 1H), 2.85-2.94 (m, 2H), 2.53-2.57 (m, 1H), 2.21 (s, 3H), 1.94-2.06 (m, 2H), 1.66-1.83 (m, 4H); MS m/z: 563.3 [M+1]$^+$. Second eluting peak (084) (4 mg, 31% yield, 99:1 er): $[\alpha]^{20}_{D}$ +56.0 (c=0.25, MeOH); $^{1}$H NMR (DMSO-$d_6$) δ: 12.74 (br s, 1H), 10.08 (br s, 1H), 3.06 (s, 1H), 7.93 (d, 1H), 7.73 (d, 1H), 7.44-7.69 (m, 5H), 7.39 (d, 2H), 7.08-7.24 (m, 3H), 6.89-7.00 (m, 1H), 6.60-6.71 (m, 1H), 5.07-5.20 (m, 1H), 4.37-4.51 (m, 1H), 2.84-2.95 (m, 2H), 2.53-2.58 (m, 1H), 2.21 (s, 3H), 1.93-2.06 (m, 2H), 1.64-1.84 (m, 4H)); MS m/z: 563.2 [M+1]$^+$.

Compound 085: 2-[(5-fluoro-2-hydroxy-phenyl)-(4-methyl-1H-imidazol-2-yl)methyl]-6-[4-(1-methyl-4-piperidyl)phenyl]isoindolin-1-one Scheme 11

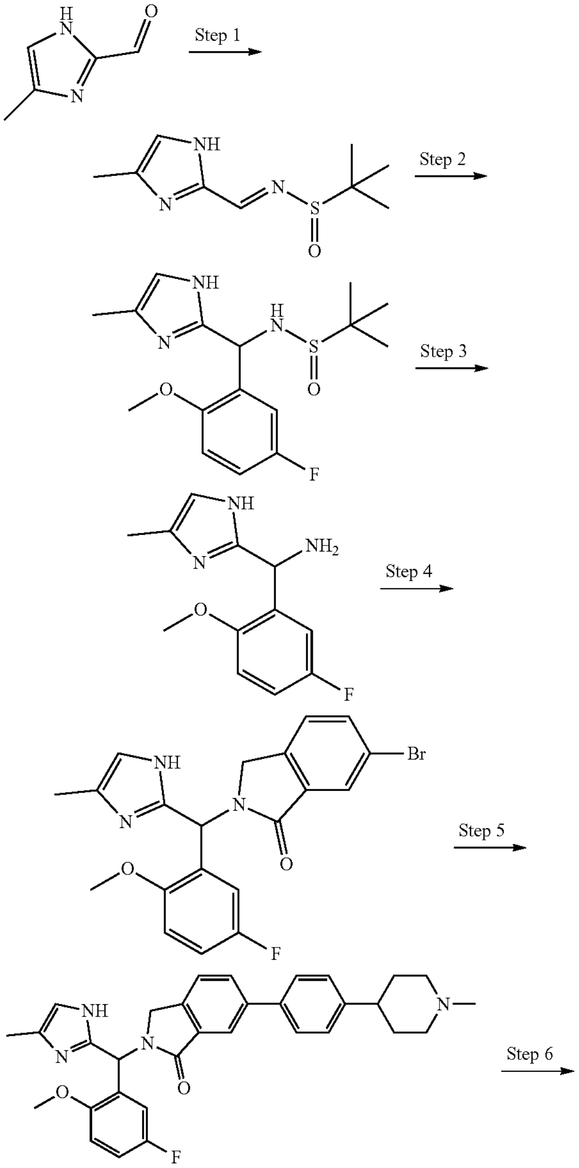

-continued

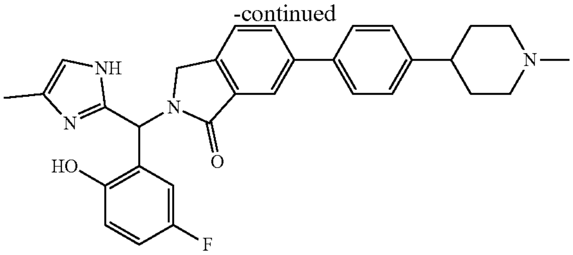

Step 1. 2-methyl-N-[(4-methyl-1H-imidazol-2-yl) methylene]propane-2-sulfinamide

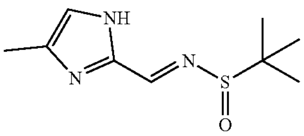

To a solution of 4-methyl-1H-imidazole-2-carboxaldehyde (5.00 g, 45.4 mmol) and 2-methylpropane-2-sulfinamide (8.25 g, 68.1 mmol) in THF (80 mL) was added tetraethyl orthotitanate (15.5 g, 68.1 mmol). After stirring at 75 CC for 16 h, the reaction mixture was quenched by water and extracted with ethyl acetate three times. The combined organic extracts were washed with brine, dried over sodium sulfate, filtered and concentrated under reduced pressure. The crude product was purified by silica gel column chromatography eluting with 0-100% ethyl acetate in petroleum ether to give the title compound (3 g, 31%). $^1$H NMR (400 MHz, $CDCl_3$) δ: 10.13-10.62 (m, 1H), 8.41 (s, 1H), 6.76-7.04 (m, 1H), 2.19-2.45 (m, 3H), 1.09-1.25 (m, 9H); MS m/z: 214.2 [M+1].

Step 2. N-[(5-fluoro-2-methoxy-phenyl)-(4-methyl-1H-imidazol-2-yl)methyl]-2-methyl-propane-2-sulfinamide

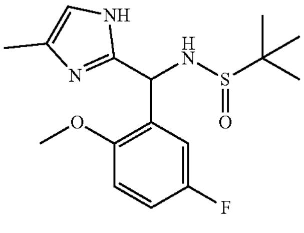 [SMILES: COc1ccc(F)cc1C(NS(=O)C(C)(C)C)c1nc(C)c[nH]1]

To a solution of 2-methyl-N-[(4-methyl-1H-imidazol-2-yl)methylene]propane-2-sulfinamide (2.30 g, 10.7 mmol) in THF (50 mL) was added dropwise a solution of 5-fluoro-2-methoxyphenylmagnesium bromide in THF (0.5 M, 64.0 mL, 32.0 mmol) at −78° C. After stirring at room temperature for 16 h, the reaction mixture was poured into sat. ammonium chloride solution and extracted with ethyl acetate three times. The combined organic extracts were washed with brine, dried over sodium sulfate, filtered and concentrated under reduced pressure. The crude product was purified by silica gel column chromatography eluting with 0-10% methanol in ethyl acetate to give the title compound (0.5 g, 14%). MS m/z: 340.1 $[M+1]^+$.

Step 3. (5-fluoro-2-methoxy-phenyl)-(4-methyl-1H-imidazol-2-yl)methanamine

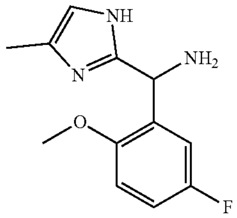 [SMILES: COc1ccc(F)cc1C(N)c1nc(C)c[nH]1]

To a solution of N-[(5-fluoro-2-methoxy-phenyl)-(4-methyl-1H-imidazol-2-yl)methyl]-2-methyl-propane-2-sulfinamide (0.560 g, 1.64 mmol) in methanol (10 mL) was added HCl in dioxane (4 M, 1.23 mL, 4.92 mmol) at 0 After stirring at room temperature for 16 h, the solvent was removed under reduced pressure to give the title compound (0.385 g, quant.) which was used in the next reaction without further purification. MS m/z: 236.0 $[M+1]^+$.

Step 4. 6-bromo-2-[(5-fluoro-2-methoxy-phenyl)-(4-methyl-1H-imidazol-2-yl)methyl]isoindolin-1-one

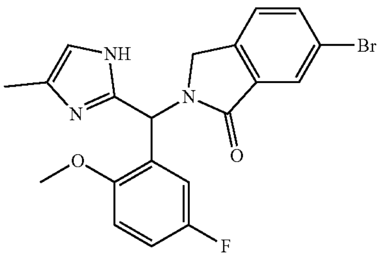 [SMILES: COc1ccc(F)cc1C(c1nc(C)c[nH]1)N1Cc2ccc(Br)cc2C1=O]

To a solution of (5-fluoro-2-methoxy-phenyl)-(4-methyl-1H-imidazol-2-yl)methanamine (0.380 g, 1.61 mmol) in DMF (5 mL) was added DIPEA (1.31 mL, 8.04 mmol). The reaction mixture was stirred at room temperature for 5 min before methyl 5-bromo-2-(bromomethyl)-benzoate (0.495 g, 1.61 mmol) was added. The reaction mixture was heated at 90° C. for 16 h. After cooling to room temperature, the reaction mixture was poured into water and extracted with ethyl acetate three times. The combined organic extracts were washed with water, brine, dried over sodium sulfate, filtered and concentrated under reduced pressure. The crude product was purified by silica gel column chromatography eluting with 0-100% ethyl acetate in petroleum ether to give the title compound (0.28 g, 40%). $^1$H NMR (DMSO-$d_6$) δ: 11.76-12.10 (m, 1H), 7.75-7.84 (m, 2H), 7.50-7.60 (m, 1H), 7.17-7.26 (m, 1H), 7.02-7.13 (m, 1H), 6.88-6.96 (m, 1H), 6.74-6.83 (m, 1H), 6.56 (s, 1H), 4.64-4.75 (m, 1H), 3.96-4.08 (m, 1H), 3.72 (d, 3H), 2.10 (d, 3H).

Step 5. 2-[(5-fluoro-2-methoxy-phenyl)-(4-methyl-1H-imidazol-2-yl)methyl]-6-[4-(1-methyl-4-piperidyl)phenyl]isoindolin-1-one

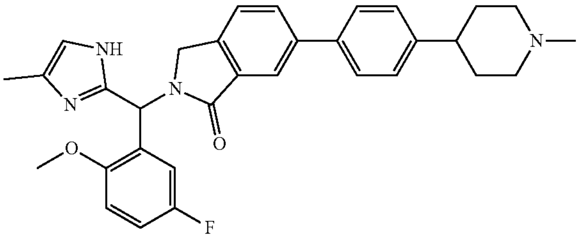

A mixture of 6-bromo-2-[(5-fluoro-2-methoxy-phenyl)-(4-methyl-1H-imidazol-2-yl)methyl]isoindolin-1-one (0.280 g, 0.650 mmol), 1-methyl-4-(4-(4,4,5,5-tetramethyl-1,3,2-dioxaborolan-2-yl)phenyl)piperidine (0.293 g, 0.975 mmol), Pd(dppf)$Cl_2$ (0.024 g, 0,033 mmol) and potassium carbonate (0.271 g, 1.95 mmol) in dioxane:water (9:1, 5 mL) was heated at 100° C. for 16 h under nitrogen. After cooling, the reaction mixture was filtered, and the filtrate was concentrated under reduced pressure, and purified by reverse phase HPLC eluting with 0-100% ACN/water ACN/water (0.05% HCl modifier) to give the title compound (0.2 g, 59%). MS m/z: 525.3 $[M+1]^+$.

Step 6. 2-[(5-fluoro-2-hydroxy-phenyl)-(4-methyl-1H-imidazol-2-yl)methyl]-6-[4-(1-methyl-4-piperidyl)phenyl]isoindolin-1-one

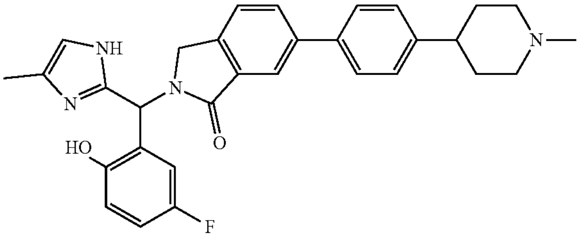

To a solution of 2-[(5-fluoro-2-methoxy-phenyl)-(4-methyl-1H-imidazol-2-yl)methyl]-6-[4-(1-methyl-4-piperidyl)phenyl]isoindolin-1-one (0.150 g, 0.285 mmol) in dichloromethane (15 mL) at 0° C. was added boron tribromide (0.713 g, 2.85 mmol). After stirring at room temperature for 2 h, the reaction mixture was diluted with dichloromethane and poured into ice-water. The aqueous phase was extracted with dichloromethane three times. The combined organic extracts were washed with brine, dried over sodium sulfate, filtered and concentrated under reduced pressure. The crude product was purified by reverse phase HPLC eluting with 0-100% ACM/water containing 10 mM ammonium acetate to give the title compound (0.068 g, 47%). NMR (400 MHz, DMSO-$d_6$) δ: 11.81-12.07 (m, 1H), 10.05 (br s, 1H), 7.80-7.95 (m, 2H), 7.59-7.6 (m, 3H), 7.35 (d, 2H), 6.96-7.08 (m, 1H), 6.53-6.90 (m, 4H), 4.72 (d, 1H), 4.10 (d, 1H), 2.89 (d, 2H), 2.53-2.57 (m, 1H), 2.21 (s, 3H), 1.90-2.12 (m, 5H), 1.62-1.80 (m, 4H); MS m/z: 511.4 $[M+1]^+$.

The following compounds were prepared by a similar method to Compound 085 from (5-fluoro-2-methoxy-phenyl)-(4-methyl-1H-imidazol-2-yl)methanamine and methyl 6-(bromomethyl)-3-chloro-2-fluorobenzoate:

| No. | Structure/Name | m/z $[M + 1]^+$ | $^1H$ NMR (DMSO-$d_6$) δ |
|---|---|---|---|
| 093 | 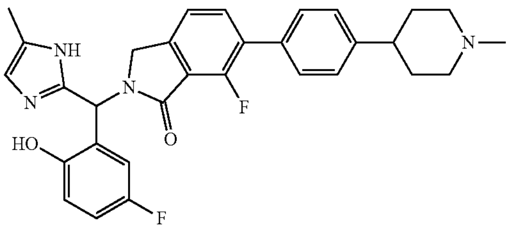 [SMILES: Cc1cnc(C(c2cc(F)ccc2O)N2Cc3ccc(-c4ccc(C5CCN(C)CC5)cc4)c(F)c3C2=O)[nH]1] 7-Fluoro-2-[(5-fluoro-2-hydroxy-phenyl)-(5-methyl-1H-imidazol-2-yl)methyl]-6-[4-(1-methyl-4-piperidyl)phenyl]isoindolin-1-one | 529.5 | 11.87-12.06 (m, 1H), 10.04 (br s, 1H), 7.65-7.73 (m, 1H), 7.42-7.53 (m, 3H), 7.32-7.39 (m, 2H), 6.97-7.06 (m, 1H), 6.74-6.88 (m, 3H), 6.72 (s, 1H), 4.73 (d, 1H), 4.08 (d, 1H). 3.29-3.32 (m, 1H), 2.83-2.93 (m, 2H), 2.20 (s, 3H), 2.05-2.16 (m, 3H), 1.92-2.02 (m, 2H), 1.61-1.82 (m, 4H). |

Compound 086: 2-[(3-fluorophenyl)-(4-methyl-1H-imidazol-2-yl)methyl]-6-[4-(1-methyl-4-piperidyl)phenyl]isoindolin-1-one

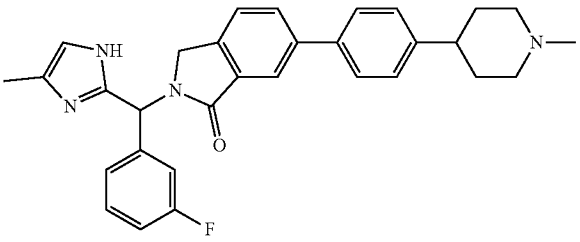

The title compound was prepared in a similar manner to Compound 085 from 2-methyl-N-[(4-methyl-1H-imidazol-2-yl)methylene]propane-2-sulfinamide and 3-fluorophenylmagnesium bromide. $^1$H NMR (DMSO-$d_6$) δ: 11.80-12.26 (m, 1H), 8.19 (s, 1H), 7.86-7.96 (m, 2H), 7.63-7.71 (m, 3H), 7.41-7.49 (m, 1H), 7.37 (d, 2H), 7.15-7.23 (m, 1H), 7.02-7.12 (m, 2H), 6.72 (s, 1H), 4.82 (d, 1H), 4.28 (d, 1H), 2.93-3.01 (m, 2H), 2.56-2.62 (m, 1H), 2.29 (s, 3H), 2.09-2.19 (m, 5H), 1.67-1.84 (m, 4H); MS m/z: 495.3 [M+1]$^+$ Compound 087: 2-[(4,5-dimethyl-1H-imidazol-2-yl)-(5-fluoro-2-hydroxy-phenyl)methyl]-6-[4-(1-methyl-4-piperidyl)phenyl]isoindolin-1-one

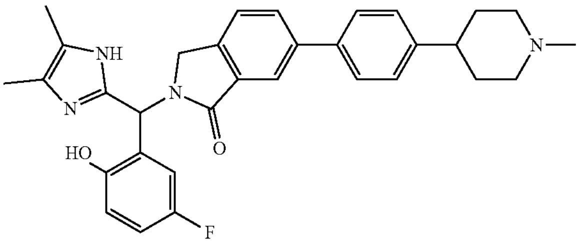

The title compound was prepared in a similar manner to Compound 085 from 4,5-dimethyl-1H-imidazole-2-carbaldehyde and 2-methylpropane-2-sulfinamide. $^1$H NMR (DMSO-$d_6$) δ: 11.75 (br s, 1H), 10.19 (br s, 1H), 7.84-7.89 (m, 2H), 7.59-7.70 (m, 3H), 7.36 (d, 2H), 6.98-7.08 (m, 1H), 6.80-6.91 (m, 2H), 6.72 (s, 1H), 4.69 (d, 1H), 4.13 (d, 1H), 2.89 (d, 2H), 2.45-2.49 (m, 1H), 2.21 (s, 3H), 1.94-2.12 (m, 8H), 1.63-1.84 (m, 4H); MS m/z: 525.3[M+1]$^+$ Compound 088: 2-[(5-fluoro-2-hydroxy-phenyl)-(2-methyl-1H-imidazol-5-yl)methyl]-6-[4-(1-methyl-4-piperidyl)phenyl]isoindolin-1-one;dihydrochloride

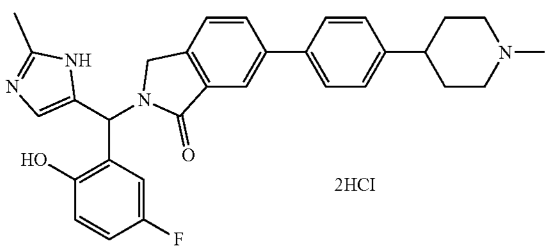 [SMILES: Cc1ncc(C(c2cc(F)ccc2O)N2Cc3ccc(-c4ccc(C5CCN(C)CC5)cc4)cc3C2=O)[nH]1]

2HCl

The title compound was prepared in a similar manner to Compound 085 from 2-methyl-1H-imidazole-5-carbaldehyde and 2-methylpropane-2-sulfinamide. $^1$H NMR (DMSO-$d_6$) δ: 10.54 (br s, 1H), 10.11 (br s, 1H), 7.86-7.99 (m, 2H), 7.62-7.75 (m, 3H), 7.33-7.44 (m, 3H), 7.05-7.15 (m, 1H), 6.87-7.01 (m, 2H), 6.75 (s, 1H), 4.54 (d, 1H), 4.22 (d, 1H), 3.49-3.52 (m, 2H), 2.99-3.12 (m, 2H), 2.70-2.91 (m, 4H), 2.54 (s, 3H), 1.94-2.10 (m, 4H); MS m/z: 511.2 [M+1]$^+$.

Compound 089: 2-[(5-fluoro-2-hydroxy-phenyl)-(5-methyl-4H-1,2,4-triazol-3-yl)methyl]-6-[4-(1-methyl-4-piperidyl)phenyl]isoindolin-1-one;hydrochloride Scheme 12

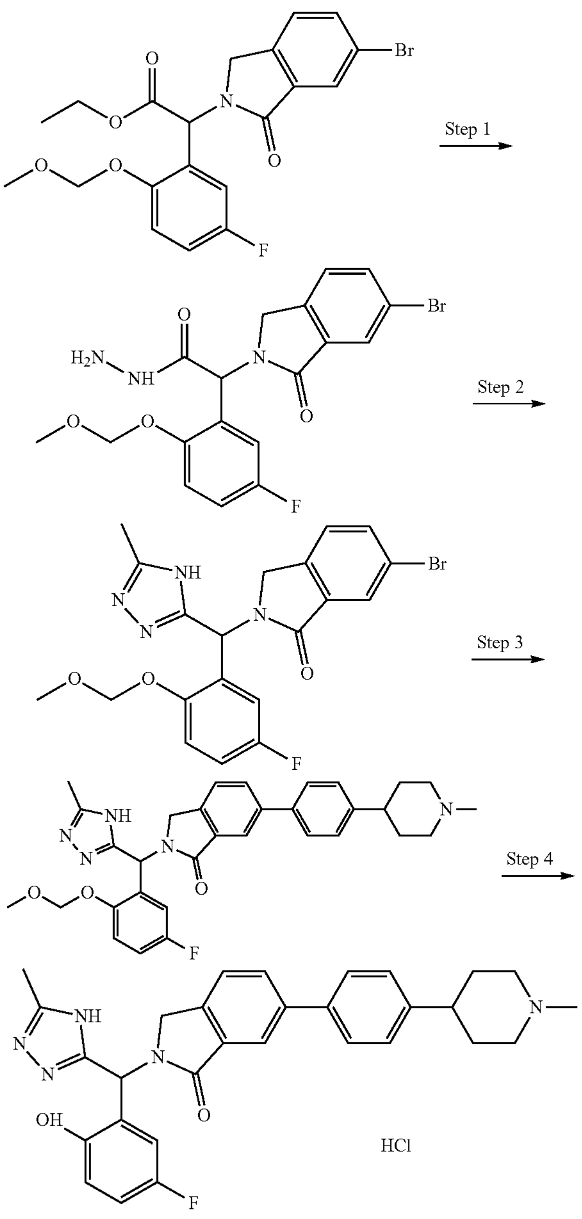

HCl

Step 1. 2-(6-bromo-1-oxo-isoindolin-2-yl)-2-[5-fluoro-2-(methoxymethoxy)phenyl]-acetohydrazide

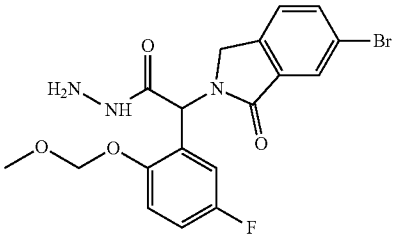 [SMILES: COCOc1ccc(F)cc1C(C(=O)NN)N1Cc2ccc(Br)cc2C1=O]

To a solution of ethyl 2-(6-bromo-1-oxo-isoindolin-2-yl)-2-[5-fluoro-2-(methoxymethoxy)-phenyl]acetate (0.900 g, 1.98 mmol) in ethanol (30 mL) was added hydrazine (0.618 mL, 19.7 mmol). After stirring at 80 CC for 16 h, the reaction mixture was concentrated under reduced pressure to give the title compound (0.75 g, 86%). $^1$H NMR (DMSO-$d_6$) δ: 9.62 (s, 1H), 8.92 (br s, 2H), 7.73-7.89 (m, 2H), 7.52 (d, 1H), 7.04-7.25 (m, 3H), 6.11 (s, 1H), 5.02-5.20 (m, 2H), 4.63 (d, 1H), 3.88 (d, 1H), 3.19 (s, 3H); MS m/z: 438.1 $[M+1]^+$.

Step 2. 6-bromo-2-[[5-fluoro-2-(methoxymethoxy)phenyl]-(5-methyl-4H-1,2,4-triazol-3-yl)methyl]isoindolin-1-one

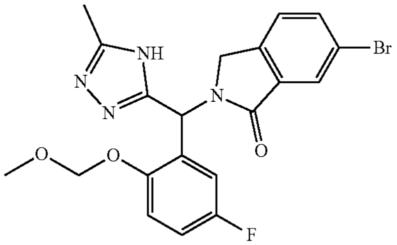 [SMILES: COCOc1ccc(F)cc1C(c1nnc(C)[nH]1)N1Cc2ccc(Br)cc2C1=O]

To a suspension of 2-(6-bromo-1-oxo-isoindolin-2-yl)-2-[5-fluoro-2-(methoxymethoxy)-phenyl]acetohydrazide (0.400 g, 0.912 mmol) and ethanimidamide hydrochloride (0.258 g, 2.73 mmol) in butanol (80 mL) was added potassium tert-butoxide in THE (1 M, 2.73 mL, 2.73 mmol). The reaction mixture was heated at 120° C. for 16 h. After cooling to room temperature, the reaction mixture was poured into water and extracted with ethyl acetate three times. The combined organic extracts were washed with water, brine, dried over sodium sulfate, filtered and concentrated under reduced pressure. The crude product was purified by silica gel column chromatography eluting with 0-10% methanol in dichloromethane to give the title compound (0.185 g, 44%). $^1$H NMR (DMSO-$d_6$) δ: 13.63 (br s, 1H), 7.72-7.86 (m, 2H), 7.54 (d, 1H), 7.09-7.25 (m, 2H), 6.81-6.98 (m, 2H), 5.14 (d, 2H), 4.65 (d, 1H), 3.95-4.08 (m, 1H), 3.21 (s, 3H), 2.34 (s, 3H); MS m/z: 461.0 $[M+1]^+$.

Step 3, 2-[[5-fluoro-2-(methoxymethoxy)phenyl](5-methyl-4H-1,2,4-triazol-3-yl)methyl]-6-[4-(1-methyl-4-piperidyl)phenyl]isoindolin-1-one

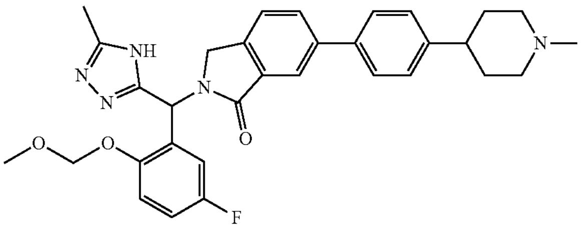

A mixture of 6-bromo-2-[[5-fluoro-2-(methoxymethoxy)phenyl]-(5-methyl-4H-1,2,4-triazol-3-yl)methyl]isoindolin-1-one (0,100 g, 0.216 mmol), [4-(1-methylpiperidin-4-yl)phenyl]boronic acid (0.057 g, 0.259 mmol), Pd(dppf)$Cl_2$ (0.016 g, 0.022 mmol) and sodium carbonate (0.071 g, 0.648 mmol) in dioxane:water (4:1, 5 mL) was heated at 100° C. for 16 h under nitrogen. After cooling, the reaction mixture was poured into water and extracted with ethyl acetate three times. The combined organic extracts were washed with water, brine, dried over sodium sulfate, filtered and concentrated under reduced pressure. The crude product was purified by silica gel column chromatography eluting with 15% methanol in dichloromethane to give the title compound (0.07 g, 58%). MS m/z: 556.3 $[M+1]^+$.

Step 4. 2-[(5-fluoro-2-hydroxy-phenyl)-(5-methyl-4H-1,2,4-triazol-3-yl)methyl]-6-[4-(1-methyl-4-piperidyl)phenyl]isoindolin-1-one;hydrochloride

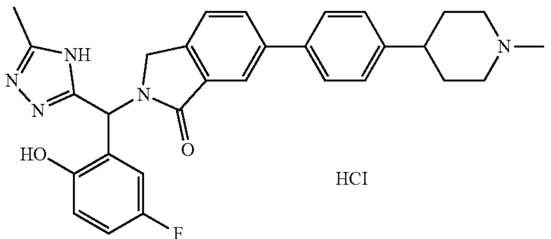 [SMILES: Cc1nnc(C(c2cc(F)ccc2O)N2Cc3ccc(-c4ccc(C5CCN(C)CC5)cc4)cc3C2=O)[nH]1 ; "HCI"]

HCl

The title compound was prepared in a similar manner to Example 076, step 4 from 2-[[5-fluoro-2-(methoxymethoxy)phenyl]-(5-methyl-4H-1,2,4-triazol-3-yl)methyl]-6-[4-(1-methyl-4-piperidyl)phenyl]isoindolin-1-one. $^1$H NMR (400 MHz, methanol-$d_4$) δ: 8.02 (d, 1H), 7.85-7.93 (m, 1H), 7.60-7.69 (m, 3H), 7.41 (d, 2H), 7.03-7.10 (m, 2H), 6.87-6.99 (m, 2H), 4.76 (d, 1H), 4.24 (d, 1H), 3.64 (d, 2H), 3.14-3.25 (m, 2H), 2.86-3.01 (m, 4H), 2.62 (s, 3H), 2.00-2.21 (m, 4H), MS m/z: 512.4 $[M+1]^+$.

Example 10: Preparation of 3-((1H-benzo[d]imidazol-2-yl)(phenyl)methyl-5-fluoro-6-(4-(1-methylpiperidin-4-yl)phenyl)quinazolin-4(3H)-one 2,2,2-trifluoroacetate (Compound 003)

Scheme 13.

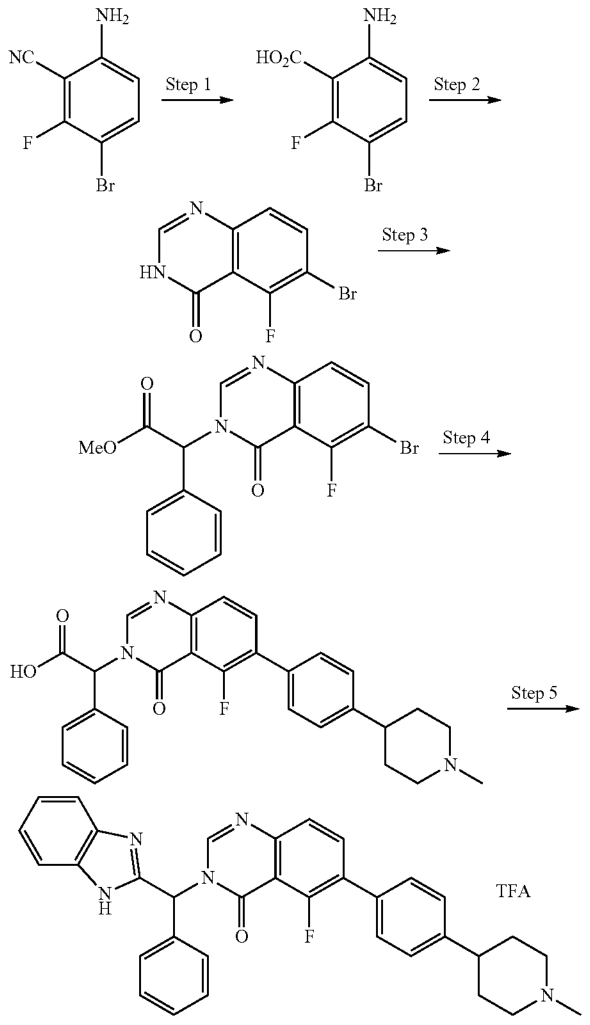

003

Step 1. 6-Amino-3-bromo-2-fluorobenzoic add

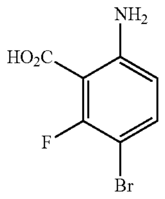 [SMILES: Nc1ccc(Br)c(F)c1C(=O)O]

A mixture of 6-amino-3-bromo-2-fluorobenzonitrile (2.56 mg, 11.8 mmol), lithium hydroxide monohydrate (4.99 g, 118 mmol) and water (70 mL) was heated at reflux for 1 h. After cooling, the solution was treated with 6N HCl to pH 4. The resulting precipitate was filtered, washed with water and dried to give the title compound (2.51 g, 92%). $^1H$ NMR (500 MHz, DMSO-$d_6$) d ppm 7.39 (dd, 1H) 6.57 (dd, 1H); MS m/z: 234.0 $[M+1]^+$.

Step 2. 6-Bromo-5-fluoroquinazolin-4(3H)-one

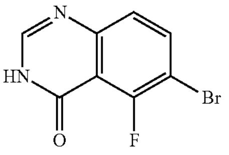

A mixture of 6-amino-3-bromo-2-fluorobenzoic acid (950 mg, 4.0 mmol) and formamide (20 mL) was heated at 160° C. for 8 h. After cooling, the reaction mixture was poured into water (100 mL) and extracted three times with EtOAc. The combine organic extracts were washed saturated brine, dried over $MgSO_4$, filtered and concentrated under reduced pressure. The residue was purified by silica gel flash chromatograph eluting with 0-35% EtOAc in hexane to give the title compound (490 mg, 50%). $^1H$ NMR (500 MHz, DMSO-$d_6$) d ppm 8.13 (d, 1H) 8.05 (dd, 1H) 7.45 (dd, 1H); MS m/z: 241.9 $[M+1]^+$.

Step 3. Methyl 2-(6-bromo-5-fluoro-4-oxoquinazolin-3(4H)-yl-2-phenylacetate

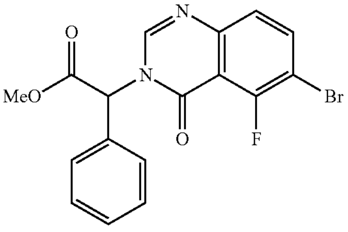 [SMILES: COC(=O)C(c1ccccc1)n1cnc2ccc(Br)c(F)c2c1=O]

Methyl 2-bromo-2-phenylacetate (349 mL, 2.2 mmol) was added to 6-bromo-5-fluoroquinazolin-4(3H)-one (440 mg, 1.9 mmol) and $Cs_2CO_3$ (1.20 g, 3.7 mmol) in DMF (3 mL), and the mixture was heated to 30° C. for 1 h. After cooling, the reaction mixture was poured into water (250 mL) and extracted with EtOAc three times. The combined organic extracts were washed with saturated brine; dried over $MgSO_4$, filtered and concentrated under reduced pressure. The residue was purified by silica gel flash chromatography, eluting with 0-30% EtOAc in hexane to give the title compound (290 mg, 39%). $^1H$ NMR (500 MHz, $CDCl_3$-d) d ppm 7.82-7.91 (m, 2H) 7.45-7.52 (m, 3H) 7.33-7.43 (m, 3H) 6.72 (s, 1H) 3.88 (s, 3H); MS m/z: 390.0 $[M+1]^+$.

Step 4. 2-(5-Fluoro-6-(4-(1-methylpiperidin-4-yl)phenyl)-4-oxoquinazolin-3(4H)-yl)-2-phenylacetic acid

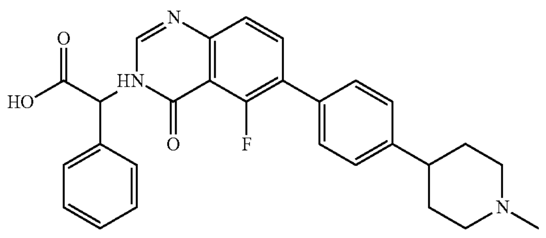 [SMILES: CN1CCC(c2ccc(-c3ccc4ncn(C(C(=O)O)c5ccccc5)c(=O)c4c3F)cc2)CC1]

The title compound was prepared in a similar manner to Example 9, step 5, from methyl 2-(6-bromo-5-fluoro-4-oxoquinazolin-3(4H)-yl)-2-phenylacetate and 1-methyl-4-(4-(4,4,5,5-tetramethyl-1,3,2-dioxaborolan-2-yl)phenyl)piperidine. $^1$H NMR (500 MHz, DMSO-$d_6$) d ppm 9.35 (br s, 1H) 8.11 (s, 1H) 7.94-7.99 (m, 1H) 7.60 (m, 3H) 7.52-7.56 (m, 2H) 7.43-7.51 (m, 3H) 7.40 (m, 2H) 6.49 (s, 1H) 3.56 (d, 2H) 3.06-3.16 (m, 2H) 2.84 (d, 4H) 2.05-2.13 (m, 2H) 1.80-1.93 (m, 2H); MS m/z: 472.2 $[M+1]^+$.

Step 5. 3-((1H-Benzo[d]imidazol-2-yl)(phenyl)methyl)-5-fluoro-6-(4-(1-methylpiperidin-4-yl)phenyl)quinazolin-4(3H)-one 2,2,2-trifluoroacetate (Compound 003)

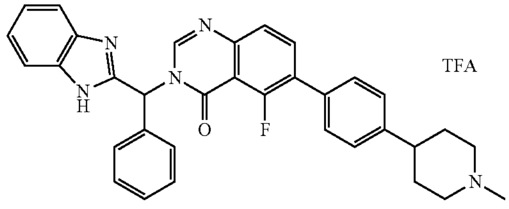 [SMILES: CN1CCC(c2ccc(-c3ccc4ncn(C(c5ccccc5)c5nc6ccccc6[nH]5)c(=O)c4c3F)cc2)CC1]

The title compound was prepared in a similar manner to Example 9, step 6, from 2-(5-fluoro-6-(4-(1-methylpiperidin-4-yl)phenyl)-4-oxoquinazolin-3(4H)-yl)-2-phenylacetic acid. $^1$H NMR (500 MHz, DMSO-d6) d ppm 9.29 (br s, 1H) 8.32 (s, 1H) 7.94-8.03 (m, 1H) 7.56-7.64 (m, 5H) 7.54 (s, 1H) 7.44-7.49 (m, 3H) 7.35-7.42 (m, 4H) 7.17-7.29 (m, 2H) 3.50-3.59 (m, 2H) 3.04-3.16 (m, 2H) 2.84 (m, 4H) 2.04-2.13 (m, 2H) 1.79-1.93 (m, 2H); MS m/z: 544.3 $[M+1]^+$.

Example 11: Preparation of Intermediates

Scheme 14.

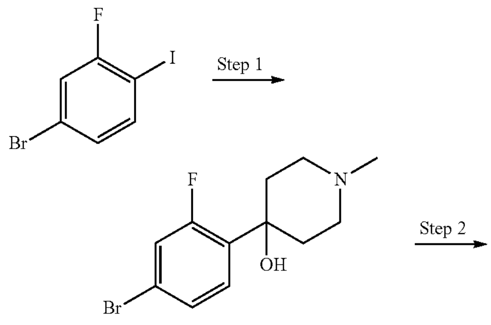

-continued

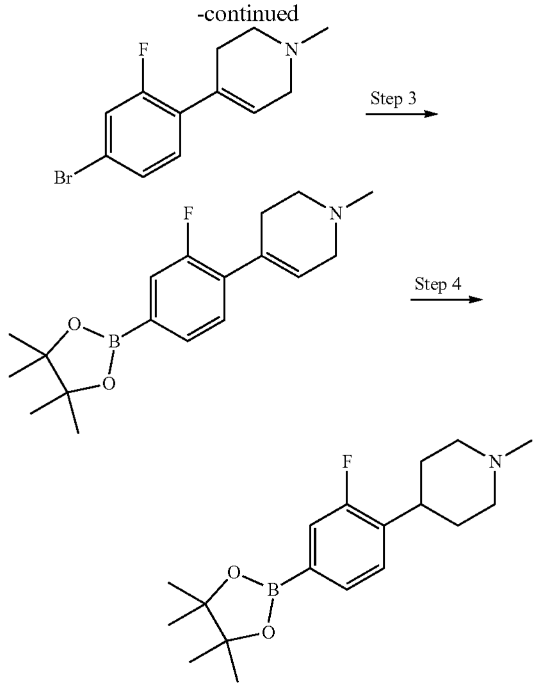

Step 1. 4-(4-Bromo-2-fluoro-phenyl)-1-methyl-piperidin-4-oi

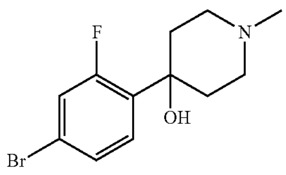 [SMILES: CN1CCC(O)(c2ccc(Br)cc2F)CC1]

To a solution of 4-bromo-2-fluoro-1-iodo-benzene (24.0 g, 79.7 mmol) in THF (400 mL) at −70° C. was added dropwise n-butyllithium (2.5 Min hexane, 31.9 mL, 79.7 mmol). After stirring at −70° C. for 30 min, a solution of 1-methylpiperidin-4-one (9.01 g, 79.7 mmol) in THF (20 mL) was added dropwise. After stirring at −70° C. for 1 h, the reaction mixture was poured into sat. ammonium chloride solution and extracted with ethyl acetate three times. The combined organic extracts were washed with brine, dried over sodium sulfate, filtered and concentrated under reduced pressure. The crude product was purified by silica gel column chromatography eluting with 5-66% ethyl acetate in petroleum ether to give the title compound (13.0 g, 57%). MS m/z: 289.8 $[M+1]^+$.

Step 2. 4-(4-Bromo-2-fluoro-phenyl)-1-methyl-3,6-dihydro-2H-pyridine

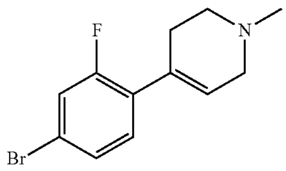

A mixture of 4-(4-bromo-2-fluoro-phenyl)-1-methyl-piperidin-4-ol (13.0 g, 45.1 mmol) and 6 M HCl (70 mL) was heated at 85° C. overnight. After cooling to room temperature, the reaction mixture was poured into water, adjusted to pH 8 by sat, sodium bicarbonate and extracted with ethyl acetate three times. The combined organic extracts were washed with brine, dried over sodium sulfate, filtered and concentrated under reduced pressure. The crude product was purified by silica gel column chromatography eluting with 5-66% ethyl acetate in petroleum ether to give the title compound (4.0 g, 31%). MS m/z: 271.7 $[M+1]^+$.

Step 3. 4-[2-Fluoro-4-(4,4,5,5-tetramethyl-1,3,2-dioxaborolan-2-yl)phenyl]-1-methyl-3,6-dihydro-2H-pyridine

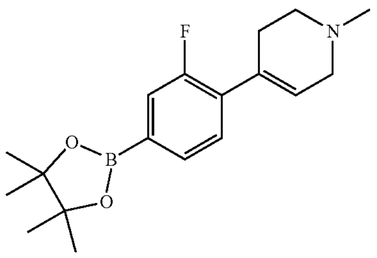

A mixture of 4-(4-bromo-2-fluoro-phenyl)-1-methyl-3,6-dihydro-2H-pyridine (3.00 g, 11.1 mmol), 4,4,5,5-tetramethyl-2-(4,4,5,5-tetramethyl-1,3,2-dioxaborolan-2-yl)-1,3,2-dioxaborolane (2.81 g, 11.1 mmol), [1,1'-bis(diphenylphosphino)ferrocene]dichloropalladium(II) (0.812 g, 1.11 mmol), potassium acetate (3.26 g, 33.3 mmol) and dioxane (30 mL) was degassed under nitrogen twice. The reaction mixture was heated at 90° C. for 16 h. After cooling to room temperature, the reaction mixture was poured into water and extracted with ethyl acetate three times. The combined organic extracts were washed with brine, dried over sodium sulfate, filtered and concentrated under reduced pressure. The crude product was purified by silica gel column chromatography eluting with 5-50% ethyl acetate in petroleum ether to give the title compound (3.0 g, 85%). $^1$H NMR (400 MHz, methanol-$d_4$) δ: 7.49 (dd, 1H), 7.27-7.40 (m, 2H), 6.01-6.03 (m, 1H), 3.18-3.21 (m, 2H), 2.72-2.80 (m, 2H) 2.57-2.65 (m, 2H), 2.43 (s, 3H) 1.30-1.39 (m, 12H).

Step 4. 4-[2-Fluoro-4-(4,4,5,5-tetramethyl-1,3,2-dioxaborolan-2-yl)phenyl]-1-methyl-piperidine

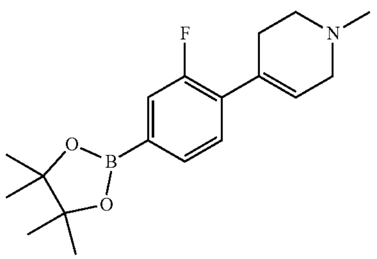

To a solution of palladium (10% on carbon, 1.10 g, 0.945 mmol) in methanol (200 mL) was added 4-[2-fluoro-4-(4,4,5,5-tetramethyl-1,3,2-dioxaborolan-2-yl)phenyl]-1-methyl-3,6-dihydro-2H-pyridine (3.00 g, 9.45 mmol). The flask was evacuated and backfilled with hydrogen and the reaction mixture was allowed to stir at 30° C. under an atmosphere of hydrogen (30 psi) for 16 h. The reaction mixture was filtered through a pad of Celite which was washed several times with methanol. The filtrate was concentrated under reduced pressure to give the title compound (2.7 g, 85%). $^1$H NMR (400 MHz, methanol-$d_4$) δ: 7.49 (d, 1H), 7.26-7.36 (m, 2H), 3.00-3.10 (m, 2H), 2.83-2.98 (m, 1H), 2.37 (s, 3H), 2.18-2.31 (m, 2H), 1.79-1.89 (m, 4H), 1.27-1.39 (m, 12H).

Scheme SM-1

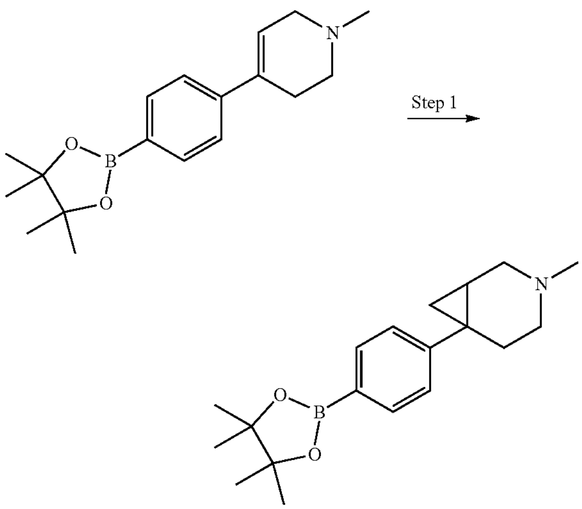

Step 1. 3-methyl-6-[4-(4,4,5,5-tetramethyl-1,3,2-dioxaborolan-2-yl)phenyl]-3-azabicyclo-[4.1.0]heptane

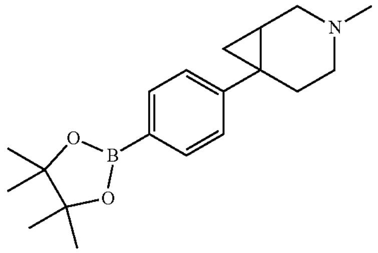

To a solution of diethylzinc (1 Min hexanes, 10.0 mL, 10.0 mmol) in dichloromethane (5 mL) at 0° C. was added diiodomethane (2.67 g, 10.0 mmol). After stirring at the same temperature for 0.5 h, a solution of 4-(1-methyl-1,2,3,6-tetrahydropyridin-4-yl)phenylboronic acid pinacol ester (0,500 g, 1.67 mmol) in dichloromethane (5 mL) was added dropwise to the reaction mixture. After stirring at room temperature for 18 h, the reaction mixture was poured into sat. ammonium chloride solution and extracted with ethyl acetate three times. The combined organic extracts were washed with brine, dried over sodium sulfate, filtered and concentrated under reduced pressure. The crude product was purified by silica gel column chromatography eluting with 5-50% ethyl acetate in petroleum ether to give the title compound (0.310 g, 59%). MS m/z: 314.2 $[M+1]^+$.

Scheme SM-2

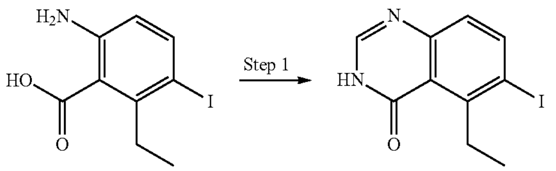

Step 1. 5-ethyl-6-iodo-3H-quinazolin-4-one

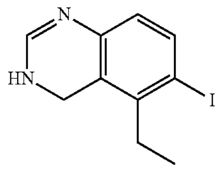

To a solution of 6-amino-2-ethyl-3-iodobenzoic acid (3.50 g, 12.0 mmol) in ethanol (70 mL) was added formamidine acetate (5.94 g, 57.1 mmol) and the reaction mixture was heated at 95° C. for 6 h. After cooling to room temperature, the resulting solid was collected by filtration and washed with ethanol to give the title compound (2.10 g, 58%). $^1$H NMR (DMSO-$d_6$) δ: 8.19 (d, 1H), 8.06 (s, 1H), 7.26 (d, 1H), 3.41-3.59 (m, 2H), 1.04-1.16 (m, 3H).

Example 12: Preparation of 2-((1H-benzo[d]imidazol-2-yl)(5-fluoro-2-hydroxyphenyl)methyl-d)-6-(4-(1-methylpiperidin-4-yl)phenyl)isoindolin-1-one (compound 036)

Scheme 15.

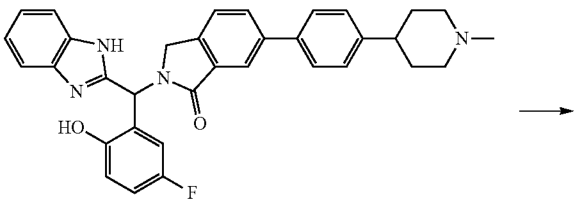

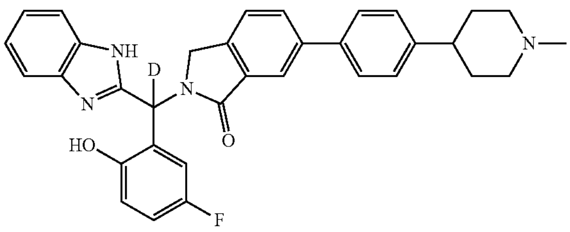

036

2-((1H-Benzo[d]imidazol-2-0(5-fluoro-2-hydroxyphenyl)methyl)-6-(4-(1-methylpiperidin-4-yl)phenyl) isoindolin-1-one (101 mg, 0.185 mmol) was stirred in $CD_3OD$ (10 g) and $D_2O$ (1 mL) to give a heterogeneous mixture. Formic acid (40 uL, 1.07 mmol) was then added and the resulting solution was stirred overnight. After 16 hours, $^1$H NMR (methanol-d4) of the reaction solution indicated ~50% incorporation of deuterium on the methine carbon based on the integration area of methine peak @ 7.16 ppm. The reaction was heated to 50° C. and stirred for an additional 8 hours, with $^1$H NMR (methanol-$d_4$) indicating >90% incorporation of deuterium. Additional formic acid 40 uL formic acid (1.07 mmol) was added and the reaction stirred at 50° C. with stirring under a nitrogen atmosphere for another 6 hours. $^1$H NMR (methanol-$d_4$) indicated 100% incorporation of deuterium on the methine carbon. A solution of DCI (100 uL, 35 weight % in D20) was added to the reaction solution. After 10 minutes, the reaction solution was concentrated, and the residue was dried under vacuum overnight to give 96 mg of a white solid.

The crude product was purified by silica chromatography, eluting with 100% ethyl acetate to 60% ethyl acetate/40% [10% (28% ammonia in water)/90% MeOH] to give the title compound as a white powder. $^1$H NMR (400 MHz, methanol-d4) δ: 8.02 (s, 1H), 7.84-7.90 (m, 1H), 7.52-7.63 (m, 5H), 7.33-7.39 (m, 2H), 7.20-7.27 (m, 2H), 6.97-7.05 (m, 1H), 6.86-6.91 (m, 1H), 6.73-6.79 (m, 1H), 4.76 (d, 1H), 4.26 (d, 1H), 2.99-3.08 (m, 2H), 2.56-2.66 (m, 1H), 2.35 (s, 3H), 2.21 (m, 2H), 1.77-1.94 (m, 4H); MS m/z: 548.3 $[M+1]^+$.

Compounds 037 and 038 were prepared following the procedure of Example 12. The crude product was then purified to separate enantiomers using a Chiralpak IA (10× 250 mm 5 micron) column eluting with 45% (0.3% TEA in MeOH)/55% $CO_2$ at Back Pressure Regulator (BPR) value of 10 MPa and flow rate of 10 mL/min on a Jasco semi-prep SFC. Absolute configuration of the chiral center for each isolated enantiomer is unknown. First eluting peak (27.4 mg, 27%); $^1$H NMR (400 MHz, methanol-$d_4$) δ: 8.02 (s, 1H), 7.84-7.90 (m, 1H), 7.52-7.63 (m, 5H), 7.33-7.39 (m, 2H), 7.20-7.27 (m, 2H), 6.97-7.05 (m, 1H), 6.86-6.91 (m, 1H), 6.73-6.79 (m, 1H), 4.76 (d, 1H), 4.26 (d, 1H), 2.99-3.08 (m, 2H), 2.56-2.66 (m, 1H), 2.35 (s, 3H), 2.21 (m, 2H), 1.77-1.94 (m, 4H); MS m/z: 548.3 $[M+1]^+$. Second eluting peak (31 mg, 28%); $^1$H NMR (400 MHz, methanol-$d_4$) δ: 8.02 (s, 1H), 7.84-7.89 (m, 1H), 7.52-7.64 (m, 5H), 7.36 (d, 2H), 7.20-7.27 (m, 2H), 6.96-7.06 (m, 1H), 6.86-6.92 (m, 1H), 6.74-6.79 (m, 1H), 4.76 (d, 1H), 4.27 (d, 1H), 3.00-3.09 (m, 2H), 2.56-2.68 (m, 1H), 2.36 (s, 3H), 2.23 (m, 2H), 1.78-1.94 (m, 4H); MS m/z: 548.3 [M+1]'.

Example 13: Preparation of 2-((1H-Benzo[d]imidazol-2-yl)(5-fluoro-2-hydroxyphenyl)methyl-d)-6-(4-(1-methylpiperidin-4-yl)phenyl)isoindolin-1-one-3, 3-$d_2$ (Compound 039)

Scheme 16.

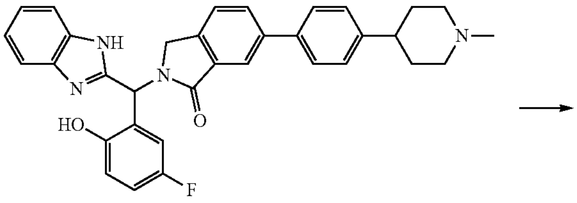

-continued

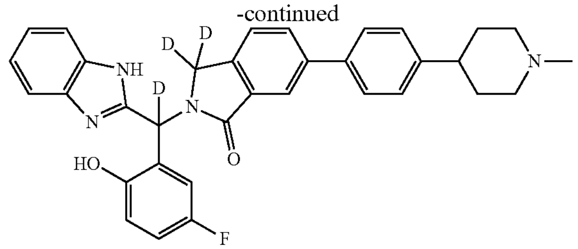

039

2-((1H-Benzo[d]imidazol-2-yl)(5-fluoro-2-hydroxyphenyl)methyl)-6-(4-(1-methylpiperidin-4-yl)phenyl) isoindolin-1-one (24.5 mg, 0.047 mmol) was stirred in $CD_3OD$ (1 g). $D_2O$ (0.5 mL) and sodium carbonate (9.84 mg, 0.093 mmol) were added and the mixture was stirred in a sealed vial at 50° C. for 18 hours. $^1H$ NMR of the reaction mixture (methanol-$d_4$) indicated >95% incorporation of deuterium on the methine carbon, based on integration area of the methine peak @ 7.16 ppm as well as ~60% incorporation of deuterium on the lactam methylene carbon. The reaction was stirred at 60° C. for an additional 48 hours. $^1H$ NMR of the reaction mixture (methanol-$d_4$) indicated complete deuteration of both the methine carbon and the lactam methylene carbon. The reaction was cooled to room temperature then a solution of 35 weight % DCI in $D_2O$ (50 uL, 0.48 mmol) was added. After stirring a few minutes, the reaction was concentrated and the residue purified by silica chromatography, eluting with 100% DCM to 100% (10% 7N NH3 in MeOH/DCM) to give the title compound (18 mg, 70%) as a white powder. $^1H$ NMR (400 MHz, DMSO-$d_6$) δ ppm 12.08-13.11 (m, 1H) 9.72-10.71 (m, 1H) 7.86-7.92 (m, 2H) 7.60-7.69 (m, 3H) 7.52 (br s, 2H) 7.35 (d, J=8.19 Hz, 2H) 7.17 (br dd, J=5.81, 3.00 Hz, 2H) 7.01-7.11 (m, 1H)) 6.91 (dd, J=8.80, 4.77 Hz, 1H) 6.80 (dd, J=9.41, 3.06 Hz, 1H) 3.05-3.21 (m, 1H) 2.87 (br d, J=11.25 Hz, 2H) 1.87-2.06 (m, 2H) 2.19 (s, 3H) 1.62-1.81 (m, 4H); MS m/z: 550.3 [M+1]$^+$.

Example 14: 2-[1H-benzimidazol-2-yl-(5-fluoro-2-hydroxy-phenyl)methyl]-6-[4-[2-(dimethyl-amino) ethoxy]phenyl]isoindolin-1-one;hydrochloride (Compound 040)

Scheme 17

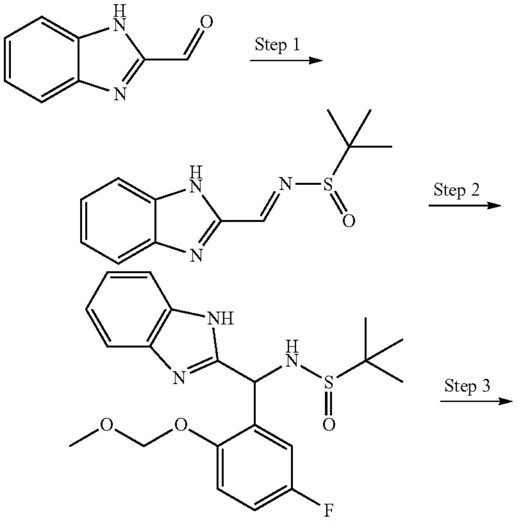

-continued

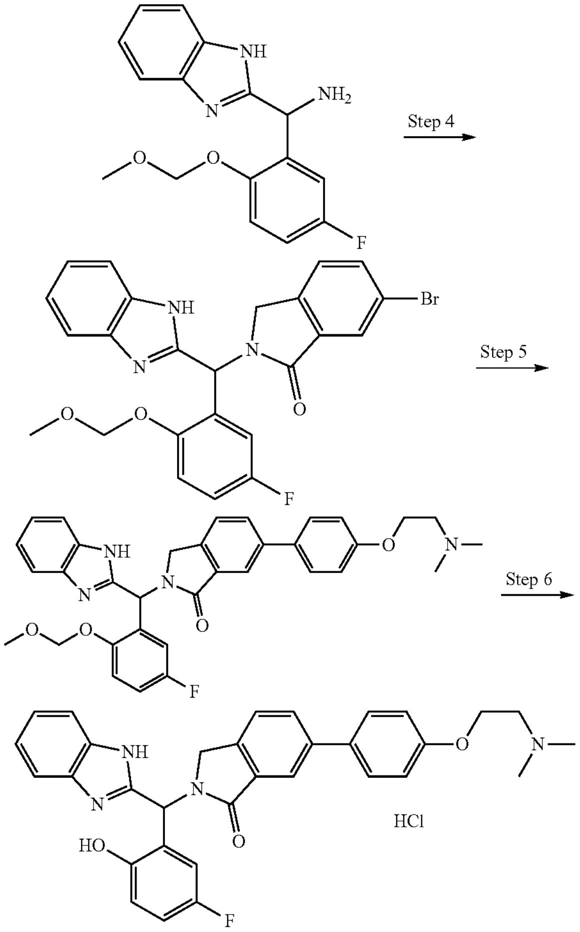

Step 1. N-(1H-benzimidazol-2-ylmethylene)-2-methyl-propane-2-sulfinamide

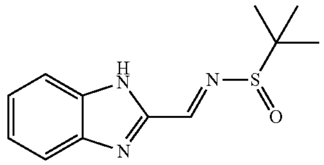 [SMILES: CC(C)(C)S(=O)/N=C/c1nc2ccccc2[nH]1]

To a solution of 1H-1,3-benzodiazole-2-carbaldehyde (75.0 g, 513 mmol) and 2-methyl-2-propanesulfinamide (93.2 g, 769 mmol) in THF (1 L) was added titanium (IV) ethoxide (175 g, 769 mmol). After stirring at 75° C. far 16 h, water was added and the reaction mixture was extracted with ethyl acetate three times. The combined organic extracts were washed with brine, dried over sodium sulfate, filtered and concentrated under reduced pressure. A solution of ethyl acetate and petroleum ether (1/1) was added to the residue and the resulting solid was isolated via filtration to give the title compound (65 g, 51%). $^1H$ NMR (400 MHz, $CDCl_3$) δ: 10.92 (s, 1H), 8.70-8.91 (m, 1H), 7.89 (d, 1H), 7.53 (d, 1H), 7.37 (dd, 2H), 1.19-1.32 (m, 9H).

Step 2. N-[1H-benzimidazol-2-yl-[5-fluoro-2-(methoxymethoxy)phenyl]methyl]-2-methyl-propane-2-sulfinamide

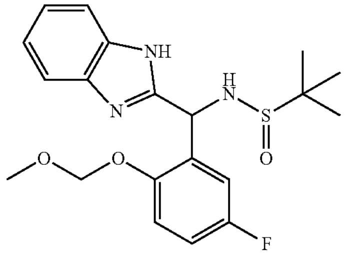 [SMILES: COCOc1ccc(F)cc1C(NS(=O)C(C)(C)C)c1nc2ccccc2[nH]1]

To a solution of 2-bromo-4-fluoro-1-(methoxymethoxy) benzene (84.6 g, 360 mmol) in THF (600 mL) at −65° C. was added dropwise n-butyllithium (2.5 M in hexane, 158 mL, 396 mmol). After stirring at −65° C. for 20 minutes, the reaction mixture was cannulated to a pre-cooled (−65° C.) solution of N-(1H-benzimidazol-2-ylmethylene)-2-methyl-propane-2-sulfinamide (45.0 g, 180 mmol) in THF (1100 mL). After stirring at −65° C. for 40 minutes, the reaction mixture was allowed to warm to 15° C. The reaction mixture was quenched by saturated ammonium chloride solution and extracted with ethyl acetate three times. The combined organic extracts were washed with brine, dried over sodium sulfate, filtered and concentrated under reduced pressure. The crude product was purified by silica gel column chromatography eluting with 33-100% ethyl acetate in petroleum ether to give the title compound (40 g, 38%). $^1$H NMR (400 MHz, $CDCl_3$) δ: 11.26 (s, 1H), 7.32-7.77 (m, 2H), 7.14-7.23 (m, 3H), 7.10 (dd, 1H), 6.87-7.02 (m, 1H), 5.96 (d, 1H), 5.13 (d, 1H), 4.93-5.05 (m, 2H), 3.29 (s, 3H), 1.27-1.41 (m, 9H).

Step 3. 1H-benzimidazol-2-yl-[5-fluoro-2-(methoxymethoxy)phenyl]methanamine

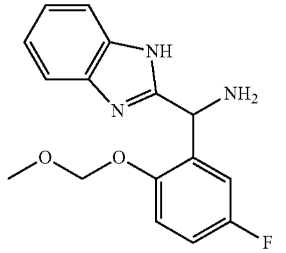 [SMILES: COCOc1ccc(F)cc1C(N)c1nc2ccccc2[nH]1]

To a solution of N-[1H-benzimidazol-2-yl-[5-fluoro-2-(methoxymethoxy)phenyl]methyl]-2-methyl-propane-2-sulfinamide (30.0 g, 73.9 mmol) in methanol (600 mL) was added HCl in dioxane (4 M, 55.2 mL, 221 mmol) at 0° C. After stirring 15 h at room temperature, the reaction mixture was diluted with water and adjusted to pH 8 by saturated sodium bicarbonate solution. The aqueous phase was extracted with ethyl acetate three times. The combined organic extracts were washed with brine, dried over sodium sulfate, filtered and concentrated under reduced pressure to give the title compound (30.0 g, quant.). $^1$H NMR (400 MHz, $CDCl_3$) δ: 7.56 (s, 2H), 7.19-7.26 (m, 2H), 7.06-7.12 (m, 2H), 6.89-6.97 (m, 1H), 5.64 (s, 1H), 5.12 (d, 2H), 3.32-3.41 (m, 3H). MS m/z: 302.3 $[M+1]^+$.

Step 4. 2-[1H-benzimidazol-2-yl-[5-fluoro-2-(methoxymethoxy)phenyl]methyl]-6-bromo-isoindolin-1-one

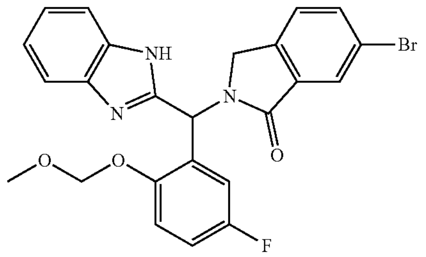 [SMILES: COCOc1ccc(F)cc1C(c1nc2ccccc2[nH]1)N1Cc2ccc(Br)cc2C1=O]

To a solution of 1H-benzimidazol-2-yl-[5-fluoro-2-(methoxymethoxy)phenyl]methanamine (23.0 g, 76.3 mmol) in DMF (250 mL) was added DIPEA (37.5 mL, 228 mmol). The reaction mixture was stirred at room temperature for 5 min and then methyl 5-bromo-2-(bromomethyl)-benzoate (28.1 g, 91.5 mmol) was added. The reaction mixture was heated at 90 for 16 h. After cooling to room temperature, the reaction mixture was poured into water and extracted with ethyl acetate three times. The combined organic extracts were washed with water, brine, dried over sodium sulfate, filtered and concentrated under reduced pressure to give the title compound (29.5 g, 78%). $^1$H NMR (400 MHz, DMSO-$d_6$) δ: 12.69 (s, 1H), 7.87 (d, 1H), 7.80 (dd, 1H), 7.54-7.64 (m, 2H), 7.47 (d, 1H), 7.13-7.25 (m, 4H), 7.09 (s, 1H), 6.92 (dd, 1H), 5.10-5.22 (m, 2H), 4.74 (d, 1H), 4.17 (d, 1H), 3.14-3.23 (m, 3H); MS m/z: 496.1 $[M+1]^+$.

Step 5. 2-[1H-benzimidazol-2-yl-[5-fluoro-2-(methoxymethoxy)phenyl]methyl]-6-[4-[2-(dimethylamino)ethoxy]phenyl]isoindolin-1-one

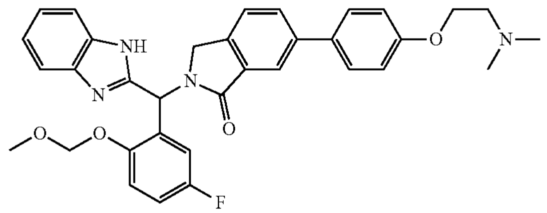

A mixture of 2-[1H-benzimidazol-2-yl-[5-fluoro-2-(methoxymethoxy)phenyl]methyl]-6-bromo-isoindolin-1-one (160 mg, 0.322 mmol), N-[2-(dimethylamino)ethyl]-N-methyl-4-(4,4,5,5-tetramethyl-1,3,2-dioxaborolan-2-yl) aniline (132 mg, 0.436 mmol), sodium carbonate (89.0 mg, 0.840 mmol) and dioxane/water (5 mL, 4/1) was degassed under nitrogen twice. [1,1'-bis(diphenylphosphino)ferrocene]dichloropalladium(II), complex with dichloromethane (41.1 mg, 0.050 mmol) was added and then the reaction mixture was degassed under nitrogen once more. The reaction mixture was heated at 100° C. for 2 h. After cooling to room temperature, the reaction mixture was poured into water and extracted with ethyl acetate three times. The combined organic extracts were washed with brine, dried over sodium sulfate, filtered and concentrated under reduced pressure. The crude product was purified by reverse phase HPLC eluting with 0-55% ACN/water containing 0.1% formic acid to give the title compound (101 mg, 53%), $^1$H NMR (400 MHz, methanol-$d_4$) δ: 8.00 (s, 1H), 7.84 (dd, 1H); 7.51-7.64 (m, 5H); 7.19-7.27 (m, 4H), 7.09-7.17 (m, 1H), 7.05 (d, 2H), 6.86 (dd, 1H), 5.06-5.19 (m, 2H), 4.70 (d, 1H) 4.28 (d, 1H), 4.16 (m, 2H), 3.20 (s, 3H), 2.80 (m, 2H), 2.36 (s, 6H); MS m/z: 581.3 $[M+1]^+$.

Step 6. 2-[1H benzimidazol-2-yl-(5-fluoro-2-hydroxy-phenyl)methyl]-6-[4-[2-(dimethylamino)-ethoxy]phenyl]isoindolin-1-one;hydrochloride (Compound 040)

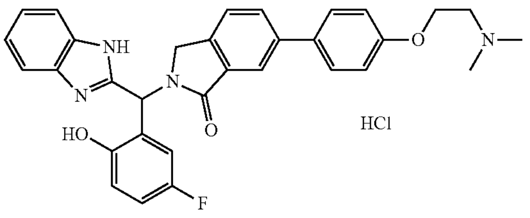 [SMILES: CN(C)CCOc1ccc(-c2ccc3c(c2)C(=O)N(C(c2nc4ccccc4[nH]2)c2cc(F)ccc2O)C3)cc1 ; Cl]

To a solution of 2-[1H-benzimidazol-2-yl-[5-fluoro-2-(methoxymethoxy)phenyl]methyl]-6-[4-[2-(dimethylamino)ethoxy]phenyl]isoindolin-1-one (0,108 g, 0.185 mmol) in dichloromethane (3.97 mL) was added HCl in dioxane (4 M, 0.462 mL, 1.85 mmol). After stirring 1 h at room temperature the solvent was removed under reduced pressure. Diethyl ether was added to the residue and the resulting solid was isolated via filtration to give the title compound (91 mg, 86%). $^1$H NMR (400 MHz, DMSO-$d_6$) δ: 10.37 (br s, 1H), 10.22 (br s, 1H), 7.83-7.89 (m, 2H), 7.60-7.69 (m, 5H), 7.34-7.45 (m, 2H), 7.01-7.13 (m, 5H), 6.94 (dd, 1H), 4.71 (d, 1H), 4.35 (t, 2H), 4.19 (d, 1H), 3.42-3.49 (m, 2H), 2.79 (d, 6H); MS m/z: 537.3 $[M+1]^+$.

Example 15: 2-[1H-benzimidazol-2-yl-(5-fluoro-2-hydroxy-phenyl)methyl]-6-[4-(1-methylazetidin-3-yl)phenyl]isoindolin-1-one (Compound 049)

Scheme 18

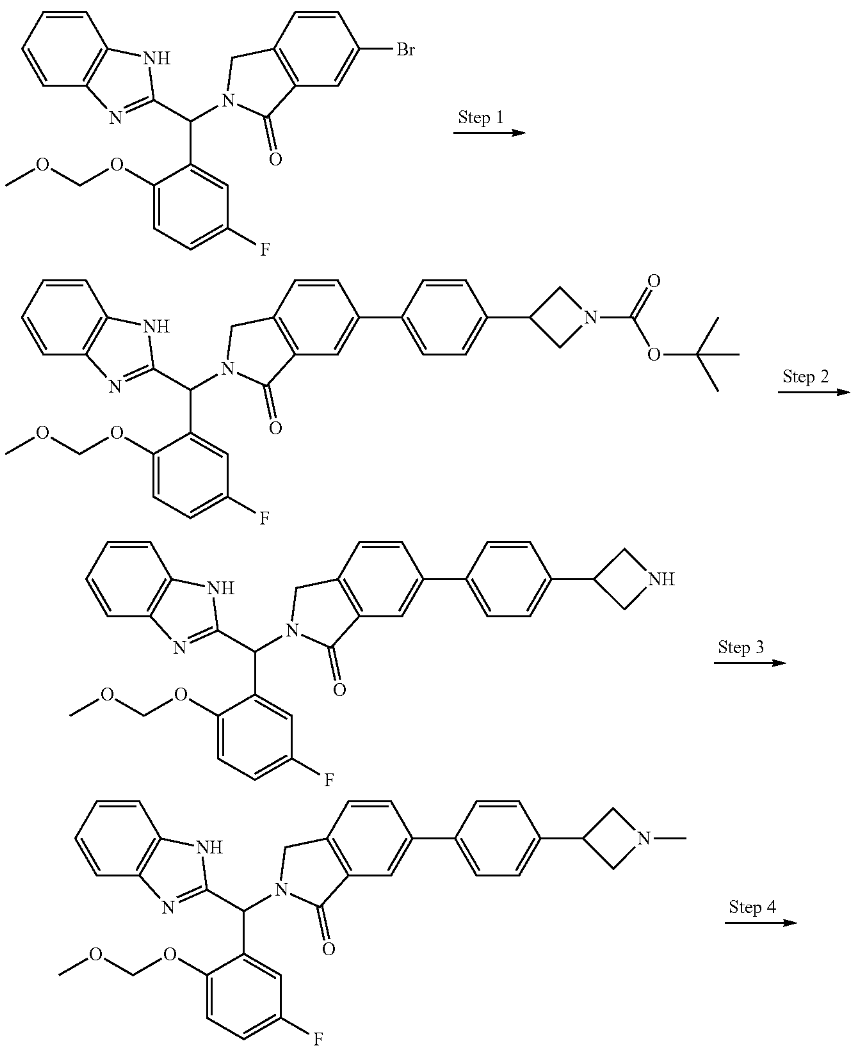

-continued

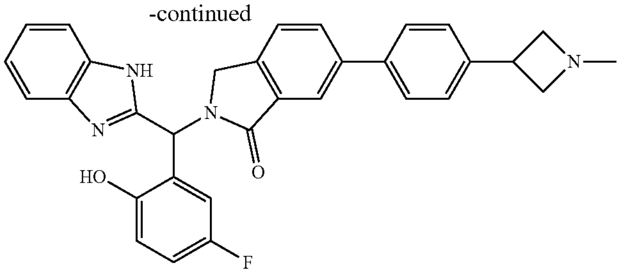

Step 1. tert-butyl 3-[4-[2-[1H-benzimidazol-2-yl-[5-fluoro-2-(methoxymethoxy)phenyl]methyl]-3-oxo-isoindolin-5-yl]phenyl]azetidine-1-carboxylate

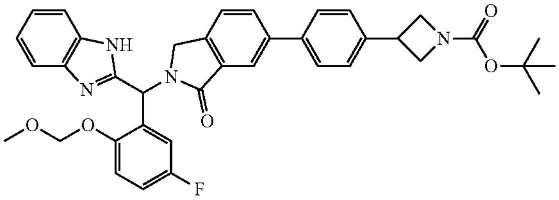 [SMILES: COCOc1ccc(F)cc1C(c1nc2ccccc2[nH]1)N1Cc2ccc(-c3ccc(C4CN(C(=O)OC(C)(C)C)C4)cc3)cc2C1=O]

A mixture of 2-[1H-benzimidazol-2-yl-[5-fluoro-2-(methoxymethoxy)phenyl]methyl]-6-bromo-isoindolin-1-one (191 mg, 0.384 mmol), tert-butyl 3-[4-(4,4,5,5-tetramethyl-1,3,2-dioxaborolan-2-yl)phenyl]-1-azetidinecarboxylate (158 mg, 0,441 mmol), sodium carbonate (105 mg, 0.990 mmol) and dioxane/water (9 mL, 4/1) was degassed under nitrogen twice. [1,1'-bis(diphenylphosphino)ferrocene]dichloropalladium(II), complex with dichloromethane (62.7 mg, 0.077 mmol) was added and then the reaction mixture was degassed under nitrogen once more. The reaction mixture was heated at 100° C. for 1 h. After cooling to room temperature, the reaction mixture was poured into water and extracted with ethyl acetate three times. The combined organic extracts were washed with brine, dried over sodium sulfate, filtered and concentrated under reduced pressure. The crude product was purified by silica gel column chromatography eluting with 0-75% ethyl acetate in hexanes to give the title compound (164 mg, 66%). $^1$H NMR (400 MHz, methanol-$d_4$) δ: 8.08 (s, 1H), 7.89-7.96 (m, 1H), 7.68-7.75 (m, 2H), 7.45-7.67 (m, 5H), 7.21-7.31 (m, 4H), 7.12-7.19 (m, 1H), 6.86-6.93 (m, 1H), 5.12-5.19 (m, 2H), 4.75 (d, 1H), 4.36-4.45 (m, 2H), 4.33 (d, 1H), 3.96-4.04 (m, 2H), 3.90 (d, 1H), 3.23 (s, 3H), 1.50 (s, 9H); MS m/z: 649.3 $[M+1]^+$.

Step 2. 6-[4-(azetidin-3-yl)phenyl]-2-[1H-benzimidazol-2-yl-[5-fluoro-2-(methoxymethoxy)-phenyl]methyl]isoindolin-1-one

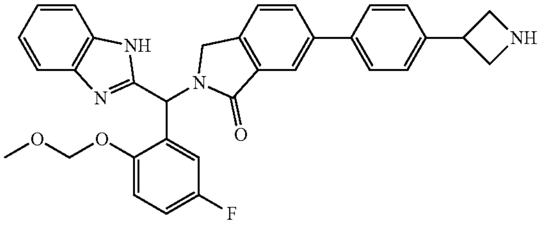 [SMILES: COCOc1ccc(F)cc1C(c1nc2ccccc2[nH]1)N1Cc2ccc(-c3ccc(C4CNC4)cc3)cc2C1=O]

To a solution of tert-butyl 3-[4-[2-[1H-benzimidazol-2-yl-[5-fluoro-2-(methoxymethoxy)-phenyl]methyl]-3-oxo-isoindolin-5-yl]phenyl]azetidine-1-carboxylate (164 mg, 0.252 mmol) in dichloromethane (5 mL) was added ethanol (73.5 μL, 1.26 mmol) and zinc bromide (283 mg, 1.26 mmol). After stirring overnight at room temperature, the reaction mixture was added to a mixture of 1N NaOH solution and methanol and the resulting solid was isolated via filtration to give the title compound (44 mg, 32%). MS m/z: 549.3 $[M+1]^+$.

Step 3, 2-[1H-benzimidazol-2-yl-[5-fluoro-2-(methoxymethoxy)phenyl]methyl]-6-[4-(1-methylazetidin-3-yl)phenyl]isoindolin-1-one

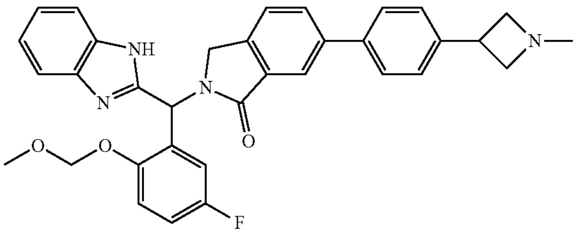

To a solution of 6-[4-(azetidin-3-yl)phenyl]-2-[1H-benzimidazol-2-yl-[5-fluoro-2-(methoxymethoxy)phenyl]methyl]isoindolin-1-one (45 mg, 0.082 mmol) in methanol (0.983 mL) was added formaldehyde (37% in water, 60.9 μL, 0.164 mmol) The reaction mixture was stirred at room temperature for 5 min and then sodium cyanoborohydride (10.3 mg, 91.5 mmol) was added. The reaction mixture was stirred at room temperature for 5 h. The reaction mixture was quenched with saturated sodium bicarbonate solution and extracted with ethyl acetate three times. The combined organic extracts were washed with water, brine, dried over sodium sulfate, filtered and concentrated under reduced pressure. The crude product was purified by reverse phase HPLC eluting with 10-100% ACN/water containing 0.1% formic acid to give the title compound (14 mg, 30%). $^1$H NMR (400 MHz, methanol-$d_4$) δ: 8.57 (s, 1H), 8.07 (d, 1H), 7.89-7.96 (m, 1H), 7.53-7.74 (m, 5H), 7.44-7.49 (m, 2H), 7.22-7.29 (m, 4H), 7.10-7.18 (m, 1H), 6.85-6.91 (m, 1H), 5.13-5.18 (m, 2H), 4.75 (d, 1H), 4.33 (d, 1H), 4.04-4.14 (m, 2H), 3.91-4.03 (m, 1H), 3.59-3.73 (m, 2H), 3.23 (s, 3H), 2.65 (s, 3H); MS m/z: 563.3 $[M+1]^+$.

Step 4. 2-[1H-benzimidazol-2-yl-(5-fluoro-2-hydroxy-phenyl)methyl]-6-[4-(1-methylazetidin-3-yl)phenyl]isoindolin-1-one (Compound 049)

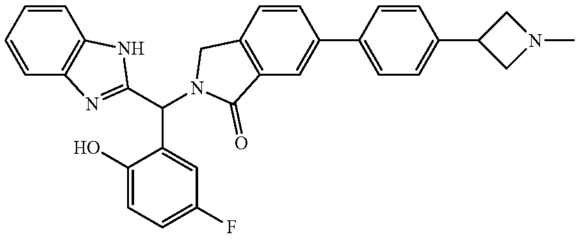 [SMILES: CN1CC(c2ccc(-c3ccc4c(c3)C(=O)N(C(c3nc5ccccc5[nH]3)c3cc(F)ccc3O)C4)cc2)C1]

To a solution of 2-[1H-benzimidazol-2-yl-[5-fluoro-2-(methoxymethoxy)phenyl]methyl]-6-[4-(1-methylazetidin-3-yl)phenyl]isoindolin-1-one (14.0 mg, 0.0248 mmol) in dichloromethane (1 mL) was added HCl in dioxane (4 M, 62.0 µL, 0.248 mmol). After stirring overnight at room temperature, the solvent was removed under reduced pressure. The crude product was purified by reverse phase HPLC eluting with 10-100% ACN/water containing 0.1% formic acid to give the title compound (3 mg, 23%). $^1$H NMR (400 MHz, methanol-$d_4$) δ: 8.06 (s, 1H), 7.88-7.94 (m, 1H), 7.68-7.74 (m, 2H), 7.63-7.67 (m, 1H), 7.52-7.61 (m, 2H), 7.44-7.51 (m, 2H), 7.23-7.29 (m, 2H), 7.16 (s, 1H), 7.00-7.07 (m, 1H), 6.89-6.95 (m, 1H), 6.75-6.81 (m, 1H), 4.74-4.82 (m, 1H), 4.29 (d, 1H), 4.09-4.19 (m, 2H), 3.94-4.06 (H), 3.70-3.80 (m, 2H), 2.70 (s, 3H); MS m/z: 519.2 [M+1]$^+$.

Example 16: 2-[1H-benzimidazol-2-yl-(5-fluoro-2-hydroxy-phenyl)methyl]-6-[4-(1-methylazetidin-3-yl)oxyphenyl]isoindolin-1-one;dihydrochloride (Compound 056)

Scheme 19

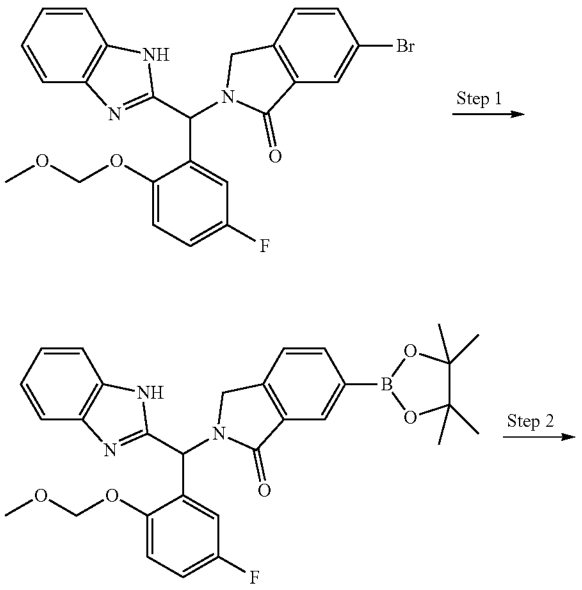

-continued

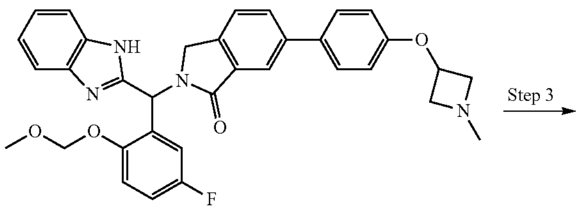

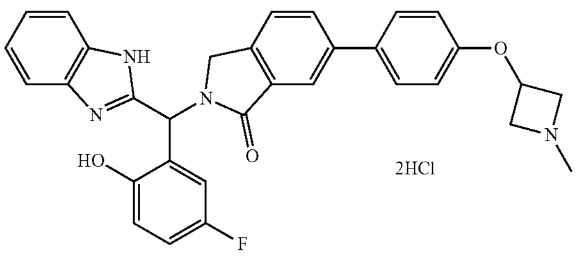

Step 1. 2-[1H-benzimidazol-2-yl-[5-fluoro-2-(methoxymethoxy)phenyl]methyl-6-(4,4,5,5-tetramethyl-1,3,2-dioxaborolan-2-yl)isoindolin-1-one

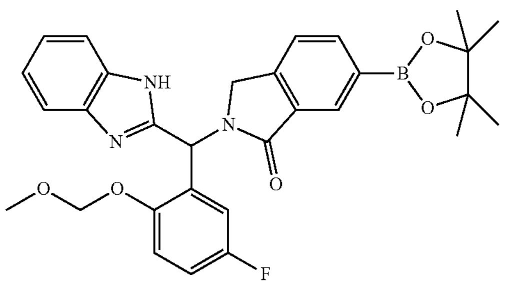

A mixture of 2-[1H-benzimidazol-2-yl-[5-fluoro-2-(methoxymethoxy)phenyl]methyl]-6-bromo-isoindolin-1-one (6.30 g, 12.6 mmol), bis(pinacolato)diboron (3.19 g, 12.6 mmol), potassium acetate (3.70 g, 37.8 mmol) and dioxane (160 mL) was degassed under nitrogen twice. [1,1'-bis(diphenylphosphino)ferrocene]dichloropalladium (II), complex with dichloromethane (0.921 mg, 1.26 mmol) was added and then the reaction mixture was degassed under nitrogen once more. The reaction mixture was heated at 100° C. for 12 h. After cooling to room temperature, the reaction mixture was filtered through a pad of Celite. The filtrate was concentrated and triturated with a mixture of ethyl acetate and petroleum ether (1/1) to give the title compound (5.10 g, 75%). $^1$H NMR (400 MHz, $CDCl_3$) δ: 11.78 (br s, 1H), 8.17 (s, 1H), 7.89 (d, 1H), 7.75 (s, 1H), 7.35-7.47 (m, 2H), 7.16-7.26 (m, 4H), 6.94 (dd, 2H), 4.75-4.83 (m, 2H), 4.69 (d, 1H), 4.45 (d, 1H), 2.98 (s, 3H), 1.33 (d, 12H); MS m/z: 544.1 [M+1]$^+$.

Step 2. 2-[1H-benzimidazol-2-yl-[5-fluoro-2-(methoxymethoxy)phenyl]methyl]-6-[4-(1-methyl-azetidin-3-yl)oxyphenyl]isoindolin-1-one

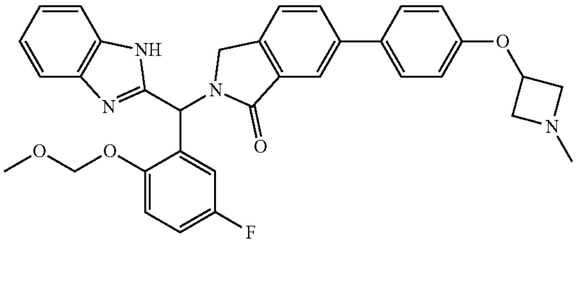

A mixture of 2-[1H-benzimidazol-2-yl-[5-fluoro-2-(methoxymethoxy)phenyl]methyl]-6-(4,4,5,5-tetramethyl-1,3,2-dioxaborolan-2-yl)isoindolin-1-one (0,309 g, 0.569 mmol), 3-(4-iodophenoxy)-1-methylazetidine (0.150 g, 0.518 mmol), potassium carbonate (0.215 g, 1.55 mmol) and dioxane/water (6 mL, 10/1) was degassed under nitrogen twice. [1,1'-bis(diphenyl-phosphino)ferrocene]dichloropalladium(II), complex with dichloromethane (75.3 mg, 0.259 mmol) was added and then the reaction mixture was degassed under nitrogen once more. The reaction mixture was heated at 150° C. for 4 h. After cooling to room temperature, the reaction mixture was poured into water and extracted with ethyl acetate three times. The combined organic extracts were washed with brine, dried over sodium sulfate, filtered and concentrated under reduced pressure. The crude product was purified by silica gel column chromatography eluting with 11% methanol in dichloromethane to give the title compound (150 mg, 50%). MS m/z: 579.1 $[M+1]^+$.

Step 3. 2-[1H-benzimidazol-2-yl-(5-fluoro-2-hydroxy-phenyl)methyl]-6-[4-(1-methylazetidin-3-yl)oxyphenyl]isoindolin-1-one;dihydrochloride (Compound 056)

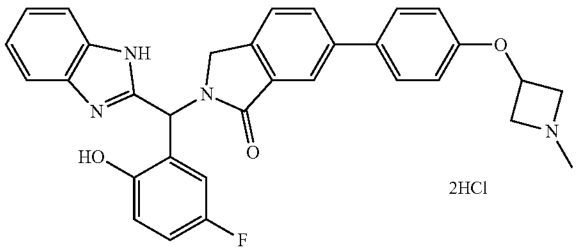 [SMILES: CN1CC(Oc2ccc(-c3ccc4c(c3)C(=O)N(C(c3nc5ccccc5[nH]3)c3cc(F)ccc3O)C4)cc2)C1]

To a solution of 2-[1H-benzimidazol-2-yl-[5-fluoro-2-(methoxymethoxy)phenyl]methyl]-6-[4-(1-methylazetidin-3-yl)oxyphenyl]isoindolin-1-one (0.150 g, 0.259 mmol) in dioxane (5 mL) was added HCl in dioxane (4 M, 3.0 mL, 12.0 mmol). After stirring 3 h at room temperature, the solvent was removed under reduced pressure. The crude product was purified by reverse phase HPLC eluting with 0-100% ACN/water (0.05% HCl modifier) to give the title compound (22 mg, 15%). $^1H$ NMR (400 MHz, DMSO-$d_6$) δ: 10.59-10.96 (m, 1H), 10.28 (br s, 1H), 7.91-7.96 (m, 2H), 7.67-7.77 (m, 5H), 7.46 (s, 2H), 7.07-7.22 (m, 3H), 6.96-7.05 (m, 3H), 5.02-5.30 (m, 1H), 4.70-4.84 (m, 2H), 4.39-4.47 (m, 1H), 4.22-4.33 (m, 2H), 4.04-4.12 (m, 1H), 2.92 (m, 3H); MS m/z: 535.2 $[M+1]^+$.

The following examples were prepared by a similar method to Example 14 from 2-[1H-benzimidazol-2-yl-[5-fluoro-2-(methoxymethoxy)phenyl]methyl]-6-bromo-isoindolin-1-one and the corresponding boronate starting materials:

| No. | Structure/Name | m/z $[M + 1]^+$ | $^1H$ NMR (DMSO-$d_6$) δ | Starting materials |
|---|---|---|---|---|
| 057 | 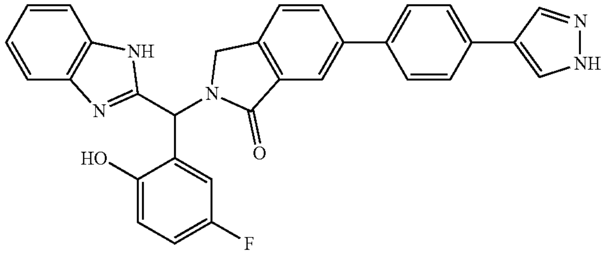 [SMILES: O=C1c2cc(-c3ccc(-c4cn[nH]c4)cc3)ccc2CN1C(c1nc2ccccc2[nH]1)c1cc(F)ccc1O] 2-[1H-benzimidazol-2-yl-(5-fluoro-2-hydroxy-phenyl)-methyl]-6-[4-(1H-pyrazol-4-yl)-phenyl]isoindolin-1-one | 516.2 | 8.05-8.20 (m, 2H), 7.92-7.97 (m, 2H), 7.67-7.75 (m, 5H), 7.47-7.57 (m, 2H), 7.11-7.24 (m, 2H), 6.98-7.08 (m, 2H), 6.87-6.97 (m, 1H), 6.79 (m, 1H), 4.81 (d, 1H), 4.21 (d, 1H) | 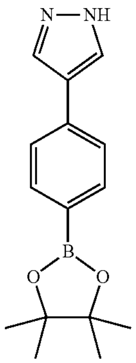 |

-continued

| No. | Structure/Name | m/z [M + 1]$^+$ | $^1$H NMR (DMSO-$d_6$) δ | Starting materials |
|---|---|---|---|---|
| 058 | 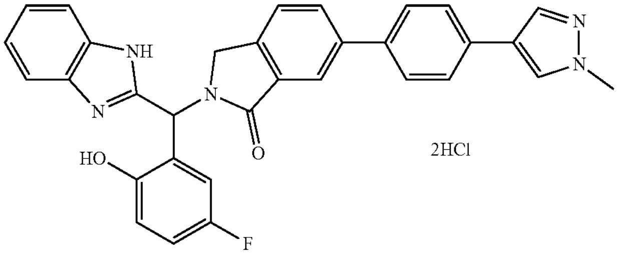 [SMILES: Cn1cc(-c2ccc(-c3ccc4c(c3)C(=O)N(C(c3nc5ccccc5[nH]3)c3cc(F)ccc3O)C4)cc2)cn1] 2HCl 2-[1H-benzimidazol-2-yl-(5-fluoro-2-hydroxy-phenyl)-methyl]-6-[4-(1-methylpyrazol-4-yl)phenyl]isoindolin-1-one; dihydrochloride | 530.2 | 10.25 (br s, 1H), 8.14 (s, 1H), 7.90-7.98 (m, 2H), 7.85 (s, 1H), 7.55-7.73 (m, 7H), 7.38-7.50 (m, 2H), 7.05-7.17 (m, 3H), 6.89-6.99 (m, 1H), 4.70 (d, 1H), 4.21 (d, 1H), 3.81 (s, 3H) | 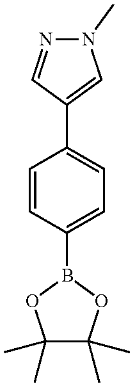 |
| 059 | 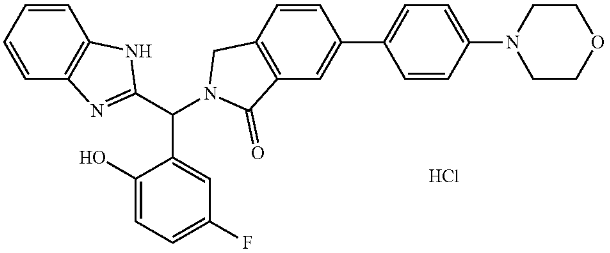 [SMILES: O=C1c2cc(-c3ccc(N4CCOCC4)cc3)ccc2CN1C(c1nc2ccccc2[nH]1)c1cc(F)ccc1O ; Cl] HCl 2-(1H-benzimidazol-2-yl-(5-fluoro-2-hydroxy-phenyl)-methyl]-6-(4-morpholinopheny)-isoindolin-1-one; hydrochloride | 535.2 | 7.90-7.95 (m, 2H), 7.72-7.79 (m, 2H), 7.63-7.71 (m, 3H), 7.51-7.57 (m, 2H), 7.17-7.25 (m, 2H), 7.03-7.17 (m, 4H), 4.76 (d, 1H), 4.27 (d, 1H), 3.75-3.82 (m, 4H), 3.14-3.26 (m, 4H) | 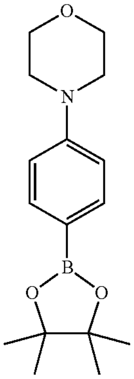 |
| 060 | 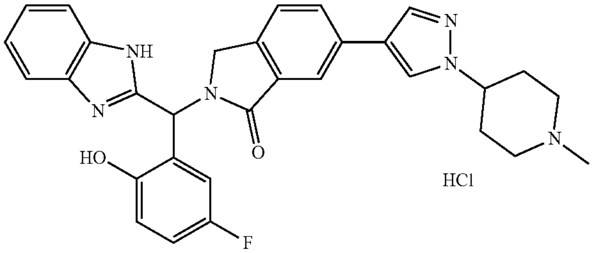 [SMILES: CN1CCC(n2cc(-c3ccc4c(c3)C(=O)N(C(c3nc5ccccc5[nH]3)c3cc(F)ccc3O)C4)cn2)CC1 ; Cl] HCl 2-[1H-benzimidazol-2-yl-(5-fluoro-2-hydroxy-phenyl)-methyl]-6-[1-(1-methyl-4-piperidyl)pyrazol-4-yl]isoindolin-1-one; hydrochloride | 537.2 | 10.99 (br s, 1H), 10.45 (br s, 1H), 8.45 (s, 1H), 8.08-8.13 (m, 1H), 7.99-8.05 (m, 1H), 7.90-7.96 (m, 1H), 7.73-7.80 (m, 2H), 7.61-7.68 (m, 1H), 7.52-7.59 (m, 2H), 7.13-7.24 (m, 3H), 7.03-7.11 (m, 1H), 4.71-4.80 (m, 1H), 4.43-4.50 (m, 1H), 4.24 (d, 1H), 3.49-3.60 (m, 2H), 3.18 (d, 2H), 2.73-2.81 (m, 3H), 2.29-2.40 (m, 4H) | 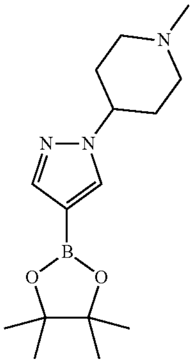 |
| 061 | 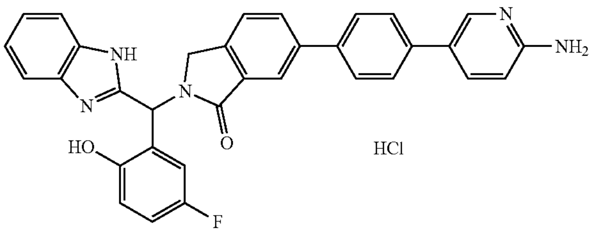 [SMILES: Nc1ccc(-c2ccc(-c3ccc4c(c3)C(=O)N(C(c3nc5ccccc5[nH]3)c3cc(F)ccc3O)C4)cc2)cn1 ; Cl] HCl 6-[4-(6-amino-3-pyridyl)phenyl]-2-[1H-benzimidazol-2-yl-(5-fluoro-2-hydroxy-phenyl)-methyl]isoindolin-1-one; hydrochloride | 542.2 | 10.31 (br s, 1H), 8.36-8.42 (m, 2H), 8.15-8.31 (m, 2H), 8.00-8.08 (m, 2H), 7.87-7.93 (m, 2H), 7.66-7.85 (m, 5H), 7.38-7.51 (m, 2H), 6.99-7.25 (m, 5H), 4.83 (d, 1H), 4.29 (d, 1H) | 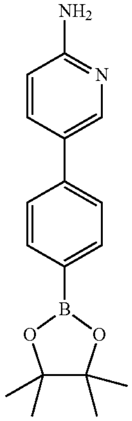 |

-continued

| No. | Structure/Name | m/z [M + 1]+ | $^1$H NMR (DMSO-$d_6$) δ | Starting materials |
|---|---|---|---|---|
| 062 | 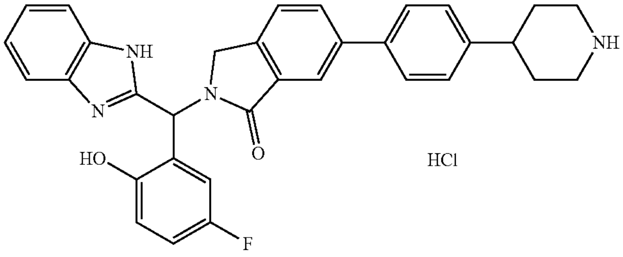 [SMILES: O=C1c2cc(-c3ccc(C4CCNCC4)cc3)ccc2CN1C(c1nc2ccccc2[nH]1)c1cc(F)ccc1O ; Cl] HCl<br>2-[1H-benzimidazol-2-yl-(5-fluoro-2-hydroxy-phenyl)-methyl]-6-[4-(4-piperidyl)-phenyl]isoindolin-1-one; hydrochloride | 533.3 | 10.31 (br s, 1H), 8.82-9.05 (m, 2H), 7.94-8.00 (m, 2H), 7.68-7.77 (m, 5H). 7.43-7.55 (m, 2H), 7.37 (d, 2H), 7.09-7.22 (m, 3H), 6.96-7.09 (m, 1H), 4.79 (d, 1H), 4.27 (d, 1H), 3.35-3.42 (m, 2H), 2.87-3.07 (m, 3H), 1.86-2.01 (m, 4H) | 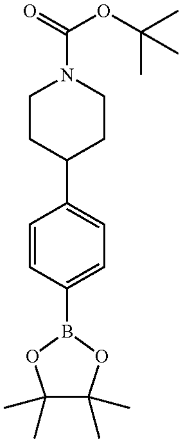 [SMILES: CC(C)(C)OC(=O)N1CCC(c2ccc(B3OC(C)(C)C(C)(C)O3)cc2)CC1] |
| 041 | 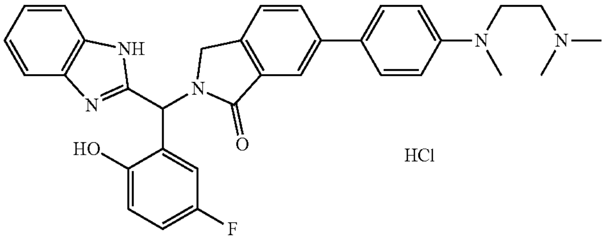 [SMILES: CN(C)CCN(C)c1ccc(-c2ccc3c(c2)C(=O)N(C(c2nc4ccccc4[nH]2)c2cc(F)ccc2O)C3)cc1 ; Cl] HCl<br>2-[1H-benzimidazol-2-yl-(5-fluoro-2-hydroxy-phenyl)-methyl]-6-[4-[2-(dimethylamino)-ethyl-methyl-amino]phenyl]-isoindolin-1-one; hydrochloride | 550.3 | 10.74 (br s, 1H), 10.30 (br s, 1H), 7.80-7.86 (m, 2H), 7.52-7.69 (m, 5H), 7.41-7.49 (m, 2H), 7.03-7.16 (m, 3H), 6.98 (d, 1H), 6.87 (d, 2H), 4.68 (d, 1H), 4.19 (d, 1H), 3.73 (m, 2H), 3.11-3.20 (m, 2H), 2.91 (s, 3H), 2.73 (d, 6H) | 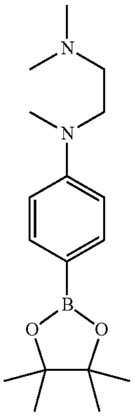 |
| 029 | 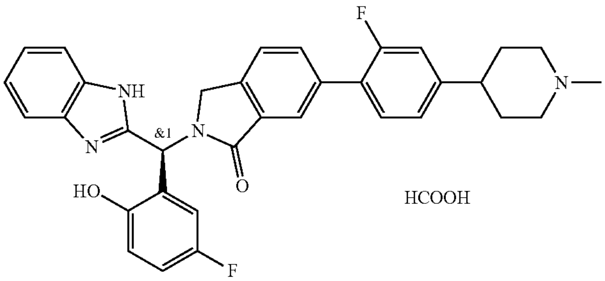 [SMILES: CN1CCC(c2ccc(-c3ccc4c(c3)C(=O)N([C@H](c3nc5ccccc5[nH]3)c3cc(F)ccc3O)C4)c(F)c2)CC1 ; "HCOOH"] HCOOH<br>2-[1H-benzimidazol-2-yl-(5-fluoro-2-hydroxy-phenyl)-methyl]-6-[2-fluoro-4-(1-methyl-4-piperidyl)phenyl]isoindolin-1-one; formic acid | 565.3 | 12.61 (br s, 1H), 9.99 (br s, 1H), 8.24 (s, 1H), 7.76-7.85 (m, 2H), 7.65-7.73 (m, 1H), 7.41-7.63 (m, 3H), 7.15-7.26 (m, 4H), 7.06-7.14 (m, 1H), 7.03 (s, 1H), 6.88-6.96 (m, 1H), 6.77-6.84 (m, 1H), 4.83 (d, 1H), 4.19 (d, 1H), 2.87-2.93 (m, 2H), 2.55-2.62 (m, 1H), 2.22 (s, 3H), 1.96-2.05 (m, 2H), 1.66-1.84 (m, 4H) | 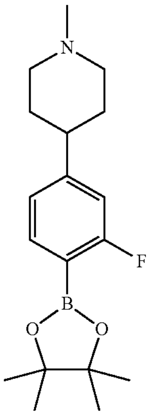 [SMILES: CN1CCC(c2ccc(B3OC(C)(C)C(C)(C)O3)c(F)c2)CC1] |

The following examples were prepared by a similar method to Example 14 from the corresponding halogen-substituted phenol and boronate starting materials. The corresponding phenol was protected as methoxymethyl derivative prior to react with the sulfinamide:

| No. | Structure/Name | m/z $[M + 1]^+$ | $^1H$ NMR (DMSO-$d_6$) δ | Starting materials |
|---|---|---|---|---|
| 042 | 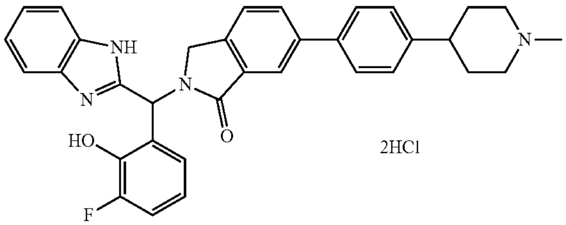 [SMILES: CN1CCC(c2ccc(-c3ccc4c(c3)C(=O)N(C(c3nc5ccccc5[nH]3)c3cccc(F)c3O)C4)cc2)CC1 ; "2HCl"] 2HCl 2-[1H-benzimidazol-2-yl-(3-fluoro-2-hydroxy-phenyl)-methyl]-6-[4-(1-methyl-4-piperidyl)phenyl]isoindolin-1-one; dihydrochloride | 547.3 | 10.64 (br s, 1H), 10.45 (br s, 1H), 7.94-8.00 (m, 2H), 7.68-7.76 (m, 5H), 7.43-7.52 (m, 2H), 7.29-7.42 (m, 3H), 7.22 (s, 1H), 7.02-7.10 (m, 1H), 6.89-6.98 (m, 1H), 4.78 (d, 1H), 4.24 (d, 1H), 3.45-3.54 (m, 2H), 3.07 (d, 2H), 2.83-2.92 (m, 1H), 2.77 (d, 3H), 1.92-2.15 (m, 4H) | 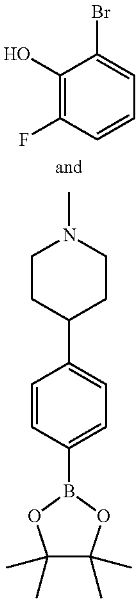 |
| 043 | 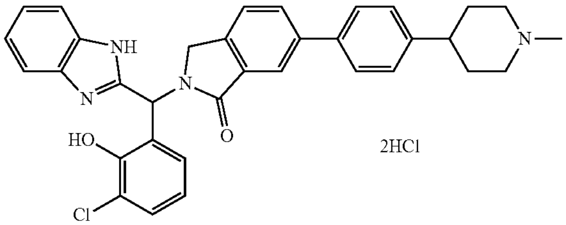 [SMILES: CN1CCC(c2ccc(-c3ccc4c(c3)C(=O)N(C(c3nc5ccccc5[nH]3)c3cccc(Cl)c3O)C4)cc2)CC1 ; "2HCl"] 2HCl 2-[1H-benzimidazol-2-yl-(3-chloro-2-hydroxy-phenyl)-methyl]-6-[4-(1-methyl-4-piperidyl)phenyl]isoindolin-1-one; dihydrochloride | 564.3 | 10.82 (br s, 1H), 10.18 (br s, 1H), 7.95-8.01 (m, 2H), 7.70-7.78 (m, 5H), 7.47-7.57 (m, 3H), 7.38 (d, 2H), 7.21-7.28 (m, 2H), 7.00 (m, 1H), 4.78 (d, 1H), 4.27 (d, 1H), 3.46-3.53 (m, 2H), 3.02-3.14 (m, 2H), 2.74-2.92 (m, 4H), 1.94-2.16 (m, 4H) | 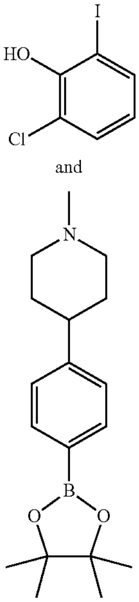 |

-continued

| No. | Structure/Name | m/z [M + 1]+ | 1H NMR (DMSO-d6) δ | Starting materials |
|---|---|---|---|---|
| 044 | 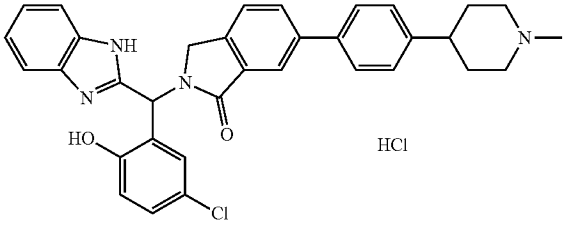 [SMILES: CN1CCC(c2ccc(-c3ccc4c(c3)C(=O)N(C(c3nc5ccccc5[nH]3)c3cc(Cl)ccc3O)C4)cc2)CC1 ; Cl] HCl 2-[1H-benzimidazol-2-yl-(5-chloro-2-hydroxy-phenyl)-methyl]-6-[4-(1-methyl-4-piperidyl)phenyl]isoindolin-1-one; hydrochloride | 564.3 | 10.66 (br s, 2H), 7.95-8.01 (m, 2H), 7.68-7.79 (m, 5H), 7.45-7.53 (m, 2H), 7.29-7.44 (m, 4H), 7.14 (s, 1H), 7.06 (d, 1H), 4.80 (d, 1H), 4.28 (d, 1H), 3.46-3.55 (m, 2H), 2.97-3.14 (m, 2H), 2.84-2.92 (m, 1H), 2.78 (d, 3H), 1.93-2.16 (m, 4H) | 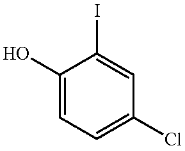 and 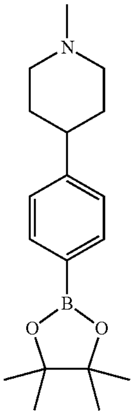 |

The following example was prepared by a similar method to Example 14 from the corresponding aldehyde and boronate starting materials:

| No. | Structure/Name | m/z [M + 1]+ | 1H NMR (DMSO-d6) δ | Starting materials |
|---|---|---|---|---|
| 045 | 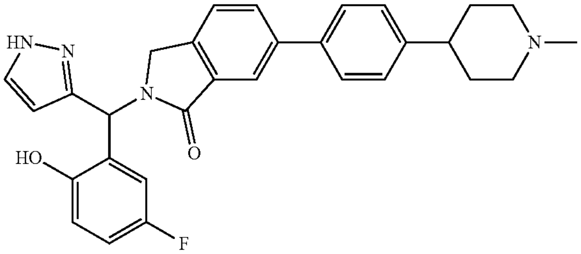 [SMILES: CN1CCC(c2ccc(-c3ccc4c(c3)C(=O)N(C(c3cc[nH]n3)c3cc(F)ccc3O)C4)cc2)CC1] 2-[(5-fluoro-2-hydroxy-phenyl)-(1H-pyrazol-3-yl)methyl]-6-[4-(1-methyl-4-piperidyl)phenyl]-isoindolin-1-one | 497.2 | 12.84 (br s, 1H), 9.78 (br s, 1H), 7.84-7.96 (m, 2H), 7.60-7.80 (m, 4H), 7.31-7.49 (m, 2H), 7.00-7.12 (m, 1H), 6.79-6.98 (m, 3H), 6.22 (s, 1H), 4.61 (d, 1H), 4.19 (d, 1H), 3.17-3.23 (m, 1H), 2.86-3.00 (m, 2H), 2.26 (s, 3H), 1.98-2.12 (m, 2H), 1.66-1.90 (m, 4H) | 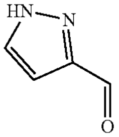 and 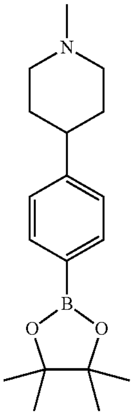 |

The following examples were prepared by a similar method to Example 2 from ethyl 2-amino-2-[5-fluoro-2-(methoxymethoxy)phenyl]acetate and either methyl 5-bromo-2-(bromo-methyl)-benzoate or methyl 6-bromo-3-(bromomethyl)picolinate; and the corresponding diamino aryl starting materials:

| No. | Structure/Name | m/z $[M + 1]^+$ | $^1H$ NMR (DMSO-$d_6$) δ | Starting materials |
|---|---|---|---|---|
| 046 | 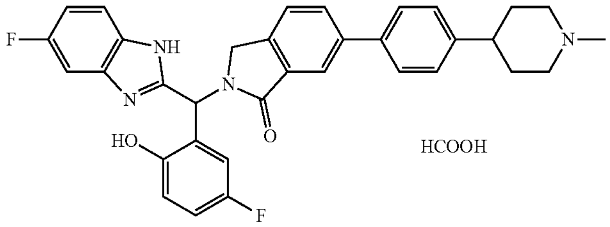 [SMILES: CN1CCC(c2ccc(-c3ccc4c(c3)C(=O)N(C(c3nc5cc(F)ccc5[nH]3)c3cc(F)ccc3O)C4)cc2)CC1 ; "HCOOH"] HCOOH 2-[(5-fluoro-1H-benzimidazol-2-yl)-(5-fluoro-2-hydroxy-phenyl)-methyl]-6-[4-(1-methyl-4-piperidyl)phenyl]isoindolin-1-one; formic acid | 565.3 | $^1H$ NMR (methanol-$d_4$) δ: 8.53-8.57 (m, 1H), 8.04 (s, 1H), 7.87-7.92 (m, 1H), 7.61-7.70 (m, 3H), 7.51-7.56 (m, 1H), 7.38-7.44 (m, 2H), 7.23-7.29 (m, 1H), 7.14 (s, 1H), 7.00-7.08 (m, 2H), 6.89-6.95 (m, 1H), 6.77-6.83 (m, 1H), 4.80 (d, 1H), 4.29 (d, 1H), 3.45-3.55 (m, 2H), 2.77-3.04 (m, 6H), 2.06-2.17 (m, 2H), 1.94-2.06 (m, 2H) | 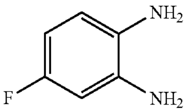 |
| 047 | 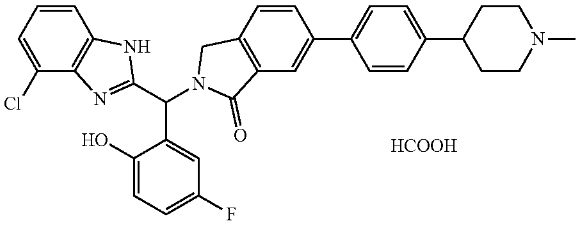 [SMILES: CN1CCC(c2ccc(-c3ccc4c(c3)C(=O)N(C(c3nc5c(Cl)cccc5[nH]3)c3cc(F)ccc3O)C4)cc2)CC1 ; "HCOOH"] HCOOH 2-[(4-chloro-1H-benzimidazol-2-yl)-(5-fluoro-2-hydroxy-phenyl)-methyl]-6-[4-(1-methyl-4-piperidyl)phenyl]isoindolin-1-one; formic acid | 581.3 | 8.21 (s, 1H), 7.88-7.96 (m, 2H), 7.64-7.72 (m, 3H), 7.43-7.55 (m, 1H), 7.37 (d, 2H), 7.17-7.30 (m, 2H), 7.01-7.13 (m, 2H), 6.90-6.95 (m, 1H), 6.77-6.85 (m, 1H), 4.79 (d, 1H), 4.21 (d, 1H), 2.90-3.00 (m, 2H), 2.54-2.63 (m, 1H), 2.25-2.30 (m, 3H), 2.03-2.16 (m, 2H), 1.67-1.83 (m, 4H) | 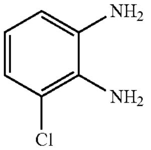 |
| 048 | 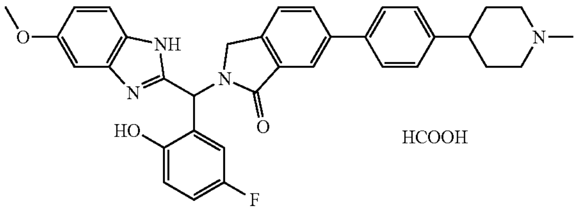 HCOOH 2-[(5-fluoro-2-hydroxy-phenyl)-(5-methoxy-1H-benzimidazol-2-yl)methyl]-6-[4-(1-methyl-4-piperidyl)phenyl]isoindolin-1-one; formic acid | 577.3 | 8.22 (s, 1H), 7.86-7.94 (m, 2H), 7.67 (d, 3H), 7.32-7.47 (m, 3H), 7.04-7.10 (m, 1H), 7.00 (s, 1H), 6.89-6.94 (m, 1H), 6.76-6.84 (m, 2H), 4.81 (d, 1H), 4.17 (d, 1H), 3.77 (s, 3H), 2.96-3.05 (m, 2H), 2.55-2.64 (m, 1H), 2.32 (s, 3H), 2.13-2.24 (m, 2H), 1.69-1.85 (m, 4H) | 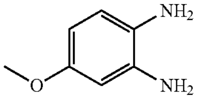 |
| 050 | 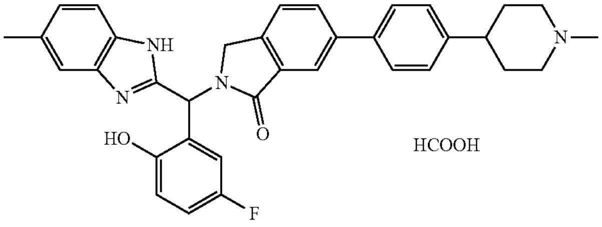 HCOOH 2-[(5-fluoro-2-hydroxy-phenyl)-(5-methyl-1H-benzimidazol-2-yl)methyl]-6-[4-(1-methyl-4-piperidyl)phenyl]isoindolin-1-one; formic acid | 561.3 | 8.20 (s, 1H), 7.86-7.95 (m, 2H), 7.64-7.69 (m, 3H), 7.24-7.49 (m, 4H), 7.05-7.11 (m, 1H), 6.95-7.04 (m, 2H), 6.88-6.93 (m, 1H), 6.74-6.81 (m, 1H), 4.81 (d, 1H), 4.17 (d, 1H), 2.88-2.98 (m, 2H), 2.53-2.60 (m, 1H), 2.41 (s, 3H), 2.24 (s, 3H), 1.99-2.10 (m, 2H), 1.66-1.82 (m, 4H) | 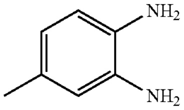 |

-continued

| No. | Structure/Name | m/z $[M+1]^+$ | $^1H$ NMR (DMSO-$d_6$) δ | Starting materials |
|---|---|---|---|---|
| 051 | 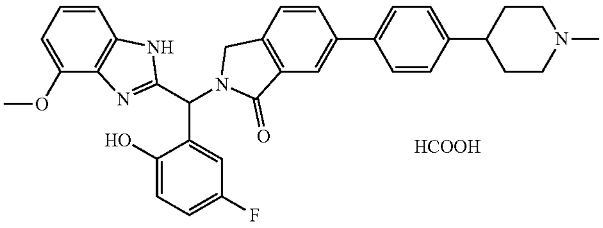 HCOOH<br>2-[(5-fluoro-2-hydroxy-phenyl)-(4-methoxy-1H-benzimidazol-2-yl)methyl-6-[4-(1-methyl-4-piperidyl)phenyl]isoindolin-1-one; formic acid | 577.3 | 8.12-8.19 (m, 1H). 7.79-7.86 (m, 2H), 7.55-7.63 (m, 3H), 7.28 (d, 2H), 6.90-7.07 (m, 4H), 6.79-6.86 (m, 1H), 6.59-6.74 (m, 2H), 4.72 (d, 1H). 4.09 (d, 1H), 3.81 (s, 3H), 2.83-2.98 (m, 2H), 2.46-2.54 (m, 1H), 2.19-2.29 (m, 3H), 2.00-2.17 (m, 2H), 1.60-1.79 (m, 4H) | 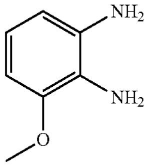 |
| 052 | 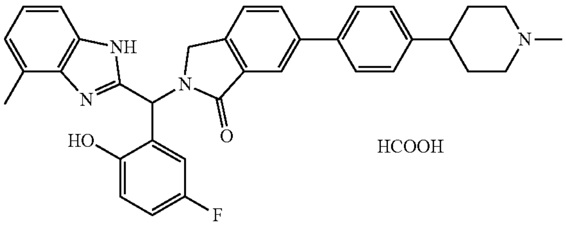 [SMILES: Cc1cccc2[nH]c(C(c3cc(F)ccc3O)N3Cc4ccc(-c5ccc(C6CCN(C)CC6)cc5)cc4C3=O)nc12 ; "HCOOH"] HCOOH<br>2-[(5-fluoro-2-hydroxy-phenyl)-(4-methyl-1H-benzimidazol-2-yl)methyl]-6-[4-(1-methyl-4-piperidyl)phenyl]isoindolin-1-one; formic acid | 561.3 | 8.23 (s, 1H), 7.87-7.93 (m, 2H), 7.63-7.71 (m, 3H), 7.25-7.45 (m, 3H), 7.03-7.10 (m, 3H), 6.96-7.01 (m, 1H), 6.86-6.95 (m, 1H), 6.72-6.85 (m, 1H), 4.85 (d, 1H), 4.18 (d, 1H), 2.89-2.99 (m, 2H), 2.54-2.60 (m, 1H), 2.48 (s, 3H), 2.25 (s, 3H), 2.02-2.12 (m, 2H), 1.65-1.86 (m, 4H) | 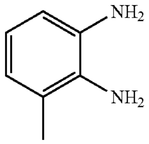 |
| 028 | 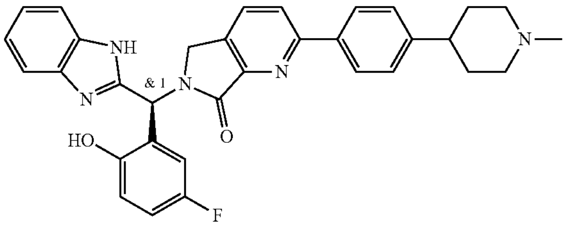<br>6-[1H-benzimidazol-2-yl-(5-fluoro-2-hydroxy-phenyl)-methyl]-2-[4-(1-methyl-4-piperidyl)phenyl]-5H-pyrrolo-[3,4-b]pyridin-7-one | 548.3 | 12.65 (br s, 1H), 9.98 (br s, 1H), 8.05-8.17 (m, 4H), 7.54-7.65 (m, 1H), 7.35-7.52 (m, 3H), 7.15-7.26 (m, 2H), 7.04-7.12 (m, 2H), 6.90-6.98 (m, 1H), 6.80-6.88 (m, 1H), 4.81 (d, 1H), 4.20 (d, 1H), 2.89-3.00 (m, 2H), 2.55-2.62 (m, 1H), 2.25 (s, 3H), 2.01-2.16 (m, 2H) 1.68-1.84 (m, 4H) | 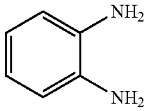 |

The following examples were prepared by a similar method to Example 6 from methyl 2-bromo-2-(5-fluoro-2-methoxy-phenyl)acetate and the corresponding bicyclic starting materials:

| No. | Structure/Name | m/z $[M + 1]^+$ | $^1H$ NMR (DMSO-$d_6$) δ | Starting materials |
|---|---|---|---|---|
| 053 | 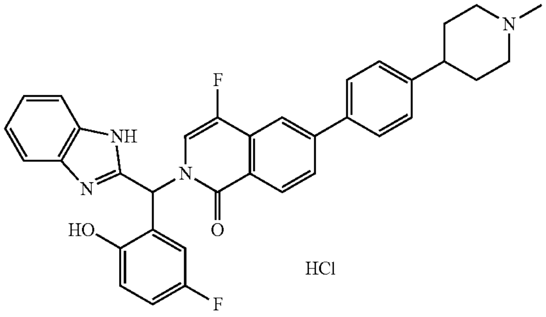 [SMILES: CN1CCC(c2ccc(-c3ccc4c(=O)n(C(c5nc6ccccc6[nH]5)c5cc(F)ccc5O)cc(F)c4c3)cc2)CC1 ; Cl] HCl 2-[1H-benzimidazol-2-yl-(5-fluoro-2-hydroxy-phenyl)-methyl]-4-fluoro-6-[4-(1-methyl-4-piperidyl)phenyl]isoquinolin-1-one; hydrochloride | 577.3 | 10.19-10.46 (m, 2H), 8.33-8.39 (m, 1H), 7.98-8.05 (m, 2H), 7.86 (d, 2H), 7.60-7.71 (m. 3H), 7.34-7.51 (m, 5H), 7.15-7.23 (m, 1H), 6.89-7.03 (m, 2H), 3.49-3.54 (m, 2H), 3.05-3.16 (m, 2H), 2.76-2.92 (m, 4H), 2.00-2.09 (m, 4H) | 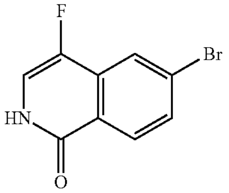 [SMILES: O=c1[nH]cc(F)c2cc(Br)ccc12] |
| 054 | 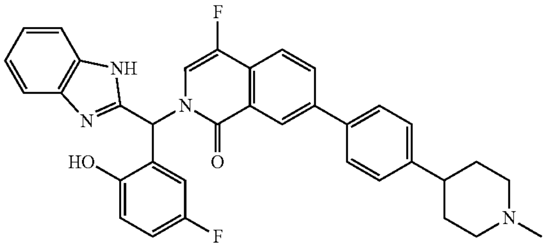 [SMILES: CN1CCC(c2ccc(-c3ccc4c(F)cn(C(c5nc6ccccc6[nH]5)c5cc(F)ccc5O)c(=O)c4c3)cc2)CC1] 2-[1H-benzimidazol-2-yl-(5-fluoro-2-hydroxy-phenyl)-methyl]-4-fluoro-7-[4-(1-methy-4-piperidyl)phenyl]isoquinolin-1-one | 577.3 | 12.78 (br s, 1H), 10.03 (br s, 1H), 8.51 (s, 1H), 8.18-8.23 (m, 1H), 7.88 (d, 1H), 7.73 (d, 2H), 7.58-7.67 (m, 2H), 7.46-7.55 (m, 1H), 7.36-7.43 (m, 3H), 7.17-7.27 (m, 2H), 7.10-7.16 (m, 1H), 6.90-6.95 (m, 1H), 6.72-6.77 (m, 1H), 2.91-3.01 (m, 2H), 2.54-2.62 (m, 1H), 2.27 (s, 3H), 2.04-2.17 (m, 2H), 1.66-1.85 (m, 4H) | 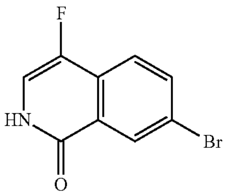 [SMILES: O=c1[nH]cc(F)c2ccc(Br)cc12] |

The following examples were prepared by a similar method to Example 6 from methyl 2-bromo-2-(5-fluoro-2-methoxy-phenyl)acetate or methyl 2-bromo-2-(5-fluoro-2-(methoxymethoxy)phenyl)acetate and the corresponding bicyclic starting materials:

| No. | Structure/Name | m/z $[M + 1]^+$ | $^1H$ NMR (DMSO-$d_6$) δ | Starting materials |
|---|---|---|---|---|
| 096 | 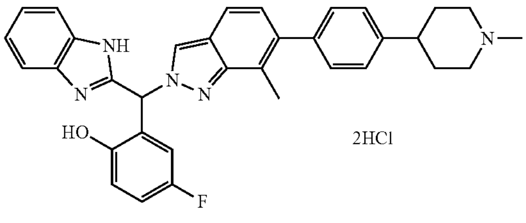 [SMILES: Cc1c(-c2ccc(C3CCN(C)CC3)cc2)ccc2cn(C(c3nc4ccccc4[nH]3)c3cc(F)ccc3O)nc12 ; "2HCl"] 2HCl 2-[1H-Benzimidazol-2-yl-[7-methyl-6-[4-(1-methyl-4-piperidyl)phenyl]indazol-2-yl]methyl]-4-fluoro-phenol; dihydrochloride | 546.4 | 10.92 (br s, 1H), 10.61 (br s, 1H), 8.64 (s, 1H), 7.91 (s, 1H), 7.75 (dd, 2H), 7.65 (d, 1H), 7.50 (dd, 2H), 7.26-7.42 (m, 4H), 7.14-7.23 (m, 1H), 7.05-7.13 (m, 1H), 7.01 (d, 1H), 6.78 (dd, 1H), 3.47 (d, 2H), 3.02-3.12 (m, 2H), 2.82-2.88 (m, 1H), 2.74 (d, 3H), 2.39 (s, 3H), 2.05-2.16 (m, 2H), 1.88-2.04 (m, 2H). | 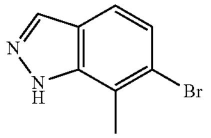 |

-continued

| No. | Structure/Name | m/z [M + 1]+ | $^1$H NMR (DMSO-$d_6$) δ | Starting materials |
|---|---|---|---|---|
| 097 | 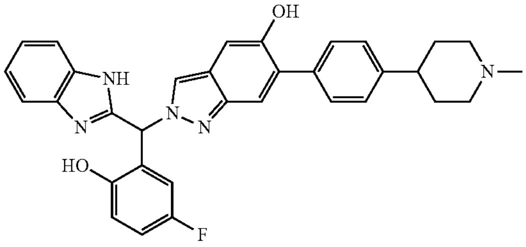 [SMILES: CN1CCC(c2ccc(-c3cc4nn(C(c5nc6ccccc6[nH]5)c5cc(F)ccc5O)cc4cc3O)cc2)CC1] 2-[1H-Benzimidazol-2-yl-(5-fluoro-2-hydroxy-phenyl)methyl]-6-[4-(1-methyl-4-piperidyl)phenyl]indazol-5-ol | 548.1 | 12.60 (br s, 1H), 12.46 (br s, 1H), 9.37 (br s, 1H), 8.14 (s, 1H), 7.52-7.60 (m, 2H), 7.33-7.49 (m, 4H), 7.15-7.28 (m, 4H), 7.04-7.13 (m, 1H), 7.01 (s, 1H), 6.89 (dd, 1H), 6.83 (dd, 1H), 3.26-3.31 (m, 1H), 2.88 (d, 2H), 2.20 (s, 3H), 1.92-2.04 (m, 2H) 1.63-1.79 (m, 4H). | 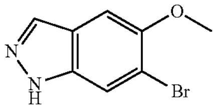 |
| 098 | 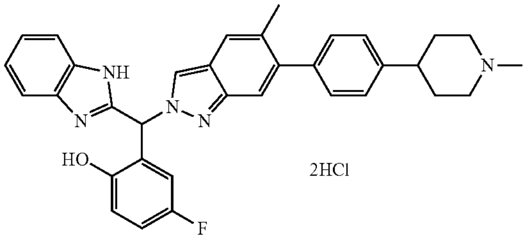 [SMILES: Cc1cc2cn(C(c3nc4ccccc4[nH]3)c3cc(F)ccc3O)nc2cc1-c1ccc(C2CCN(C)CC2)cc1] 2HCl 2-[1H-Benzimidazol-2-yl-[5-methyl-6-[4-(1-methyl-4-piperidyl)phenyl]-indazol-2-yl]methyl]-4-fluoro-phenol; dihydrochloride | 546.1 | 10.78 (br s, 1H), 8.60 (s, 1H), 7.85 (s, 1H), 7.74 (dd, 2H), 7.66 (s, 1H), 7.49 (dd, 2H), 7.39 (s, 1H), 7.26-7.36 (m, 4H), 7.11-7.21 (m, 1H), 7.04 (dd, 1H), 6.64 (dd, 1H), 3.47 (d, 2H), 3.04-3.12 (m, 2H) 2.83-2.87 (m, 1H), 2.75 (d, 3H), 2.21 (s, 3H), 1.97-2.13 (m, 4H). | 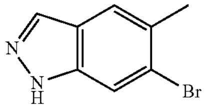 |
| 099 | 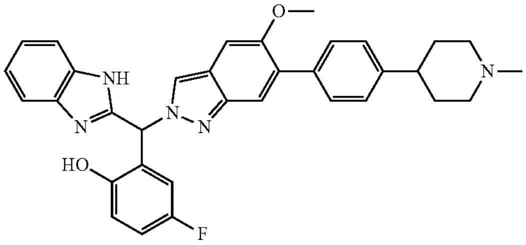 [SMILES: COc1cc2cn(C(c3nc4ccccc4[nH]3)c3cc(F)ccc3O)nc2cc1-c1ccc(C2CCN(C)CC2)cc1] 2-[1H-Benzimidazol-2-yl-[5-methoxy-6-[4-(1-methyl-4-piperidyl)phenyl]indazol-2-yl]methyl]-4-fluoro-phenol | 562.6 | 8.27 (s, 1H), 7.43-7.64 (m, 4H), 7.39 (d, 2H), 7.26 (d, 2H), 7.15-7.23 (m, 2H), 7.13 (s, 1H), 7.04-7.12 (m, 1H), 6.90 (dd, 1H), 6.83 (dd, 1H), 3.73 (s, 3H), 3.31-3.32 (m, 1H), 2.87 (d, 2H), 2.19 (s, 3H), 1.89-2.02 (m, 2H), 1.62-1.80 (m, 4H). | 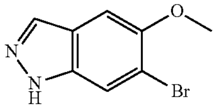 |
| 100 | 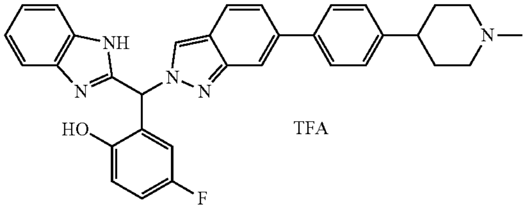 [SMILES: CN1CCC(c2ccc(-c3ccc4cn(C(c5nc6ccccc6[nH]5)c5cc(F)ccc5O)nc4c3)cc2)CC1] TFA 2-((1H-Benzo[d]imidazol-2-yl)(6-(4-(1-methylpiperidin-4-yl)phenyl)-2H-indazol-2-yl)methyl)-4-fluorophenol; trifluoroacetate | 531.9 | 10.20 (br s, 1H), 9.43 (br s, 1H), 8.50 (s, 1H), 7.84 (s, 1H), 7.83 (d, 1H), 7.70 (d, 2H), 7.60 (m, 3H), 7.39 (dd, 1H), 7.34 (d, 2H), 7.27 (m, 2H), 7.13 (m, 1H), 6.94 (dd, 1H), 6.86 (dd, 1H), 3.54 (m, 2H), 3.10 (m, 2H), 2.85 (m, 1H), 2.83 (d, 3H), 2.06 (m, 2H), 1.86 (m, 2H) | 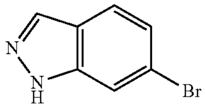 |

-continued

| No. | Structure/Name | m/z [M + 1]+ | $^1H$ NMR (DMSO-$d_6$) δ | Starting materials |
|---|---|---|---|---|
| 101 | 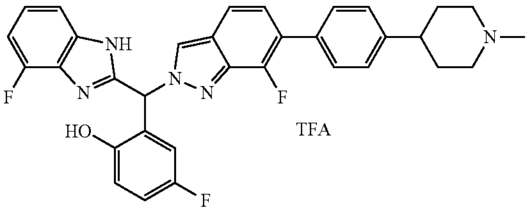 [SMILES: CN1CCC(c2ccc(-c3ccc4cn(C(c5nc6c(F)cccc6[nH]5)c5cc(F)ccc5O)nc4c3F)cc2)CC1] TFA 4-Fluoro-2-((4-fluoro-1H-benzo[d]-imidazol-2-yl)(7-fluoro-6-(4-(1-methylpiperidin-4-yl)phenyl)-2H-indazol-2-yl)methyl)phenol; trifluoroacetate | 567.9 | 10.21 (br s, 1H), 9.49 (br s, 1H), 8.59 (d, 1H), 7.64 (d, 1H), 7.59 (m, 3H), 7.38 (d, 2H), 7.22 (m, 1H), 7.16 (m, 2H), 7.03 (dd, 1H), 6.95 (dd, 1H), 6.90 (dd, 1H), 3.56 (m, 2H), 3.10 (m, 2H), 2.87 (m, 1H), 2.83 (d, 3H), 2.07 (m, 2H), 1.88 (m, 2H) | 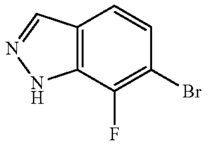 and 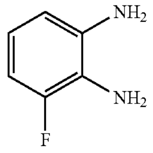 |
| 102 | 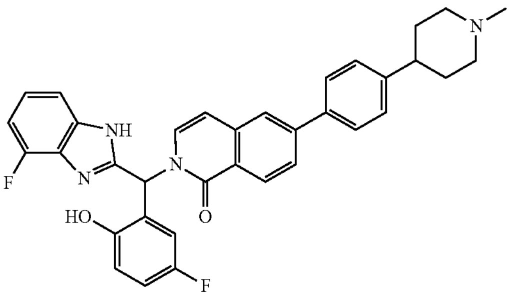 [SMILES: CN1CCC(c2ccc(-c3ccc4c(=O)n(C(c5nc6c(F)cccc6[nH]5)c5cc(F)ccc5O)ccc4c3)cc2)CC1] 2-((4-Fluoro-1H-benzo[d]imidazol-2-yl)(5-fluoro-2-hydroxyphenyl)methyl)-6-(4-(1-methylpiperidin-4-yl)phenyl)isoquinolin-1(2H)-one | 576.9 | 10.05 (br s, 1H), 9.48 (br s, 1H), 8.30 (d, 1H), 7.97 (d, 1H), 7.85 (dd, 1H), 7.80 (d, 2H), 7.66 (s, 1H), 7.40 (d, 2H), 7.36 (d, 1H), 7.29 (d, 1H), 7.20 (m, 1H), 7.13 (m, 1H), 7.03 (dd, 1H), 6.92 (dd, 1H), 6.73 (d, 1H), 6.67 (dd, 1H), 3.56 (m, 2H), 3.10 (m, 2H), 2.88 (m, 1H), 2.83 (d, 3H), 2.07 (m, 2H), 1.88 (m, 2H) | 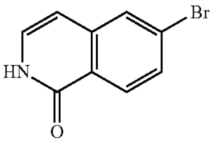 and 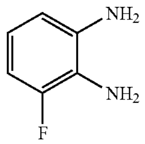 |

The following examples were prepared by a similar method to Example 7 from ethyl 2-amino-2-[5-fluoro-2-(methoxymethoxy)phenyl]acetate and the corresponding boronate and acid starting materials:

| No. | Structure/Name | m/z [M + 1]+ | $^1H$ NMR (DMSO-$d_6$) δ | Starting materials |
|---|---|---|---|---|
| 055 | 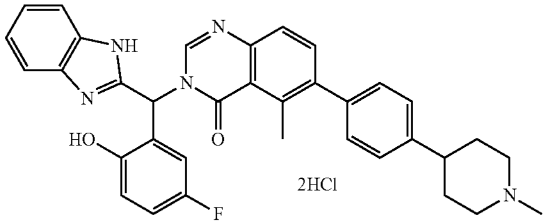 [SMILES: Cc1c(-c2ccc(C3CCN(C)CC3)cc2)ccc2ncn(C(c3nc4ccccc4[nH]3)c3cc(F)ccc3O)c(=O)c12] 2HCl 3-[1H-benzimidazol-2-yl-(5-fluoro-2-hydroxy-phenyl)-methyl]-5-methyl-6-[4-(1-methyl-4-piperidyl)phenyl]-quinazolin-4-one; dihydrochloride | 574.3 | 10.29-10.47 (m, 2H), 8.21 (s, 1H), 7.64-7.71 (m, 3H), 7.57-7.64 (m, 1H), 7.47-7.54 (m, 1H), 7.30-7.44 (m, 6H), 7.17-7.24 (m, 1H), 7.00-7.06 (m, 1H), 6.91-6.98 (m, 1H), 3.46-3.55 (m, 2H), 3.01-3.14 (m, 2H), 2.84-2.94 (m, 1H), 2.79 (d, 3H), 2.64 (s, 3H), 1.93-2.15 (m, 4H) | 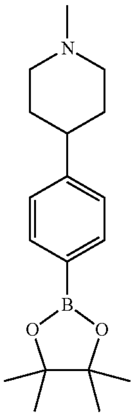 and 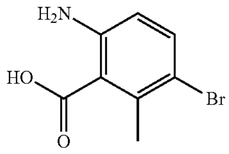 |

-continued

| No. | Structure/Name | m/z $[M + 1]^+$ | $^1H$ NMR ($DMSO-d_6$) δ | Starting materials |
|---|---|---|---|---|
| 007 | 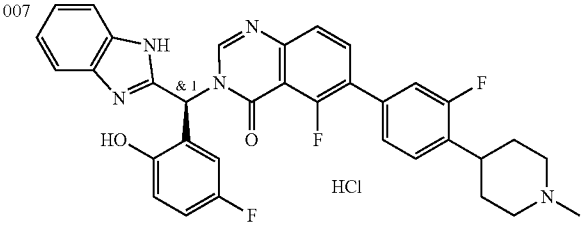 3-[1H-benzimidazol-2-yl-(5-fluoro-2-hydroxy-phenyl)methyl]-5-fluoro-6-[3-fluoro-4-(1-methyl-4-piperidyl)phenyl]quinazolin-4-one; hydrochloride | 596.3 | 10.20-10.48 (m. 2H), 8.29 (s, 1H), 7.99-8.06 (m, 1H), 7.61-7.70 (m, 3H), 7.40-7.54 (m, 4H), 7.33-7.38 (m, 2H), 7.17-7.23 (m, 1H), 6.99-7.05 (m, 1H), 6.90-6.97 (m, 1H), 3.49-3.55 (m, 2H), 3.07-3.21 (m, 3H), 2.69-2.86 (m, 3H), 1.96-2.17 (m, 4H) | 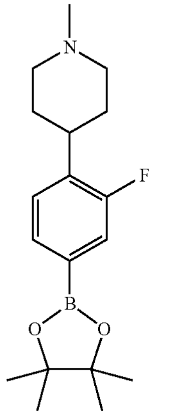 and 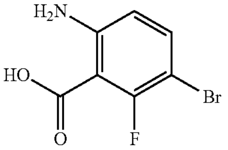 |

The following example was prepared by a similar method to Example 8 from 2-[1H-Benzimidazol-2-yl-[1-(2-trimethylsilylethoxymethyl)-5,6-dihydro-4H-cyclopenta[c]pyrazol-3-yl]methyl]-6-bromo-isoindolin-1-one and 5-ethynylpyridin-2-amine in a similar manner to Example 4, step 3:

| No. | Structure/Name | m/z $[M + 1]^+$ | $^1H$ NMR ($DMSO-d_6$) δ |
|---|---|---|---|
| 030 | 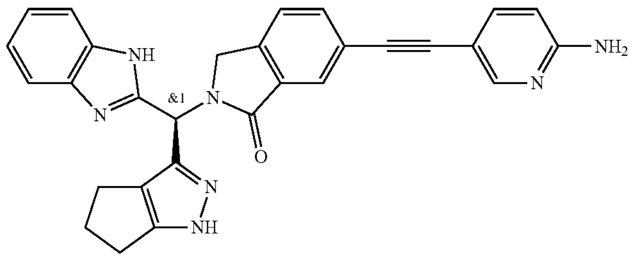 [SMILES: Nc1ccc(C#Cc2ccc3c(c2)C(=O)N([C@H](c2nc4ccccc4[nH]2)c2n[nH]c4c2CCC4)C3)cn1] 6-[2-(6-amino-3-pyridyl)ethynyl-2-[1H-benzimidazol-2-yl(1,4,5,6-tetrahydrocyclopenta-[c]pyrazol-3-yl)methyl]-isoindolin-1-one | 486.2 | 12.28-12.77 (m, 2H), 8.16 (d, 1H), 7.78 (s, 1H), 7.61-7.75 (m, 2H), 7.54 (m, 3H), 7.09-7.26 (m, 2H), 6.81 (s, 1H), 6.39-6.50 (m, 3H), 4.91 (d, 1H), 4.27-4.43 (m, 1H), 2.54-2.66 (m, 2H), 2.13-2.37 (m, 3H), 1.86-2.00 (m, 1H) |

The following compounds were prepared by a similar method to Example 16 from 2-[1-H-benzimidazol-2-yl-[5-fluoro-2-(methoxymethoxy)phenyl]methyl]-6-(4,4,5,5-tetramethyl-1,3,2-dioxaborolan-2-yl)isoindolin-1-one and the corresponding aryl halide starting materials:

| No. | Structure/Name | m/z [M + 1]$^+$ | $^1$H NMR (DMSO-$d_6$) δ | Starting materials |
|---|---|---|---|---|
| 090 | 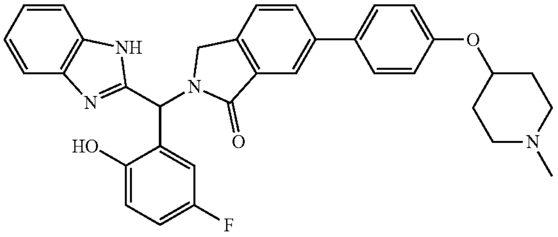 [SMILES: CN1CCC(Oc2ccc(-c3ccc4c(c3)C(=O)N(C(c3nc5ccccc5[nH]3)c3cc(F)ccc3O)C4)cc2)CC1] 2-[1H-benzimidazol-2-yl-(5-fluoro-2-hydroxy-phenyl)methyl]-6-[4-[(1-methyl-4-piperidyl)oxy]phenyl]isoindolin-1-one | 563.4 | 12.61 (br s, 1H), 9.94 (br s, 1H), 7.83-7.94 (m, 2H), 7.54-7.70 (m, 4H), 7.39-7.48 (m, 1H), 7.12-7.23 (m, 2H), 7.00-7.10 (m, 4H), 6.83-6.94 (m, 1H), 6.72-6.80 (m, 1H), 4.79 (d, 1H), 4.33-4.48 (m, 1H), 4.16 (d, 1H), 2.53-2.67 (m, 2H), 2.10-2.28 (m, 5H) 1.88-2.00 (m, 2H), 1.68-1.81 (m, 2H) | 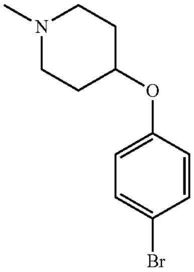 |
| 091 | 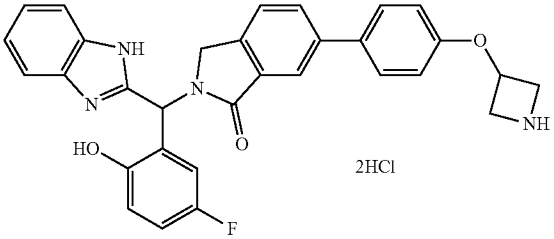 [SMILES: O=C1c2cc(-c3ccc(OC4CNC4)cc3)ccc2CN1C(c1nc2ccccc2[nH]1)c1cc(F)ccc1O] 2HCl 6-[4-(azetidin-3-yloxy)phenyl]-2-[1H-benzimidazol-2-yl-(5-fluoro-2-hydroxy-phenyl)methyl]isoindolin-1-one; dihydrochloride | 521.3 | 1H), 9.15 (br s, 1H), 7.89-7.99 (m, 2H), 7.61-7.80 (m, 5H), 7.36-7.51 (m, 2H), 6.92-7.24 (m, 6H), 5.09-5.20 (m, 1H), 4.78 (d, 1H), 4.46-4.51 (m, 2H), 4.23 (d, 1H), 3.93-4.05 (m, 2H) | 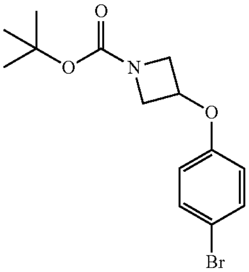 [SMILES: CC(C)(C)OC(=O)N1CC(Oc2ccc(Br)cc2)C1] |

Example 17: Preparation of 4-[3-fluoro-4-(4,4,5,5-tetramethyl-dioxaborolan-2-yl)-phenyl]-1-methyl-piperdine Scheme 20

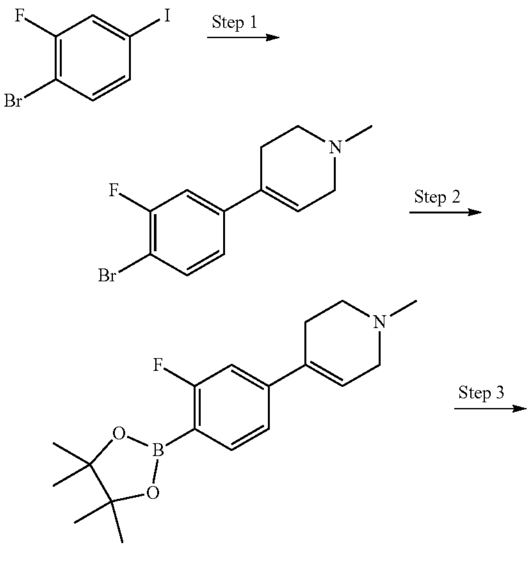

-continued

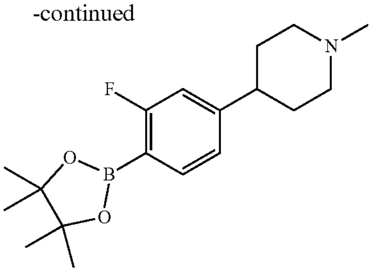

Step 1. 4-(4-bromo-3-fluoro-phenyl)-1-methyl-3,6-dihydro-2H-pyridine

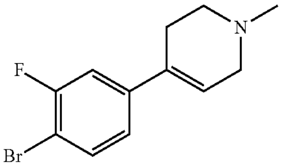

A mixture of 1-bromo-2-fluoro-4-iodobenzene (10.0 g, 33.2 mmol), 1-methyl-4-(4,4,5,5-tetramethyl-1,3,2-dioxaborolan-2-yl-1,2,3,6-tetrahydropyridine (7.40 g, 33.2 mmol), sodium carbonate (10.9 g, 99.6 mmol), [1,1'-bis(diphenylphosphino)ferrocene]dichloropalladium (II) (2.42 g, 3.32 mmol), and dioxane/water (100 mL, 411) was degassed under nitrogen twice. The reaction mixture was heated at 100° C. for 16 h. After cooling to room temperature, the reaction mixture was poured into water and extracted with ethyl acetate three times. The combined organic extracts were washed with brine, dried over sodium sulfate, filtered and concentrated under reduced pressure. The crude product was purified by silica gel column chromatography eluting with 50-67% ethyl acetate in petroleum ether to give the title compound (7.00 g, 78%). $^1$H NMR (400 MHz, methanol-$d_4$) δ: 7.51-7.59 (m, 1H), 7.25-7.31 (m, 1H), 7.13-7.23 (m, 1H), 8.21-8.24 (m, 1H), 3.10-3.18 (m, 2H), 2.87-2.75 (m, 2H) 2.52-2.61 (m, 2H), 2.39 (s, 3H); MS m/z: 271.8 $[M+1]^+$.

Step 2. 4-[3-fluoro-4-(4,4,5,5-tetramethyl-1,3,2-dioxaborolan-2-yl)phenyl]-1-methyl-3,6-dihydro-2H-pyridine

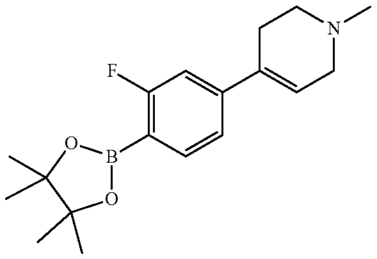

A mixture of 4-(4-bromo-3-fluoro-phenyl)-1-methyl-3,6-dihydro-2H-pyridine (1.00 g, 3.70 mmol), 4,4,5,5-tetramethyl-2-(4,4,5,5-tetramethyl-1,3,2-dioxaborolan-2-yl)-1,3,2-dioxaborolane (1.40 g, 5.55 mmol), [1,1'-bis(diphenylphosphino)ferrocene]dichloropalladium(II) (0.541 g, 0.740 mmol), potassium acetate (1.08 g, 11.1 mmol) and dioxane (20 mL) was degassed under nitrogen twice. The reaction mixture was heated at 100° C. for 3 h. After cooling to room temperature, the reaction mixture was poured into water and extracted with ethyl acetate three times. The combined organic extracts were washed with brine, dried over sodium sulfate, filtered and concentrated under reduced pressure. The crude product was purified by silica gel column chromatography eluting with 50-100% ethyl acetate in petroleum ether to give the title compound (0.432 g, 37%). $^1$H NMR (400 MHz, methanol-$d_4$) δ: 7.60-7.68 (m, 1H), 7.22-7.27 (m, 1H), 7.06-7.13 (m, 1H), 6.20-6.27 (m, 1H), 3.16-3.23 (m, 2H), 2.74-2.81 (m, 2H), 2.57-2.64 (m, 2H), 2.44 (s, 3H), 1.34 (s, 12H); MS m/z: 318.1 $[M+1]^+$.

Step 3. 4-[3-fluoro-4-(4,4,5,5-tetramethyl-1,3,2-dioxaborolan-2-yl)phenyl]-1-methyl-piperidine

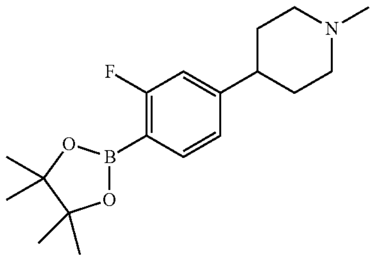

To a solution of palladium (10% on carbon, 0.900 g, 0.851 mmol) in methanol (54 mL) was added 4-[3-fluoro-4-(4,4,5,5-tetramethyl-1,3,2-dioxaborolan-2-yl)phenyl]-1-methyl-3,6-dihydro-2H-pyridine (2.70 g, 8.51 mmol). The flask was evacuated and backfilled with hydrogen and the reaction mixture was allowed to stir at 30 CC under an atmosphere of hydrogen (50 psi) for 48 h. The reaction mixture was filtered through a pad of Celite which was washed several times with methanol. The filtrate was concentrated under reduced pressure to give the title compound (1.89 g, 70%). $^1$H NMR (400 MHz, methanol-$d_4$) δ: 7.61-7.67 (m, 1H), 7.06-7.11 (m, 1H), 6.89-7.00 (m, 1H), 2.98-3.11 (m, 2H), 2.53-2.69 (m, 1H), 2.37 (s, 3H) 2.16-2.27 (m, 2H), 1.72-1.93 (m, 4H) 1.35 (s, 12H); MS m/z: 320.1 $[M+1]^+$.

Example 18: Preparation of 7-fluoro-2-[(R)-(5-fluoro-2-hydroxy-phenyl)-(4-methyl-1H-imidazol-2-yl)methyl]-6-[4-(1-methyl-4-piperidyl)phenyl]isoindolin-1-one and 7-fluoro-2-[(S)-(5-fluoro-2-hydroxy-phenyl)-(4-methyl-1H-imidazol-2-yl)methyl]-6-[4-(1-methyl-4-piperidyl)phenyl]isoindolin-1-one (094 and 095)

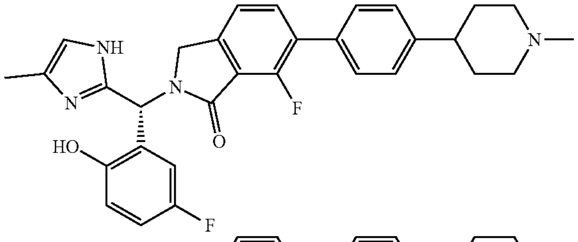

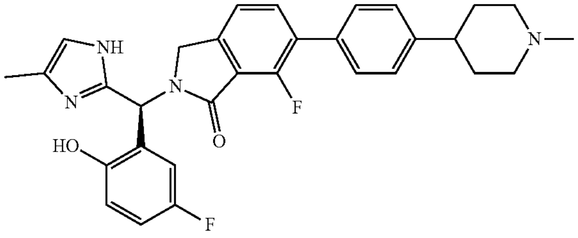

7-Fluoro-2-[(5-fluoro-2-hydroxy-phenyl)-(5-methyl-1H-imidazol-2-yl)methyl]-6-[4-(1-methyl-4-piperidyl)phenyl]isoindolin-1-one (093, 0.020 g, 0.038 mmol) was purified by prep SFC with a Chiral Technologies Chiralpak IA (5 micron 250×10 mm) column @ 40 CC eluting with 45% (0.3% TEA in MeOH)/55% $CO_2$ at 10 MPa to separate enantiomers. Absolute configuration of the chiral center for each isolated enantiomer is unknown. First eluting peak (094) (6 mg, 30% yield, 100:0 er); $[\alpha]^{20}_{D}$ −78.3 (c=0.035, MeOH); $^1$H NMR (DMSO-$d_6$) δ: 11.77-12.05 (m, 1H), 10.08 (br s, 1H), 7.65-7.74 (m, 1H), 7.43-7.50 (m, 3H), 7.37 (d, 2H), 6.97-7.07 (m, 1H), 6.77-6.88 (m, 2H), 6.73 (s, 1H), 6.53-6.65 (m, 1H), 4.73 (d, 1H), 4.09 (d, 1H), 2.88 (d, 2H), 2.41-2.49 (m, 1H), 2.20 (s, 3H), 2.12 (s, 3H), 1.94-2.03 (m, 2H), 1.64-1.81 (m, 4H); MS m/z: 529.3 $[M+1]^+$. Second eluting peak (095) (6 mg, 30% yield, 97.8:2.2 er); $[\alpha]^{20}_{D}$ +55.3 (c=0.038, MeOH); $^1$H NMR (DMSO-$d_6$) δ: 11.78-12.05 (m, 1H), 10.06 (br s, 1H), 7.66-7.75 (m, 1H), 7.44-7.51 (m, 3H), 7.38 (d, 2H), 6.97-7.07 (m, 1H), 6.77-6.88 (m, 2H), 6.73 (s, 1H), 6.52-6.65 (m, 1H), 4.74 (d, 1H), 4.10 (d, 1H), 2.89 (d, 2H), 2.41-2.49 (m, 1H), 2.21 (s, 3H), 2.13 (s, 3H), 1.94-2.05 (m, 2H), 1.64-1.82 (m, 4H); MS m/z: 529.3 $[M+1]^+$.

Example 19: 2-[(5-Fluoro-2-hydroxy-phenyl)-[5-(trifluoromethyl)-1H-imidazol-2-yl]methyl]-6-[4-(1-methyl-4-piperidyl)phenyl]isoindolin-1-one;hydrochloride (103)

Scheme 21

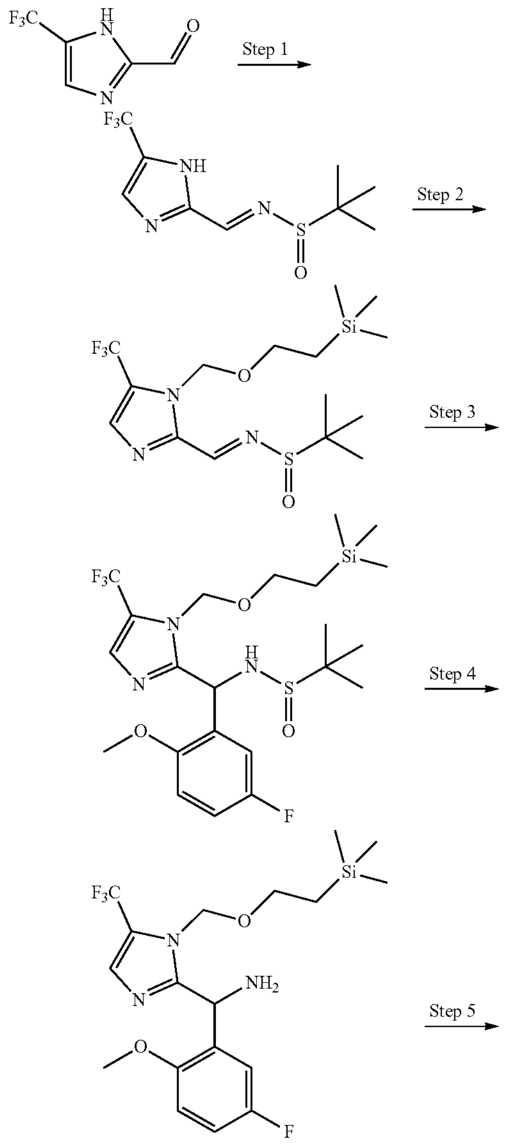

-continued

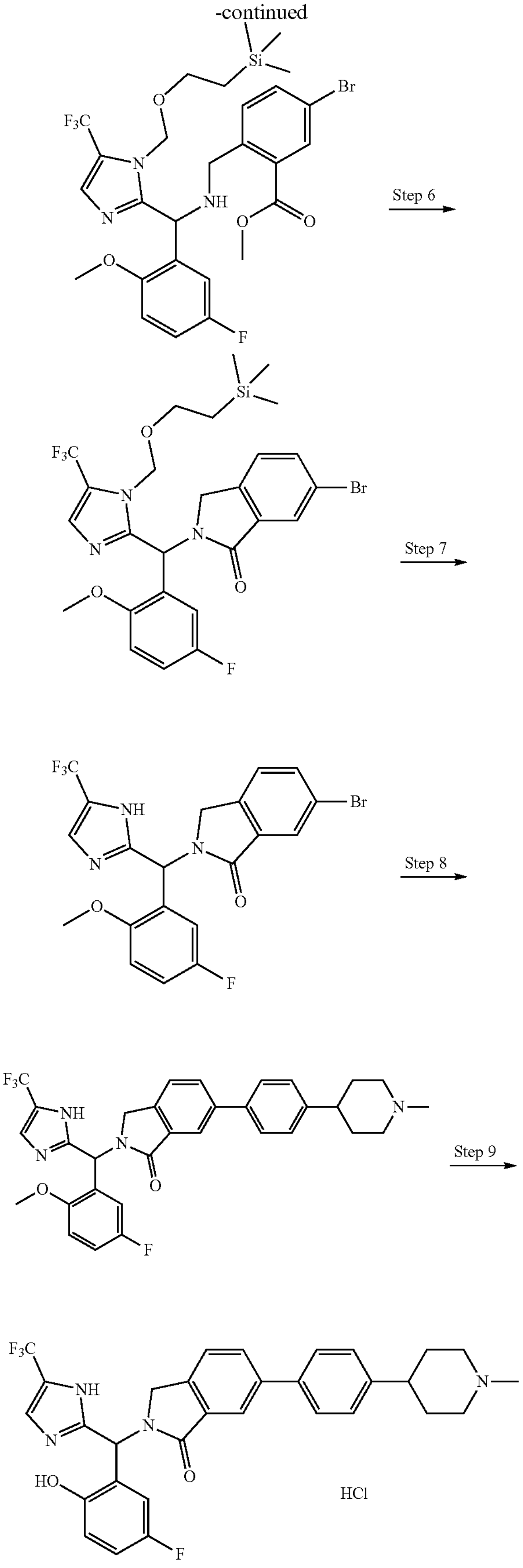

Step 1. 2-Methyl-N-[[5-(trifluoromethyl)-1H-imidazol-2-yl]methylene]propane-2-sulfinamide

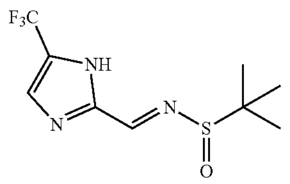 [SMILES: CC(C)(C)S(=O)/N=C/c1ncc(C(F)(F)F)[nH]1]

To a solution of 5-(trifluoromethyl)-1H-imidazole-2-carbaldehyde (9.80 g, 59.7 mmol) and 2-methylpropane-2-sulfinamide (10.8 g, 98.5 mmol) in THF (300 mL) was added tetraethyl orthotitanate (20.4 g, 89.5 mmol). After stirring at 75° C. for 5 h, the reaction mixture was quenched by water and extracted with ethyl acetate three times. The combined organic extracts were washed with brine, dried over sodium sulfate, filtered and concentrated under reduced pressure. The crude product was purified by silica gel column chromatography eluting with 0-100% ethyl acetate in petroleum ether to give the title compound (9.6 g, 60%). $^1$H NMR (400 MHz, $CDCl_3$) δ: 11.34 (br s, 1H); 8.52 (s, 1H), 7.49 (s, 1H), 1.16 (s, 9H); MS m/z: 267.9 $[M+1]^+$.

Step 2. 2-Methyl-N-[[5-(trifluoromethyl)-1-(2-trimethylsilylethoxymethyl)imidazol-2-yl]methylene] propane-2-sulfinamide

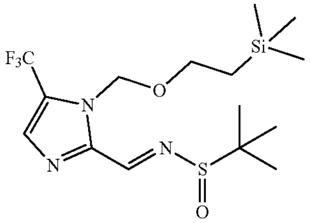 [SMILES: CC(C)(C)S(=O)/N=C/c1ncc(C(F)(F)F)n1COCC[Si](C)(C)C]

To a solution of 2-methyl-N-[[5-(trifluoromethyl)-1H-imidazol-2-yl]methylene]propane-2-sulfinamide (9.60 g; 35.9 mmol) in DMF (200 mL) was added sodium hydride (1.29 g, 53.8 mmol) at 0° C. After stirring at the same temperature for 15 min, 2-(trimethylsilyl)ethoxymethyl chloride (8.96 g, 53.8 mmol) was added. After stirring at room temperature for 2 h, the reaction mixture was quenched by water and extracted with ethyl acetate three times. The combined organic extracts were washed with brine, dried over sodium sulfate; filtered and concentrated under reduced pressure. The crude product was purified by silica gel column chromatography eluting with 0-10% ethyl acetate in petroleum ether to give the title compound (6.5 g, 46%). $^1$H NMR (400 MHz; $CDCl_3$) δ: 8.65 (s, 1H), 7.60 (s, 1H), 5.90 (d, 1H), 5.71 (d, 1H), 3.50-3.68 (m, 2H), 1.28 (s, 9H), 0.87-0.97 (m, 2H), −0.01-0.01 (m, 9H); MS m/z: 398.0 $[M+1]^+$.

Step 3. N-[(5-Fluoro-2-methoxy-phenyl)-[5-(trifluoromethyl)-1-(2-trimethylsilylethoxymethyl)-imidazol-2-yl]methyl]-2-methyl-propane-2-sulfinamide

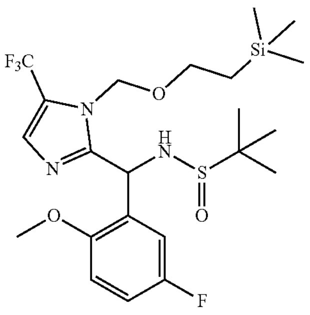

To a solution of 2-methyl-N-[[5-(trifluoromethyl)-1-(2-trimethylsilylethoxymethyl)imidazol-2-yl]methylene]propane-2-sulfinamide (6.50 g, 16.3 mmol) in THF (100 mL) was added dropwise a solution of 5-fluoro-2-methoxyphenylmagnesium bromide in THF (0.5 M; 97.8 mL, 48.9 mmol) at −78° C. After stirring at room temperature for 16 h, the reaction mixture was poured into sat. ammonium chloride solution and extracted with ethyl acetate three times. The combined organic extracts were washed with brine, dried over sodium sulfate, filtered and concentrated under reduced pressure. The crude product was purified by reverse phase HPLC eluting with 0-100% ACN/water containing 10 mM ammonium acetate to give the title compound (1.9 g, 22%). $^1$H NMR (400 MHz, $CDCl_3$) δ: 7.24-7.33 (m, 1H), 6.93-7.07 (m, 2H), 6.84 (dd, 1H), 6.15 (d, 1H), 5.17-5.26 (m, 2H), 4.92 (d, 1H), 3.85 (s, 3H), 3.24-3.45 (m, 2H), 1.21 (s, 9H), 0.74-0.89 (m, 2H), −0.06-0.00 (m, 9H); MS m/z: 524.1 $[M+1]^+$.

Step 4. (5-Fluoro-2-methoxy-phenyl)-[5-(trifluoromethyl)-1-(2-trimethylsilylethoxymethyl)-imidazol-2-yl]methanamine

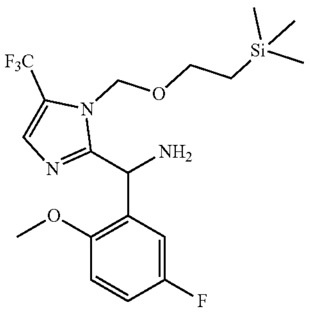

To a solution of N-[(5-fluoro-2-methoxy-phenyl)-[5-(trifluoromethyl)-1-(2-trimethylsilyl-ethoxymethyl)imidazol-2-yl]methyl]-2-methyl-propane-2-sulfinamide (1.90 g, 3.62 mmol) in methanol (80 mL) was added HCl in methanol (4 M, 9.05 mL, 36.2 mmol) at 0° C. After stirring at room temperature for 2 h, the solvent was removed under reduced pressure. The crude product was purified by reverse phase HPLC eluting with 0-100% ACN/water containing 10 mM ammonium acetate to give the title compound (1.1 g, 73%). $^1$H NMR (400 MHz, $CDCl_3$) δ: 7.24-7.33 (m, 1H), 6.90-6.98

(m, 1H), 6.79-6.89 (m, 2H), 5.63 (s, 1H), 5.02-5.13 (m, 2H), 3.85 (s, 3H), 3.24-3.41 (m, 2H), 0.70-0.86 (m, 2H), −0.03 (s, 9H); MS m/z: 420.0 [M+1]$^+$.

Step 5. Methyl 5-bromo-2-[[[(5-fluoro-2-methoxy-phenyl)-[5-(trifluoromethyl)-1-(2-trimethylsilylethoxymethyl)imidazol-2-yl]methyl]amino]methyl] benzoate

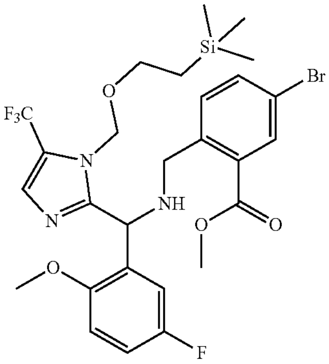 [SMILES: COC(=O)c1cc(Br)ccc1CNC(c1cc(F)ccc1OC)c1ncc(C(F)(F)F)n1COCC[Si](C)(C)C]

To a solution of (5-fluoro-2-methoxy-phenyl)-[5-(trifluoromethyl)-1-(2-trimethylsilylethoxymethyl)imidazol-2-yl] methanamine (1.05 g, 2.50 mmol) and methyl 5-bromo-2-(bromomethyl)benzoate (0.846 g, 2.75 mmol) in DMF (50 mL) was added DIPEA (2.05 mL, 12.5 mmol). The reaction mixture was heated at 90° C. for 1 h. After cooling to room temperature, the reaction mixture was poured into water and extracted with ethyl acetate three times. The combined organic extracts were washed with water, brine, dried over sodium sulfate, filtered and concentrated under reduced pressure to give the title compound (1.61 g, quant.) which was used in the next reaction without further purification. MS m/z: 646.0 [M+1]$^+$.

Step 6. 6-Bromo-2-[(5-fluoro-2-methoxy-phenyl)-[5-(trifluoromethyl)-1-(2-trimethylsilylethoxymethyl]imidazol-2-yl]methyl]isoindolin-1-one

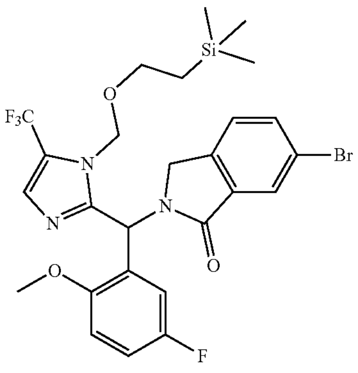 [SMILES: COc1ccc(F)cc1C(c1ncc(C(F)(F)F)n1COCC[Si](C)(C)C)N1Cc2ccc(Br)cc2C1=O]

To a solution of methyl 5-bromo-2-[[[(5-fluoro-2-methoxy-phenyl)-[5-(trifluoromethyl)-1-(2-trimethylsilylethoxymethyl)imidazol-2-yl]methyl]amino]methyl]benzoate (1.61 g, 2.49 mmol) in toluene (50 mL) was added trimethylaluminum (0.179 g, 2.49 mmol). The reaction mixture was heated at 90° C. for 16 h. After cooling to room temperature, the solvent was removed under reduced pressure. The crude product was purified by reverse phase HPLC eluting with 0-100% ACN/water containing 10 mM ammonium acetate to give the title compound (1.2 g, 78%). $^1$H NMR (400 MHz, $CDCl_3$) δ: 7.98 (d, 1H), 7.65 (dd, 1H), 7.29-7.35 (m, 2H), 7.26 (s, 1H), 7.18 (dd, 1H), 6.98-7.07 (m, 1H), 6.86 (dd, 1H), 5.59 (d, 1H), 5.22 (d, 1H), 4.96 (d, 1H), 4.06 (d, 1H), 3.75-3.84 (m, 3H), 3.21-3.44 (m, 2H), 0.53-0.78 (m, 2H), −0.12-0.00 (m, 9H); MS m/z: 614.1 [M+1]$^+$.

Step 7. 6-Bromo-2-[(5-fluoro-2-methoxy-phenyl)-[5-(rifluoromethyl)-1H-imidazol-2-yl]methyl]isoindolin-1-one

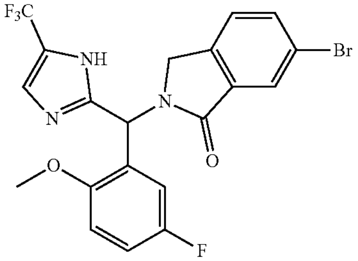 [SMILES: COc1ccc(F)cc1C(c1ncc(C(F)(F)F)[nH]1)N1Cc2ccc(Br)cc2C1=O]

To a solution of 6-bromo-2-[(5-fluoro-2-methoxy-phenyl)-[5-(trifluoromethyl)-1-(2-trimethylsilylethoxymethyl) imidazol-2-yl]methyl]isoindolin-1-one (0.540 g, 0.878 mmol) in methanol (5 mL) was added aq. HCl (12 M, 10.0 mL, 120 mmol) at 0° C. After stirring at room temperature for 4 h, the solvent was removed under reduced pressure and lyophilized to give the title compound (0.425 g, quant.). $^1$H NMR (400 MHz, methanol-$d_4$) δ: 7.94 (d, 1H), 7.69-7.82 (m, 2H), 7.48 (d, 1H), 7.07-7.29 (m, 2H), 6.82-7.03 (m, 2H), 4.65 (d, 1H), 4.13-4.18 (m, 1H), 3.79 (s, 3H); MS m/z: 485.9 [M+1]$^+$.

Step 8, 2-[(5-Fluoro-2-methoxy-phenyl)-[5-(trifluoromethyl)-1H-imidazol-2-yl]methyl]-6-[4-(1-methyl-4-piperidyl)phenyl]isoindolin-1-one

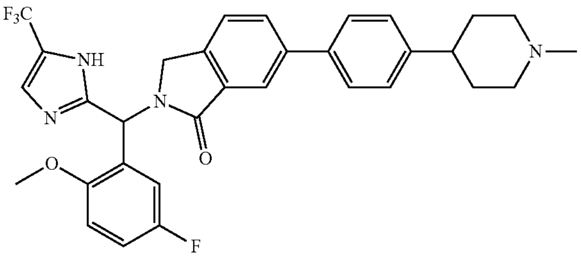

A mixture of 6-bromo-2-[(5-fluoro-2-methoxy-phenyl)-[5-(trifluoromethyl)-1H-imidazol-2-yl]methyl]isoindolin-1-one (0.425 g, 0.878 mmol), 1-methyl-4-(4-(4,4,5,5-tetramethyl-1,3,2-dioxaborolan-2-yl)phenyl)piperidine (0.403 g, 1.34 mmol), Pd(dppf)$Cl_2$ (0.032 g, 0.044 mmol) and potassium carbonate (0.372 g, 2.68 mmol) in dioxane:water (9:1, 10 mL) was heated at 100° C. for 2 h under nitrogen. After cooling, the reaction mixture was filtered, and the filtrate was concentrated under reduced pressure, and purified by silica gel column chromatography eluting with 0-15% methanol in dichloromethane to give the title compound (0.3 g, 58%). $^1$H NMR (400 MHz, $CDCl_3$) δ: 7.94 (d, 1H), 7.72-7.79 (m, 1H), 7.45-7.55 (m, 3H), 7.32-7.41 (m, 4H), 6.96-7.07 (m, 1H), 6.89-6.95 (m, 1H), 6.71-6.82 (m, 1H), 4.82-4.96 (m, 1H), 4.34-4.53 (m, 1H), 3.57-3.67 (m, 3H), 2.99-3.09 (m, 2H), 2.48-2.63 (m, 1H), 2.34-2.39 (m, 4H), 2.07-2.16 (m, 3H), 1.86-1.97 (m, 2H); MS m/z: 579.3 $[M+1]^+$.

Step 9, 2-[(5-Fluoro-2-hydroxy-phenyl)-(5-(trifluoromethyl)-1H-imidazol-2-yl]methyl]-6-[4-(1-methyl-4-piperidyl)phenyl]isoindolin-1-one;hydrochloride

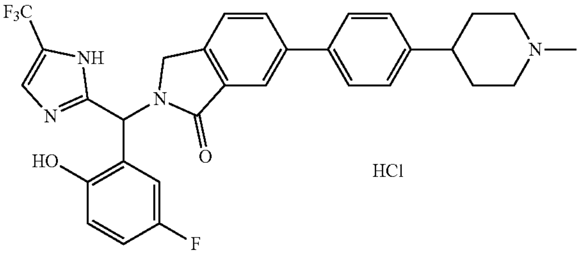 [SMILES: CN1CCC(c2ccc(-c3ccc4c(c3)C(=O)N(C(c3ncc(C(F)(F)F)[nH]3)c3cc(F)ccc3O)C4)cc2)CC1 ; Cl]

HCl

To a solution of 2-[(5-fluoro-2-methoxy-phenyl)-[5-(trifluoromethyl)-1H-imidazol-2-yl]methyl]-6-[4-(1-methyl-4-piperidyl)phenyl]isoindolin-1-one (0.250 g, 0.432 mmol) in dichloromethane (5 mL) at 0° C. was added boron tribromide (0.407 g, 4.32 mmol). After stirring at room temperature for 1 h, the reaction mixture was diluted with dichloromethane and poured into ice-water. The aqueous phase was extracted with dichloromethane three times. The combined organic extracts were washed with brine, dried over sodium sulfate, filtered and concentrated under reduced pressure. The crude product was purified by reverse phase HPLC eluting with 0-100% ACN/water (0.05% HCl modifier) to give the title compound (0.122 g, 50%). NMR (400 MHz, DMSO-$d_6$) δ: 10.58 (br s, 1H), 9.98 (br s, 1H), 7.88-7.96 (m, 2H), 7.80 (d, 1H), 7.63-7.76 (m, 3H), 7.36 (d, 2H), 7.02-7.12 (m, 1H), 6.84-6.98 (m, 2H), 6.70 (dd, 1H), 4.67 (d, 1H), 4.12 (d, 1H), 3.49 (d, 2H), 2.99-3.16 (m, 2H), 2.80-2.89 (m, 1H), 2.77 (d, 3H), 1.96-2.12 (m, 4H); MS m/z: 565.5 [M+1]+.

Example 20: Preparation of 2-[(R)-(5-fluoro-2-hydroxy-phenyl)-(4-methyl-1H-imidazol-2-yl)methyl]-6-[4-(1-methyl-4-piperidyl)phenyl]isoindolin-1-one and 2-[(S)-(5-fluoro-2-hydroxy-phenyl)-(4-methyl-1H-imidazol-2-yl)methyl]-6-[4-(1-methyl-4-piperidyl)phenyl]isoindolin-1-one (104 and 105)

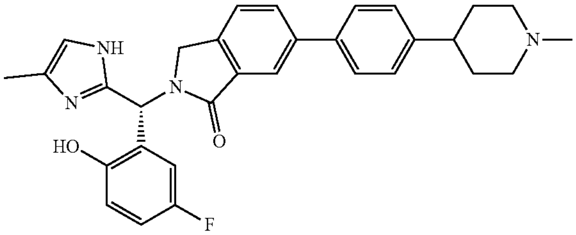

-continued

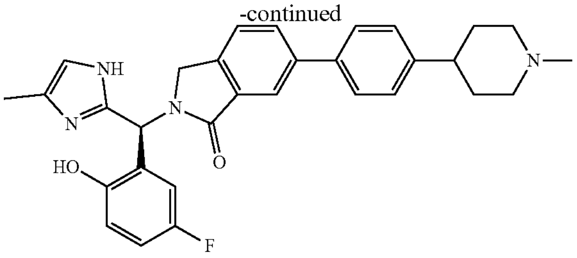

2-[(5-Fluoro-2-hydroxy-phenyl)-(4-methyl-1H-imidazol-2-yl)methyl]-6-[4-(1-methyl-4-piperidyl)phenyl]isoindolin-1-one (085, 0.020 g, 0.039 mmol) was purified by prep SFC with a Chiral Technologies Chiralpak IA (5 micron 250×10 mm) column @ 40° C. eluting with 35% (0.3% TEA in MeOH)/65% CO2 at 12 MPa to separate enantiomers. Absolute configuration of the chiral center for each isolated enantiomer is unknown. First eluting peak (104) (6.5 mg, 33% yield, 97.9:2.1 er); $[\alpha]^{\circ}_{D}$ −88.2 (c=0.0465, MeOH); $^1$H NMR (DMSO-$d_6$) δ: 11.74-12.04 (m, 1H), 10.06 (br s, 1H), 7.84-7.88 (m, 2H), 7.64 (br d, J=8.2 Hz, 3H), 7.35 (d, J=8.2 Hz, 2H), 7.02 (td, J=8.5, 3.1 Hz, 1H), 6.51-6.90 (m, 4H), 4.72 (br d, J=17.7 Hz, 1H), 4.11 (br d, J=17.4 Hz, 1H), 2.88 (br d, J=10.9 Hz, 2H), 2.20 (s, 3H), 2.08-2.17 (m, 3H), 1.92-2.02 (m, 2H), 1.59-1.81 (m, 4H); MS m/z: 511.3 $[M+1]^+$. Second eluting peak (105) (7.3 mg, 37% yield, 97.7:2.3 er); $[\alpha]^{\circ}_{D}$ +67.3 (c=0.049, MeOH); $^1$H NMR (DMSO-d6) δ: 11.74-12.20 (m, 1H), 10.08 (br s, 1H), 7.82-7.90 (m, 2H), 7.65 (br d, J=8.2 Hz, 3H), 7.36 (d, J=8.2 Hz, 2H), 7.02 (td, J=8.6, 3.2 Hz, 1H), 6.52-6.91 (m, 4H), 4.72 (d, J=17.9 Hz, 1H), 4.11 (d, J=17.9 Hz, 1H), 2.88 (br d, J=11.1 Hz, 2H), 2.21 (s, 3H), 2.13 (s, 3H), 1.98 (td, J=11.3, 2.1 Hz, 2H), 1.59-1.84 (m, 4H); MS m/z: 511.3 $[M+1]^+$.

Example 21: Preparation of 6-[(R)-1-H-benzimidazol-2-yl-(5-fluoro-2-hydroxy-phenyl)methyl]-2-[4-(1-methyl-4-piperidyl)phenyl]-5H-pyrrolo[3,4-b]pyridin-7-one and 6-[(S)-1H-benzimidazol-2-yl-(5-fluoro-2-hydroxy-phenyl)methyl]-2-[4-(1-methyl-4-piperidyl)phenyl]-5H-pyrrolo[3,4-b]pyridin-7-one (106 and 107)

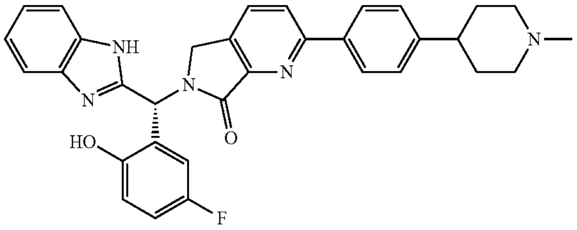

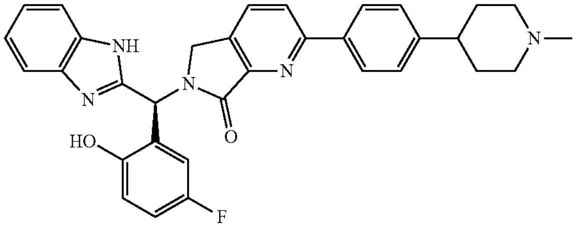

6-[1H-Benzimidazol-2-yl-(5-fluoro-2-hydroxy-phenyl)methyl]-2-[4-(1-methyl-4-piperidyl)phenyl]-5H-pyrrolo[3, 4-b]pyridin-7-one (028, 0.020 g, 0.037 mmol) was purified by prep SFC with a Chiral Technologies Chiralpak IA (5 micron 250×19 mm) column 40° C. eluting with 55% (0.3% TEA in MeOH)/45% 002 at 10 MPa to separate enantiomers. Absolute configuration of the chiral center for each isolated enantiomer is unknown. First eluting peak (106) (2.8 mg, 14% yield, 98.5:1.5 er); $[\alpha]^{20}_{D}$ −12.3 (c=0.06, MeOH); $^1$H NMR (DMSO-$d_6$) δ: 7.96-8.09 (m, 4H), 7.39-7.51 (m, 2H), 7.33 (d, J=8.3 Hz, 2H), 7.06-7.16 (m, 2H), 6.94-7.06 (m, 2H), 6.83 (dd, J=8.9, 4.8 Hz, 1H), 6.76 (dd, J=9.3, 3.1 Hz, 1H), 4.72 (d, J=17.9 Hz, 1H), 4.14 (br d, J=17.7 Hz, 1H), 2.75-2.86 (m, 2H), 2.13 (s, 3H), 1.91 (td, J=11.0, 1.5 Hz, 2H), 1.56-1.78 (m, 4H); MS m/z: 548.3 $[M+1]^+$. Second eluting peak (107) (6.1 mg, 30% yield, 97.2:2.8 er); $[\alpha]^{\circ}_{D}$ +21.8 (c=0.055, MeOH); $^1$H NMR (DMSO-$d_6$) δ: 12.56 (br s, 1H), 9.92 (br s, 1H), 7.94-8.13 (m, 4H), 7.46-7.57 (m, 1H), 7.36-7.44 (m, 1H), 7.33 (d, J=8.3 Hz, 2H), 7.11 (br s, 2H), 7.00-7.05 (m, 1H), 6.99 (s, 1H), 6.84 (dd, J=8.9, 4.8 Hz, 1H), 6.75 (dd, J=9.3, 3.1 Hz, 1H), 4.73 (d, J=17.9 Hz, 1H), 4.11 (d, J=17.9 Hz, 1H), 2.73-2.88 (m, 2H), 2.13 (s, 3H), 1.80-1.97 (m, 2H), 1.53-1.78 (m, 4H); MS m/z: 548.3 $[M+1]^+$.

The following examples were prepared by a similar method to Compound 069 from methyl 2-bromo-2-(5-fluoro-2-(methoxymethoxy)phenyl)acetate and the corresponding boronate starting material:

| No. | Structure/Name | m/z $[M + 1]^+$ | $^1$H NMR (DMSO-$d_6$) δ | Starting materials |
|---|---|---|---|---|
| 108 | 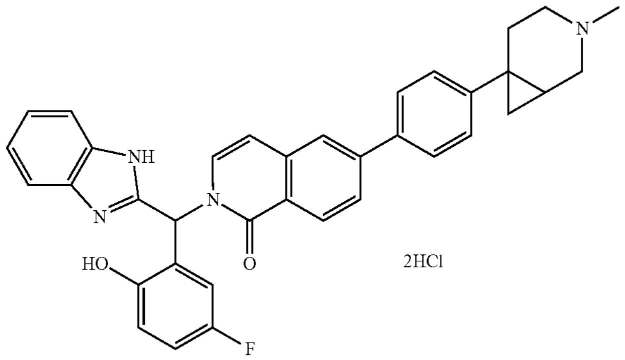 [SMILES: CN1CCC2(c3ccc(-c4ccc5c(=O)n(C(c6nc7ccccc7[nH]6)c6cc(F)ccc6O)ccc5c4)cc3)CC2C1] 2-[1H-Benzimidazol-2-yl-(5-fluoro-2-hydroxy-phenyl)methyl]-6-[4-(3-methyl-3-azabicyclo[4.1.0]heptan-6-yl)phenyl]isoquinolin-1-one; dihydrochloride | 571.3 | 10.15-10.41 (m, 2H), 8.29 (d, J = 8.3 Hz, 1H), 8.01 (s, 1H), 7.86 (br d, J = 8.4 Hz, 1H), 7.78 (d, J = 8.3 Hz, 2H), 7.43-7.70 (m, 5H), 7.28-7.42 (m, 3H), 7.12-7.22 (m, 1H), 6.96-7.05 (m, 1H), 6.84-6.94 (m, 1H), 6.70-6.82 (m, 1H), 3.80-3.94 (m, 1H), 3.23-3.36 (m, 1H), 2.99-3.12 (m, 1H), 2.84-2.96 (m, 1H), 2.70 (br d, J = 4.4 Hz, 4H), 2.27-2.41 (m, 1H), 1.47-1.61 (m, 1H), 1.08-1.38 (m, 2H) | 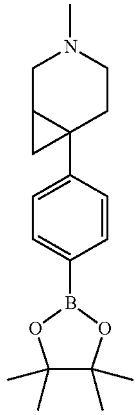 |
| 109 | 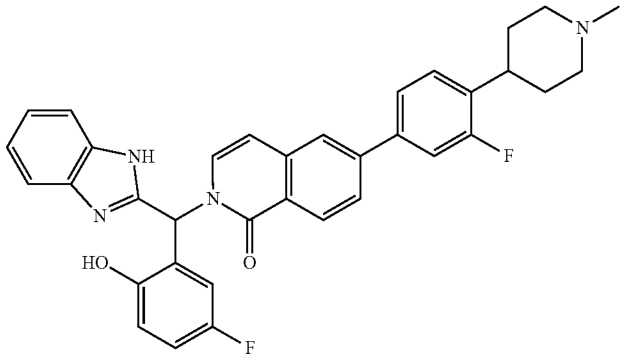 [SMILES: CN1CCC(c2ccc(-c3ccc4c(=O)n(C(c5nc6ccccc6[nH]5)c5cc(F)ccc5O)ccc4c3)cc2F)CC1] 2-[1H-Benzimidazol-2-yl-(5-fluoro-2-hydroxy-phenyl)methyl]-6-[3-fluoro-4-(1-methyl-4-piperidyl)phenyl]isoquinolin-1-one; dihydrochloride | 577.3 | 10.48 (br s, 1H), 10.26 (br s, 1H), 8.30 (d, J = 8.3 Hz, 1H), 8.07 (s, 1H), 7.90 (br d, J = 8.3 Hz, 1H), 7.71 (br d, J = 10.0 Hz, 2H), 7.61-7.67 (m, 3H), 7.44 (br t, J = 7.8 Hz, 1H), 7.31-7.40 (m, 3H), 7.12-7.23 (m, 1H), 6.96-7.06 (m, 1H), 6.89 (br d, J = 7.8 Hz, 1H), 6.78 (d, J = 7.6 Hz, 1H), 3.43-3.57 (m, 2H), 3.06-3.22 (m, 3H), 2.73-2.85 (m, 3H), 1.83-2.22 (m, 4H) | 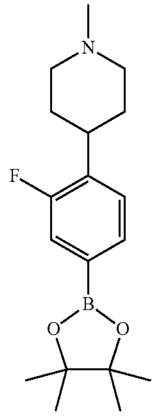 |

The following examples were prepared by a similar method to Compound 070 from methyl 2-bromo-2-(5-fluoro-2-(methoxymethoxy)phenyl)acetate and the corresponding boronate starting material:

| No. | Structure/Name | m/z [M + 1]+ | $^1$H NMR (DMSO-$d_6$) δ | Starting materials |
|---|---|---|---|---|
| 110 | 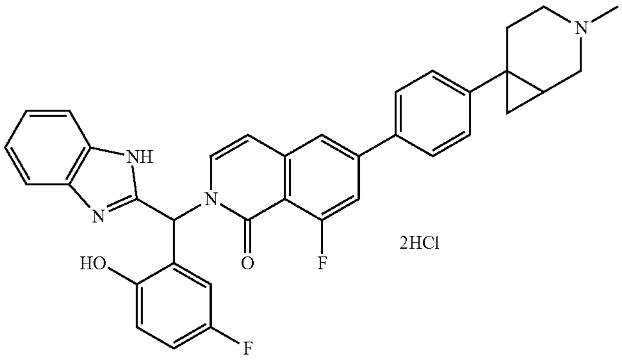 [SMILES: CN1CCC2(c3ccc(-c4cc(F)c5c(=O)n(C(c6nc7ccccc7[nH]6)c6cc(F)ccc6O)ccc5c4)cc3)CC2C1] 2-[1H-Benzimidazol-2-yl-(5-fluoro-2-hydroxy-phenyl)methyl]-8-fluoro-6-4-(3-methyl-3-azabicyclo[4.1.0]-heptan-6-yl)phenyl]isoquinolin-1-one; dihydrochloride | 589.3 | 10.06-10.33 (m, 1H), 7.80-7.89 (m, 3H), 7.45-7.69 (m, 6H), 7.28-7.41 (m, 3H), 7.17 (br s, 1H), 6.93-7.02 (m, 1H), 6.79-6.91 (m, 1H), 6.68-6.78 (m, 1H), 3.81-3.96 (m, 2H), 3.24-3.38 (m, 1H), 2.99-3.12 (m, 1H), 2.84-2.99 (m, 1H), 2.64-2.83 (m, 4H), 2.24-2.39 (m, 1H), 1.46-1.62 (m, 1H), 1.07-1.30 (m, 2H) | 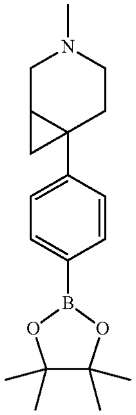 |
| 111 | 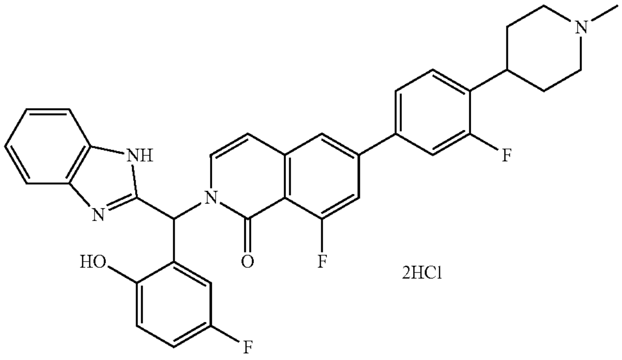 [SMILES: CN1CCC(c2ccc(-c3cc(F)c4c(=O)n(C(c5nc6ccccc6[nH]5)c5cc(F)ccc5O)ccc4c3)cc2F)CC1] 2-[1H-Benzimidazol-2-yl-(5-fluoro-2-hydroxy-phenyl)methyl]-8-fluoro-6-[3-fluoro-4-(1-methyl-4-piperidyl)-phenyl]isoquinolin-1-one; dihydrochloride | 595.3 | 10.41 (br s, 1H), 10.25 (br s, 1H), 7.93 (s, 1H), 7.61-7.81 (m, 5H), 7.57 (s, 1H), 7.44 (br t, J = 8.0 Hz, 1H), 7.32-7.40 (m, 3H), 7.11-7.23 (m, 1H), 6.95-7.03 (m, 1H), 6.83-6.93 (m, 1H), 6.75 (br d, J = 7.2 Hz, 1H), 3.45-3.57 (m, 2H), 3.06-3.22 (m, 3H), 2.75-2.84 (m, 3H), 1.92-2.16 (m, 4H) | 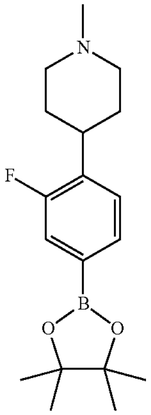 [SMILES: CN1CCC(c2ccc(B3OC(C)(C)C(C)(C)O3)cc2F)CC1] |

Example 22: 2-[1H-Benzimidazol-2-yl-deuterio-(5-fluoro-2-hydroxy-phenyl)methyl]-6-[4-(1-methyl-4-piperidyl)phenyl]isoquinolin-1-one (112)

Scheme 22

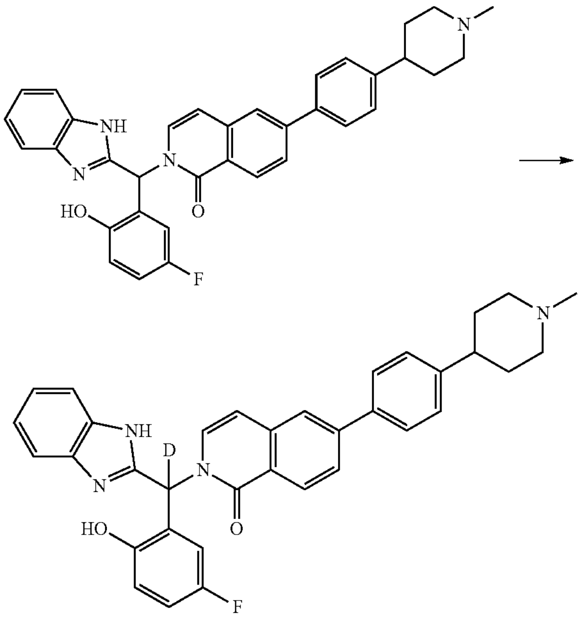

Rac-2-(1H-1,3-benzodiazol-2-yl)(5-fluoro-2-hydroxy-phenyl)methyl]-6-[4-(1-methylpiperidin-4-yl)phenyl]-1,2-dihydroisoquinolin-1-one (069, 20.4 mg, 0.0365 mmol) was dissolved in dry tetrahydrofuran (1 ml) in a vial equipped with a stir bar. Deuterium oxide (350 μL, 19.3 mmol) was then added with stirring followed by N; N-diisopropylethylamine (38.1 μL, 219 μmol). The reaction vial was sealed and the reaction was allowed to stir at 70° C. for 60 hours. An $^1$HNMR (DMSO-$d_6$) of the reaction solution indicated ~100% incorporation of deuterium on the methine carbon based on the disappearance of the methine peak @ ~7.67 ppm. The reaction was cooled to room temperature and the solvents were removed under reduced pressure. The crude product was purified by silica gel column chromatography eluting with 0-15% (7N $NH_3$ in methanol) in DOM to give the title compound (14 mg, 68%), $^1$H NMR (DMSO-de, 400 MHz) δ: 11.9-13.5 (m, 1H), 9.6-10.9 (m, 1H), 8.28 (d, 1H), 7.94 (s, 1H), 7.81 (d, 1H), 7.7-7.8 (m, 2H), 7.54 (br s, 2H), 7.3-7.4 (m, 2H), 7.29 (d, 1H), 7.19 (br dd, 2H), 7.08 (dt, 1H), 6.88 (dd, 1H), 6.6-6.7 (m, 2H), 2.88 (br d, 2H), 2.5-2.7 (m, 1H), 2.20 (s, 3H), 1.9-2.0 (m, 2H), 1.6-1.8 (m, 4H); MS m/z: 560.3 $[M+1]^+$.

The following example was prepared by a similar method to Example 22 from 2-[1H-benzimidazol-2-yl-(5-fluoro-2-hydroxy-phenyl)methyl]-8-fluoro-6-[4-(1-methyl-4-piperidyl) phenyl]isoquinolin-1-one (070):

| No. | Structure/Name | m/z $[M + 1]^+$ | $^1$H NMR (DMSO-$d_6$) δ |
|---|---|---|---|
| 113 | 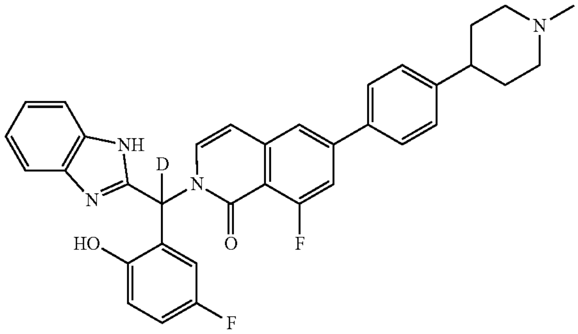 [SMILES: [2H]C(c1nc2ccccc2[nH]1)(c1cc(F)ccc1O)n1ccc2cc(-c3ccc(C4CCN(C)CC4)cc3)cc(F)c2c1=O] 2-[1H-Benzimidazol-2-yl-deuterio-(5-fluoro-2-hydroxy-phenyl)methyl]-8-fluoro-6-[4-(1-methyl-4-piperidyl)phenyl]isoquinolin-1-one | 578.3 | 12.7-12.8 (m, 1H), 9.9-10.1 (m, 1H), 7.7-7.8 (m, 3H), 7.4-7.6 (m, 3H), 7.39 (br d, 2H, J = 7.9 Hz), 7.29 (d, 1H, J = 7.6 Hz), 7.20 (br s, 2H), 7.0-7.2 (m, 1H), 6.90 (dd, 1H, J = 4.8, 8.7 Hz), 6.6-6.7 (m, 2H), 2.89 (br d, 2H, J = 10.6 Hz), 2.5-2.6 (m, 1H), 2.21 (s, 3H), 2.00 (br t, 2H, J = 10.8 Hz), 1.6-1.8 (m, 4H) |

Example 23: Preparation of 2-[(S)-1H-benzimidazol-2-yl-deuterio-(5-fluoro-2-hydroxy-phenyl)methyl]-6-[4-(1-methyl-4-piperidyl)phenyl]isoquinolin-1-one and 2-[(R)-1H-benzimidazol-2-yl-deuterio-(5-fluoro-2-hydroxy-phenyl)methyl]-6-[4-(1-methyl-4-piperidyl)phenyl]isoquinolin-1-one (114 and 115)

Scheme 23

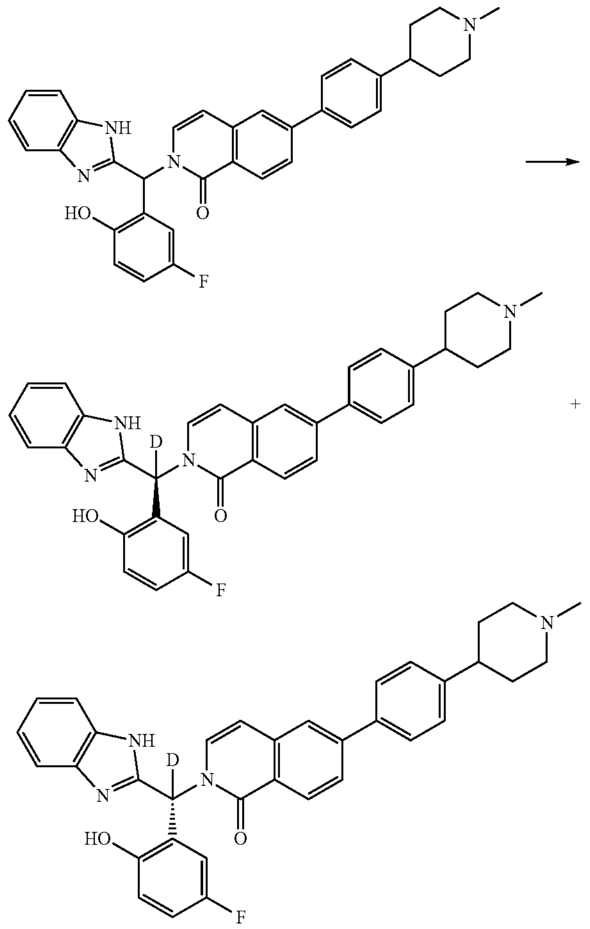

Rac-2-(1H-1,3-benzodiazol-2-yl)(5-fluoro-2-hydroxyphenyl)methyl]-6-[4-(1-methylpiperidin-4-yl)phenyl]-1,2-dihydroisoquinolin-1-one (069, 50 mg, 0.090 mmol) was dissolved in dry tetrahydrofuran (2 ml) in a vial equipped with a stir bar. Deuterium oxide (1000 µL, 55.4 mmol) was then added with stirring followed by N,N-diisopropylethylamine (62.2 µL, 358 µmol). The reaction vial was sealed then the reaction was allowed to stir at 70° C. for 60 hours. An $^1$HNMR (DMSO-$d_6$) of the reaction solution indicated ~100% incorporation of deuterium on the methine carbon based on the disappearance of the methine peak @ ~7.67 ppm. The reaction was cooled to room temperature then evaporated to leave crude product which was dissolved in 5 ml THF. 75 uL of a 35 wt % DCI in $D_2O$ solution was then added dropwise with stirring. After 10 minutes, the reaction solution was concentrated, and the residue was dried under vacuum overnight to give crude product as the bis DCI salt. The crude product was purified to separate enantiomers using a Chiralpak IG (10×250 mm 5 micron) column eluting with 55% (0.3% TEA in MeOH)/45% CO2 at back pressure regulator (BPR) value of 10 MPa and flow rate of 7 mL/min on a Jasco semi-prep SFC. Absolute configuration of the chiral center for each isolated enantiomer is unknown. First eluting peak (114) (19.7 mg, 37%, 100:0 er); $[\alpha]^{20}_D$ −13.6 (c=0.0515, MeOH); $^1$H NMR (DMSO-$d_6$, 400 MHz) δ: 11.9-13.5 (m, 1H), 9.6-10.9 (m, 1H), 8.28 (d, 1H), 7.94 (s, 1H), 7.81 (d, 1H), 7.7-7.8 (m, 2H), 7.54 (br s, 2H), 7.3-7.4 (m, 2H), 7.29 (d, 1H), 7.19 (br dd, 2H), 7.08 (dt, 1H), 6.88 (dd, 1H), 6.6-6.7 (m, 2H), 2.88 (br d, 2H), 2.5-2.7 (m, 1H), 2.20 (s, 3H), 1.9-2.0 (m, 2H), 1.6-1.8 (m, 4H); MS m/z: 560.3 $[M+1]^+$. Second eluting peak (115) (18.8 mg, 36%, 99.7:0.3 er); $[\alpha]^{20}_D$ +14.2 (c=0.0705, MeOH); $^1$H NMR (DMSO-$d_6$, 400 MHz) δ: 11.9-13.5 (m, 1H), 9.6-10.9 (m, 1H), 8.28 (d, 1H), 7.94 (s, 1H), 7.81 (d, 1H), 7.7-7.8 (m, 2H), 7.54 (br s, 2H), 7.3-7.4 (m, 2H), 7.29 (d, 1H), 7.19 (br dd, 2H), 7.08 (dt, 1H), 6.88 (dd, 1H), 6.6-6.7 (m, 2H), 2.88 (br d, 2H), 2.5-2.7 (m, 1H), 2.20 (s, 3H), 1.9-2.0 (m, 2H), 1.6-1.8 (m, 4H); MS m/z: 560.3 $[M+1]^+$.

The following examples were prepared by a similar method to Example 23 from 2-[1H-benzimidazol-2-yl-(5-fluoro-2-hydroxy-phenyl)methyl]-8-fluoro-6-[4-(1-methyl-4-piperidyl)phenyl]isoquinolin-1-one (070). The absolute configuration of the chiral center for each isolated enantiomer is unknown:

| No. | Structure/Name | m/z $[M + 1]^+$ | $^1$H NMR (DMSO-$d_6$) δ | Optical rotation |
|---|---|---|---|---|
| 116 | 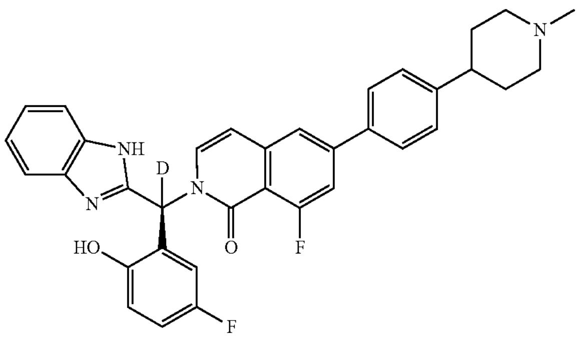 [SMILES: [2H][C@](c1nc2ccccc2[nH]1)(c1cc(F)ccc1O)n1ccc2cc(-c3ccc(C4CCN(C)CC4)cc3)cc(F)c2c1=O] | 578.3 | 12.7-12.8 (m, 1H), 9.9-10.1 (m, 1H), 7.7-7.8 (m, 3H), 7.4-7.6 (m, 3H), 7.39 (br d, 2H, J = 7.9 Hz), 7.29 (d, 1H, J = 7.6 Hz), 7.20 (br s, 2H), 7.0-7.2 (m, 1H), 6.90 (dd, 1H, J = 4.8, 8.7 Hz), 6.6-6.7 (m, 2H), 2.89 (br d, 2H, J = 10.6 Hz), 2.5-2.6 (m, 1H), 2.21 (s, 3H), 2.00 (br t, 2H, J = 10.8 Hz), 1.6-1.8 (m, 4H) | $[\alpha]^{20}_D$-11.8 (c = 0.0595, MeOH) |

-continued

| No. | Structure/Name | m/z [M + 1]+ | $^1$H NMR (DMSO-$d_6$) δ | Optical rotation |
|---|---|---|---|---|
| | 2-[1H-Benzimidazol-2-yl-(5-fluoro-2-hydroxy-phenyl)methyl]-8-fluoro-6-4-(3-methyl-3-azabicyclo[4.1.0]-heptan-6-yl)phenyl]isoquinolin-1-one; dihydrochloride | | | |
| 117 | 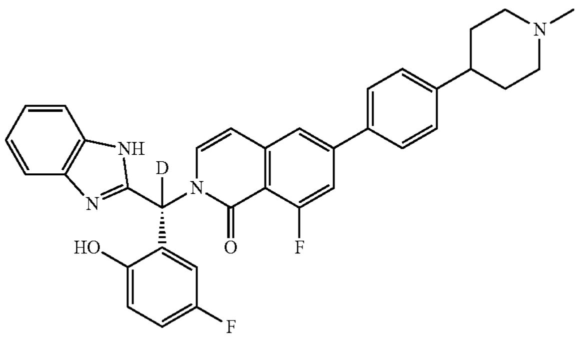 [SMILES: [2H][C@@](c1nc2ccccc2[nH]1)(c1cc(F)ccc1O)n1ccc2cc(-c3ccc(C4CCN(C)CC4)cc3)cc(F)c2c1=O] 2-[1H-Benzimidazol-2-yl-(5-fluoro-2-hydroxy-phenyl)methyl-8-fluoro-6-[3-fluoro-4-(1-methyl-4-piperidyl)phenyl]isoquinolin-1-one; dihydrochloride | 578.3 | 12.7-12.8 (m, 1H), 9.9-10.1 (m, 1H), 7.7-7.8 (m, 3H), 7.4-7.6 (m, 3H), 7.39 (br d, 2H, J = 7.9 Hz), 7.29 (d, 1H, J = 7.6 Hz), 7.20 (br s, 2H), 7.0-7.2 (m, 1H), 6.90 (dd, 1H, J = 4.8, 8.7 Hz), 6.6-6.7 (m, 2H), 2.89 (br d, 2H, J = 10.6 Hz), 2.5-2.6 (m, 1H), 2.21 (s, 3H), 2.00 (br t, 2H, J = 10.8 Hz), 1.6-1.8 (m, 4H) | $[\alpha]^{20}_D$ 14.8 (c = 0.061, MeOH) |

Example 24: 2-((1H-Benzo[d]imidazol-2-yl)(5-fluoro-6-(4-(1-methylpiperidin-4-yl)phenyl)-2H-indazol-2-yl)methyl)-4-fluorophenol (118)

Scheme 24

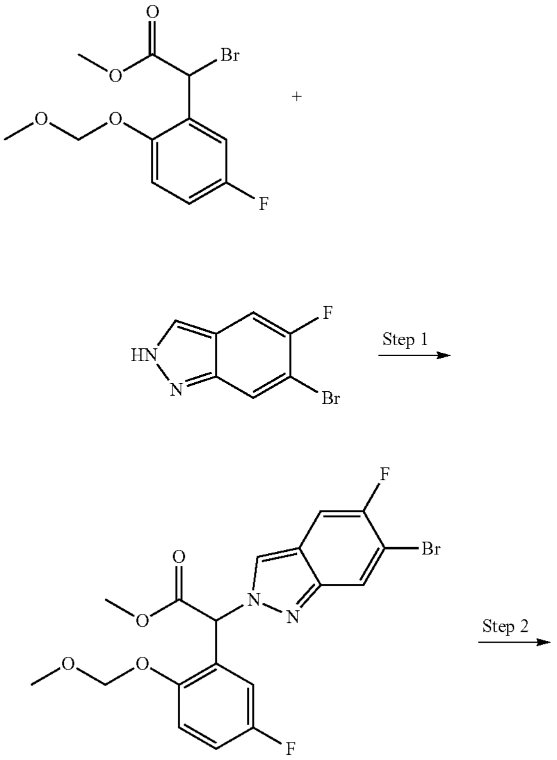

-continued

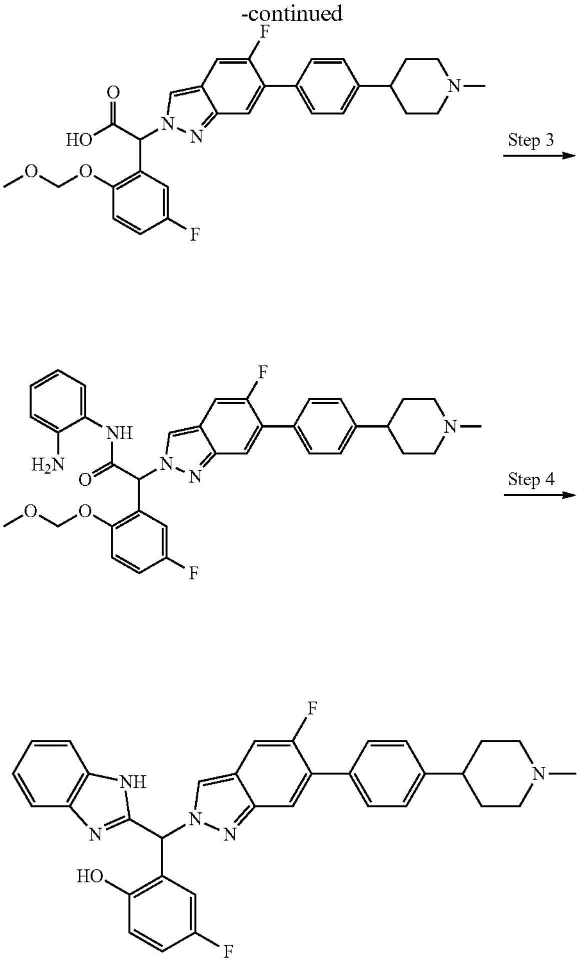

Step 1. Methyl 2-(6-bromo-5-fluoro-2H-indazol-2-yl)-2-(5-fluoro-2-(methoxymethoxy)phenyl) acetate

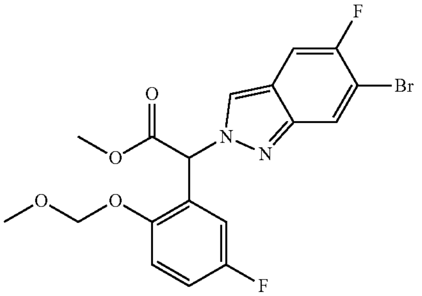 [SMILES: COCOc1ccc(F)cc1C(C(=O)OC)n1cc2cc(F)c(Br)cc2n1]

Methyl 2-bromo-2-(5-fluoro-2-(methoxymethoxy)phenyl)acetate (513 mg, 1.67 mmol) was added to a suspension of 6-bromo-5-fluoro-2H-indazole (360 mg, 1.67 mmol) and cesium carbonate (651 mg, 2.09 mmol) In $CH_3CN$ (16 mL) and the mixture was stirred at 0° C. for 1 hr, and then at RT for 16 hrs. The mixture was partitioned between water and EtOAc, and the aqueous layer extracted with EtOAc (3×30 mL). The combined organic layer was washed with brine, dried ($Na_2SO_4$), filtered and the residue purified by silica chromatography (0-20% EtOAc in Hex) to give the title compound (204 mg, 19%) as a solid. $^1$H NMR (CDCl3-d) δ: 8.00 (d, 1H); 7.92 (s, 1H), 7.31 (d, 1H), 7.20 (dd, 1H), 7.13 (m, 1H), 7.11 (d, 1H), 6.80 (s, 1H), 5.18 (d, 1H), 5.14 (d, 1H), 3.86 (s, 3H), 3.35 (s; 3H); MS m/z: 442.8 $[M+1]^+$.

Step 2. 2-(5-Fluoro-2-(methoxymethoxy)phen)-2-(5-fluoro-6-(4-(1-methylpiperidin-4-yl)phenyl)-2H-indazol-2-yl)acetic acid

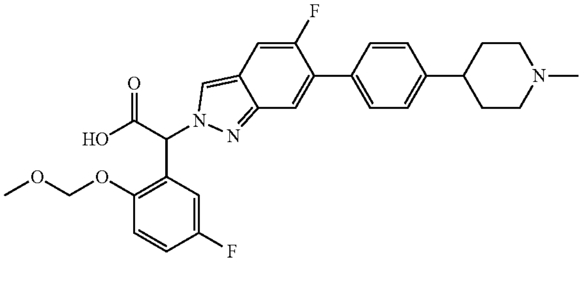

A mixture of methyl 2-(6-bromo-5-fluoro-2H-indazol-2-yl)-2-(5-fluoro-2-(methoxymethoxy)-phenyl)acetate (205 mg, 0.47 mmol), 1-methyl-4-(4-(4,4,5,5-tetramethyl-1,3,2-dioxaborolan-2-yl)phenyl)piperidine (147 mg, 0.49 mmol), Pd(dppf)$Cl_2$·DCM (38 mg, 0.047 mmol) and sodium carbonate (149 mg, 1.41 mmol) in dioxane:water (3:1, 3 mL) was degassed and re-suffused with nitrogen three times. The mixture was heated at 100° C. for 4 hours under nitrogen. After cooling, the reaction mixture was filtered and purified by reverse phase HPLC, eluting with 0-80% ACN/water (0.035% TFA modifier) to give the title compound (117 mg, 48%). $^1$H NMR (DMSO-$d_6$) δ: 9.35 (br s, 1H), 8.47 (s, 1H), 7.72 (d, 1H); 7.56 (m, 3H), 7.36 (d, 2H), 7.27 (m, 1H), 7.22 (dd, 1H), 7.16 (dd, 1H), 6.83 (s, 1H), 5.25 (d, 2H), 5.22 (d, 2H), 3.56 (d, 2H), 3.32 (s, 3H), 3.11 (m, 2H), 2.87 (m, 1H), 2.84 (d, 3H), 2.08 (m, 2H), 1.87 (m, 2H); MS m/z: 521.9 $[M+1]^+$.

Step 3. N-(2-Aminophenyl)-2-(5-fluoro-2-(methoxymethoxy)phenyl)-2-(5-fluoro-6-(4-methylpiperidin-4-yl)phenyl)-2H-indazol-2-yl)acetamide

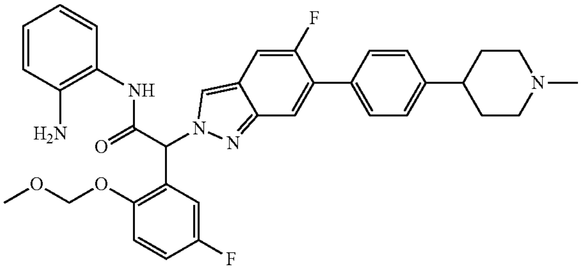

A mixture of 2-(6-bromo-(5-Fluoro-2-(methoxymethoxy) phenyl)-2-(5-fluoro-6-(4-(1-methylpiperidin-4-yl)phenyl)-2H-indazol-2-yl)acetic acid (117 mg, 0.48 mmol), benzene-1,2-diamine (156 mg, 1.44 mmol), HATU (365 mg, 0.96 mmol), DEA (250 mL, 1.44 mmol) and degassed DMF (3 mL) was stirred for 1 hour. The reaction mixture was purified by reverse phase HPLC, eluting with 0-80% ACN/water (0.035% TFA modifier) to give the title compound. $^1$H NMR (DMSO-$d_6$) δ: 9.92 (s, 1H), 9.33 (br s, 1H), 8.31 (s, 1H), 7.73 (d, 1H), 7.57 (m, 3H), 7.36 (d, 2H), 7.29 (m, 1H), 7.27 (dd, 1H), 7.18 (dd, 1H), 7.01 (dd, 1H), 6.99 (s, 1H), 6.96 (m, 1H), 6.74 (d, 1H), 6.58 (m, 1H), 5.24 (d, 1H), 5.19 (d, 1H), 3.55 (d, 2H), 3.25 (s, 3H), 3.11 (m, 2H), 2.87 (m, 1H), 2.84 (d, 3H), 2.08 (m, 2H), 1.86 (m, 2H).

Step 4. 2-((1H-Benzo[d]imidazol-2-yl)(5-fluoro-6-(4-(1-methylpiperidin-4-yl)phenyl)-2H-indazol-2-yl) methyl)-4-fluorophenol (118)

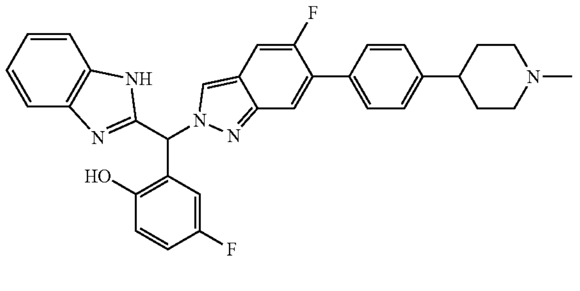 [SMILES: CN1CCC(c2ccc(-c3cc4nn(C(c5nc6ccccc6[nH]5)c5cc(F)ccc5O)cc4cc3F)cc2)CC1]

The material from step 3 was heated in AcOH (5 mL) at 100° C. for 1 hr. The solvent was removed under reduced pressure, and the residue was dissolved in 1:1 TFA:DCM (5 mL) for 5 hrs. The reaction mixture was purified by reverse phase HPLC, eluting with 0-80% ACN/water (0,035% TFA modifier) to give the title compound (39 mg, 13% over 3 steps). $^1$H NMR (DMSO-$d_6$) δ: 10.18 (br s, 1H), 9.36 (br s, 1H), 8.46 (s, 1H), 7.71 (d, 1H), 7.59 (d, 2H), 7.57 (m, 4H), 7.35 (d, 2H), 7.24 (m, 2H), 7.12 (dd, 1H), 6.93 (dd, 1H), 6.87 (dd, 1H), 3.54 (d, 2H), 3.10 (m, 2H), 2.86 (m, 1H), 2.84 (d, 3H), 2.08 (m, 2H), 1.86 (m, 2H); MS m/z: 550.0 $[M+1]^+$.

The following example was prepared by a similar method to Example 24 from methyl 2-bromo-2-(5-fluoro-2-(methoxymethoxy)phenyl)acetate and the corresponding bicyclic starting material:

| No. | Structure/Name | m/z $[M + 1]^+$ | $^1H$ NMR (DMSO-$d_6$) δ | Starting materials |
|---|---|---|---|---|
| 119 | 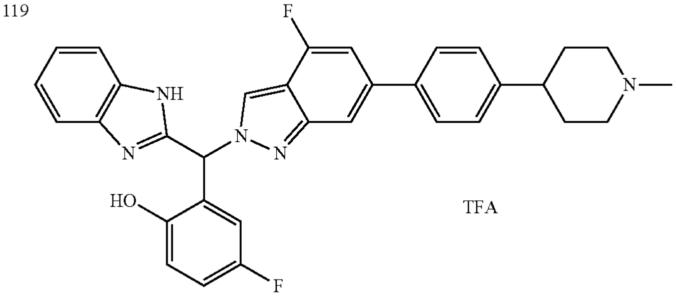 TFA 2-((1H-Benzo[d]imidazol-2-yl)(4-fluoro-6-(4-(1-methylpiperidin-4-yl)phenyl)-2H-indazol-2-yl)methyl)-4-fluorophenol; trifluoroacetate | 550.0 | 10.21 (br s, 1H), 9.43 (br s, 1H), 8.70 (s, 1H), 7.74 (m, 3H), 7.61 (s, 1H), 7.58 (m, 2H), 7.34 (d, 2H), 7.24 (m, 2H), 7.20 (d, 2H), 7.13 (m, 1H), 6.94 (m, 2H), 3.54 (d, 2H), 3.10 (m, 2H), 2.85 (m, 1H), 2.83 (d, 3H), 2.06 (m, 2H), 1.86 (m, 2H) | 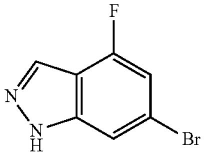 [SMILES: Fc1cc(Br)cc2[nH]ncc12] |

Scheme 25

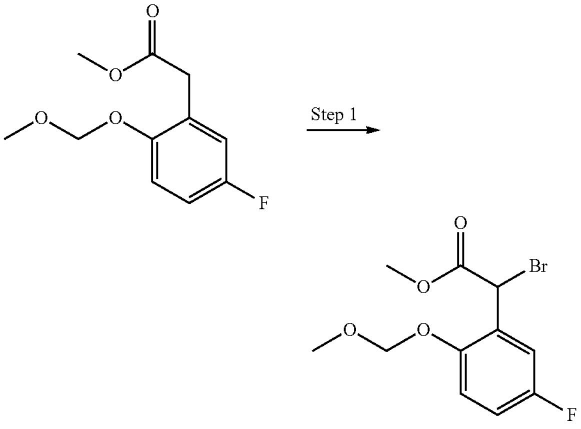

Step 1. methyl 2-bromo-2-(5-fluoro-2-(methoxymethoxy)phenyl)acetate

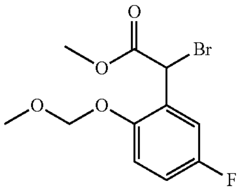 [SMILES: COCOc1ccc(F)cc1C(Br)C(=O)OC]

To a solution of methyl 5-fluoro-2-(methoxymethoxy) benzeneacetate (5.00 g, 21.9 mmol) in chloroform (80 mL) was added N-bromosuccinimide (4.66 g, 26.2 mmol) and benzoyl peroxide (0.530 g, 2.19 mmol). After stirring at 80° C. for 16 h, the solvent was removed under reduced pressure. The crude compound was purified by silica gel column chromatography eluting with 0-5% ethyl acetate in petroleum ether to give the title compound (2.4 g, 36%). $^1H$ NMR (400 MHz, $CDCl_3$) δ: 7.31 (dd, 1H), 6.97-7.03 (m, 1H), 6.87-6.95 (m, 1H), 5.76 (s, 1H), 5.12 (d, 2H), 3.72 (s, 3H), 3.41 (s, 3H).

Example 25: HTRF-Based EGFR Biochemical Assays

EGFR biochemical activity measurements were carried out using the homogeneous time-resolved fluorescence (HTRF) assay (Cisbio), inhibitors and DMSO normalizations were first dispensed to empty black low-volume 384-well plates (Corning) with 0300 digital liquid dispenser (HP). All reactions were carried out at room temperature and solutions were added to plates with a Multidrop Combi Reagent Dispenser (ThermoFisher). The reaction mixture (10 μL final volume) contained 1 μM tyrosine kinase peptide-biotin substrate and mutant EGFR in a reaction buffer (50 mM HEPES pH 7.0, 5 mM $MgCl_2$, 1 mM $MnCl_2$, 0.01% BSA, 2 mM TCEP, 0.1 mM $NaVO_4$). Enzyme concentrations were adjusted to accommodate varying kinase activities (L858R 0.1 nM, L858R/T790M 0.02 nM). Enzyme reaction solution (2× concentrations, 5 μL) was added to 384-well plates containing compounds and incubated for 30 mins. Enzyme reactions were initiated with the addition of 5 μL of ATP to a final concentration of 100 μM and reacted for 20 mins. Reactions were quenched with the addition of 10 μL of phospho-tyrosine antibody-Europium(III) cryptate (1-to-180 volume ratio) and Streptavidin-XL665 (46.7 nM) in EDTA-containing detection buffer, then incubated at room temperature for 1 hour, and read with a PHERAstar plate reader (excitation=337 nm, emission=620 nm and 665 nm). $IC_{50}$ values were determined by inhibition curves (11-point curves from 1.0 μM to 0.130 nM or 23-point curves from 1.0 μM to 0.130 μM) in triplicate with non-linear least squares fit in GraphPad Prism 7.0d. The data obtained are shown in Table 7 below.

TABLE 7

| No. | HTRF $IC_{50}$ EGFR L858R/T790M, nM | HTRF $IC_{50}$ EGFR L858R, nM |
|---|---|---|
| 001 | 0.4 | 1 |
| 002 | 4 | 17 |
| 003 | 2 | 9 |
| 004 | 0.4 | 1 |
| 005 | 1 | 8 |
| 006 | 0.5 | 2 |
| 007 | 0.4 | 1 |
| 008 | 5 | 42 |

TABLE 7-continued

| No. | HTRF $IC_{50}$ EGFR L858R/T790M, nM | HTRF $IC_{50}$ EGFR L858R, nM |
|---|---|---|
| 009 | 0.4 | 3 |
| 010 | 4 | 12 |
| 011 | 10 | 15 |
| 012 | 6 | 48 |
| 013 | 33 | 22 |
| 014 | 0.3 | 2 |
| 015 | 2 | 15 |
| 016 | 0.7 | 3 |
| 017 | 0.4 | 1 |
| 018 | 5 | 9 |
| 019 | 1 | 4 |
| 021 | 2 | 6 |
| 022 | 0.1 | 0.3 |
| 023 | 1 | 6 |
| 024 | 0.5 | 2 |
| 025 | 11 | 150 |
| 026 | 7 | 26 |
| 028 | 0.3 | 2 |
| 029 | 0.6 | 2 |
| 030 | 35 | 80 |
| 031 | 8 | 45 |
| 032 | 0.3 | 2 |
| 033 | 6 | 24 |
| 034 | 0.7 | 4 |
| 035 | 42 | 507 |
| 036 | 0.7 | 2.6 |
| 037 | 0.5 | 1.4 |
| 038 | 6 | 18 |
| 039 | 0.5 | 2.9 |
| 040 | 2 | 7 |
| 041 | 2 | 5 |
| 042 | 13 | 31 |
| 043 | 73 | 49 |
| 044 | 2 | 6 |
| 045 | 18 | 32 |
| 046 | 0.7 | 4 |
| 047 | 2 | 14 |
| 048 | 4 | 35 |
| 049 | 2 | 6 |
| 050 | 2 | 21 |
| 051 | 1 | 10 |
| 052 | 2 | 5 |
| 053 | 1 | 6 |
| 054 | 0.4 | 2 |
| 055 | 1 | 2 |
| 056 | 8 | 12 |
| 057 | 17 | 37 |
| 058 | 12 | 67 |
| 059 | 13 | >100 |
| 060 | 18 | 27 |
| 061 | 11 | 69 |
| 062 | 0.7 | 3 |
| 063 | 2 | 9 |
| 064 | 20 | 31 |
| 065 | 0.5 | 2 |
| 066 | 3 | 14 |
| 067 | 4 | 11 |
| 068 | 166 | 756 |
| 069 | 5 | 9 |
| 070 | 1 | 4 |
| 071 | 20 | >100 |
| 073 | 14 | 21 |
| 074 | 1 | 2 |
| 075 | 0.7 | 1 |
| 076 | 2 | 2 |
| 077 | 2 | 2 |
| 078 | 1 | 3 |
| 079 | 0.8 | 3 |
| 080 | 0.6 | 3 |
| 081 | 0.8 | 6 |
| 082 | 0.6 | 3 |
| 083 | 0.6 | 1 |
| 084 | 232 | 219 |
| 085 | 28 | 13 |
| 086 | 25 | >100 |
| 087 | 25 | >100 |

TABLE 7-continued

| No. | HTRF $IC_{50}$ EGFR L858R/T790M, nM | HTRF $IC_{50}$ EGFR L858R, nM |
|---|---|---|
| 090 | 8 | 11 |
| 091 | 6 | 12 |
| 092 | 1 | 4 |
| 093 | 4 | 3 |
| 94 | 2 | 1 |
| 095 | 59 | 92 |
| 096 | 0.8 | 3 |
| 097 | 36 | 16 |
| 098 | 4 | 6 |
| 099 | 8 | 10 |
| 100 | 4 | 14 |
| 101 | 0.8 | 4 |
| 102 | 4 | 6 |
| 104 | 2 | 1 |
| 105 | 49 | 65 |
| 106 | 0.8 | 3 |
| 107 | 17 | 71 |
| 108 | 2 | 5 |
| 109 | 2 | 4 |
| 110 | 0.6 | 3 |
| 111 | 0.6 | 3 |
| 112 | 2 | 3 |
| 113 | 4 | 14 |
| 114 | 0.9 | 2 |
| 115 | 157 | 132 |
| 116 | 0.2 | 0.8 |
| 117 | 81 | >100 |
| 118 | 6 | 16 |
| 119 | 3 | 11 |

Example 26: Ba/F3 Cell Proliferation Models

The EGFR mutant L858R and L858R/T790M Ba/F3 cells have been previously described (Zhou, W., et al. *Nature* 462, 2009, 1070-1074). All cell lines were maintained in RPM 1640 (Cellgro; Mediatech Inc., Herndon. CA) supplemented with 10% FBS, 100 units/mL penicillin, 100 units/mL streptomycin. The EGFR I941R mutation was introduced via site directed mutagenesis using the Quick Change Site-Directed Mutagenesis kit (Stratagene; La Jolla, CA) according to the manufacturer's instructions. All constructs were confirmed by DNA sequencing. The constructs were shuttled into the retroviral vector JP1540 using the Cre-recombination system (Agilent Technologies, Santa Clara, CA). Ba/F3 cells were then infected with retrovirus per standard protocols, as described previously (Zhou, et al, *Nature* 2009). Stable clones were obtained by selection in puromycin (2 μg/ml).

Growth and inhibition of growth was assessed by the Cell Titer Glo® assay (Promega, Madison, WI) and was performed according to the manufacturer's instructions. The Cell Titer Glo® assay is a luminescence-based method used to determine the number of viable cells based on quantitation of the ATP present, which is directly proportional to the amount of metabolically active cells present. Ba/F3 cells of different EGFR genotypes were exposed to compounds as a single agent or in combination with 1 μg/mL cetuximab for 72 hours and the number of cells used per experiment was determined empirically as has been previously established (Zhou, et al., Nature 2009). All experimental points were set up in triplicates in 384-well plates and all experiments were repeated at least three times. The luminescent signal was detected using a spectrometer and the data was graphically displayed using GraphPad Prism® version 5.0 for Windows®, (GraphPad Software; www.graphpad.com). The curves were fitted using a non-linear regression model with a sigmoidal dose response. The results of this assay for the compounds disclosed herein are shown in Table 8.

TABLE 8

| No. | Cell $IC_{50}$ BaF3 EGFR L858R/T790M, uM | Cell $IC_{50}$ BaF3 EGFR L858R/T790M (+cetux.), uM | Cell $IC_{50}$ BaF3 EGFR L858R, uM | Cell $IC_{50}$ BaF3 EGFR L858R (+cetux.), uM |
|---|---|---|---|---|
| 001 | 0.32 | 0.009 | | |
| 002 | 4.45 | 0.14 | | |
| 003 | 1.4 | 0.05 | | |
| 004 | 0.09 | 0.01 | 0.24 | 0.03 |
| 005 | 1.22 | 0.02 | | |
| 006 | 0.28 | 0.005 | 1.10 | 0.06 |
| 007 | 0.52 | 0.009 | | |
| 008 | 5.41 | 0.17 | | |
| 009 | 0.94 | 0.02 | 3.89 | 0.18 |
| 010 | 1.93 | 0.02 | | |
| 011 | 1.92 | 0.01 | | |
| 012 | 0.62 | 0.01 | | |
| 013 | >10 | 0.26 | | |
| 014 | 0.71 | 0.01 | 0.81 | 0.06 |
| 015 | 1.1 | 0.02 | | |
| 016 | 0.59 | 0.01 | | |
| 017 | 0.26 | 0.006 | | |
| 018 | 3.49 | 0.02 | | |
| 019 | 1.87 | 0.01 | | |
| 020 | 0.44 | 0.006 | 1.36 | 0.17 |
| 021 | 1.65 | 0.02 | | |
| 022 | 0.38 | 0.005 | 0.64 | 0.04 |
| 023 | 0.95 | 0.02 | | |
| 024 | 0.44 | 0.007 | 1.18 | 0.06 |
| 025 | 3.05 | 0.18 | | |
| 026 | 2.28 | 0.08 | | |
| 028 | 1.36 | 0.03 | | |
| 029 | 0.76 | 0.02 | | |
| 030 | >10 | 0.33 | | |
| 031 | >10 | 0.37 | | |
| 032 | 0.21 | 0.007 | 0.96 | 0.05 |
| 033 | 5.23 | 0.34 | | |
| 034 | 0.42 | 0.005 | 1.43 | 0.06 |
| 035 | 3.6 | 0.53 | | |
| 036 | 0.17 | 0.007 | | |
| 037 | 0.16 | 0.004 | | |
| 038 | 0.93 | 0.041 | | |
| 039 | 0.28 | 0.014 | | |
| 040 | 1.57 | 0.01 | | |
| 041 | 0.95 | 0.02 | | |
| 042 | 4.00 | 0.24 | | |
| 043 | 4.94 | 0.58 | | |
| 044 | 1.50 | 0.05 | | |
| 045 | 3.74 | 1.17 | | |
| 046 | 0.86 | 0.02 | | |
| 047 | 1.84 | 0.08 | | |
| 048 | 4.76 | 0.76 | | |
| 049 | 2.54 | 0.02 | | |
| 050 | 3.85 | 0.85 | | |
| 051 | 3.92 | 1.05 | | |
| 052 | 4.18 | 0.37 | | |
| 053 | 0.56 | 0.005 | | |
| 054 | 1.06 | 0.02 | | |
| 055 | 0.10 | 0.01 | | |
| 056 | 1.28 | 0.01 | | |
| 057 | 0.55 | 0.01 | | |
| 058 | 1.42 | 0.02 | | |
| 059 | 0.79 | 0.01 | | |
| 060 | 5.50 | 0.11 | | |
| 061 | 0.79 | 0.02 | | |
| 062 | 0.65 | 0.02 | | |
| 063 | 0.89 | 0.05 | 1.05 | |
| 064 | 0.22 | 0.02 | 0.67 | |
| 065 | 0.03 | | 0.13 | |
| 069 | 0.52 | 0.01 | 0.36 | |
| 070 | 0.07 | 0.005 | 0.16 | |
| 071 | 1.38 | 0.33 | 1.21 | |
| 073 | 0.58 | 0.02 | 0.93 | |
| 074 | 0.12 | 0.02 | 0.11 | |
| 075 | 0.09 | 0.02 | 0.1 | |

TABLE 8-continued

| No. | Cell $IC_{50}$ BaF3 EGFR L858R/T790M, uM | Cell $IC_{50}$ BaF3 EGFR L858R/T790M (+cetux.), uM | Cell $IC_{50}$ BaF3 EGFR L858R, uM | Cell $IC_{50}$ BaF3 EGFR L858R (+cetux.), uM |
|---|---|---|---|---|
| 076 | 0.14 | 0.03 | 0.09 | |
| 077 | 0.45 | 0.05 | 0.91 | |
| 078 | 0.31 | 0.02 | 0.69 | |
| 079 | 0.19 | 0.007 | 0.83 | |
| 080 | 0.21 | 0.01 | 0.5 | |
| 081 | 0.21 | | | |
| 082 | 0.22 | 0.02 | 0.67 | |
| 083 | 0.2 | | 0.63 | |
| 085 | 1.29 | 0.05 | 0.78 | |
| 086 | 3.22 | | 3.64 | |
| 087 | 1.32 | | 1.37 | |
| 089 | 5.95 | | 4.53 | |
| 090 | 0.86 | 0.02 | 1.43 | |
| 091 | 1.05 | 0.12 | 1.78 | |
| 092 | 0.1 | 0.01 | 0.82 | |
| 100 | 0.53 | | 2 | |
| 118 | 1.31 | | 4.08 | |
| 119 | 0.42 | | 0.78 | |

The disclosed subject matter is not to be limited in scope by the specific embodiments and examples described herein. Indeed, various modifications of the disclosure in addition to those described will become apparent to those skilled in the art from the foregoing description and accompanying FIGURES. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes. Other embodiments are within the following claims.

The invention claimed is:

1. A compound of Formula Ia:

(Ia)

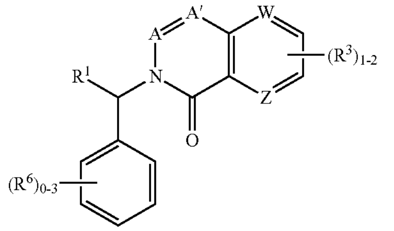

or a pharmaceutically acceptable salt thereof;

wherein:

A and A' are each, independently, CH or N;

W and Z are each, independently, CH or C-halo;

$R^1$ is selected from the group consisting of:

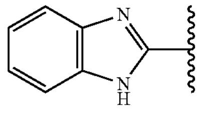

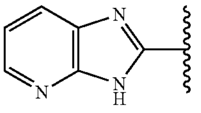

-continued

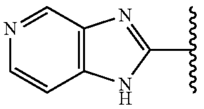
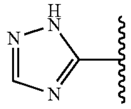
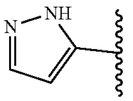
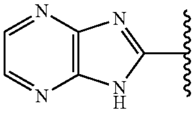
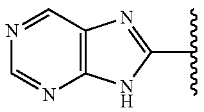
and
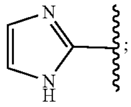
;

$R^3$ is phenyl optionally substituted one time with piperidine, wherein piperidine is substituted one time with $R^7$;

$R^6$ is independently, at each occurrence, hydroxy or halo; and $R^7$ is independently, at each occurrence, $C_1$-$C_6$ alkyl.

2. The compound of claim 1, wherein $R^1$ is

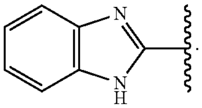
.

3. The compound of claim 1, wherein W is CH.

4. The compound of claim 1, wherein Z is CF.

5. The compound of claim 1, wherein there is one occurrence of $R^3$, and $R^3$ is phenyl substituted one time with piperidine, wherein piperidine is substituted one time with $R^7$.

6. The compound of claim 1, wherein $R^7$ is $C_1$-$C_3$ alkyl.

7. The compound of claim 1, wherein the compound of Formula Ia is selected from the group consisting of

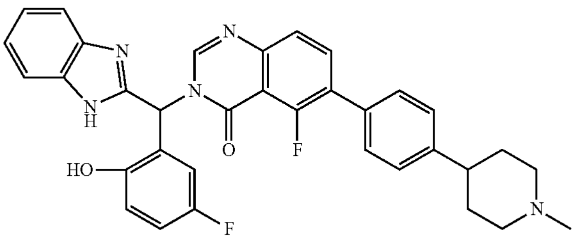

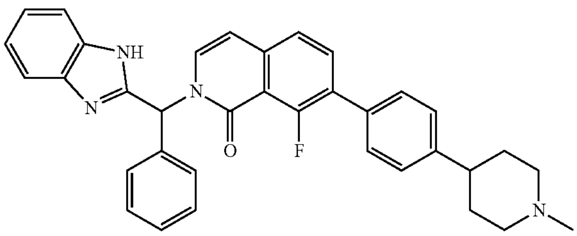

-continued

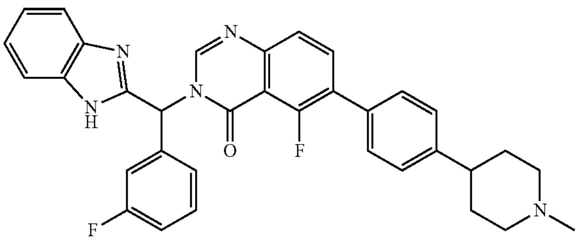

or a pharmaceutically acceptable salt thereof.

8. The compound of claim 1, wherein the compound of Formula Ia is

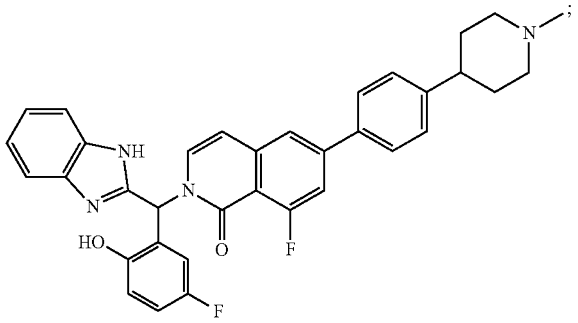
;

or a pharmaceutically acceptable salt thereof.

9. The compound of claim 1, wherein the compound of Formula Ia is

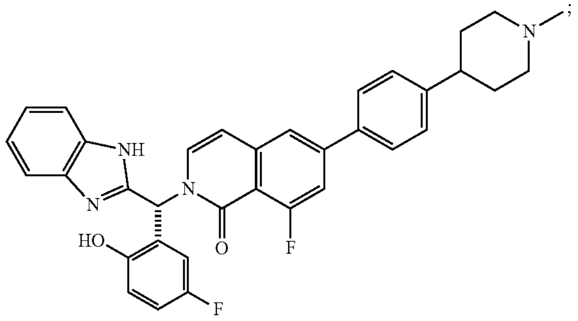 [SMILES: CN1CCC(c2ccc(-c3cc(F)c4c(=O)n(C(c5nc6ccccc6[nH]5)c5cc(F)ccc5O)ccc4c3)cc2)CC1]
;

or a pharmaceutically acceptable salt thereof.

10. The compound of claim 1, wherein the compound of Formula Ia is selected from the group consisting of

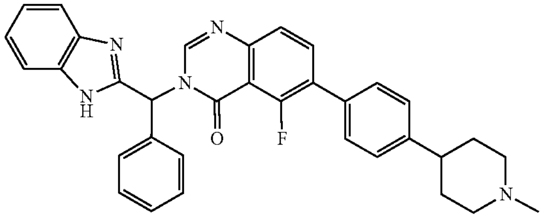

-continued

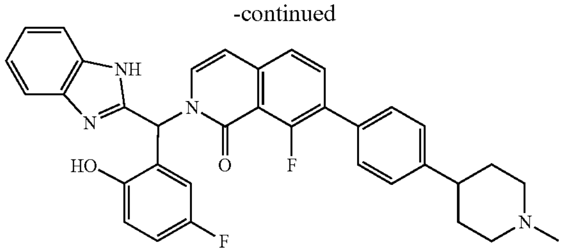

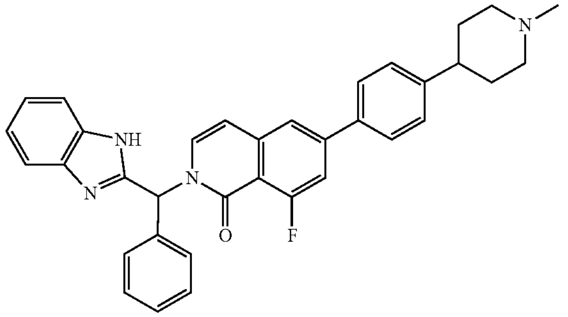

and

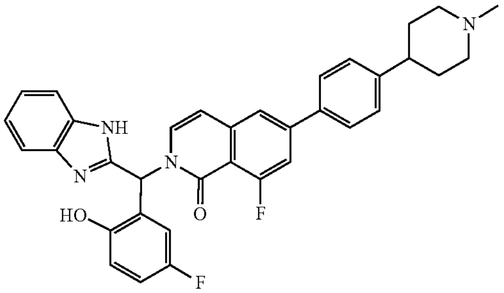

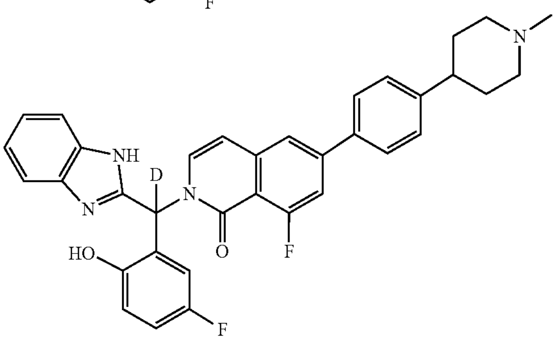

, or a pharmaceutically acceptable salt thereof.

11. A compound of Formula Ia:

(Ia)

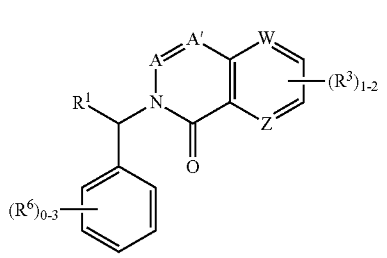

or a pharmaceutically acceptable salt thereof; wherein:

A and A' are each, independently, CH, $CR^8$, or N;

W and Z are each, independently, N, CH, C-halo, C—($C_1$-$C_3$ alkyl), or C—($C_1$-$C_3$ alkoxy);

provided that at least one of W or Z is CH;

$R^1$ is selected from the group consisting of:

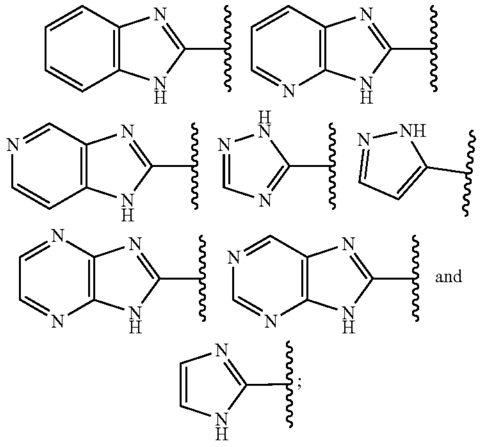

and

;

all of which are optionally substituted with one, two, or three $R^8$ $R^3$ is independently, at each occurrence, selected from the group consisting of $C_2$-$C_6$ alkynyl or $C_6$-$C_{10}$ aryl, wherein alkynyl is optionally substituted one, two, or three times with $R^4$, and wherein aryl is optionally substituted one, two, or three times with $R^5$;

$R^4$ is independently, at each occurrence, selected from the group consisting of H, $(CH_2)_{0-3}$—($C_3$-$C_7$ cycloalkyl), $(CH_2)_{0-3}$—($C_4$-$C_7$ cycloalkenyl), $(CH_2)_{0-3}$—($C_6$-$C_{10}$ aryl), $(CH_2)_{0-3}$-(5-6 membered heteroaryl), and $(CH_2)_{0-3}$-(5-7 membered heterocyclyl), wherein the aryl, heteroaryl, or heterocyclyl are each optionally substituted one, two, or three times with $R^5$;

$R^5$ is independently, at each occurrence, selected from the group consisting of $C_1$-$C_6$ alkyl, $C_1$-$C_6$ haloalkyl, $C_1$-$C_6$ alkoxy, $C_1$-$C_6$ haloalkoxy, $C_1$-$C_3$ alkylamine, 3-10 membered cycloalkyl, halogen, COOH, C(O)O($C_1$-$C_6$ alkyl), $O(CH_2)_{1-3}$—OH, $NH_2$, NH($C_1$-$C_6$ alkyl), N($C_1$-$C_6$ alkyl)$_2$, OH, CN, $(CH_2)_{0-3}$—($C_6$-$C_{10}$ aryl), $(CH_2)_{0-3}$-(5-6 membered heteroaryl), and $(CH_2)_{0-3}$-(5-7 membered heterocyclyl), wherein the aryl, heteroaryl, or heterocyclyl are each optionally substituted one, two, or three times with $R^7$;

$R^6$ is independently, at each occurrence, selected from the group consisting of $C_1$-$C_3$ alkyl, $C_1$-$C_3$ haloalkyl, $C_1$-$C_3$ alkoxy, $C_1$-$C_3$ haloalkoxy, $C_1$-$C_3$ alkylamine, halogen, OH, $NO_2$, $NH_2$, NH($C_1$-$C_6$ alkyl), N($C_1$-$C_6$ alkyl)$_2$, $(CH_2)_{1-4}OH$, $S(O)_{0-2}H$, $S(O)_{0-2}NH_2$, or CN;

alternatively, two $R^6$, together with the atoms to which they are attached, can form 5-10 membered heteroaryl, 6-10 membered aryl, 3-10 membered heterocycloalkyl, or 3-10 membered cycloalkyl;

$R^7$ is independently, at each occurrence, selected from the group consisting of substituents independently selected from $C_1$-$C_6$ alkyl, $C_1$-$C_6$ haloalkyl, $C_1$-$C_6$ alkoxy, $C_1$-$C_6$ haloalkoxy, halogen, $NH_2$, NH($C_1$-$C_6$ alkyl), N($C_1$-$C_6$ alkyl)$_2$, $SO_2NH_2$, $SO_2NH$($C_1$-$C_6$ alkyl), $SO_2N$($C_1$-$C_6$ alkyl)$_2$, $(CH_2)_{1-2}$—OH, $C(O)(CH_2)_{1-2}$—OH, C(O)($C_1$-$C_6$ alkyl), and C(O)O($C_1$-$C_6$ alkyl);

alternatively, two $R^7$, together with the atoms to which they are attached, can form 5-10 membered heteroaryl, 6-10 membered aryl, 3-10 membered heterocycloalkyl, or 3-10 membered cycloalkyl; and $R^8$ is independently, at each occurrence, selected from the group consisting of $C_1$-$C_3$ alkyl, $C_1$-$C_3$ haloalkyl, $C_1$-$C_3$ alkoxy, $C_1$-$C_3$ haloalkoxy, $C_1$-$C_3$ alkylamine, 3-6 membered cycloalkyl, halogen, OH, $NO_2$, $NH_2$, $NH(C_1$-$C_6$ alkyl), $N(C_1$-$C_6$ alkyl$)_2$, $(CH_2)_{1-4}OH$, $S(O)_{0-2}H$, $S(O)_{0-2}NH_2$, or CN.

12. The compound of claim 11, or a pharmaceutically acceptable salt thereof, wherein:

A is CH and A' is CH, $CR^8$, or N;

W is CH and Z is N, CH, C-halo, C—($C_1$-$C_3$ alkyl), or C—($C_1$-$C_3$ alkoxy);

$R^1$ is benzimidazole optionally substituted with halogen;

$R^3$ is phenyl substituted one or two times with $R^5$;

$R^5$ is either halogen, piperidin-4-yl substituted with methyl, or 3-azabicyclo[4.1.0]heptan-6-yl substituted with methyl;

$R^6$ is independently, at each occurrence, selected from the group consisting of halogen and OH;

$R^8$ is or halogen.

13. The compound of claim 11, wherein $R^1$ is

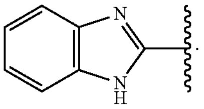 [SMILES: *c1nc2ccccc2[nH]1]

14. The compound of claim 11, wherein W is CH.

15. The compound of claim 11, wherein Z is CF.

16. The compound of claim 11, wherein there is one occurrence of $R^3$, and $R^3$ is phenyl substituted one time with piperidine, wherein piperidine is substituted one time with $R^7$.

17. The compound of claim 11, wherein $R^7$ is $C_1$-$C_3$ alkyl.

18. A pharmaceutical composition comprising a compound of claim 1, or a pharmaceutically acceptable salt thereof, and at least one pharmaceutically acceptable carrier.

19. A pharmaceutical composition comprising a compound of claim 9, or a pharmaceutically acceptable salt thereof, and at least one pharmaceutically acceptable carrier.

20. A pharmaceutical composition comprising a compound of claim 11, or a pharmaceutically acceptable salt thereof, and at least one pharmaceutically acceptable carrier.

21. A method of treating an EGFR-mediated cancer in a subject in need thereof, comprising administering to the subject a therapeutically effective amount of a compound according to claim 1.

22. The method according to claim 21, wherein the cancer is non-small cell lung cancer (NSCLC).

23. The method of claim 21, wherein the method further comprises administering to the subject in need thereof a therapeutically effective amount of osimertinib.

24. A method of treating an EGFR-mediated cancer in a subject in need thereof, comprising administering to the subject a therapeutically effective amount of a compound according to claim 11.

25. The method according to claim 24, wherein the cancer is non-small cell lung cancer (NSCLC).

26. The method of claim 24, wherein the method further comprises administering to the subject in need thereof a therapeutically effective amount of osimertinib.

27. A method of treating an EGFR-mediated cancer in a subject in need thereof, comprising administering to the subject a therapeutically effective amount of a compound according to claim 9.

28. The method according to claim 27, wherein the cancer is non-small cell lung cancer (NSCLC).

29. The method of claim 27, wherein the method further comprises administering to the subject in need thereof a therapeutically effective amount of osimertinib.

* * * * *